United States Patent
June et al.

(10) Patent No.: US 11,274,298 B2
(45) Date of Patent: Mar. 15, 2022

(54) RNA ENGINEERED T CELLS FOR THE TREATMENT OF CANCER

(71) Applicant: The Trustees of the University of Pennsylvania, Philadelphia, PA (US)

(72) Inventors: Carl H. June, Merion Station, PA (US); Yangbing Zhao, Lumberton, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 227 days.

(21) Appl. No.: 16/559,122

(22) Filed: Sep. 3, 2019

(65) Prior Publication Data

US 2020/0087659 A1 Mar. 19, 2020

Related U.S. Application Data

(62) Division of application No. 14/342,904, filed as application No. PCT/US2012/055760 on Sep. 17, 2012, now Pat. No. 10,421,960.

(60) Provisional application No. 61/535,608, filed on Sep. 16, 2011.

(51) Int. Cl.
| | |
|---|---|
| C12N 15/11 | (2006.01) |
| C07K 14/82 | (2006.01) |
| A61K 35/17 | (2015.01) |
| A61K 45/06 | (2006.01) |
| A61K 48/00 | (2006.01) |

(52) U.S. Cl.
CPC .............. C12N 15/11 (2013.01); A61K 35/17 (2013.01); A61K 45/06 (2013.01); C07K 14/82 (2013.01); *A61K 48/00* (2013.01); *C07K 2319/03* (2013.01); *C07K 2319/72* (2013.01); *C12N 2799/027* (2013.01)

(58) Field of Classification Search
CPC ................................ C12N 15/11; A61K 35/17
USPC ..................................... 435/372.3; 424/93.21
See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 5,993,434 | A | 11/1999 | Dev et al. |
| 6,111,095 | A | 8/2000 | Benseler et al. |
| 6,120,766 | A | 9/2000 | Hale et al. |
| 6,181,964 | B1 | 1/2001 | Hofmann et al. |
| 6,233,482 | B1 | 5/2001 | Hofmann et al. |
| 6,241,701 | B1 | 6/2001 | Hofmann et al. |
| 6,352,694 | B1 | 3/2002 | June et al. |
| 6,516,223 | B2 | 2/2003 | Hofmann et al. |
| 6,534,055 | B1 | 3/2003 | June et al. |
| 6,567,694 | B2 | 5/2003 | Hayakawa et al. |
| 6,678,556 | B1 | 1/2004 | Nolan et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,171,264 | B1 | 1/2007 | Hofmann et al. |
| 7,172,869 | B2 | 2/2007 | June et al. |
| 7,173,116 | B2 | 2/2007 | Fewell et al. |
| 7,175,843 | B2 | 2/2007 | June et al. |
| 7,232,566 | B2 | 6/2007 | June et al. |
| 8,242,248 | B2 | 8/2012 | Soper et al. |
| 8,450,112 | B2 | 5/2013 | Peshwa et al. |
| 9,132,153 | B2 | 9/2015 | Peshwa et al. |
| 9,669,058 | B2 | 6/2017 | Li et al. |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2004/0101519 | A1 | 5/2004 | June et al. |
| 2005/0052630 | A1 | 3/2005 | Smith et al. |
| 2005/0070841 | A1 | 3/2005 | Mathiesen et al. |
| 2005/0118185 | A1 | 6/2005 | Hombach et al. |
| 2006/0034810 | A1 | 2/2006 | Riley et al. |
| 2006/0121005 | A1 | 6/2006 | Berenson et al. |
| 2007/0128708 | A1 | 6/2007 | Gamelin et al. |
| 2008/0014208 | A1 | 1/2008 | Reiter et al. |
| 2008/0260706 | A1 | 10/2008 | Rabinovich et al. |
| 2010/0137010 | A1 | 6/2010 | Counts et al. |
| 2010/0324278 | A1 | 12/2010 | Srivastava et al. |
| 2011/0044953 | A1 | 2/2011 | Allison et al. |

FOREIGN PATENT DOCUMENTS

| | | | |
|---|---|---|---|
| WO | 2007031081 | A2 | 3/2007 |
| WO | 2008097926 | A3 | 10/2008 |
| WO | 2009091826 | A2 | 7/2009 |
| WO | WO-2009091826 | A2 * | 7/2009 ......... C07K 16/2803 |

(Continued)

OTHER PUBLICATIONS

Tammana (Jan. 2010, Human Gene Therapy, 21:75-86.*
Holtkamp (Blood, 2006, 108: 4009-4017).*
Kuhn, RNA Biology, Jan. 2011, 8:35-43.*
Carpenito, 2009, PNAS, 106:3360-3365.*
Barrett, 2011, Human Gene Therapy, 22:1575-1586, published online Aug. 12, 2011.*
Zhao (2010, Cancer Res, 70:9053-9061.*
Chinese Patent Application No. 201280056518.6—First Office Action dated Dec. 2, 2015.

(Continued)

*Primary Examiner* — Valarie E Bertoglio
(74) *Attorney, Agent, or Firm* — Saul Ewing Arnstein & Lehr LLP; Kathryn Doyle

(57) ABSTRACT

The present invention relates to compositions and methods for generating RNA Chimeric Antigen Receptor (CAR) transfected T cells. The RNA-engineered T cells can be used in adoptive therapy to treat cancer.

15 Claims, 58 Drawing Sheets
Specification includes a Sequence Listing.

(56) References Cited

FOREIGN PATENT DOCUMENTS

| WO | 2010025177 A1 | 3/2010 |
|---|---|---|
| WO | 2011041093 A1 | 4/2011 |

OTHER PUBLICATIONS

Eurasian Patent Application No. 201490636—Office Action dated Oct. 2015.
European Supplementary Search Report for EP12832609.7 dated Mar. 25, 2015.
Indian Patent Application No. 1744/DELNP/2014—First Examination Report dated Nov. 12, 2018.
"International Search Report dated Mar. 18, 2013—PCT/US2012/055760".
Banerjee, "5'-Terminal Cap Structure in Eucaryotic Messenger Ribonucleic Acids.", 1980, Microbiological Reviews 44(2):175-205.
Barrett, et al., "Determinants of intracellular RNA pharmacokinetics: Implications for RNA based immuntotherapeutics.", RNA Biol. Jan.-Feb. 2011;8(1):35-43.
Barrett, et al., "Treatment of Advanced Leukemia in Mice with mRNA Engineered T Cells", Human Gene Therapy 22, Dec. 2011, 1575-1586.
Berg, et al., "Selective expansion of a peripheral blood CD8+ memory T cell subset expressing both granzyme B and L-selectin during primary viral infection in renal allograft recipients", Transplant Proc. 30(8), 1998, 3975-3977.
Betts, et al., "Detection of T-Cell Degranulation: CD107a and b.", 2004 Methods Cell Biol 75:497-512.
Bierer, et al., "Cyclosporin A and FK506: molecular mechanisms of immunosuppression.", Curr Opin Immunol. Oct. 1993;5(5):763-73.
Bird, et al., "Single-chain antigen-binding proteins", 1988, Science 242:423-426.
Birkholz, et al., "Transfer of mRNA encoding recombinant immunoreceptors reprograms CD4+ and CD8+ T cells for use in the adoptive immunotherapy of cancer.", Gene Therapy (2009) 16, 596-604.
Brentjens, et al., "Genetically Targeted T Cells Eradicate Systemic Acute Lymphoblastic Leukemia Xenografts", 2007, Clin Cancer Res 13:5426-5435.
Brentjens, et al., "Treatment of Chronic Lymphocytic Leukemia With Genetically Targeted Autologous T Cells: Case Report of an Unforeseen Adverse Event in a Phase I Clinical Trial", Molecular Therapy 18:666-668.
Brocker, et al., "Adoptive Tumor Immunity Mediated by Lymphocytes Bearing Modified Antigen-Specific Receptors.", 1998, Adv Immunol 68:257-269.
Buning, et al., "Do CARs Need a Driver's License? Adoptive Cell Therapy with Chimeric Antigen Receptor-Redirected T Cells Has Caused Serious Adverse Events.", Human Gene Therapy 21:1039-1042 (Sep. 2010).
Bushman, "Retroviral integration and human gene therapy.", 2007 J Clin Invest 117(8):2083-2086.
Cao, et al., "Development and Application of a Multiplexable Flow Cytometry-Based Assay to Quantify Cell-Mediated Cytolysis.", 2010, Cytometry Part A 77:534-45.
Carpenito, et al., "Control of large, established tumor xenografts with genetically retargeted human T cells containing CD28 and CD137 domains", Proc. Natl. Acad. Sci 106:3360-3365.
Cheadle, et al., "Natural Expression of the CD19 Antigen Impacts the Long-Term Engraftment but Not Antitumor Activity of CD19-Specific Engineered T Cells.", J Immunol 2010; 184:1885-1896.
Cougot, et al., "'Cap-tabolism'.", Trends Biochem Sci. Aug. 2004;29(8):436-44. (Abstract).
Deeks, et al., "A phase II randomized study of HIV-specific T-cell gene therapy in subjects with undetectable plasma viremia on combination antiretroviral therapy.", 2002, Mol Ther 5(6):788-797.

Dobrenkov, et al., "Monitoring the Efficacy of Adoptively Transferred Prostate Cancer-Targeted Human T Lymphocytes with PET and Bioluminescence Imaging.", J Nucl Med. Jul. 2008; 49(7): 1162-1170.
Elango, et al., "Optimized transfection of mRNA transcribed from a d(A/T)100 tail-containing vector", 2005, Biochim. Biophys. Res. Commun., 330:958-966 (Abstract).
Eshhar, "Specific activation and targeting of cytotoxic lymphocytes through chimeric single chains consisting of antibody-binding domains and the gamma or zeta subunits of the immunoglobulin and T-cell receptors", 1993, Proc Natl Acad Sci U S A 90(2):720-724.
Eshhar, et al., "Tumor-specific T-bodies: towards clinical application.", Cancer Immunol Immunother. Nov.-Dec. 1997;45(3-4):131-6. (Abstract).
Garland, et al., "The use of Teflon cell culture bags to expand functionally active CD8+ cytotoxic T lymphocytes.", J. Immunol Meth. 227(1-2):53-63, 1999.
Haanen, et al., "Selective Expansion of Cross-reacitve CD8+ Memory T Cells by Viral Variants.", 1999, J Exp Med 190(9):1319-1328.
Hacein-Bey-Abina, et al., "Insertional oncogenesis in 4 patients after retrovirus-mediated gene therapy of SCID-X1.", 2008, J Clin Invest 118(9)L3134-3142.
Hassan, et al., "Localization of Mesothelin in Epithelial Ovarian Cancer", Appl. Immunohistochem Mol MorphoL 13:243-247 (2005) Abstract.
Henderson, et al., "Comparison of the effects of FK-506, cyclosporin A and rapamycin on IL-2 production.", Immunology (1991) 73:316-321.
Hermans, et al., "The VITAL assay: a versatile fluorometric technique for assessing CTL- CTLand NKT-mediated cytotoxicity against multiple targets in vitro and in vivo.", J Immunol Methods. Feb. 1, 2004;285(1):25-40. (Abstract).
Heslop, "Safer CARS", 2010, Molecular Therapy 18(4):661-662.
Holtkamp, et al., "Modification of antigen-encoding RNA increases stability, translational efficacy, and T-cell stimulatory capacity of dendritic cells.", 2006, Blood 108:4009-17.
Horowitz, "Graft-Versus-Leukemia Reactions After Bone Marrow Transplantation.", 1990, Blood 75(3):555-562.
Hotkamp, et al., "Modification of antigen-encoding RNA increases stability, translational efficacy, and T-cell stimulatory capacity of dendritic cells.", Blood. Dec. 15, 2006;108(13):4009-17.
Huston, et al., "Protein engineering of antibody binding sites: Recovery of specific activity in an anti-digoxin single-chain Fv analogue produced in *Escherichia coli*.", 1988, Proc Natl Acad Sci USA 85:5879-5883.
Imai, et al., "Chimeric receptors with 4-1BB signaling capacity provoke potent cytotoxicity against acute lymphoblastic leukemia.", Leukemia 18(4):, 2004, 676-684.
James, et al., "Mathematical Modeling of Chimeric TCR Triggering Predicts the Magnitude of Target Lysis and Its Impairment by TCR Downmodulation.", 2010, J Immunol 184:4284-4294.
June, "Adoptive T cell therapy for cancer in the clinic", J Clin Invest. 117, 2007, 1466-1476.
June, et al., "Engineering lymphocyte subsets: tools, trials and tribulations.", Nat Rev Immunol Oct. 2009; 9(10):704-716.
Kalchenko, et al., "Use of lipophilic near-infrared dye in whole-body optical imaging of hematopoietic cell homing.", 2006, J Biomed Opt 11(5):050507-1 (3 pages).
Kershaw, et al., "A Phase I Study on Adoptive Immunotherapy Using Gene-Modified T Cells for Ovarian Cancer.", Clin Cancer Res 2006; 12:6106-6115.
Kochenderfer, et al., "GenBank Accession No. HM852952 .", Sep. 9, 2010.
Koronfel, "GenBank Accession No. FJ040214.", Sep. 3, 2008.
Koronfel, et al., "GenBank Accession No. FJ230962.", Dec. 9, 2008.
Kuhn, et al., "Determinants of intracellular RNA pharmacokinetics: Implications for RNA-based immunotherapeutics.", RNA Biol, 8:35-43, 2011.

(56) References Cited

OTHER PUBLICATIONS

Lamers, et al., "Treatment of metastatic renal cell carcinoma with autologous T-lymphocytes genetically retargeted against carbonic anhydrase IX: first clinical experience." 2006, J Clin Oncol 24:e20-e22.
Levine, et al., "Effects of CD28 costimulation on long-term proliferation of CD4+ T cells in the absence of exogenous feeder cells.", 1997, J. Immunol 159:5921-30.
Li, et al., "Expression of a chimeric antigen receptors in natural killer cells with a regulatory-compliant non-viral method.", 2010, Cancer Gene Ther 17(3):147.
Liu, et al., "Calcineurin Is a Common Target of Cyclophilin-Cyclosporin A and FKBP-FK506 Complexes.", Liu et al., Cell 66:807-815, 1991.
Malone, et al., "Cationic liposome-mediated RNA transfection.", 1989 Proc Natl Acad Sci USA 86:6077-6081.
Marktel, et al., "Immunologic potential of donor lymphocytes expressing a suicide gene for early immune reconstitution after hematopoietic T-cell-depleted stem cell transplantation.", 2003, Blood 101(4):1290-1298.
Masters, "Short tandem repeat profiling provides an international reference standard for human cell lines.", 2001, Proc Natl Acad Sci USA 98(14)8012-8017.
Mehta, "Graft-Versus-Leukemia Reactions in clinical bone marrow transplantation.", Leuk Lymphoma Aug. 1993; 10(6):427-32 (Abstract).
Milone, et al., "Chimeric Receptors Containing C137 Signal Transduction Domains Mediate Enhanced Survival of T Cells and Increased Antileukemic Efficacy In Vivo.", 2009, Mol Ther 17:1453-1464.
Mitchell, et al., "Selective Modification of Antigen-Specific T Cells by RNA Electroporation.", Hum Gene Ther. May 2008 ; 19(5): 511-521.
Morgan, et al., "Case report of a serious adverse event following the administration of T cells transduced with a chimeric antigen receptor recognizing ERBB2." 2010, Molecular Therapy 18(4):843-851.
Nadler, et al., "B4, a human B lymphocyte-associated antigen expressed on normal, mitogen-activated, and malignant B lymphocytes.", 1983, J Immunol 131(1):244-250.
Nienhuis, et al., "Genotoxicity of retroviral integration in hematopoietic cells.", 2006 Molecular Therapy 13(6):1031-1049.
Nishikawa, et al., "Nonviral vectors in the new millennium: delivery barriers in gene transfer", Hum. Gene Ther. 12(8), 2001, 861-870 (abstract only).
Pinthus, et al., "Adoptive immunotherapy of prostate cancer bone lesions using redirected effector lymphocytes.", 2004, J Clin Invest 114(12):1774-1781.
Plosker, et al., "Rituximab: a review of its use in non-Hodgkin's lymphoma and chronic lymphocytic leukaemia.", 2003 Drugs 63(8):803-843.
Porter, et al., "Chimeric antigen receptor-modified T cells in chronic lymphoid leukemia", New England J Med 365(8), 2011, 725-733.
Pule, et al., "Virus-specific T cells engineered to coexpress tumor-specific receptors: persistence and antitumor activity in individuals with neuroblastoma." 2008, Nat Med 14:1264-1270.
Rabinovich, et al., "Chimeric receptor mRNA transfection as a tool to generate antineoplastic lymphocytes.", 2009 Hum Gene Ther 20(1):51-61.
Rosenberg, et al., "Adoptive cell transfer: a clinical path to effective cancer immunotherapy", 2008, Nat Rev Cancer 8:299-308.
Sadelain, et al., "The promise and potential pitfalls of chimeric antigen receptors." 2009 Curr. Opin. Immunol. 21:215-223.
Sato, et al., "Engineered human tmpk/AZT as a novel enzyme/prodrug axis for suicide gene therapy", 2007, Mol. Ther. 15(5):962-970.
Schafi, et al., "A new way to generate cytolytic tumor-specific T cells: electroporation of RNA coding for a T cell receptor into T lymphocytes.", 2006, Cancer Immunol Immunother 55:1132-41.
Shaffer, et al., "T cells redirected against CD70 for the immunotherapy of CD70-positive malignancies.", 2011, Blood 117(16):4304-1.
Singh, et al., "Redirecting Specificity of T-Cell Populations for CD19 Using the Sleeping Beauty System", 2008, Cancer Research 68:2961-2971.
Smits, et al., "RNA-based gene transfer for adult stem cells and T cells", Leukemia (2004) 18, 1898-1902.
Stein, "Translation of vascular endothelial growth factor mRNA by internal ribosome entry: implications for translation under hypoxia", 1998, Mol Cell Biol 18:3112-9.
Stepinski, et al., "Synthesis and properties of mRNAs containing the novel "anti-reverse" cap analogs 7-methyl(3'-0-methyl)GpppG and 7-methyl(3'-deoxy)GpppG", RNA 7, 2001, 1468-1495.
Suhoski, et al., "Engineering artificial antigen-presenting cells to express a diverse array of co-stimulatory molecules", 2007 Mol. Ther. 15:981-988.
Tammana, et al., "Comparison of T Cell Activities Mediated by Human TCRs and CARs That Use the Same Recognition Domains.", Hum Gene Ther. Jan. 2010;21(1):75-86.
Teachey, et al., "mTOR inhibitors are synergistic with methotrexate: an effective combination to treat acute lymphoblastic leukemia.", 2008, Blood 112(5): 2020-2023.
Teachey, et al., "The mTOR inhibitor CCI-779 induces apoptosis and inhibits growth in preclinical models of primary adult human ALL.", 2006, Blood 107(3): 1149-1155.
Teague, et al., "Interleukin-15 rescues tolerant CD8+ T cells for use in adoptive immunotherapy of established tumors.", 2006, Nat Med 12:335-41.
Till, et al., "Adoptive immunotherapy for indolent non-Hodgkin lymphoma and mantle cell lymphoma using genetically modified autologous CD20-specific T cells." 2008, Blood, 112:2261-2271.
Van Vollenhoven, et al., "Longterm safety of patients receiving rituximab in rheumatoid arthritis clinical trials.", 2010, J Rheumatol 37(3):558-567.
Wolfl, et al., "Activation-induced expression of CD137 permits detection, isolation, and expansion of the full repertoire of CD8+ T cells responding to antigen without requiring knowledge of epitope specificities", Blood. 110(1), Jul. 1, 2007, 201-210.
Yoon, et al., "Adoptive immunotherapy using human peripheral blood lymphocytes transferred with RNA encoding Her-2/neu-specific chimeric immune receptor in ovarian cancer xenograft model.", 2009, Cancer Gene Ther 16(6):489-497.
Zhao, et al., "A Herceptin-Based Chimeric Antigen Receptor with Modified Signaling domains Leads to Enhanced Survival of Transduced T Lymphocytes and Antitumor Activity.", J Immunol 183(9), 2009, 5563-5574.
Zhao, et al., "Emission spectra of bioluminescent reporters and interaction with mammalian tissue determine the sensitivity of detection in vivo.", 2005, J Biomed Opt 10(4):41210.
Zhao, et al., "High-Efficiency Transfection of Primary Human and Mouse T Lymphocytes Using RNA Electroporation", 2006, Mol Ther 13(1):151-159.
Zhao, et al., "Multiple injections of electroporated autologous T cells expressing a chimeric antigen receptor mediate regression of human disseminated tumor", Cancer Res. Nov. 15, 2010; 70(22): 9053-9061.
Zhao, et al., "Primary Human Lymphocytes Transduced with NY-ESO-1 Antigen-Specific TCR Genes Recognize and Kill Diverse Human Tumor Cell Lines", The Journal of Immunology, vol. 174, No. 7, pp. 4415-4423, Apr. 1, 2005.
Zhong, et al., "Chimeric antigen receptors combining 4-1BB and CD28 signaling domains augment PI3kinase/AKT/Bcl-XL activation and CD8+ T cell-mediated tumor eradication", Mol Ther, 18:413-420 (2009).
Yoon, et al. "Modification of antigen-encoding RNA increases stability, translational efficacy, and T-cell stimulatory capacity of dendritic cells" Blood Dec. 15, 2006;108(13):4009-17.

* cited by examiner

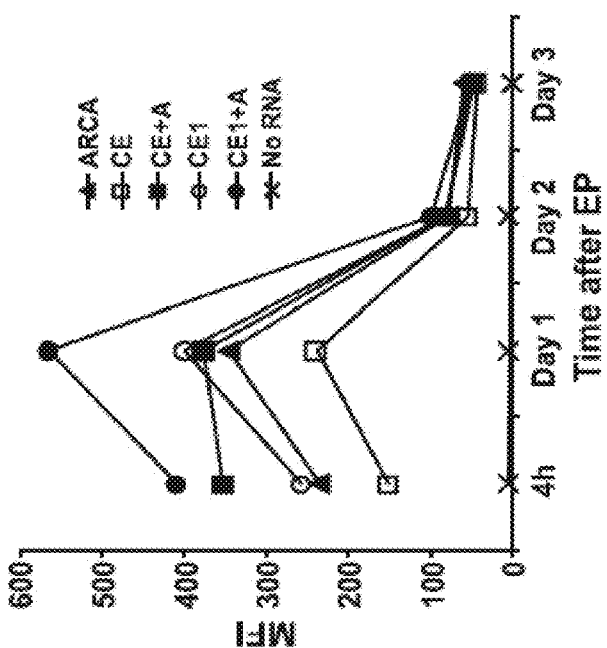
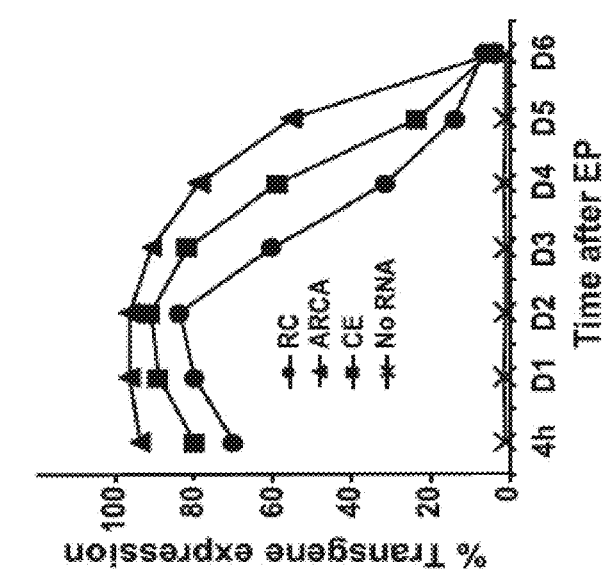
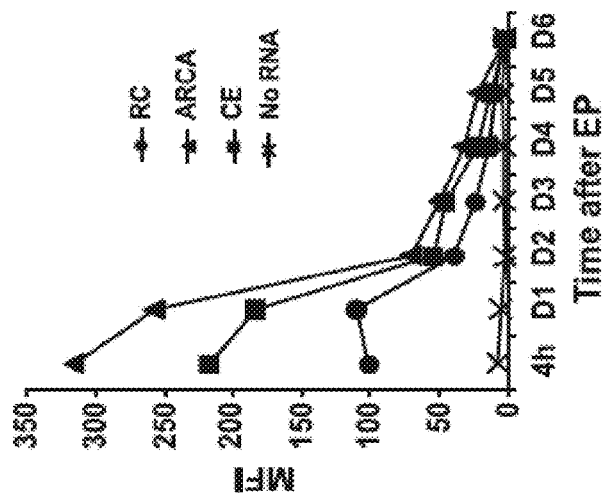

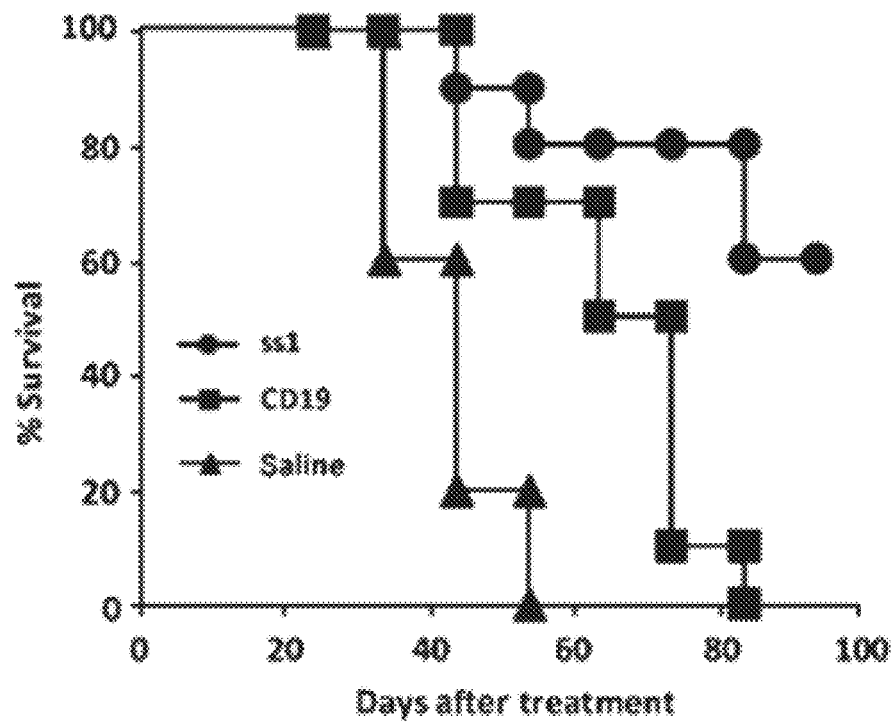
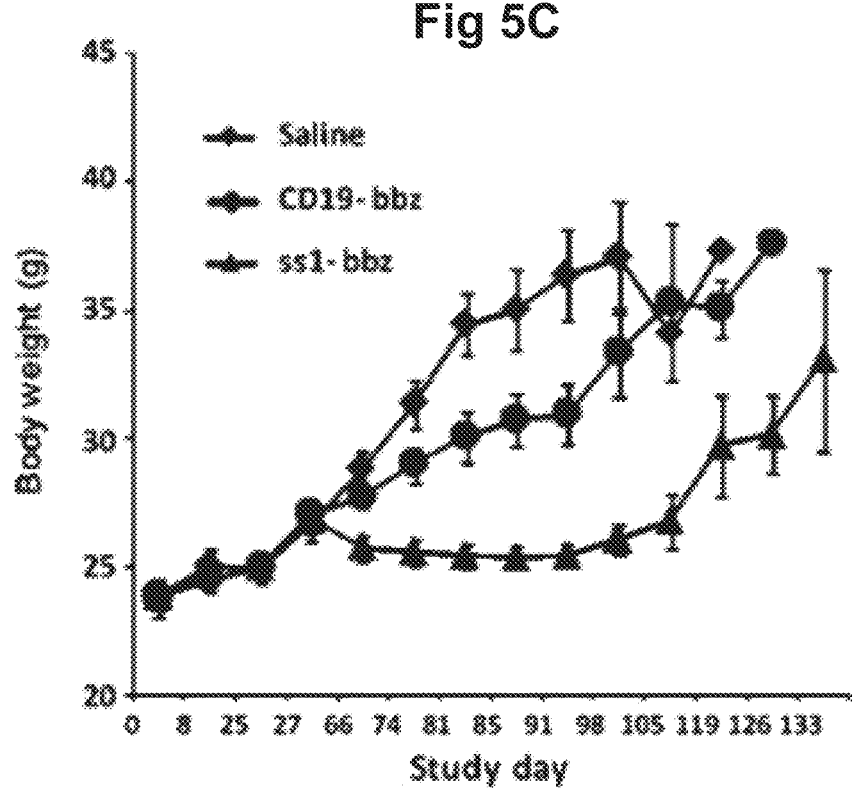

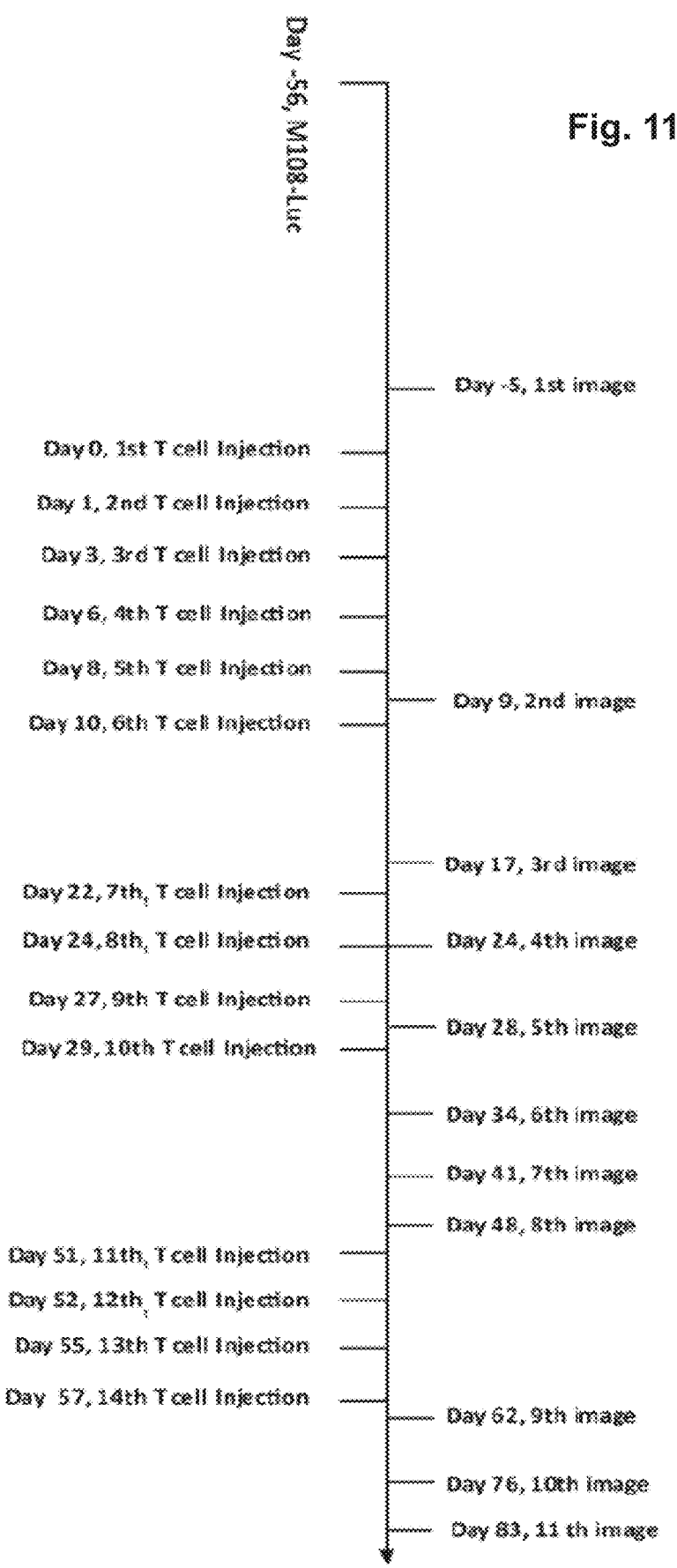

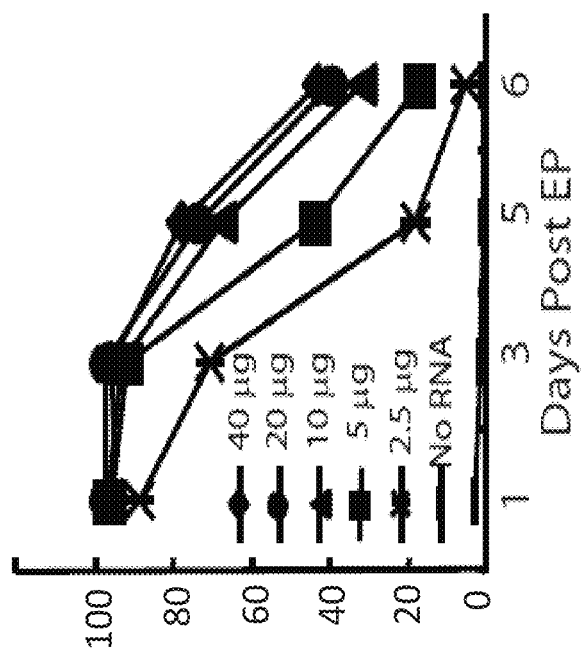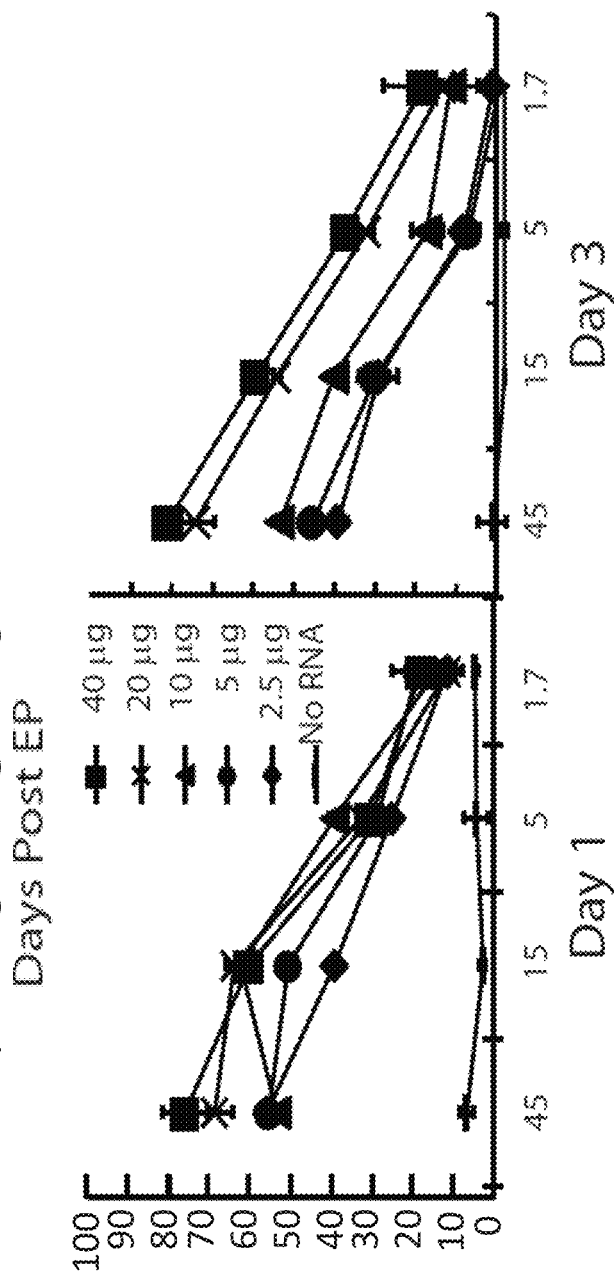
Fig. 13B
Fig. 13C

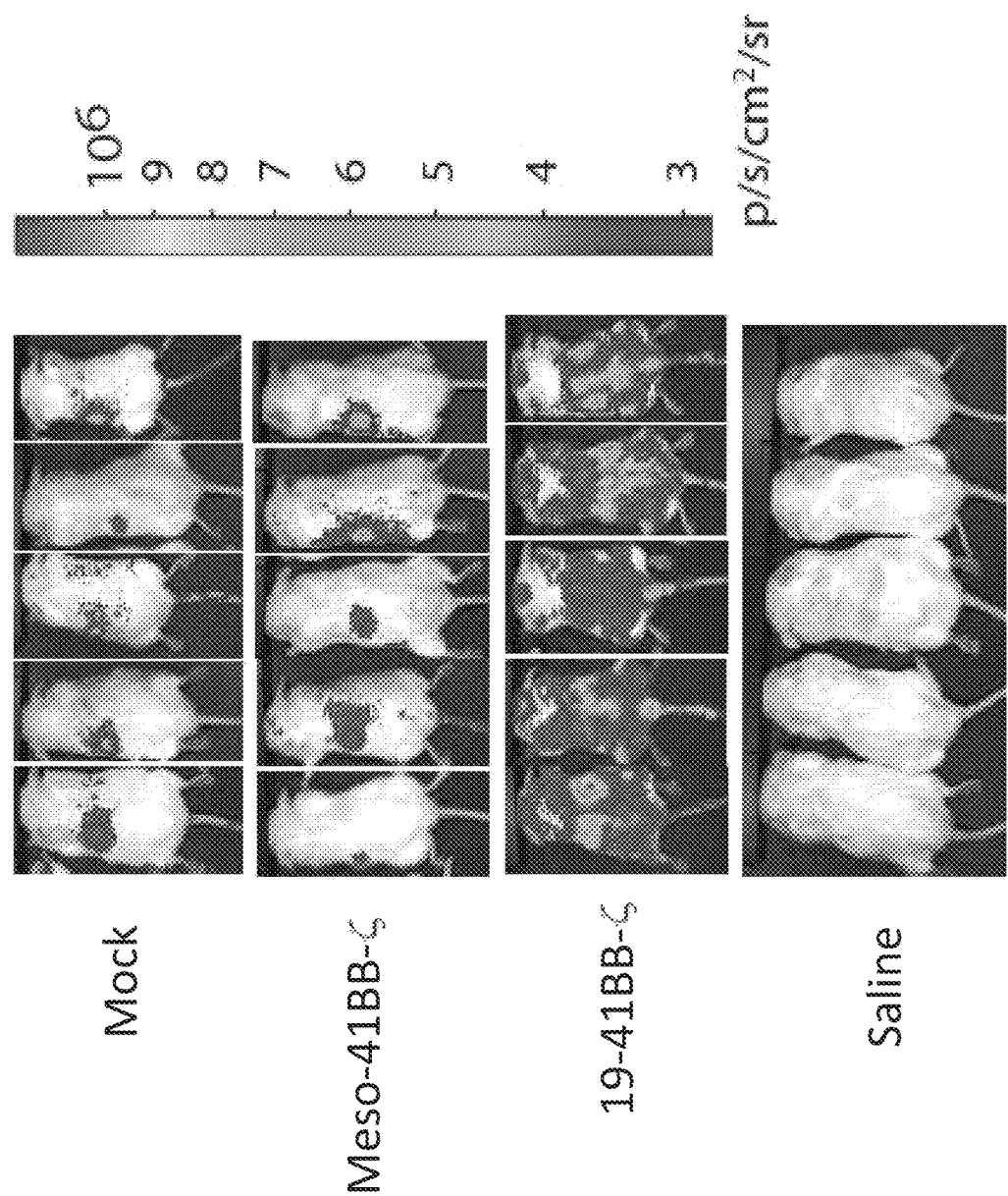

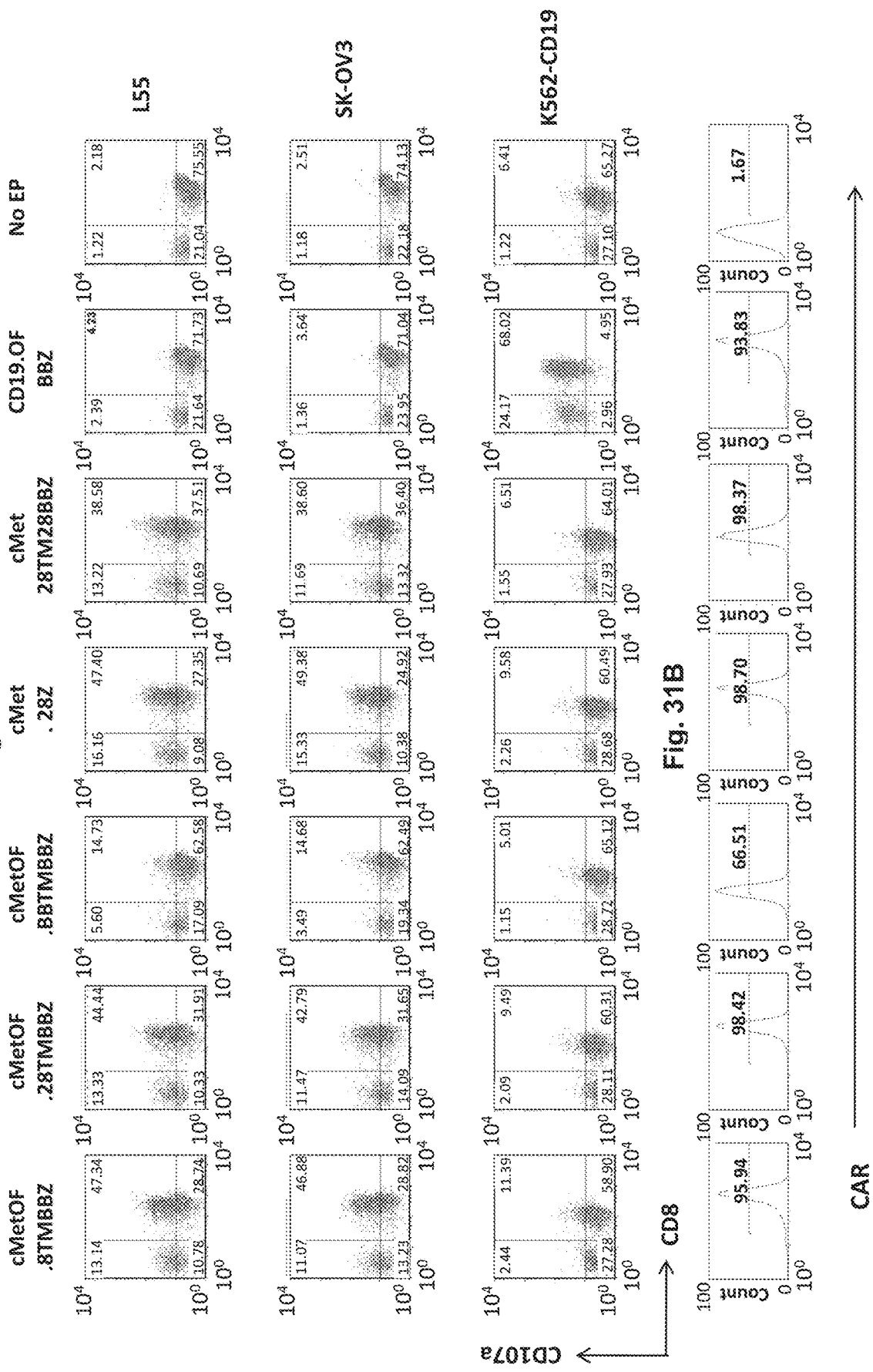

SKOV3 epithelial ovarian carcinoma cells (wild type cells express c-MET)

| Group | Mice (#) | Tumor Cells s.c. | Treatment i.t. Injection T cells |
|---|---|---|---|
| cMET CAR + Cytoxan | 9 | SKOV3-Luc | cMET CAR + Cytoxan |
| CD19CAR + Cytoxan | 9 | SKOV3-Luc | CD19 CAR + Cytoxan |
| PBS | 7 | SKOV3-Luc | PBS |

Experimental design
Establish vascularized flank xenograft tumors with SkOV3/luc tumors on day 0 in female NSG mice (n=7 to 9 mice per group)

Treatment beginning at week 6, 7, 9 and 11: 1x10e7 CAR cells injected IT
Cytoxan i.p. injection 24 hour before treatment at weeks 7, 9 and 11

Endpoints: survival and tumor burden (bioluminescence)

Fig. 37

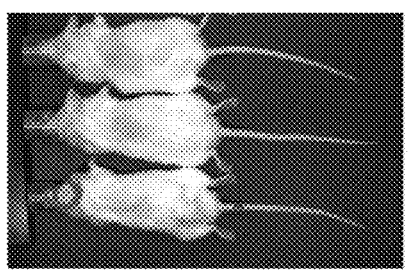
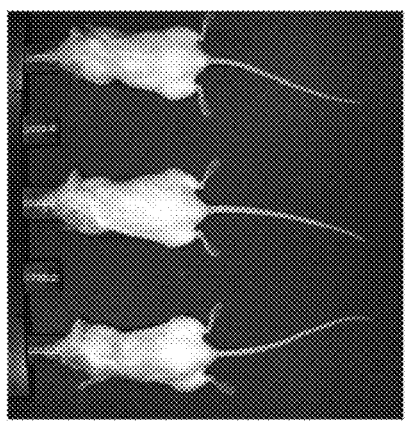
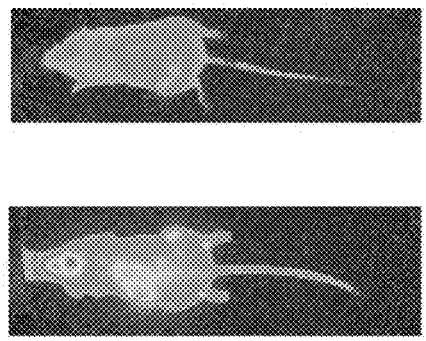
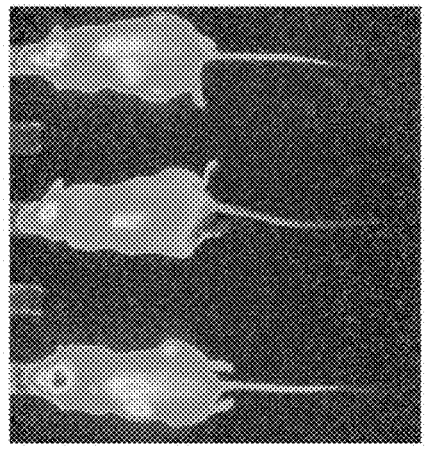
Fig. 47

SEQUENCE LISTING

<160> NUMBER OF SEQ ID NOS: 28

<210> SEQ ID NO 1
<211> LENGTH: 32
<212> TYPE: DNA
<213> ORGANISM: Artificial sequence
<220> FEATURE:
<223> OTHER INFORMATION: Chemically synthesized

<400> SEQUENCE: 1
cctaagctta ccgccatggc cttaccagtg ac                                      32

<210> SEQ ID NO 2
<211> LENGTH: 36
<212> TYPE: DNA
<213> ORGANISM: Artificial sequence
<220> FEATURE:
<223> OTHER INFORMATION: Chemically synthesized

<400> SEQUENCE: 2
cctaagctta ccgccatggc cttaccagtg accgcc                                  36

<210> SEQ ID NO 3
<211> LENGTH: 30
<212> TYPE: DNA
<213> ORGANISM: Artificial sequence
<220> FEATURE:
<223> OTHER INFORMATION: Chemically synthesized

<400> SEQUENCE: 3
cctgcggccg cttagcgagg gggcagggcc                                         30

<210> SEQ ID NO 4
<211> LENGTH: 4893
<212> TYPE: DNA
<213> ORGANISM: Artificial sequence
<220> FEATURE:
<223> OTHER INFORMATION: Chemically synthesized

<400> SEQUENCE: 4
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagctcta     240
atacgactca ctatagggaa agctcgagct taccgccatg gccttaccag tgaccgcctt     300
gctcctgccg ctggccttgc tgctccacgc cgccaggccg ggatcccagg tacaactgca     360
gcagtctggg cctgagctgg agaagcctgg cgcttcagtg aagatatcct gcaaggcttc     420
tggttactca ttcactggct acaccatgaa ctgggtgaag cagagccatg aaagagcct      480
tgagtggatt ggacttatta ctccttacaa tggtgcttct agctacaacc agaagttcag     540
gggcaaggcc acattaactg tagacaagtc atccagcaca gcctacatgg acctcctcag     600
tctgacatct gaagactctg cagtctattt ctgtgcaagg gggggttacg acgggagggg     660
ttttgactac tggggccaag gaccacggt caccgtctcc tcaggtggag gcggttcagg     720
cggcggtggc tctagcggtg gcggatcgga catcgagctc actcagtctc cagcaatcat     780
gtctgcatct caggggagaa ggtcaccat gacctgcagt gccagctcaa gtgtaagtta     840
catgcactgg taccagcaga agtcaggcac ctcccccaaa agatggattt acgacacatc     900
caaactggct tctggagtcc caggtcgctt cagtggcagt gggtctggaa actcttactc     960
tctcacaatc agcagcgtgg aggctgaaga cgacgcaact tattactgcc agcagtggag    1020
taagcaccct ctcacgtacg gtgctgggac aaagttggaa atcaaagcta gcaccacgac    1080
gccagcgccg cgaccaccaa caccggcgcc accatcgcg tcgcagcccc tgtccctgcg    1140
cccagaggcg tgccggccag cggcgggggg cgcagtgcac acgagggggc tggacttcgc    1200

```
ctgtgatatc tacatctggg cgcccttggc cgggacttgt ggggtccttc tcctgtcact    1260
ggttatcacc ctttactgca aacggggcag aaagaaactc ctgtatatat tcaaacaacc    1320
atttatgaga ccagtacaaa ctactcaaga ggaagatggc tgtagctgcc gatttccaga    1380
agaagaagaa ggaggatgtg aactgagagt gaagttcagc aggagcgcag acgccccgc     1440
gtacaagcag ggccagaacc agctctataa cgagctcaat ctaggacgaa gagaggagta    1500
cgacgttttg gacaagagac gtggccggga ccctgagatg gggggaaagc cgagaaggaa    1560
gaaccctcag gaaggcctgt acaatgaact gcagaaagat aagatggcgg aggcctacag    1620
tgagattggg atgaaaggcg agcgccgagg gggcaagggg cacgatggcc tttaccaggg    1680
tctcagtaca gccaccaagg acacctacga cgcccttcac atgcaggccc tgcccctcg     1740
ctaagcggcc gcctcgagag ctcgctttct tgctgtccaa tttctattaa aggttccttt    1800
gttccctaag tccaactact aaactggggg atattatgaa gggccttgag catctggatt    1860
ctgcctaata aaaacattt attttcattg ctgcgtcgag agctcgcttt cttgctgtcc      1920
aatttctatt aaaggttcct tgttccctaa gtccaactaa ctaaactggg ggatattatg    1980
aagggccttg agcatctgga ttctgcctaa taaaaaacat ttattttcat tgctgcgtcg    2040
acgaattcaa aaaaaaaaaa aaaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaga agagcactag tggcgcctga   2220
tgcggtattt tctccttacg catctgtgcg gtatttcaca ccgcataggc cgctgtattc    2280
tatagtgtca cctaaatggc cgcacaattc actggccgtc gttttacaac gtcgtgactg    2340
ggaaaaccct ggcgttaccc aacttaatcg ccttgcagca catcccccctt tcgccagctg   2400
gcgtaatagc gaagaggccc gcaccgatcg cccttcccaa cagttgcgca gcctgaatgg    2460
cgaatggaaa ttgtaagcgt taatattttg ttaaaattcg cgttaaattt tgttaaatc     2520
agctcatttt ttaaccaata ggccgaaatc ggcaaaatcc cttataaatc aaaagaatag    2580
accgagatag ggttgagtgt tgttccagtt tggaacaaga gtccactatt aaagaacgtg    2640
gactccaacg tcaaagggcg aaaaaccgtc tatcagggcg atggcccact acgtgaacca    2700
tcaccctaat caagttttttt ggggtcgagg tgccgtaaag cactaaatcg aaccctaaa    2760
gggagccccc gatttagagc ttgacgggga aagccggcga acgtggcgag aaaggaaggg    2820
aagaaagcga aaggagcggg cgctagggcg ctggcaagtg tagcggtcac gctgcgcgta    2880
accaccacac ccgccgcgct taatgcgccg ctacagggcg cgtcaggtgg cacttttcgg    2940
ggaaatgtgc gcggaacccc tatttgttta ttttttctaaa tacattcaaa tatgtatccg    3000
ctcatagtca ggcaactatg gatgaacgaa atagacagat cgctgagata ggtgcctcac    3060
tgattaagca ttggtaactg tcagaccaag tttactcata tatactttag attgatttaa    3120
aacttcattt ttaatttaaa aggatctagg tgaagatcct ttttgataat ctcatgaaca    3180
ataaaactgt ctgcttacat aaacagtaat acaaggggtg ttatgagcca tattcaacgg    3240
gaaacgtctt gctctaggcc gcgattaaat tccaacatgg atgctgattt atatgggtat    3300
aaatgggctc gcgataatgt cgggcaatca ggtgcgacaa tctatcgatt gtatgggaag    3360
cccgatgcgc cagagttgtt tctgaaacat ggcaaaggta gcgttgccaa tgatgttaca    3420
gatgagatgg tcagactaaa ctggctgacg gaatttatgc ctcttccgac catcaagcat    3480
tttatccgta ctcctgatga tgcatggtta ctcaccactg cgatcccggg gaaaacagca    3540
ttccaggtat tagaagaata tcctgattca ggtgaaaata ttgttgatgc gctggcagtg    3600
```

```
ttcctgcgcc ggttgcattc gattcctgtt tgtaattgtc cttttaacag cgatcgcgta    3660
tttcgtctcg ctcaggcgca atcacgaatg aataacggtt tggttgatgc gagtgatttt    3720
gatgacgagc gtaatggctg gcctgttgaa caagtctgga agaaatgca taaacttttg    3780 ccattctcac cggattcagt cgtcactcat ggtgatttct cacttgataa ccttattttt    3840 gacgaggga aattaatagg ttgtattgat gttggacgag tcggaatcgc agaccgatac    3900
caggatcttg ccatcctatg gaactgcctc ggtgagtttt ctccttcatt acagaaacgg    3960 cttttttcaaa aatatggtat tgataatcct gatatgaata aattgcagtt tcatttgatg    4020
ctcgatgagt ttttctaaga attaattcat gaccaaaatc ccttaacgtg agttttcgtt    4080
ccactgagcg tcagacccccg tagaaaagat caaaggatct tcttgagatc ctttttttct    4140
gcgcgtaatc tgctgcttgc aaacaaaaaa accaccgcta ccagcggtgg tttgtttgcc    4200
ggatcaagag ctaccaactc ttttttccgaa ggtaactggc ttcagcagag cgcagatacc    4260
aaatactgtc cttctagtgt agccgtagtt aggccaccac ttcaagaact ctgtagcacc    4320
gcctacatac ctcgctctgc taatcctgtt accagtggct gctgccagtg cgataagtc    4380 gtgtcttacc gggttggact caagacgata gttaccggat aaggcgcagc ggtcgggctg    4440 aacgggggt tcgtgcacac agcccagctt ggagcgaacg acctacaccg aactgagata    4500
cctacagcgt gagctatgag aaagcgccac gcttcccgaa gggagaaagg cggacaggta    4560
tccggtaagc ggcagggtcg gaacaggaga gcgcacgagg gagcttccag ggggaaacgc    4620
ctggtatctt tatagtcctg tcgggtttcg ccacctctga cttgagcgtc gatttttgtg    4680
atgctcgtca gggggggcgga gcctatggaa aaacgccagc aacgcggcct ttttacggtt    4740
cctggccttt tgctggcctt tgctcacat gttctttcct gcgttatccc ctgattctgt    4800
ggataaccgt attaccgcct ttgagtgagc tgataccgct cgccgcagcc gaacgaccga    4860
gcgcagcgag tcagtgagcg aggaagcgga aga                                  4893

<210> SEQ ID NO 5
<211> LENGTH: 4888
<212> TYPE: DNA
<213> ORGANISM: Artificial sequence
<220> FEATURE:
<223> OTHER INFORMATION: Chemically synthesized

<400> SEQUENCE: 5
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagctcta     240
atacgactca ctatagggaa agctcgagct taccgccatg gccttaccag tgaccgcctt     300
gctcctgccg ctggccttgc tgctccacgc cgccaggccg gacatccaga tgacacagac     360
tacatcctcc ctgtctgcct ctctgggaga cagagtcacc atcagttgca gggcaagtca     420
ggacattagt aaatatttaa attggtatca gcagaaacca gatggaactg ttaaactcct     480
gatctaccat acatcaagat tacactcagg agtcccatca aggttcagtg cagtgggtc     540 tggaacagat tattctctca ccattagcaa cctggagcaa gaagatattg ccacttactt     600
ttgccaacag ggtaatacgc ttccgtacac gttcggaggg gggaccaagc tggagatcac     660
aggtggcggt ggctcgggcg gtggtgggtc gggtggcggc ggatctgagg tgaaactgca     720
```

-continued

| | |
|---|---|
| ggagtcagga cctggcctgg tggcgccctc acagagcctg tccgtcacat gcactgtctc | 780 |
| aggggtctca ttacccgact atggtgtaag ctggattcgc cagcctccac gaaagggtct | 840 |
| ggagtggctg ggagtaatat ggggtagtga aaccacatac tataattcag ctctcaaatc | 900 |
| cagactgacc atcatcaagg acaactccaa gagccaagtt ttcttaaaaa tgaacagtct | 960 |
| gcaaactgac gacacagcca tttactactg tgccaaacat tattactacg gtggtagcta | 1020 |
| cgctatggac tactgggggcc aaggaacctc agtcaccgtc tcctcaacca cgacgccagc | 1080 |
| gccgcgacca ccaacaccgg cgcccaccat cgcgtcgcag cccctgtccc tgcgcccaga | 1140 |
| ggcgtgccgg ccagcggcgg ggggcgcagt gcacacgagg gggctggact cgcctgtga | 1200 |
| tatctacatc tgggcgccct tggccgggac ttgtggggtc cttctcctgt cactggttat | 1260 |
| cacccttac tgcaaacggg gcagaaagaa actcctgtat atattcaaac aaccatttat | 1320 |
| gagaccagta caaactactc aagaggaaga tggctgtagc tgccgatttc agaagaaga | 1380 |
| agaaggagga tgtgaactga gagtgaagtt cagcaggagc gcagacgccc ccgcgtacaa | 1440 |
| gcagggccag aaccagctct ataacgagct caatctagga cgaagagagg agtacgacgt | 1500 |
| tttggacaag agacgtggcc gggaccctga gatgggggga aagccgagaa ggaagaaccc | 1560 |
| tcaggaaggc ctgtacaatg aactgcagaa agataagatg gcggaggcct acagtgagat | 1620 |
| tgggatgaaa ggcgagcgcc ggaggggcaa ggggcacgat ggcctttacc agggtctcag | 1680 |
| tacagccacc aaggacacct acgacgcct tcacatgcag gccctgcccc ctcgctaagc | 1740 |
| ggccgcctcg agagctcgct ttcttgctgt ccaatttcta ttaaaggttc ctttgttccc | 1800 |
| taagtccaac tactaaactg ggggatatta tgaagggcct tgagcatctg gattctgcct | 1860 |
| aataaaaaac atttatttc attgctgcgt cgagagctcg ctttcttgct gtccaatttc | 1920 |
| tattaaaggt tcctttgttc cctaagtcca actactaaac tggggatat tatgaagggc | 1980 |
| cttgagcatc tggattctgc ctaataaaaa acatttattt tcattgctgc gtcgacgaat | 2040 |
| tcaaaaaaaa aaaaaaaaa aaaaaaaaa aaaaaaaaa aaaaaaaaa aaaaaaaaa | 2100 |
| aaaaaaaaaa aaaaaaaaa aaaaaaaaa aaaaaaaaa aaaaaaaaa aaaaaaaaa | 2160 |
| aaaaaaaaaa aaaaaaaaa aaaaaaaaa aagaagagca ctagtggcgc ctgatgcggt | 2220 |
| attttctcct tacgcatctg tgcggtattt cacaccgcat aggccgctgt attctatagt | 2280 |
| gtcacctaaa tggccgcaca attcactggc cgtcgtttta caacgtcgtg actgggaaaa | 2340 |
| ccctggcgtt acccaactta atcgccttgc agcacatccc cctttcgcca gctggcgtaa | 2400 |
| tagcgaagag gcccgcaccg atcgcccttc ccaacagttg cgcagcctga atggcgaatg | 2460 |
| gaaattgtaa gcgttaatat tttgttaaaa ttcgcgttaa attttgtta aatcagctca | 2520 |
| ttttttaacc aataggccga atcggcaaa atcccttata aatcaaaaga atagaccgag | 2580 |
| atagggttga gtgttgttcc agtttggaac aagagtccac tattaaagaa cgtggactcc | 2640 |
| aacgtcaaag ggcgaaaaac cgtctatcag ggcgatggcc cactacgtga accatcaccc | 2700 |
| taatcaagtt ttttggggtc gaggtgccgt aaagcactaa atcggaaccc taaagggagc | 2760 |
| ccccgattta gagcttgacg ggaaagccg gcgaacgtgg cgagaaagga agggaagaaa | 2820 |
| gcgaaaggag cgggcgctag ggcgctggca agtgtagcgg tcacgctgcg cgtaaccacc | 2880 |
| acacccgccg cgcttaatgc gccgctacag ggcgcgtcag gtggcacttt tcggggaaat | 2940 |
| gtgcgcggaa cccctatttg tttattttc taaatacatt caaatatgta tccgctcatg | 3000 |
| agtcaggcaa ctatgatga acgaaataga cagatcgctg ataggtgc ctcactgatt | 3060 |
| aagcattggt aactgtcaga ccaagtttac tcatatatac tttagattga tttaaaactt | 3120 |

```
cattttttaat ttaaaaggat ctaggtgaag atccttttttg ataatctcat gaacaataaa    3180
actgtctgct tacataaaca gtaatacaag gggtgttatg agccatattc aacgggaaac    3240
gtcttgctct aggccgcgat taaattccaa catggatgct gatttatatg ggtataaatg    3300
ggctcgcgat aatgtcgggc aatcaggtgc gacaatctat cgattgtatg ggaagcccga    3360
tgcgccagag ttgtttctga acatggcaa aggtagcgtt gccaatgatg ttacagatga    3420
gatggtcaga ctaaactggc tgacggaatt tatgcctctt ccgaccatca agcattttat    3480
ccgtactcct gatgatgcat ggttactcac cactgcgatc cccgggaaaa cagcattcca    3540
ggtattagaa gaatatcctg attcaggtga aaatattgtt gatgcgctgg cagtgttcct    3600
gcgccggttg cattcgattc ctgtttgtaa ttgtcctttt aacagcgatc gcgtatttcg    3660
tctcgctcag gcgcaatcac gaatgaataa cggtttggtt gatgcgagtg attttgatga    3720
cgagcgtaat ggctggcctg ttgaacaagt ctggaaagaa atgcataaac ttttgccatt    3780
ctcaccggat tcagtcgtca ctcatggtga tttctcactt gataaccttta tttttgacga    3840
ggggaaatta ataggttgta ttgatgttgg acgagtcgga atcgcagacc gataccagga    3900
tcttgccatc ctatggaact gcctcggtga gttttctcct tcattacaga aacggctttt    3960
tcaaaaatat ggtattgata atcctgatat gaataaattg cagtttcatt tgatgctcga    4020
tgagttttttc taagaattaa ttcatgacca aaatccctta acgtgagttt tcgttccact    4080
gagcgtcaga ccccgtagaa aagatcaaag gatcttcttg agatcctttt tttctgcgcg    4140
taatctgctg cttgcaaaca aaaaaaccac cgctaccagc ggtggtttgt ttgccggatc    4200
aagagctacc aactctttttt ccgaaggtaa ctggcttcag cagagcgcag ataccaaata    4260
ctgtccttct agtgtagccg tagttaggcc accacttcaa gaactctgta gcaccgccta    4320
catacctcgc tctgctaatc ctgttaccag tggctgctgc cagtggcgat aagtcgtgtc    4380
ttaccgggtt ggactcaaga cgatagttac cggataaggc gcagcggtcg ggctgaacgg    4440
ggggttcgtg cacacagccc agcttggagc gaacgaccta caccgaactg agatacctac    4500
agcgtgagct atgagaaagc gccacgcttc ccgaagggag aaaggcggac aggtatccgg    4560
taagcggcag ggtcggaaca ggagagcgca cgagggagct tccaggggga aacgcctggt    4620
atctttatag tcctgtcggg tttcgccacc tctgacttga gcgtcgattt ttgtgatgct    4680
cgtcaggggg gcggagccta tggaaaaacg ccagcaacgc ggccttttta cggttcctgg    4740
ccttttgctg gccttttgct cacatgttct ttcctgcgtt atcccctgat tctgtggata    4800
accgtattac cgcctttgag tgagctgata ccgctcgccg cagccgaacg accgagcgca    4860
gcgagtcagt gagcgaggaa gcggaaga                                       4888
```

<210> SEQ ID NO 6
<211> LENGTH: 1467
<212> TYPE: DNA
<213> ORGANISM: Artificial sequence
<220> FEATURE:
<223> OTHER INFORMATION: Chemically synthesized

<400> SEQUENCE: 6

```
atggccttac cagtgaccgc cttgctcctg ccgctggcct tgctgctcca cgccgccagg     60
ccgggatccc aggtacaact gcagcagtct gggcctgagc tggagaagcc tggcgcttca    120
gtgaagatat cctgcaaggc ttctggttac tcattcactg gctacaccat gaactgggtg    180
aagcagagcc atggaaagag ccttgagtgg attggactta ttactcctta caatggtgct    240
```

| | |
|---|---|
| tctagctaca accagaagtt caggggcaag gccacattaa ctgtagacaa gtcatccagc | 300 |
| acagcctaca tggacctcct cagtctgaca tctgaagact ctgcagtcta tttctgtgca | 360 |
| agggggggtt acgacgggag gggttttgac tactggggcc aagggaccac ggtcaccgtc | 420 |
| tcctcaggtg gaggcggttc aggcggcggt ggctctagcg gtggcggatc ggacatcgag | 480 |
| ctcactcagt ctccagcaat catgtctgca tctccagggg agaaggtcac catgacctgc | 540 |
| agtgccagct caagtgtaag ttacatgcac tggtaccagc agaagtcagg cacctccccc | 600 |
| aaaagatgga tttatgacac atccaaactg gcttctggag tcccaggtcg cttcagtggc | 660 |
| agtgggtctg gaaactctta ctctctcaca atcagcagcg tggaggctga agatgatgca | 720 |
| acttattact gccagcagtg gagtaagcac cctctcacgt acggtgctgg gacaaagttg | 780 |
| gaaatcaaag ctagcaccac gacgccagcg ccgcgaccac caacaccggc gcccaccatc | 840 |
| gcgtcgcagc ccctgtccct cgcccagag gcgtgccggc cagcggcggg gggcgcagtg | 900 |
| cacacgaggg ggctggactt cgcctgtgat atctacatct gggcgccctt ggccgggact | 960 |
| tgtgggtcc ttctcctgtc actggttatc acccttact gcaaacgggg cagaaagaaa | 1020 |
| ctcctgtata tattcaaaca accatttatg agaccagtac aaactactca agaggaagat | 1080 |
| ggctgtagct gccgatttcc agaagaagaa gaaggaggat gtgaactgag agtgaagttc | 1140 |
| agcaggagcg cagacgcccc cgcgtacaag cagggccaga accagctcta taacgagctc | 1200 |
| aatctaggac gaagagagga gtacgatgtt ttggacaaga cgtggccg ggaccctgag | 1260 |
| atgggggaa agccgagaag gaagaaccct caggaaggcc tgtacaatga actgcagaaa | 1320 |
| gataagatgg cggaggccta cagtgagatt gggatgaaag cgagcgccg gaggggcaag | 1380 |
| ggcacgatg gcctttacca gggtctcagt acagccacca aggacaccta cgacgccctt | 1440 |
| cacatgcagg ccctgccccc tcgctaa | 1467 |

<210> SEQ ID NO 7
<211> LENGTH: 1461
<212> TYPE: DNA
<213> ORGANISM: Artificial sequence
<220> FEATURE:
<223> OTHER INFORMATION: Chemically synthesized

<400> SEQUENCE: 7

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| gggggaccaa gctggagat cacaggtggc ggtggctcgg gcggtggtgg gtcgggtggc | 420 |
| ggcggatctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gccaaggaac ctcagtcacc | 780 |
| gtctcctcaa ccacgacgcc agcgccgcga ccaccaacac cggcgcccac catcgcgtcg | 840 |

| | |
|---|---:|
| cagcccctgt ccctgcgccc agaggcgtgc cggccagcgg cgggggggcgc agtgcacacg | 900 |
| aggggggctgg acttcgcctg tgatatctac atctgggcgc ccttggccgg gacttgtggg | 960 |
| gtccttctcc tgtcactggt tatcacccctt tactgcaaac ggggcagaaa gaaactcctg | 1020 |
| tatatattca acaaccatt tatgagacca gtacaaacta ctcaagagga agatggctgt | 1080 |
| agctgccgat ttccagaaga agaagaagga ggatgtgaac tgagagtgaa gttcagcagg | 1140 |
| agcgcagacg cccccgcgta caagcagggc cagaaccagc tctataacga gctcaatcta | 1200 |
| ggacgaagag aggagtacga tgttttggac aagagacgtg gccgggaccc tgagatgggg | 1260 |
| ggaaagccga gaaggaagaa ccctcaggaa ggcctgtaca atgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc cccctcgcta a | 1461 |

<210> SEQ ID NO 8
<211> LENGTH: 1467
<212> TYPE: DNA
<213> ORGANISM: Artificial sequence
<220> FEATURE:
<223> OTHER INFORMATION: Chemically synthesized

<400> SEQUENCE: 8

| | |
|---|---:|
| atggccttac cagtgaccgc cttgctcctg ccgctggcct tgctgctcca cgccgccagg | 60 |
| ccgggatccc aggtacaact gcagcagtct gggcctgagc tggagaagcc tggcgcttca | 120 |
| gtgaagatat cctgcaaggc ttctggttac tcattcactg gctacaccat gaactgggtg | 180 |
| aagcagagcc atggaaagag ccttgagtgg attggactta ttactcctta caatggtgct | 240 |
| tctagctaca accagaagtt caggggcaag gccacattaa ctgtagacaa gtcatccagc | 300 |
| acagcctaca tggacctcct cagtctgaca tctgaagact ctgcagtcta tttctgtgca | 360 |
| aggggggggtt acgacgggag gggttttgac tactggggcc aagggaccac ggtcaccgtc | 420 |
| tcctcaggtg aggcggttc aggcggcggt ggctctagcg gtggcggatc ggacatcgag | 480 |
| ctcactcagt ctccagcaat catgtctgca tctccagggg agaaggtcac catgacctgc | 540 |
| agtgccagct caagtgtaag ttacatgcac tggtaccagc agaagtcagg cacctccccc | 600 |
| aaaagatgga tttacgacac atccaaactg gcttctggag tcccaggtcg cttcagtggc | 660 |
| agtgggtctg gaaactctta ctctctcaca atcagcagcg tggaggctga agacgacgca | 720 |
| acttattact gccagcagtg gagtaagcac cctctcacgt acggtgctgg acaaagttgg | 780 |
| gaaatcaaag ctagcaccac gacgccagcg ccgcgaccac caacaccggc gcccaccatc | 840 |
| gcgtcgcagc cctgtccct gcgcccagag gcgtgccggc cagcggcggg gggcgcagtg | 900 |
| cacacgaggg ggctggactt cgcctgtgat atctacatct gggcgccctt ggccgggact | 960 |
| tgtgggtcc ttctcctgtc actggttatc ccctttact gcaacgggg cagaaagaaa | 1020 |
| ctcctgtata tattcaaaca accatttatg agaccagtac aaactactca agaggaagat | 1080 |
| ggctgtagct gccgatttcc agaagaagaa gaaggaggat gtgaactgag agtgaagttc | 1140 |
| agcaggagcg cagacgcccc cgcgtacaag cagggccaga accagctcta taacgagctc | 1200 |
| aatctaggac gaagagagga gtacgacgtt ttggacaaga cgtggccg ggaccctgag | 1260 |
| atggggggaa agccgagaag gaagaaccct caggaaggcc tgtacaatga actgcagaaa | 1320 |
| gataagatgg cggaggccta cagtgagatt gggatgaaag cgagcgccg gaggggcaag | 1380 |

```
gggcacgatg gcctttacca gggtctcagt acagccacca aggacaccta cgacgccctt    1440
cacatgcagg ccctgccccc tcgctaa                                         1467

<210> SEQ ID NO 9
<211> LENGTH: 1461
<212> TYPE: DNA
<213> ORGANISM: Artificial sequence
<220> FEATURE:
<223> OTHER INFORMATION: Chemically synthesized

<400> SEQUENCE: 9
atggccttac cagtgaccgc cttgctcctg ccgctggcct tgctgctcca cgccgccagg      60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg cggtggtggg gtcgggtggc    420
ggcggatctg aggtgaaact gcaggagtca ggacctggcc tggtggcgcc ctcacagagc    480
ctgtccgtca catgcactgt ctcagggttc tcattacccg actatggtgt aagctggatt    540
cgccagcctc cacgaaaggg tctggagtgg ctggagtaa tatggggtag tgaaaccaca    600
tactataatt cagctctcaa atccagactg accatcatca aggacaactc caagagccaa    660
gttttcttaa aaatgaacag tctgcaaact gacgacacag ccatttacta ctgtgccaaa    720
cattattact acggtggtag ctacgctatg gactactggg ccaaggaac ctcagtcacc    780 gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900 aggggggctgg acttcgcctg tgatatctac atctgggcgc ccttggccgg acttgtgggg    960
gtccttctcc tgtcactggt tatcaccctt tactgcaaac ggggcagaaa gaaactcctg   1020
tatatattca acaaccatt tatgagacca gtacaaacta ctcaagagga gatggctgt   1080 agctgccgat tccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga cgttttggac aagagacgtg ccgggacc tgagatgggg   1260 ggaaagccga gaaggaagaa ccctcaggaa ggcctgtaca tgaactgca gaaagataag   1320 atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcta a                                              1461

<210> SEQ ID NO 10
<211> LENGTH: 1446
<212> TYPE: DNA
<213> ORGANISM: Artificial sequence
<220> FEATURE:
<223> OTHER INFORMATION: Chemically synthesized

<400> SEQUENCE: 10
atggagtttg gctgagctg gcttttcctt gtggctattt taaaaggtgt ccagtgctct      60
agagatattt gctgacccca aactccactc tccctgcctg tcagtcttgg agatcaagcc    120
tccatctctt gcagatctag tcagagtctt gtacaccgta atggaaacac ctatttacat    180
```

```
tggtacctgc agaagccagg ccagtctcca aagctcctga ttcacaaagt ttccaaccga      240
ttttctgggg tcccagacag gttcagtggc agtggatcag ggacagattt cacactcaag      300
atcagcagag tggaggctga ggatctggga gtttatttct gttctcaaag tacacatgtt      360
cctccgctca cgttcggtgc tgggaccaag ctggagctga acgggctga tgctgcacca       420 actgtatcca tcttcccagg ctcgggcggt ggtgggtcgg gtggcgaggt gaagcttcag      480
cagtctggac ctagcctggt ggagcctggc gcttcagtga tgatatcctg caaggcttct      540
ggttcctcat tcactggcta caacatgaac tgggtgaggc agaacattgg aaagagcctt      600
gaatggattg gagctattga tccttactat ggtggaacta gctacaacca gaagttcaag      660
ggcagggcca cattgactgt agacaaatcg tccagcacag cctacatgca cctcaagagc      720
ctgacatctg aggactctgc agtctattac tgtgtaagcg gaatggagta ctggggtcaa      780
ggaacctcag tcaccgtctc ctcagccaaa acgacacccc catcagtcta tggaagggtc      840
accgtctctt cagcggagcc caaatcttgt gacaaaactc acacatgccc accgtgcccg      900
ggatccatct acatctgggc ccctctggcc ggcacctgtg gcgtgctgct gctgtccctg      960
gtcatcaccc tgtactgcaa gcggggcaga aagaagctgc tgtacatctt caagcagccc     1020
ttcatgcggc ctgtgcagac cacacaggaa gaggacggct gtagctgtag attccccgag     1080
gaagaggaag gcggctgcga gctgagagtg aagttcagca gaagcgccga cgcccctgcc     1140
tatcagcagg gccagaacca gctgtacaac gagctgaacc tgggcagacg ggaggaatac     1200
gacgtgctgg acaagagaag aggccgggac cctgagatgg gcggcaagcc cagacggaag     1260 aaccccagg aaggcctgta taacgaactg cagaaagaca gatggccgga ggcctacagc       1320
gagatcggca tgaagggcga gcggagaaga ggcaagggcc atgacggcct gtaccagggc     1380
ctgagcaccg ccaccaagga cacctacgac gccctgcaca tgcaggccct gcctccaaga     1440
tgatga                                                                1446
```

<210> SEQ ID NO 11
<211> LENGTH: 1455
<212> TYPE: DNA
<213> ORGANISM: Artificial sequence
<220> FEATURE:
<223> OTHER INFORMATION: Chemically synthesized

<400> SEQUENCE: 11

```
atggagtttg ggctgagctg gctttttctt gtggctattt taaaaggtgt ccagtgctct        60
agagatattt tgctgaccca aactccactc tccctgcctg tcagtcttgg agatcaagcc       120
tccatctctt gcagatctag tcagagtctt gtacaccgta atggaaacac ctatttacat       180
tggtacctgc agaagccagg ccagtctcca aagctcctga ttcacaaagt ttccaaccga      240
ttttctgggg tcccagacag gttcagtggc agtggatcag ggacagattt cacactcaag      300
atcagcagag tggaggctga ggatctggga gtttatttct gttctcaaag tacacatgtt      360
cctccgctca cgttcggtgc tgggaccaag ctggagctga acgggctga tgctgcacca       420 actgtatcca tcttcccagg ctcgggcggt ggtgggtcgg gtggcgaggt gaagcttcag      480
cagtctggac ctagcctggt ggagcctggc gcttcagtga tgatatcctg caaggcttct      540
ggttcctcat tcactggcta caacatgaac tgggtgaggc agaacattgg aaagagcctt      600
gaatggattg gagctattga tccttactat ggtggaacta gctacaacca gaagttcaag      660
ggcagggcca cattgactgt agacaaatcg tccagcacag cctacatgca cctcaagagc      720
```

| | |
|---|---|
| ctgacatctg aggactctgc agtctattac tgtgtaagcg aatggagta ctggggtcaa | 780 |
| ggaacctcag tcaccgtctc ctcagccaaa acgacacccc catcagtcta tggaagggtc | 840 |
| accgtctctt cagcggagcc caaatcttgt gacaaaactc acacatgccc accgtgcccg | 900 |
| ggatccttct gggtgctggt cgtggtcggc ggcgtgctgg cctgttactc cctgctggtc | 960 |
| accgtggcct tcatcatctt ttgggtcaag cggggcagaa agaagctgct gtacatcttc | 1020 |
| aagcagccct tcatgcggcc tgtgcagacc acacaggaag ggacggctg tagctgtaga | 1080 |
| ttccccgagg aagaggaagg cggctgcgag ctgagagtga agttcagcag aagcgccgac | 1140 |
| gcccctgcct atcagcaggg ccagaaccag ctgtacaacg agctgaacct gggcagacgg | 1200 |
| gaggaatacg acgtgctgga caagagaaga ggccgggacc ctgagatggg cggcaagccc | 1260 |
| agacggaaga accccagga aggcctgtat aacgaactgc agaaagacaa gatggccgag | 1320 |
| gcctacagcg agatcggcat gaaggcgag cggagaagag gcaagggcca tgacggcctg | 1380 |
| taccagggcc tgagcaccgc caccaaggac acctacgacg ccctgcacat gcaggccctg | 1440 |
| cctccaagat gatga | 1455 |

<210> SEQ ID NO 12
<211> LENGTH: 1455
<212> TYPE: DNA
<213> ORGANISM: Artificial sequence
<220> FEATURE:
<223> OTHER INFORMATION: Chemically synthesized

<400> SEQUENCE: 12

| | |
|---|---|
| atggagtttg ggctgagctg gcttttttctt gtggctattt taaaaggtgt ccagtgctct | 60 |
| agagatattt tgctgaccca aactccactc tccctgcctg tcagtcttgg agatcaagcc | 120 |
| tccatctctt gcagatctag tcagagtctt gtacaccgta atggaaacac ctatttacat | 180 |
| tggtacctgc agaagccagg ccagtctcca aagctcctga ttcacaaagt tccaaccga | 240 |
| ttttctgggg tcccagacag gttcagtggc agtggatcag gacagattt cacactcaag | 300 |
| atcagcagag tggaggctga ggatctggga gtttatttct gttctcaaag tacacatgtt | 360 |
| cctccgctca cgttcggtgc tgggaccaag ctggagctga acgggctga tgctgcacca | 420 |
| actgtatcca tcttcccagg ctcgggcggt ggtgggtcgg gtggcgaggt gaagcttcag | 480 |
| cagtctggac ctagcctggt ggagcctggc gcttcagtga tgatatcctg caaggcttct | 540 |
| ggttcctcat tcactggcta caacatgaac tgggtgaggc agaacattgg aaagagcctt | 600 |
| gaatggattg gagctattga tccttactat ggtggaacta gctacaacca gaagttcaag | 660 |
| ggcagggcca cattgactgt agacaaatcg tccagcacag cctacatgca cctcaagagc | 720 |
| ctgacatctg aggactctgc agtctattac tgtgtaagcg aatggagta ctggggtcaa | 780 |
| ggaacctcag tcaccgtctc ctcagccaaa acgacacccc catcagtcta tggaagggtc | 840 |
| accgtctctt cagcggagcc caaatcttgt gacaaaactc acacatgccc accgtgcccg | 900 |
| ggatccttct gggtgctggt cgtggtcggc ggcgtgctgg cctgttactc cctgctggtc | 960 |
| accgtggcct tcatcatctt ttgggtcaag cggggcagaa agaagctgct gtacatcttc | 1020 |
| aagcagccct tcatgcggcc tgtgcagacc acacaggaag ggacggctg tagctgtaga | 1080 |
| ttccccgagg aagaggaagg cggctgcgag ctgagagtga agttcagcag aagcgccgac | 1140 |
| gcccctgcct atcagcaggg ccagaaccag ctgtacaacg agctgaacct gggcagacgg | 1200 |
| gaggaatacg acgtgctgga caagagaaga ggccgggacc ctgagatggg cggcaagccc | 1260 |
| agacggaaga accccagga aggcctgtat aacgaactgc agaaagacaa gatggccgag | 1320 |

```
gcctacagcg agatcggcat gaagggcgag cggagaagag gcaagggcca tgacggcctg    1380
taccagggcc tgagcaccgc caccaaggac acctacgacg ccctgcacat gcaggccctg    1440
cctccaagat gatga                                                    1455
```

<210> SEQ ID NO 13
<211> LENGTH: 1443
<212> TYPE: DNA
<213> ORGANISM: Artificial sequence
<220> FEATURE:
<223> OTHER INFORMATION: Chemically synthesized

<400> SEQUENCE: 13

```
atggagtttg ggctgagctg gcttttctt gtggctattt taaaaggtgt ccagtgctct      60
agagatattt gctgacccca aactccactc tccctgcctg tcagtcttgg agatcaagcc    120
tccatctctt gcagatctag tcagagtctt gtacaccgta atggaaacac ctatttacat    180
tggtacctgc agaagccagg ccagtctcca aagctcctga ttcacaaagt tccaaccga    240 ttttctgggg tcccagacag gttcagtggc agtggatcag gacagatttt cacactcaag    300
atcagcagag tggaggctga ggatctggga gtttatttct gttctcaaag tacacatgtt    360
cctccgctca cgttcggtgc tgggaccaag ctggagctga acgggctga tgctgcacca    420 actgtatcca tcttcccagg ctcgggcggt ggtgggtcgg gtggcgaggt gaagcttcag    480
cagtctggac ctagcctggt ggagcctggc gcttcagtga tgatatcctg caaggcttct    540
ggttcctcat tcactggcta caacatgaac tgggtgaggc agaacattgg aaagagcctt    600
gaatggattg gagctattga tccttactat ggtggaacta gctacaacca gaagttcaag    660
ggcagggcca cattgactgt agacaaatcg tccagcacag cctacatgca cctcaagagc    720
ctgacatctg aggactctgc agtctattac tgtgtaagcg gaatggagta ctgggtcaa    780 ggaacctcag tcaccgtctc ctcagccaaa acgacacccc catcagtcta cggaagggtc    840
accgtctctt cagcggagcc caaatcttgt gacaaaactc acacctgccc accgtgcccg    900
ggatccatct acatctgggc ccctctggcc ggcacctgtg gcgtgctgct gctgtccctg    960
gtcatcaccc tgtactgcaa gcggggcaga aagaagctgc tgtacatctt caagcagccc    1020
ttcatgcggc ctgtgcagac cacacaggaa gaggacggct gtagctgtag attccccgag    1080
gaagaggaag gcggctgcga gctgagagtg aagttcagca gaagcgccga cgcccctgcc    1140
tatcagcagg gccagaacca gctgtacaac gagctgaacc tgggcagacg ggaggaatac    1200
gacgtgctgg acaagagaag aggccgggac cctgagatgg gcggcaagcc cagacggaag    1260 aaccccagg aaggcctgta taacgaactg cagaaagaca gatggccga ggcctacagc    1320 gagatcggca tgaagggcga gcggagaaga ggcaagggcc atgacggcct gtaccagggc    1380
ctgagcaccg ccaccaagga cacctacgac gccctgcaca tgcaggccct gcctccaaga    1440
tga                                                                1443
```

<210> SEQ ID NO 14
<211> LENGTH: 2025
<212> TYPE: DNA
<213> ORGANISM: Artificial sequence
<220> FEATURE:
<223> OTHER INFORMATION: Chemically synthesized

<400> SEQUENCE: 14

```
atgctgctgc tggtgaccag cctgctgctg tgtgagctgc cccaccccgc ctttctgctg     60
```

| | |
|---|---|
| atccccgaca tccagatgac ccagagcccc agcagcgtga gcgccagcgt gggcgaccgg | 120 |
| gtgaccatca cctgccgggc cagccagggc atcaacacct ggctggcctg gtatcagcag | 180 |
| aagcccggca aggcccccaa gctgctgatc tacgccgcca gcagcctgaa gagcggcgtg | 240 |
| cccagccggt ttagcggctc tggctctggc gccgacttca ccctgaccat cagcagcctg | 300 |
| cagcccgagg acttcgccac ctactactgc agcaggcca acagcttccc cctgaccttt | 360 |
| ggcggcggaa caaaggtgga gatcaagggc agcacctccg gcagcggcaa gcctggcagc | 420 |
| ggcgagggca gcaccaaggg ccaggtgcag ctggtgcaga gcggagccga ggtgaagaag | 480 |
| cctggcgcct ccgtcaaggt gtcctgcgag gccagcggct acaccttcac cagctacggc | 540 |
| ttcagctggg tgcggcaggc accaggccag ggcctcgagt ggatgggctg gatcagcgcc | 600 |
| agcaacggca cacctacta cgcccagaag ctgcagggca gggtcaccat gaccaccgac | 660 |
| accagcacca gcagcgccta catggaactg cggagcctga aagcgacga caccgccgtg | 720 |
| tactactgcg ccagggtgta cgccgactac gccgattact ggggccaggg caccctggtg | 780 |
| accgtgagca gcgagagcaa gtacggccct ccctgccccc cttgccctgc ccccgagttc | 840 |
| ctgggcggac ccagcgtgtt cctgttcccc ccaagcccca aggacaccct gatgatcagc | 900 |
| cggacccccg aggtgacctg tgtggtggtg gacgtgtccc aggaggaccc cgaggtccag | 960 |
| ttcaactggt acgtggacgg cgtggaggtg cacaacgcca agaccaagcc ccgggaggag | 1020 |
| cagttcaata gcacctaccg ggtggtgtcc gtgctgaccg tgctgcacca ggactggctg | 1080 |
| aacggcaagg aatacaagtg taaggtgtcc aacaagggcc tgcccagcag catcgagaaa | 1140 |
| accatcagca aggccaaggg ccagcctcgg gagccccagg tgtacaccct gcccctagc | 1200 |
| caagaggaga tgaccaagaa ccaggtgtcc ctgacctgcc tggtgaaggg cttctacccc | 1260 |
| agcgacatcg ccgtggagtg ggagagcaac ggccagcccg agaacaacta caagaccacc | 1320 |
| cccctgtgc tggacagcga cggcagcttc ttcctgtaca gccggctgac cgtggacaag | 1380 |
| agccggtggc aggagggcaa cgtctttagc tgctccgtga tgcacgaggc cctgcacaac | 1440 |
| cactacaccc agaagagcct gagcctgtcc ctgggcaagg atatcatcta catctgggcc | 1500 |
| cctctggccg gcacctgtgg cgtgctgctg ctgtccctgg tcatcaccct gtactgcaag | 1560 |
| cggggcagaa agaagctgct gtacatcttc aagcagccct tcatgcggcc tgtgcagacc | 1620 |
| acacaggaag gacggctg tagctgtaga ttccccgagg aagaggaagg cggctgcgag | 1680 |
| ctgagagtga agttcagcag aagcgccgac gcccctgcct atcagcaggg ccagaaccag | 1740 |
| ctgtacaacg agctgaacct gggcagacgg gaggaatacg acgtgctgga caagagaaga | 1800 |
| ggccgggacc ctgagatggg cggcaagccc agacggaaga ccccagga aggcctgtat | 1860 |
| aacgaactgc agaaagacaa gatggccgag gcctacagcg agatcggcat gaagggcgag | 1920 |
| cggagaagag gcaagggcca tgacggcctg taccagggcc tgagcaccgc caccaaggac | 1980 |
| acctacgacg ccctgcacat gcaggccctg cctccaagat gatga | 2025 |

<210> SEQ ID NO 15
<211> LENGTH: 2040
<212> TYPE: DNA
<213> ORGANISM: Artificial sequence
<220> FEATURE:
<223> OTHER INFORMATION: Chemically synthesized

<400> SEQUENCE: 15

| | |
|---|---|
| atgctgctgc tggtgaccag cctgctgctg tgtgagctgc ccacccccgc ctttctgctg | 60 |
| atccccgaca tccagatgac ccagagcccc agcagcgtga gcgccagcgt gggcgaccgg | 120 |

```
gtgaccatca cctgccgggc cagccagggc atcaacacct ggctggcctg gtatcagcag    180
aagcccggca aggcccccaa gctgctgatc tacgccgcca gcagcctgaa gagcggcgtg    240
cccagccggt ttagcggctc tggctctggc gccgacttca ccctgaccat cagcagcctg    300
cagcccgagg acttcgccac ctactactgc cagcaggcca cagcttccc cctgacctt    360 ggcggcggaa caaaggtgga gatcaagggc agcacctccg gcagcggcaa gcctggcagc    420
ggcgagggca gcaccaaggg ccaggtgcag ctggtgcaga gcggagccga ggtgaagaag    480
cctggcgcct ccgtcaaggt gtcctgcgag gccagcggct acaccttcac cagctacggc    540
ttcagctggg tgcggcaggc caccaggccag ggcctcgagt ggatgggctg gatcagcgcc    600
agcaacggca acacctacta cgcccagaag ctgcagggca gggtcaccat gaccaccgac    660
accagcacca gcgcgccta catggaactg cggagcctga aagcgacga caccgccgtg    720 tactactgcg ccagggtgta cgccgactac gccgattact ggggccaggg caccctggtg    780
accgtgagca gcgagagcaa gtacggcccc cctgccccc cttgccctgc ccccgagttc    840
ctgggcggac cagcgtgtt cctgttcccc ccaagccca aggacaccct gatgatcagc    900
cggacccccg aggtgacctg tgtggtggtg gacgtgtccc aggaggaccc cgaggtccag    960
ttcaactggt acgtggacgg cgtggaggtg cacaacgcca agaccaagcc ccgggaggag   1020
cagttcaata gcacctaccg ggtggtgtcc gtgctgaccg tgctgcacca ggactggctg   1080
aacggcaagg aatacaagtg taaggtgtcc aacaagggcc tgcccagcag catcgagaaa   1140
accatcagca aggccaaggg ccagcctcgg gagccccagg tgtacaccct gccccctagc   1200
caagaggaga tgaccaagaa ccaggtgtcc ctgacctgcc tggtgaaggg cttctacccc   1260
agcgacatcg ccgtggagtg ggagagcaac ggccagcccg agaacaacta caagaccacc   1320
ccccctgtgc tggacagcga cggcagcttc ttcctgtaca gccggctgac cgtggacaag   1380
agccggtggc aggagggcaa cgtctttagc tgctccgtga tgcacgaggc cctgcacaac   1440
cactacaccc agaagagcct gagcctgtcc ctgggcaagg ataatgatat cttctgggtg   1500
ctggtcgtgg tcggcggcgt gctggcctgt tactccctgc tggtcaccgt ggccttcatc   1560
atcttttggg tcaagcgggg cagaaagaag ctgctgtaca tcttcaagca gcccttcatg   1620
cggcctgtgc agaccacaca ggaagaggac ggctgtagct gtagattccc cgaggaagag   1680
gaaggcggct gcgagctgag agtgaagttc agcagaagcg ccgacgcccc tgcctatcag   1740
cagggccaga accagctgta caacgagctg aacctgggca gacgggagga atacgacgtg   1800
ctggacaaga agagggcgg ggaccctgag atgggcggca gcccagacg aagaacccc   1860 caggaaggcc tgtataacga actgcagaaa gacaagatgg ccgaggccta cagcgagatc   1920
ggcatgaagg gcgagcggag aagaggcaag ggccatgacg gcctgtacca gggcctgagc   1980
accgccacca ggacaccta cgacgccctg cacatgcagg ccctgcctcc aagatgatga   2040
```

<210> SEQ ID NO 16
<211> LENGTH: 2031
<212> TYPE: DNA
<213> ORGANISM: Artificial sequence
<220> FEATURE:
<223> OTHER INFORMATION: Chemically synthesized

<400> SEQUENCE: 16

```
atgctgctgc tggtgaccag cctgctgctg tgtgagctgc cccacccgc ctttctgctg     60 atccccgaca tccagatgac ccagagcccc agcagcgtga gcgccagcgt gggcgaccgg    120
```

```
gtgaccatca cctgccgggc cagccagggc atcaacacct ggctggcctg gtatcagcag      180
aagcccggca aggccccaa gctgctgatc tacgccgcca gcagcctgaa gagcggcgtg       240
cccagccggt ttagcggctc tggctctggc gccgacttca ccctgaccat cagcagcctg      300
cagcccgagg acttcgccac ctactactgc cagcaggca acagcttccc cctgaccttt       360
ggcggcggaa caaaggtgga gatcaagggc agcacctccg gcagcggcaa gcctggcagc      420
ggcgagggca gcaccaaggg ccaggtgcag ctggtgcaga gcggagccga ggtgaagaag      480
cctggcgcct ccgtcaaggt gtcctgcgag gccagcggct acaccttcac cagctacggc      540
ttcagctggg tgcggcaggc caggccag ggcctcgagt ggatgggctg gatcagcgcc        600
agcaacggca acacctacta cgcccagaag ctgcagggca gggtcaccat gaccaccgac      660
accagcacca gcagcgccta catggaactg cggagcctga aagcgacga caccgccgtg       720 tactactgcg ccagggtgta cgccgactac gccgattact ggggccaggg caccctggtg      780
accgtgagca gcgagagcaa gtacggcccc cctgccccc cttgccctgc ccccgagttc       840
ctgggcggac ccagcgtgtt cctgttcccc cccaagccca aggacaccct gatgatcagc      900 cggaccccg aggtgacctg tgtggtggtg gacgtgtccc aggaggaccc cgaggtccag       960
ttcaactggt acgtggacgg cgtggaggtg cacaacgcca agaccaagcc ccgggaggag     1020
cagttcaata gcacctaccg ggtggtgtcc gtgctgaccg tgctgcacca ggactggctg     1080
aacggcaagg aatacaagtg taaggtgtcc aacaagggcc tgcccagcag catcgagaaa    1140
accatcagca aggccaaggg ccagcctcgg gagccccagg tgtacaccct gccccctagc     1200
caagaggaga tgaccaagaa ccaggtgtcc ctgacctgcc tggtgaaggg cttctacccc     1260
agcgacatcg ccgtggagtg ggagagcaac ggccagcccg agaacaacta caagaccacc    1320 cccctgtgc tggacagcga cggcagcttc ttcctgtaca gccggctgac cgtggacaag     1380
agccggtggc aggagggcaa cgtctttagc tgctccgtga tgcacgaggc cctgcacaac    1440
cactaccccc agaagagcct gagcctgtcc ctgggcaagg atatcatttc tttttcctc     1500 gcgctgactt cgacagccct actgtttctg ctctttttcc tgactctcag attctcggtg    1560
gtgaagcggg gcagaaagaa gctgctgtac atcttcaagc agcccttcat gcggcctgtg     1620
cagaccacac aggaagagga cggctgtagc tgtagattcc ccgaggaaga ggaaggcggc   1680
tgcgagctga gagtgaagtt cagcagaagc gccgacgccc ctgcctatca gcagggccag   1740
aaccagctgt acaacgagct gaacctgggc agacgggagg aatacgacgt gctggacaag   1800
agaagaggcc gggaccctga gatggcggc aagcccagac ggaagaaccc ccaggaaggc    1860
ctgtataacg aactgcagaa agacaagatg gccgaggcct acagcgagat cggcatgaag    1920
ggcgagcgga agaggcaa gggccatgac ggcctgtacc agggcctgag caccgccacc    1980
aaggacacct acgacgccct gcacatgcag gccctgcctc caagatgatg a           2031
```

<210> SEQ ID NO 17
<211> LENGTH: 2157
<212> TYPE: DNA
<213> ORGANISM: Artificial sequence
<220> FEATURE:
<223> OTHER INFORMATION: Chemically synthesized

<400> SEQUENCE: 17

```
atgctgctgc tggtgaccag cctgctgctg tgtgagctgc cccacccgc ctttctgctg      60 atccccgaca tccagatgac ccagagcccc agcagcgtga cgccagcgt gggcgaccgg     120 gtgaccatca cctgccgggc cagccagggc atcaacacct ggctggcctg gtatcagcag    180
```

```
aagcccggca aggcccccaa gctgctgatc tacgccgcca gcagcctgaa gagcggcgtg    240
cccagccggt ttagcggctc tggctctggc gccgacttca ccctgaccat cagcagcctg    300
cagcccgagg acttcgccac ctactactgc cagcaggcca acagcttccc cctgaccttt    360
ggcggcggaa caaaggtgga gatcaagggc agcacctccg gcagcggcaa gcctggcagc    420
ggcgagggca gcaccaaggg ccaggtgcag ctggtgcaga gcggagccga ggtgaagaag    480
cctggcgcct ccgtcaaggt gtcctgcgag gccagcggct acaccttcac cagctacggc    540
ttcagctggg tgcggcaggc caccaggcca ggcctcgaat ggatgggctg gatcagcgcc    600
agcaacggca cacctactac gcccagaag ctgcagggca gggtcaccat gaccaccgac    660
accagcacca gcagcgccta catggaactg cggagcctga aagcgacga caccgccgtg    720 tactactgcg ccagggtgta cgccgactac gccgattact ggggccaggg caccctggtg    780
accgtgagca gcgagagcaa gtacggccct cctgcccccc cttgccctgc cccgagttc    840 ctgggcggac ccagcgtgtt cctgttcccc ccaagcccca aggacaccct gatgatcagc    900
cggacccccg aggtgacctg tgtggtggtg gacgtgtccc aggaggaccc cgaggtccag    960
ttcaactggt acgtggacgg cgtggaggtg cacaacgcca agaccaagcc ccgggaggag   1020
cagttcaata gcacctaccg ggtggtgtcc gtgctgaccg tgctgcacca ggactggctg   1080
aacggcaagg aatacaagtg taaggtgtcc aacaagggcc tgcccagcag catcgagaaa   1140
accatcagca aggccaaggg ccagcctcgg gagcccagg tgtacaccct gcccctagc   1200 caagaggaga tgaccaagaa ccaggtgtcc ctgacctgcc tggtgaaggg cttctacccc   1260
agcgacatcg ccgtggagtg ggagagcaac ggccagcccg agaacaacta caagaccacc   1320 cccctgtgc tggacagcga cggcagcttc ttcctgtaca gccggctgac cgtggacaag   1380
agccggtggc aggagggcaa cgtctttagc tgctccgtga tgcacgaggc cctgcacaac   1440
cactacaccc agaagagcct gagcctgtcc ctgggcaagg atatcttctg ggtgctggtc   1500
gtggtcggcg gcgtgctggc ctgttactcc ctgctggtca ccgtggcctt catcatcttt   1560
tgggtccgca gcaagagaag cagaggcggc cacagcgact acatgaacat gacacccaga   1620
cggccaggcc ccaccagaaa gcactaccag ccctacgccc ctcctagaga cttcgccgcc   1680
taccggtcca gcggggcag aaagaagctg ctgtacatct tcaagcagcc cttcatgcgg   1740
cctgtgcaga ccacacagga agaggacggc tgtagctgta gattccccga ggaagaggaa   1800
ggcggctgcg agctgagagt gaagttcagc agaagcgccg acgcccctgc ctatcagcag   1860
ggccagaacc agctgtacaa cgagctgaac ctgggcagac gggaggaata cgacgtgctg   1920
gacaagagaa gaggccggga ccctgagatg ggcggcaagc cagacggaa gaaccccag   1980 gaaggcctgt ataacgaact gcagaaagac aagatggccg aggcctacag cgagatcggc   2040
atgaagggcg agcggagaag aggcaagggc catgacggcc tgtaccaggg cctgagcacc   2100
gccaccaagg acacctacga cgccctgcac atgcaggccc tgcctccaag atgatga      2157
```

<210> SEQ ID NO 18
<211> LENGTH: 2025
<212> TYPE: DNA
<213> ORGANISM: Artificial sequence
<220> FEATURE:
<223> OTHER INFORMATION: Chemically synthesized

<400> SEQUENCE: 18

```
atgctgctgc tggtgaccag cctgctgctg tgtgagctgc cccacccgc ctttctgctg    60
```

| | |
|---|---|
| atccccgaca tccagatgac ccagagcccc agcagcgtga gcgccagcgt gggcgaccgg | 120 |
| gtgaccatca cctgccgggc cagccagggc atcaacacct ggctggcctg gtatcagcag | 180 |
| aagcccggca aggcccccaa gctgctgatc tacgccgcca gcagcctgaa gagcggcgtg | 240 |
| cccagccggt ttagcggctc tggctctggc gccgacttca ccctgaccat cagcagcctg | 300 |
| cagcccgagg acttcgccac ctactactgc agcaggcca acagcttccc cctgaccttt | 360 |
| ggcggcggaa caaaggtgga gatcaagggc agcacctccg gcagcggcaa gcctggcagc | 420 |
| ggcgagggca gcaccaaggg ccaggtgcag ctggtgcaga gcggagccga ggtgaagaag | 480 |
| cctggcgcct ccgtcaaggt gtcctgcgag gccagcggct acaccttcac cagctacggc | 540 |
| ttcagctggg tgcggcaggc caccaggccag ggcctcgaat ggatgggctg gatcagcgcc | 600 |
| agcaacggca acacctacta cgcccagaag ctgcagggca gggtcaccat gaccaccgac | 660 |
| accagcacca gcagcgccta catggaactg cggagcctga aagcgacga caccgccgtg | 720 |
| tactactgcg ccagggtgta cgccgactac gccgattact ggggccaggg caccctggtg | 780 |
| accgtgagca gcgagagcaa gtacggccct ccctgccccc cttgccctgc ccccgagttc | 840 |
| ctgggcggac ccagcgtgtt cctgttcccc ccaagcccca aggacaccct gatgatcagc | 900 |
| cggacccccg aggtgacctg tgtggtggtg gacgtgtccc aggaggaccc cgaggtccag | 960 |
| ttcaactggt acgtggacgg cgtggaggtg cacaacgcca agaccaagcc ccgggaggag | 1020 |
| cagttcaata gcacctaccg ggtggtgtcc gtgctgaccg tgctgcacca ggactggctg | 1080 |
| aacggcaagg aatacaagtg taaggtgtcc aacaagggcc tgcccagcag catcgagaaa | 1140 |
| accatcagca aggccaaggg ccagcctcgg gagccccagg tgtacaccct gccccctagc | 1200 |
| caagaggaga tgaccaagaa ccaggtgtcc ctgacctgcc tggtgaaggg cttctacccc | 1260 |
| agcgacatcg ccgtggagtg ggagagcaac ggccagcccg agaacaacta caagaccacc | 1320 |
| cccctgtgc tggacagcga cggcagcttc ttcctgtaca gccggctgac cgtggacaag | 1380 |
| agccgtggc aggagggcaa cgtctttagc tgctccgtga tgcacgaggc cctgcacaac | 1440 |
| cactacaccc agaagagcct gagcctgtcc ctgggcaaga tgttctgggt gctggtcgtt | 1500 |
| gtgggcggcg tgctggcctg ctacagcctg ctggtgacag tggccttcat catcttttgg | 1560 |
| gtgaggagca agcggagcag aggcggccac agcgactaca tgaacatgac ccccggagg | 1620 |
| cctggcccca cccggaagca ctaccagccc tacgcccctc caggggatttt cgccgcctac | 1680 |
| cggagccggg tgaagttcag ccggagcgcc gacgcccctg cctaccagca gggccagaac | 1740 |
| cagctgtaca cgagctgaa cctgggccgg agggaggagt acgacgtgct ggacaagcgg | 1800 |
| agaggccggg accctgagat gggcggcaag ccccggagaa agaaccccca ggagggcctg | 1860 |
| tataacgaac tgcagaaaga caagatggcc gaggcctaca gcgagatcgg catgaagggc | 1920 |
| gagcggaggc ggggcaaggg ccacgacggc ctgtaccagg gcctgagcac cgccaccaag | 1980 |
| gatacctacg acgccctgca catgcaggcc ctgccccca gatga | 2025 |

```
<210> SEQ ID NO 19
<211> LENGTH: 1335
<212> TYPE: DNA
<213> ORGANISM: Artificial sequence
<220> FEATURE:
<223> OTHER INFORMATION: Chemically synthesized

<400> SEQUENCE: 19
```

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |

```
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtgcagtgg gtctggaaca gattattctc tcaccattag caacctggag       300
caagaagata ttgccactta cttttgccaa cagggtaata cgcttccgta cacgttcgga      360
gggggaccca agctggagat cacaggtggc ggtggctcgg gcggtggtgg gtcgggtggc      420
ggcggatctg aggtgaaact gcaggagtca ggacctggcc tggtggcgcc ctcacagagc      480
ctgtccgtca catgcactgt ctcaggggtc tcattacccg actatggtgt aagctggatt      540
cgccagcctc cacgaaaggg tctggagtgg ctgggagtaa tatggggtag tgaaaccaca      600
tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
gtctcctcaa ccacgacgcc agcgccgcga ccaccaacac cggcgcccac catcgcgtcg      840
cagcccctgt ccctgcgccc agaggcgtgc cggccagcgg cgggggcgc agtgcacacg       900 aggggctgg acttcgcctg tgatatctac atctgggcgc ccttggccgg gacttgtggg       960
gtccttctcc tgtcactggt tatcacccct tactgcagag tgaagttcag caggagcgca      1020 gacgccccg cgtaccagca gggccagaac cagctctata cgagctcaa tctaggacga       1080 agagaggagt acgatgtttt ggacaagaga cgtggccggg accctgagat ggggggaaag      1140
ccgagaagga agaaccctca ggaaggcctg tacaatgaac tgcagaaaga taagatggcg      1200
gaggcctaca gtgagattgg gatgaaaggc gagcgccgga ggggcaaggg gcacgatggc      1260
ctttaccagg gtctcagtac agccaccaag gacacctacg acgcccttca catgcaggcc      1320
ctgccccctc gctaa                                                       1335
```

<210> SEQ ID NO 20
<211> LENGTH: 1473
<212> TYPE: DNA
<213> ORGANISM: Artificial sequence
<220> FEATURE:
<223> OTHER INFORMATION: Chemically synthesized

<400> SEQUENCE: 20

```
atggccttac cagtgaccgc cttgctcctg ccgctggcct tgctgctcca cgccgccagg       60
ccggacatcc agatgacaca gactacatcc tccctgtctg cctctctggg agacagagtc      120
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtgcagtgg gtctggaaca gattattctc tcaccattag caacctggag       300
caagaagata ttgccactta cttttgccaa cagggtaata cgcttccgta cacgttcgga      360
gggggaccca agctggagat cacaggtggc ggtggctcgg gcggtggtgg gtcgggtggc      420
ggcggatctg aggtgaaact gcaggagtca ggacctggcc tggtggcgcc ctcacagagc      480
ctgtccgtca catgcactgt ctcaggggtc tcattacccg actatggtgt aagctggatt      540
cgccagcctc cacgaaaggg tctggagtgg ctgggagtaa tatggggtag tgaaaccaca      600
tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
```

| | |
|---|---|
| gtctcctcaa ccacgacgcc agcgccgcga ccaccaacac cggcgcccac catcgcgtcg | 840 |
| cagcccctgt ccctgcgccc agaggcgtgc cggccagcgg cgggggggcgc agtgcacacg | 900 |
| aggggggctgg acttcgcctg tgattttttgg gtgctggtgg tggttggtgg agtcctggct | 960 |
| tgctatagct tgctagtaac agtggccttt attattttct gggtgaggag taagaggagc | 1020 |
| aggctcctgc acagtgacta catgaacatg actccccgcc gccccgggcc cacccgcaag | 1080 |
| cattaccagc cctatgcccc accacgcgac ttcgcagcct atcgctccat cgatagagtg | 1140 |
| aagttcagca ggagcgcaga cgcccccgcg taccagcagg gccagaacca gctctataac | 1200 |
| gagctcaatc taggacgaag agaggagtac gatgttttgg acaagagacg tggccgggac | 1260 |
| cctgagatgg ggggaaagcc gagaaggaag aaccctcagg aaggcctgta caatgaactg | 1320 |
| cagaaagata gatggcgga ggcctacagt gagattggga tgaaaggcga gcgccggagg | 1380 |
| ggcaaggggc acgatggcct ttaccagggt ctcagtacag ccaccaagga cacctacgac | 1440 |
| gcccttcaca tgcaggccct gccccctcgc taa | 1473 |

<210> SEQ ID NO 21
<211> LENGTH: 1593
<212> TYPE: DNA
<213> ORGANISM: Artificial sequence
<220> FEATURE:
<223> OTHER INFORMATION: Chemically synthesized

<400> SEQUENCE: 21

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| ggggggacca agctggagat cacaggtggc ggtggctcgg gcggtggtgg gtcgggtggc | 420 |
| ggcggatctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gccaaggaac ctcagtcacc | 780 |
| gtctcctcaa ccacgacgcc agcgccgcga ccaccaacac cggcgcccac catcgcgtcg | 840 |
| cagcccctgt ccctgcgccc agaggcgtgc cggccagcgg cgggggggcgc agtgcacacg | 900 |
| aggggggctgg acttcgcctg tgattttttgg gtgctggtgg tggttggtgg agtcctggct | 960 |
| tgctatagct tgctagtaac agtggccttt attattttct gggtgaggag taagaggagc | 1020 |
| aggctcctgc acagtgacta catgaacatg actccccgcc gccccgggcc cacccgcaag | 1080 |
| cattaccagc cctatgcccc accacgcgac ttcgcagcct atcgctccaa acggggcaga | 1140 |
| aagaaactcc tgtatatatt caaacaacca tttatgagac cagtacaaac tactcaagag | 1200 |
| gaagatggct gtagctgccg atttccagaa gaagaagaag gaggatgtga actgagagtg | 1260 |
| aagttcagca ggagcgcaga cgcccccgcg tacaagcagg gccagaacca gctctataac | 1320 |
| gagctcaatc taggacgaag agaggagtac gatgttttgg acaagagacg tggccgggac | 1380 |

```
cctgagatgg ggggaaagcc gagaaggaag aaccctcagg aaggcctgta caatgaactg    1440
cagaaagata agatggcgga ggcctacagt gagattggga tgaaaggcga gcgccggagg    1500
ggcaaggggc acgatggcct ttaccagggt ctcagtacag ccaccaagga cacctacgac    1560
gcccttcaca tgcaggccct gccccctcgc taa                                 1593
```

<210> SEQ ID NO 22
<211> LENGTH: 1596
<212> TYPE: DNA
<213> ORGANISM: Artificial sequence
<220> FEATURE:
<223> OTHER INFORMATION: Chemically synthesized

<400> SEQUENCE: 22

```
atggccctgc tgtgacagc tctgctgctg cctctggctc tgctcctgca tgccgctaga     60
cccgacatcc agatgaccca gaccacctcc agcctgtctg cctctctggg cgacagagtg    120
accatcagct gccgggccag ccaggacatc agcaagtacc tgaactggta tcagcagaaa    180
cccgacggca ccgtgaagct gctgatctac cacacctctc ggctgcacag cggcgtgcct    240
agcagattca gcggcagcgg ctccggcacc gactacagcc tgaccatctc caacctggaa    300
caggaagata tcgccaccta cttctgccag caaggcaaca cactgcccta ccttcggc     360 ggaggcacca gctggaaat accggcgga ggcggatctg gaggcggagg aagcggaggc    420
ggcggatccg aagtgaagct gcaggaaagc ggccctggac tggtggcccc tagccagagc    480
ctgagcgtga cctgtaccgt gtccggcgtg agcctgcctg attacggcgt gagctggatc    540
agacagcccc ccagaaaggg cctggaatgg ctgggcgtga tctggggcag cgagacaacc    600
tactacaaca gcgccctgaa gtcccggctg accatcatca aggacaacag caagagccag    660
gtgttcctga agatgaacag cctgcagacc gacgacaccg ccatctacta ctgcgccaag    720
cactactact acggcggcag ctacgctatg gattactggg gccagggcac cagcgtgacc    780
gtgtccagca ccaccacccc tgcccctaga cctccaaccc cagccccac aatcgccagc    840 cagcccctgt ctctgaggcc cgaggcctgt agaccagctg ccggcggagc cgtgcacacc    900
agaggcctgg acttcgcctg cgacttctgg gtgctggtcg tggtcggcgg cgtgctggcc    960
tgttactccc tgctggtcac cgtggccttc atcatctttt gggtccgcag caagagaagc    1020
agaggcggcc acagcgacta catgaacatg acacccagac ggccaggccc caccagaaag    1080
cactaccagc cctacgcccc tcctagagac ttcgccgcct accggtccaa gcggggcaga    1140
aagaagctgc tgtacatctt caagcagccc ttcatgcggc ctgtgcagac cacacaggaa    1200
gaggacggct gtagctgtag attccccgag gaagaggaag cggctgcga gctgagagtg    1260 aagttcagca gaagcgccga cgcccctgcc tatcagcagg gccagaacca gctgtacaac    1320
gagctgaacc tgggcagacg gaggaatac gacgtgctgg acaagagaag aggccgggac    1380
cctgagatgg gcggcaagcc cagacggaag aaccccagg aaggcctgta taacgaactg    1440
cagaaagaca agatggccga ggcctacagc gagatcggca tgaagggcga gcggagaaga    1500
ggcaagggcc atgacggcct gtaccagggc ctgagcaccg ccaccaagga cacctacgac    1560 gcccctgcaca tgcaggccct gcctccaaga tgatga                             1596
```

<210> SEQ ID NO 23
<211> LENGTH: 1593
<212> TYPE: DNA
<213> ORGANISM: Artificial sequence
<220> FEATURE:

<223> OTHER INFORMATION: Chemically synthesized

<400> SEQUENCE: 23

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| ggggggacca agctggagat cacaggtggc ggtggctcgg gcggtggtgg gtcgggtggc | 420 |
| ggcggatctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gccaaggaac ctcagtcacc | 780 |
| gtctcctcaa ccacgacgcc agcgccgcga ccaccaacac cggcgcccac catcgcgtcg | 840 |
| cagccctgt ccctgcgccc agaggcgtgc cggccagcgg cggggggcgc agtgcacacg | 900 |
| aggggctgg acttcgcctg tgattttgg gtgctggtgg tggttggtgg agtcctggct | 960 |
| tgctatagct tgctagtaac agtggccttt attattttct gggtgaggag taagaggagc | 1020 |
| aggggaggtc acagtgacta catgaacatg actccccgcc gccccgggcc cacccgcaag | 1080 |
| cattaccagc cctatgcccc accacgcgac ttcgcagcct atcgctccaa acggggcaga | 1140 |
| aagaaactcc tgtatatatt caaacaacca tttatgagac cagtacaaac tactcaagag | 1200 |
| gaagatggct gtagctgccg atttccagaa gaagaagaag aggatgtgaa actgagagtg | 1260 |
| aagttcagca ggagcgcaga cgccccgcg tacaagcagg gccagaacca gctctataac | 1320 |
| gagctcaatc taggacgaag agaggagtac gatgttttgg acaagagacg tggccgggac | 1380 |
| cctgagatgg ggggaaagcc gagaaggaag aaccctcagg aaggcctgta caatgaactg | 1440 |
| cagaaagata gatggcgga ggcctacagt gagattggga tgaaaggcga gcgccggagg | 1500 |
| ggcaagggc acgatggcct ttaccagggt ctcagtacag ccaccaagga cacctacgac | 1560 |
| gcccttcaca tgcaggccct gccccctcgc taa | 1593 |

<210> SEQ ID NO 24
<211> LENGTH: 1473
<212> TYPE: DNA
<213> ORGANISM: Artificial sequence
<220> FEATURE:
<223> OTHER INFORMATION: Chemically synthesized

<400> SEQUENCE: 24

| | |
|---|---|
| atggccctgc tgtgacagc tctgctgctg cctctggctc tgctcctgca tgccgctaga | 60 |
| cccgacatcc agatgaccca gaccacctcc agcctgtctg cctctctggg cgacagagtg | 120 |
| accatcagct gccgggccag ccaggacatc agcaagtacc tgaactggta tcagcagaaa | 180 |
| cccgacggca ccgtgaagct gctgatctac cacacctctc ggctgcacag cggcgtgcct | 240 |
| agcagattca gcggcagcgg ctccggcacc gactacagcc tgaccatctc caacctggaa | 300 |
| caggaagata tcgccaccta cttctgccag caaggcaaca cactgcccta caccttcggc | 360 |

```
ggaggcacca agctggaaat caccggcgga ggcggatctg gaggcggagg aagcggaggc    420
ggcggatccg aagtgaagct gcaggaaagc ggccctggac tggtggcccc tagccagagc    480
ctgagcgtga cctgtaccgt gtccggcgtg agcctgcctg attacggcgt gagctggatc    540
agacagcccc ccagaaaggg cctggaatgg ctgggcgtga tctggggcag cgagacaacc    600
tactacaaca gcgccctgaa gtcccggctg accatcatca aggacaacag caagagccag    660
gtgttcctga agatgaacag cctgcagacc gacgacaccg ccatctacta ctgcgccaag    720
cactactact acggcggcag ctacgctatg gattactggg gccagggcac cagcgtgacc    780
gtgtccagca ccaccacccc tgcccctaga cctccaaccc cagccccac  aatcgccagc    840 cagcccctgt ctctgaggcc cgaggcctgt agaccagctg ccggcggagc cgtgcacacc    900
agaggcctgg acttcgcctg cgacttctgg gtgctggtcg tggtcggcgg cgtgctggcc    960
tgttactccc tgctggtcac cgtggccttc atcatctttt gggtccgcag caagagaagc   1020
agaggcggcc acagcgacta catgaacatg acacccagac ggccaggccc caccagaaag   1080
cactaccagc cctacgcccc tcctagagac ttcgccgcct actgcgagct gagagtgaag   1140
ttcagcagaa gcgccgacgc ccctgcctat cagcagggcc agaaccagct gtacaacgag   1200
ctgaacctgg gcagacggga ggaatacgac gtgctggaca agagaagagg ccgggaccct   1260
gagatgggcg gcaagcccag acggaagaac ccccaggaag gcctgtataa cgaactgcag   1320
aaagacaaga tggccgaggc ctacagcgag atcggcatga agggcgagcg gagaagaggc   1380
aagggccatg acggcctgta ccagggcctg agcaccgcca ccaaggacac ctacgacgcc   1440
ctgcacatgc aggccctgcc tccaagatga tga                                1473

<210> SEQ ID NO 25
<211> LENGTH: 150
<212> TYPE: DNA
<213> ORGANISM: Artificial sequence
<220> FEATURE:
<223> OTHER INFORMATION: Chemically synthesized

<400> SEQUENCE: 25
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 26
<211> LENGTH: 290
<212> TYPE: DNA
<213> ORGANISM: Artificial sequence
<220> FEATURE:
<223> OTHER INFORMATION: Chemically synthesized

<400> SEQUENCE: 26
tcgagagctc gctttcttgc tgtccaattt ctattaaagg ttcctttgtt ccctaagtcc     60
aactactaaa ctgggggata ttatgaaggg ccttgagcat ctggattctg cctaataaaa    120
aacatttatt ttcattgctg cgtcgagagc tcgctttctt gctgtccaat ttctattaaa    180
ggttcctttg ttccctaagt ccaactacta aactggggga tattatgaag gccttgagc     240 atctggattc tgcctaataa aaaacattta ttttcattgc tgcgtcgacg                290

<210> SEQ ID NO 27
<211> LENGTH: 5449
<212> TYPE: DNA
```

<213> ORGANISM: Artificial sequence
<220> FEATURE:
<223> OTHER INFORMATION: Chemically synthesized

<400> SEQUENCE: 27

| | | | | | |
|---|---|---|---|---|---|
| taatacgact | cactataggg | aaagctcgac | gccaccatgc | tgctgctggt | gaccagcctg | 60 |
| ctgctgtgtg | agctgcccca | ccccgccttt | ctgctgatcc | ccgacatcca | gatgacccag | 120 |
| agccccagca | gcgtgagcgc | cagcgtgggc | gaccgggtga | ccatcacctg | ccgggccagc | 180 |
| cagggcatca | acacctggct | ggcctggtat | cagcagaagc | ccggcaaggc | ccccaagctg | 240 |
| ctgatctacg | ccgccagcag | cctgaagagc | ggcgtgccca | gccggtttag | cggctctggc | 300 |
| tctggcgccg | acttcaccct | gaccatcagc | agcctgcagc | ccgaggactt | cgccacctac | 360 |
| tactgccagc | aggccaacag | cttcccctg | acctttggcg | gcggaacaaa | ggtggagatc | 420 |
| aagggcagca | cctccggcag | cggcaagcct | ggcagcggcg | agggcagcac | caagggccag | 480 |
| gtgcagctgg | tgcagagcgg | agccgaggtg | aagaagcctg | gcgcctccgt | caaggtgtcc | 540 |
| tgcgaggcca | gcggctacac | cttcaccagc | tacggcttca | gctgggtgcg | gcaggcacca | 600 |
| ggccagggcc | tcgagtggat | gggctggatc | agcgccagca | acggcaacac | ctactacgcc | 660 |
| cagaagctgc | agggcagggt | caccatgacc | accgacacca | gcaccagcag | cgcctacatg | 720 |
| gaactgcgga | gcctgagaag | cgacgacacc | gccgtgtact | actgcgccag | ggtgtacgcc | 780 |
| gactacgccg | attactgggg | ccagggcacc | ctggtgaccg | tgagcagcga | gagcaagtac | 840 |
| ggccctccct | gccccccttg | ccctgccccc | gagttcctgg | gcggaccag | cgtgttcctg | 900 |
| ttccccccca | agcccaagga | caccctgatg | atcagccgga | cccccgaggt | gacctgtgtg | 960 |
| gtggtggacg | tgtcccagga | ggaccccgag | gtccagttca | actggtacgt | ggacggcgtg | 1020 |
| gaggtgcaca | acgccaagac | caagcccgg | gaggagcagt | tcaatagcac | ctaccgggtg | 1080 |
| gtgtccgtgc | tgaccgtgct | gcaccaggac | tggctgaacg | gcaaggaata | caagtgtaag | 1140 |
| gtgtccaaca | agggcctgcc | cagcagcatc | gagaaaacca | tcagcaaggc | caagggccag | 1200 |
| cctcgggagc | cccaggtgta | caccctgccc | cctagccaag | aggagatgac | caagaaccag | 1260 |
| gtgtccctga | cctgcctggt | gaagggcttc | taccccagcg | acatcgccgt | ggagtgggag | 1320 |
| agcaacggcc | agcccgagaa | caactacaag | accacccccc | ctgtgctgga | cagcgacggc | 1380 |
| agcttcttcc | tgtacagccg | gctgaccgtg | gacaagagcc | ggtggcagga | gggcaacgtc | 1440 |
| tttagctgct | ccgtgatgca | cgaggccctg | cacaaccact | acacccagaa | gagcctgagc | 1500 |
| ctgtccctgg | gcaaggatat | catctacatc | tgggcccctc | tggccggcac | ctgtggcgtg | 1560 |
| ctgctgctgt | ccctggtcat | caccctgtac | tgcaagcggg | gcagaaagaa | gctgctgtac | 1620 |
| atcttcaagc | agcccttcat | gcggcctgtg | cagaccacac | aggaagagga | cggctgtagc | 1680 |
| tgtagattcc | ccgaggaaga | ggaaggcggc | tgcgagctga | gagtgaagtt | cagcagaagc | 1740 |
| gccgacgccc | ctgcctatca | gcagggccag | aaccagctgt | acaacgagct | gaacctgggc | 1800 |
| agacgggagg | aatacgacgt | gctggacaag | agaagaggcc | gggaccctga | gatgggcggc | 1860 |
| aagcccagac | ggaagaaccc | ccaggaaggc | ctgtataacg | aactgcagaa | agacaagatg | 1920 |
| gccgaggcct | acagcgagat | cggcatgaag | ggcgagcgga | gaagaggcaa | gggccatgac | 1980 |
| ggcctgtacc | agggcctgag | caccgccacc | aaggacacct | acgacgccct | gcacatgcag | 2040 |
| gccctgcctc | caagatgatg | agcggccgcc | tcgagagctc | gctttcttgc | tgtccaattt | 2100 |
| ctattaaagg | ttcctttgtt | ccctaagtcc | aactactaaa | ctgggggata | ttatgaaggg | 2160 |
| ccttgagcat | ctggattctg | cctaataaaa | aacatttatt | ttcattgctg | cgtcgagagc | 2220 |

```
tcgctttctt gctgtccaat ttctattaaa ggttcctttg ttccctaagt ccaactacta    2280
aactggggga tattatgaag ggccttgagc atctggattc tgcctaataa aaaacattta    2340
ttttcattgc tgcgtcgacg aattcaaaaa aaaaaaaaaa aaaaaaaaaa aaaaaaaaaa    2400
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaagaaga    2520 gcactagtgg cgcctgatgc ggtattttct ccttacgcat ctgtgcggta tttcacaccg    2580
cataggccgc tgtattctat agtgtcacct aaatggccgc acaattcact ggccgtcgtt    2640
ttacaacgtc gtgactggga aaccctggcg ttacccaac ttaatcgcct tgcagcacat    2700 cccccttcg ccagctggcg taatagcgaa gaggcccgca ccgatcgccc ttcccaacag    2760
ttgcgcagcc tgaatggcga atggaaattg taagcgttaa tattttgtta aaattcgcgt    2820 taaattttg ttaaatcagc tcattttta accataggc cgaaatcggc aaaatccctt    2880
ataaatcaaa agaatagacc gagatagggt tgagtgttgt tccagtttgg aacaagagtc    2940
cactattaaa gaacgtggac tccaacgtca agggcgaaa aaccgtctat cagggcgatg    3000
gcccactacg tgaaccatca ccctaatcaa gttttttggg gtcgaggtgc cgtaaagcac    3060
taaatcggaa ccctaagggg agcccccgat ttagagcttg acggggaaag ccggcgaacg    3120
tggcgagaaa ggaagggaag aaagcgaaag gagcgggcgc tagggcgctg gcaagtgtag    3180
cggtcacgct gcgcgtaacc accacaccg ccgcgcttaa tgcgccgcta cagggcgcgt    3240
caggtggcac ttttcgggga aatgtgcgcg gaacccctat ttgtttattt ttctaaatac    3300
attcaaatat gtatccgctc atgagtcagg caactatgga tgaacgaaat agacagatcg    3360
ctgagatagg tgcctcactg attaagcatt ggtaactgtc agaccaagtt tactcatata    3420
tactttagat tgatttaaaa cttcattttt aatttaaaag gatctaggtg aagatccttt    3480
ttgataatct catgaacaat aaaactgtct gcttacataa acagtaatac aagggggtgtt    3540 atgagccata ttcaacggga aacgtcttgc tctaggccgc gattaaattc caacatggat    3600
gctgatttat atgggtataa atgggctcgc gataatgtcg ggcaatcagg tgcgacaatc    3660
tatcgattgt atgggaagcc cgatgcgcca gagttgtttc tgaaacatgg caaaggtagc    3720
gttgccaatg atgttacaga tgagatggtc agactaaact ggctgacgga atttatgcct    3780
cttccgacca tcaagcattt tatccgtact cctgatgatg catggttact caccactgcg    3840
atccccggga aaacagcatt ccaggtatta gaagaatatc ctgattcagg tgaaaatatt    3900
gttgatgcgc tggcagtgtt cctgcgccgg ttgcattcga ttcctgtttg taattgtcct    3960
tttaacagcg atcgcgtatt tcgtctcgct caggcgcaat cacgaatgaa taacggtttg    4020
gttgatgcga gtgattttga tgacgagcgt aatggctggc ctgttgaaca gtctggaaa    4080 gaaatgcata acttttgcc attctcaccg gattcagtcg tcactcatgg tgatttctca    4140
cttgataacc ttatttttga cgaggggaaa ttaataggtt gtattgatgt tggacgagtc    4200
ggaatcgcag accgatacca ggatcttgcc atcctatgga actgcctcgg tgagttttct    4260
ccttcattac agaaacggct ttttcaaaaa tatggtattg ataatcctga tatgaataaa    4320
ttgcagtttc atttgatgct cgatgagttt ttctaagaat taattcatga ccaaaatccc    4380
ttaacgtgag ttttcgttcc actgagcgtc agaccccgta gaaagatca aggatcttc    4440 ttgagatcct tttttctgc gcgtaatctg ctgcttgcaa acaaaaaaac caccgctacc    4500
agcggtggtt tgtttgccgg atcaagagct accaactctt tttccgaagg taactggctt    4560
```

```
cagcagagcg cagataccaa atactgtcct tctagtgtag ccgtagttag gccaccactt    4620
caagaactct gtagcaccgc ctacatacct cgctctgcta atcctgttac cagtggctgc    4680
tgccagtggc gataagtcgt gtcttaccgg gttggactca agacgatagt taccggataa    4740
ggcgcagcgg tcgggctgaa cggggggttc gtgcacacag cccagcttgg agcgaacgac    4800
ctacaccgaa ctgagatacc tacagcgtga gctatgagaa agcgccacgc ttcccgaagg    4860
gagaaaggcg gacaggtatc cggtaagcgg cagggtcgga acaggagagc gcacgaggga    4920
gcttccaggg ggaaacgcct ggtatcttta tagtcctgtc gggtttcgcc acctctgact    4980
tgagcgtcga ttttgtgat gctcgtcagg ggggcggagc ctatggaaaa acgccagcaa    5040
cgcggccttt ttacggttcc tggccttttg ctggcctttt gctcacatgt tctttcctgc    5100
gttatcccct gattctgtgg ataaccgtat taccgccttt gagtgagctg ataccgctcg    5160
ccgcagccga acgaccgagc gcagcgagtc agtgagcgag gaagcggaag agcgcccaat    5220
acgcaaaccg cctctccccg cgcgttggcc gattcattaa tgcagctggc acgacaggtt    5280
tcccgactgg aaagcgggca gtgagcgcaa cgcaattaat gtgagttagc tcactcatta    5340
ggcaccccag gctttacact ttatgcttcc ggctcgtatg ttgtgtggaa ttgtgagcgg    5400
ataacaattt cacacaggaa acagctatga ccatgattac gccaagctc               5449

<210> SEQ ID NO 28
<211> LENGTH: 4870
<212> TYPE: DNA
<213> ORGANISM: Artificial sequence
<220> FEATURE:
<223> OTHER INFORMATION: Chemically synthesized
<400> SEQUENCE: 28
taatacgact cactataggg aaagctcgag cttaccgcca tggagtttgg gctgagctgg      60
cttttcttg tggctatttt aaaaggtgtc cagtgctcta gagatatttt gctgacccaa     120
actccactct ccctgcctgt cagtcttgga gatcaagcct ccatctcttg cagatctagt     180
cagagtcttg tacaccgtaa tggaaacacc tatttacatt ggtacctgca gaagccaggc     240
cagtctccaa agctcctgat tcacaaagtt tccaaccgat tttctggggt cccagacagg     300
ttcagtggca gtggatcagg gacagatttc acactcaaga tcagcagagt ggaggctgag     360
gatctgggag tttatttctg ttctcaaagt acacatgttc ctccgctcac gttcggtgct     420
gggaccaagc tggagctgaa acgggctgat gctgcaccaa ctgtatccat cttcccaggc     480
tcgggcggtg gtgggtcggg tggcgaggtg aagcttcagc agtctggacc tagcctggtg     540
gagcctggcg cttcagtgat gatatcctgc aaggcttctg gttcctcatt cactggctac     600
aacatgaact gggtgaggca gaacattgga aagagccttg aatggattgg agctattgat     660
ccttactatg gtgaactag ctacaaccag aagttcaagg gcagggccac attgactgta     720
gacaaatcgt ccagcacagc ctacatgcac ctcaagagcc tgacatctga ggactctgca     780
gtctattact gtgtaagcgg aatggagtac tgggtcaag gaacctcagt caccgtctcc     840
tcagccaaaa cgacaccccc atcagtctac ggaagggtca ccgtctcttc agcggagccc     900
aaatcttgtg acaaaactca cacctgccca ccgtgcccgg gatccatcta catctgggcc     960
cctctggccg gcacctgtgg cgtgctgctg ctgtccctgg tcatcaccct gtactgcaag    1020
cggggcagaa agaagctgct gtacatcttc aagcagccct tcatgcgcc tgtgcagacc    1080
acacaggaag aggacggctg tagctgtaga ttccccgagg aagaggaagg cggctgcgag    1140
ctgagagtga agttcagcag aagcgccgac gcccctgcct atcagcaggg ccagaaccag    1200
```

```
ctgtacaacg agctgaacct gggcagacgg gaggaatacg acgtgctgga caagagaaga    1260
ggccgggacc ctgagatggg cggcaagccc agacggaaga accccccagga aggcctgtat   1320 aacgaactgc agaaagacaa gatggccgag gcctacagcg agatcggcat gaagggcgag    1380
cggagaagag gcaagggcca tgacggcctg taccagggcc tgagcaccgc caccaaggac    1440
acctacgacg ccctgcacat gcaggccctg cctccaagat gagcggccgc ctcgagagct    1500
cgctttcttg ctgtccaatt tctattaaag gttcctttgt tccctaagtc caactactaa    1560
actgggggat attatgaagg gccttgagca tctggattct gcctaataaa aacatttat    1620 tttcattgct gcgtcgagag ctcgcttcct tgctgtccaa tttctattaa aggttccttt    1680
gttccctaag tccaactact aaactggggg atattatgaa gggccttgag catctggatt    1740
ctgcctaata aaaacatttt atttttcattg ctgcgtcgac gaattcaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaagaag agcactagtg gcgcctgatg cggtattttc tccttacgca    1980
tctgtgcggt atttcacacc gcataggccg ctgtattcta tagtgtcacc taaatggccg    2040
cacaattcac tggccgtcgt tttacaacgt cgtgactggg aaaaccctgg cgttacccaa    2100
cttaatcgcc ttgcagcaca tccccctttc gccagctggc gtaatagcga agaggcccgc    2160
accgatcgcc cttcccaaca gttgcgcagc ctgaatggcg aatggaaatt gtaagcgtta    2220
atattttgtt aaaattcgcg ttaaattttt gttaaatcag ctcatttttt aaccaatagg    2280
ccgaaatcgg caaaatccct tataaatcaa agaatagac cgagataggg ttgagtgttg    2340
ttccagtttg gaacaagagt ccactattaa agaacgtgga ctccaacgtc aaagggcgaa    2400
aaaccgtcta tcagggcgat ggcccactac gtgaaccatc accctaatca gttttttgg    2460 ggtcgaggtg ccgtaaagca ctaaatcgga acctaaagg gagcccccga tttagagctt    2520
gacggggaaa gccggcgaac gtggcgagaa aggaagggaa gaaagcgaaa ggagcgggcg    2580
ctagggcgct ggcaagtgta gcggtcacgc tgcgcgtaac caccacaccc gccgcgctta    2640
atgcgccgct acagggcgcg tcaggtggca cttttcgggg aaatgtgcgc ggaacccta    2700 tttgttatt tttctaaata cattcaaata tgtatccgct catgagtcag gcaactatgg    2760
atgaacgaaa tagacagatc gctgagatag gtgcctcact gattaagcat tggtaactgt    2820
cagaccaagt ttactcatat atactttaga ttgatttaaa acttcatttt taatttaaaa    2880
ggatctaggt gaagatcctt tttgataatc tcatgaacaa taaaactgtc tgcttacata    2940
aacagtaata caagggtgt tatgagccat attcaacggg aaacgtcttg ctctaggccg    3000
cgattaaatt ccaacatgga tgctgattta tatgggtata aatgggctcg cgataatgtc    3060
gggcaatcag gtgcgacaat ctatcgattg tatgggaagc ccgatgcgcc agagttgttt    3120
ctgaaacatg gcaaaggtag cgttgccaat gatgttacag atgagatggt cagactaaac    3180
tggctgacgg aatttatgcc tcttccgacc atcaagcatt ttatccgtac tcctgatgat    3240
gcatggttac tcaccactgc gatccccggg aaaacagcat tccaggtatt agaagaatat    3300
cctgattcag gtgaaaatat tgttgatgcg ctggcagtgt tcctgcgccg gttgcattcg    3360
attcctgttt gtaattgtcc ttttaacagc gatcgcgtat ttcgtctcgc tcaggcgcaa    3420
tcacgaatga ataacggttt ggttgatgcg agtgattttg atgacgagcg taatggctgg    3480
cctgttgaac aagtctggaa agaaatgcat aaacttttgc cattctcacc ggattcagtc    3540
```

-continued

```
gtcactcatg gtgatttctc acttgataac cttattttg acgagggaa attaataggt      3600 tgtattgatg ttggacgagt cggaatcgca gaccgatacc aggatcttgc catcctatgg    3660
aactgcctcg gtgagttttc tccttcatta cagaaacggc ttttcaaaa atatggtatt     3720 gataatcctg atatgaataa attgcagttt catttgatgc tcgatgagtt tttctaagaa    3780
ttaattcatg accaaaatcc cttaacgtga gttttcgttc cactgagcgt cagacccgt     3840 agaaaagatc aaaggatctt cttgagatcc ttttttctg cgcgtaatct gctgcttgca     3900 aacaaaaaa ccaccgctac cagcggtggt ttgtttgccg gatcaagagc taccaactct    3960
ttttccgaag gtaactggct tcagcagagc gcagatacca aatactgtcc ttctagtgta    4020
gccgtagtta ggccaccact tcaagaactc tgtagcaccg cctacatacc tcgctctgct    4080
aatcctgtta ccagtggctg ctgccagtgg cgataagtcg tgtcttaccg ggttggactc    4140
aagacgatag ttaccggata aggcgcagcg gtcgggctga acgggggtt cgtgcacaca     4200 gcccagcttg gagcgaacga cctacaccga actgagatac ctacagcgtg agctatgaga    4260
aagcgccacg cttcccgaag ggagaaaggc ggacaggtat ccggtaagcg gcagggtcgg    4320
aacaggagag cgcacgaggg agcttccagg gggaaacgcc tggtatcttt atagtcctgt    4380
cgggtttcgc cacctctgac ttgagcgtcg atttttgtga tgctcgtcag gggggcggag    4440
cctatggaaa aacgccagca acgcggcctt tttacggttc ctggccttt gctggccttt      4500 tgctcacatg ttctttcctg cgttatcccc tgattctgtg gataaccgta ttaccgcctt    4560
tgagtgagct gataccgctc gccgcagccg aacgaccgag cgcagcgagt cagtgagcga    4620
ggaagcggaa gagcgcccaa tacgcaaacc gcctctcccc gcgcgttggc cgattcatta    4680
atgcagctgg cacgacaggt ttcccgactg gaaagcgggc agtgagcgca acgcaattaa    4740
tgtgagttag ctcactcatt aggcacccca ggctttacac tttatgcttc cggctcgtat    4800
gttgtgtgga attgtgagcg gataacaatt tcacacagga aacagctatg accatgatta    4860
cgccaagctc                                                           4870
```

RNA ENGINEERED T CELLS FOR THE TREATMENT OF CANCER

CROSS-REFERENCE TO RELATED APPLICATION

This application is a divisional of U.S. patent application Ser. No. 14/342,904, filed Mar. 5, 2014, issued as U.S. Pat. No. 10,421,960, which is a U.S. national phase application filed under 35 U.S.C. § 371 claiming benefit to International Patent Application No. PCT/US2012/055760, filed on Sep. 17, 2012, which is entitled to priority under 35 U.S.C. § 119(e) to U.S. Provisional Application No. 61/535,608, filed Sep. 16, 2011, each of which is hereby incorporated by reference in its entirety.

STATEMENT REGARDING FEDERALLY SPONSORED RESEARCH OR DEVELOPMENT

This invention was made with government support under RO1CA120409, PO1CA066726 and RO1CA102646 awarded by the National Institutes of Health (NIH). The government has certain rights in the invention.

BACKGROUND OF THE INVENTION

While a graft-versus-leukemia (GVL) effect has been established in patients who undergo hematopoietic stem cell transplant (SCT), suggesting acute lymphoblastic leukemia (ALL) may be controlled by cellular immune-mediated pathways, the relative lack of efficacy of donor lymphocyte infusion for ALL suggests that leukemic cells are poorly immunogenic. New methods that can overcome poor tumor immunogenicity and have the potential to be efficacious for treatment of ALL with less toxicity than standard approaches used to treat high risk and relapsed disease, including SCT, need to be pursued (Horowitz, et al., 1990, Blood 75(3): 555-562; Mehta, 1993, Leuk Lymphoma 10(6):427-432).

Chimeric antigen receptors (CAR) are molecules combining antibody-based specificity for tumor-associated surface antigens with T cell receptor-activating intracellular domains with specific anti-tumor cellular immune activity (Eshhar, 1997, Cancer Immunol Immunother 45(3-4) 131-136; Eshhar et al., 1993, Proc Natl Acad Sci USA 90(2): 720-724; Brocker and Karjalainen, 1998, Adv Immunol 68:257-269). These CARs allow a T cell to achieve MHC-independent primary activation through single chain Fv (scFv) antigen-specific extracellular regions fused to intracellular domains that provide T cell activation and co-stimulatory signals. Second and third generation CARs also provide appropriate co-stimulatory signals via CD28 and/or CD137 (4-1BB) intracellular activation motifs, which augment cytokine secretion and anti-tumor activity in a variety of solid tumor and leukemia models (Pinthus, et al, 2004, J Clin Invest 114(12):1774-1781; Milone, et al., 2009, Mol Ther 17(8):1453-1464; Sadelain, et al., 2009, Curr Opin Immunol 21(2):215-223).

Most investigators have achieved efficient CAR gene transfer of human tumor and HIV antigens into human T cells via retrovirus or HIV-derived lentivirus, and some of these cell therapy products have advanced to Phase I/II trials (Deeks et al., 2002, Mol Ther 5(6):788-797; Kershaw, et al., 2006, Clin Cancer Res 12(20 Pt 1):6106-6115; Pule, et al., 2008, Nat Med 14(11):1264-1270; Till, et al., 2008, Blood 112(6):2261-2271). Recently, the use of CD19-targeted CAR+ T cells in three patients with CLL has been reported (Porter et al., 2011, N Eng J Med, 365: 725-733). Two of three of these patients with refractory disease and high tumor burdens entered a complete remission after 4 weeks. These responses have been sustained and the CAR+ T cells persisted for >6 months, suggesting the efficacy of this technology. Approaches using integrating viral vectors have clear advantages, including long-term expression of the CAR on infused cells across multiple cell divisions. However, iterative clinical trials which rapidly incorporate CAR design innovations may be difficult to implement using viral vectors, because of the complexity of release testing and the high expense of vector production. In addition, there are regulatory concerns using this approach. This has clearly been seen in the case of a retroviral vector used in gene modification of hematopoietic stem cells in the treatment of X-linked severe combined immunodeficiency (Hacein-Bey-Abina et al., 2008, J Clin Invest 118(9):3132-3142). In the case of lentiviral vectors, or in the setting of gene modification of mature lymphocytes, this is a theoretical concern, but it is an issue for regulators of gene and cell therapy technologies.

Electroporation-mediated mRNA transfection is a potentially complementary approach for gene expression that does not result in permanent genetic modification of cells. The use of mRNA for gene therapy applications was first described by Malone et al. in the context of liposome-mediated transfection (Malone, et al., 1989, Proc Natl Acad Sci USA 86(16):6077-6081). Successful electroporation of mRNA into primary T lymphocytes has now been developed and used for efficient TCR gene transfer (Zhao, et al., 2006, Mol Ther 13(1):151-159; Zhao, et al., 2005, J Immunol. 174(7):4415-4423). More recently, CARs directed against the Her2/neu antigen were introduced into T cells by mRNA electroporation and were found to be more effective than Her2/neu antibodies in a breast cancer xenograft model (Yoon, et al., 2009, Cancer Gene Ther 16(6):489-497). Other human target antigen-directed CARs introduced into T cells by mRNA electroporation include those targeting CEA and ErbB2 (Birkholz et al., 2009, Gene Ther 16(5):596-604). While a number of articles report efficacy using this approach in solid tumors after intratumoral injection or in local injection intraperitoneal models, similar success has not been demonstrated in disseminated leukemia pre-clinical models possibly due to the difficulty in achieving efficacy in a disseminated model using a transient expression system (Rabinovich, et al., 2009, Hum Gene Ther 20(1):51-61).

CD19 is a surface antigen restricted to B cells, and is expressed on early pre-B cells and a majority of B cell leukemias and lymphomas (Nadler, et al., 1983 J Immunol 131(1):244-250). This makes CD19 an attractive antigen for targeted therapy as it is expressed on the malignant cell lineage and a specific subset of early and mature B lymphocytes but not hematopoietic stem cells. It has been postulated that CD19 depletion allows for eventual restoration of a normal B cell pool from the CD19 negative precursor population (Cheadle et al., 2010, J Immunol 184(4):1885-1896). Experience with rituximab, the anti-CD20 monoclonal antibody used for treatment of B cell malignancies and autoimmune disorders, has shown that therapy induced B cell deficiency is well tolerated (Plosker and Figgitt, 2003, Drugs 63(8):803-843; van Vollenhoven, et al., 2010, J Rheumatol 37(3):558-567).

Adoptive transfer of CTLs has shown great promise in both viral infections and cancers. After many years of disappointing results with chimeric antigen receptor (CAR) T-cell therapy, improved culture systems and cell engineering technologies are leading to CAR T cells with more potent antitumor effects (Sadelain et al., 2009, Curr Opin Immunol 21:215-23). Results from recent clinical trials indicate improved clinical results with CARs introduced with retroviral vectors (Till et al., 2008, Blood 112:2261-71; Pule et al., 2008, Nat Med 14:1264-70). Perhaps not surprisingly, these CAR T cells also exhibit enhanced toxicity (Brentjens et al., 2010, Mol Ther 18:666-8; Morgan et al., 2010, Mol Ther 18:843-51). Recent editorials have discussed the need for safer CARs (Heslop, 2010, Mol Ther 18:661-2; Buning et al., 2010, Hum Gene Ther 21:1039-42).

Thus, there is an urgent need in the art for compositions and methods for providing additional compositions and methods to affect adoptive transfer of CTLs. The present invention addresses this need.

SUMMARY OF THE INVENTION

The present invention provides an in vitro transcribed RNA or synthetic RNA comprising a nucleic acid encoding an extracellular domain, a transmembrane domain, a costimulatory signaling region, and a signaling domain of CD3-zeta. In one embodiment, the extracellular domain comprises an antigen binding moiety. In one embodiment, the antigen binding moiety binds to a tumor antigen. In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one embodiment, the RNA is transcribed from an in vitro transcription vector, wherein the vector is pD-A.ss1.OF.BBZ.2bg.150A. In one embodiment, the vector comprises the nucleic acid sequence of SEQ ID NO: 4. In one embodiment, the DNA from which the RNA is transcribed comprises a sequence selected from the group consisting SEQ ID NO: 6, and SEQ ID NO: 8.

In one embodiment, the RNA is transcribed from an in vitro transcription vector, wherein the vector is pD-A.19.OF.2bg.150A. In one embodiment, the vector comprises the nucleic acid sequence of SEQ ID NO: 5. In one embodiment, the DNA from which the RNA is transcribed comprises a sequence selected from the group consisting of SEQ ID NO: 7, SEQ ID NO: 9, SEQ ID NO: 19, SEQ ID NO: 20, SEQ ID NO: 21, SEQ ID NO: 22, SEQ ID NO: 23 and SEQ ID NO: 24.

In one embodiment, the RNA is transcribed from an in vitro transcription vector, wherein the vector is pD-A.GD2.OF.8TMBBZ.2bg.150A. In one embodiment, the vector comprises the nucleic acid sequence of SEQ ID NO: 28. In one embodiment, the DNA from which the RNA is transcribed comprises a sequence selected from the group consisting of SEQ ID NO: 10, SEQ ID NO: 11, SEQ ID NO: 12 and SEQ ID NO: 13.

In one embodiment, the RNA is transcribed from an in vitro transcription vector, wherein the vector is pD-A.cMet.OF.8TMBBZ.2bgUTR.150A. In one embodiment, the vector comprises the nucleic acid sequence of SEQ ID NO: 27. In one embodiment, the DNA from which the RNA is transcribed comprises a sequence selected from the group consisting of SEQ ID NO: 14, SEQ ID NO: 15, SEQ ID NO: 16, SEQ ID NO: 17 and SEQ ID NO: 18.

In one embodiment, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the nucleic acid sequence comprises a poly(A) tail comprising about 150 adenosine bases. In one embodiment, the nucleic acid sequence comprises a 3'UTR comprising at least one repeat of a 3'UTR derived from human beta-globulin.

The present invention also provides a T cell comprising an in vitro transcribed RNA or synthetic RNA comprising a nucleic acid encoding an extracellular domain, a transmembrane domain, a costimulatory signaling region, and a signaling domain of CD3-zeta. In one embodiment, the extracellular domain comprises an antigen binding moiety. In one embodiment, the antigen binding moiety binds to a tumor antigen. In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one embodiment, the RNA is transcribed from an in vitro transcription vector, wherein the vector is pD-A.ss1.OF.BBZ.2bg.150A. In one embodiment, the vector comprises the nucleic acid sequence of SEQ ID NO: 4. In one embodiment, the DNA from which the RNA is transcribed comprises a sequence selected from the group consisting SEQ ID NO: 6, and SEQ ID NO: 8.

In one embodiment, the RNA is transcribed from an in vitro transcription vector, wherein the vector is pD-A.19.OF.2bg.150A. In one embodiment, the vector comprises the nucleic acid sequence of SEQ ID NO: 5. In one embodiment, the DNA from which the RNA is transcribed comprises a sequence selected from the group consisting of SEQ ID NO: 7, SEQ ID NO: 9, SEQ ID NO: 19, SEQ ID NO: 20, SEQ ID NO: 21, SEQ ID NO: 22, SEQ ID NO: 23 and SEQ ID NO: 24.

In one embodiment, the RNA is transcribed from an in vitro transcription vector, wherein the vector is pD-A.GD2.OF.8TMBBZ.2bg.150A. In one embodiment, the vector comprises the nucleic acid sequence of SEQ ID NO: 28. In one embodiment, the DNA from which the RNA is transcribed comprises a sequence selected from the group consisting of SEQ ID NO: 10, SEQ ID NO: 11, SEQ ID NO: 12 and SEQ ID NO: 13.

In one embodiment, the RNA is transcribed from an in vitro transcription vector, wherein the vector is pD-A.cMet.OF.8TMBBZ.2bgUTR.150A. In one embodiment, the vector comprises the nucleic acid sequence of SEQ ID NO: 27. In one embodiment, the DNA from which the RNA is transcribed comprises a sequence selected from the group consisting of SEQ ID NO: 14, SEQ ID NO: 15, SEQ ID NO: 16, SEQ ID NO: 17 and SEQ ID NO: 18.

In one embodiment, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the nucleic acid sequence comprises a poly(A) tail comprising about 150 adenosine bases. In one embodiment, the nucleic acid sequence comprises a 3'UTR comprising at least one repeat of a 3'UTR derived from human beta-globulin.

The present invention also provides a method of generating a population of RNA-engineered T cells transiently expressing exogenous RNA. The method comprises introducing an in vitro transcribed RNA or synthetic RNA into a T cell, where the RNA comprises a nucleic acid encoding an extracellular domain, a transmembrane domain, a costimulatory signaling region, and a signaling domain of CD3-zeta. In one embodiment, the extracellular domain comprises an antigen binding moiety. In one embodiment, the antigen binding moiety binds to a tumor antigen. In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one embodiment, the RNA is transcribed from an in vitro transcription vector, wherein the vector is pD-A.ss1.OF.BBZ.2bg.150A. In one embodiment, the vector comprises the nucleic acid sequence of SEQ ID NO: 4. In one embodiment, the DNA from which the RNA is transcribed comprises a sequence selected from the group consisting SEQ ID NO: 6, and SEQ ID NO: 8.

In one embodiment, the RNA is transcribed from an in vitro transcription vector, wherein the vector is pD-A.19.OF.2bg.150A. In one embodiment, the vector comprises the nucleic acid sequence of SEQ ID NO: 5. In one embodiment, the DNA from which the RNA is transcribed comprises a sequence selected from the group consisting of SEQ ID NO: 7, SEQ ID NO: 9, SEQ ID NO: 19, SEQ ID NO: 20, SEQ ID NO: 21, SEQ ID NO: 22, SEQ ID NO: 23 and SEQ ID NO: 24.

In one embodiment, the RNA is transcribed from an in vitro transcription vector, wherein the vector is pD-A.GD2.OF.8TMBBZ.2bg.150A. In one embodiment, the vector comprises the nucleic acid sequence of SEQ ID NO: 28. In one embodiment, the DNA from which the RNA is transcribed comprises a sequence selected from the group consisting of SEQ ID NO: 10, SEQ ID NO: 11, SEQ ID NO: 12 and SEQ ID NO: 13.

In one embodiment, the RNA is transcribed from an in vitro transcription vector, wherein the vector is pD-A.cMet.OF.8TMBBZ.2bgUTR.150A. In one embodiment, the vector comprises the nucleic acid sequence of SEQ ID NO: 27. In one embodiment, the DNA from which the RNA is transcribed comprises a sequence selected from the group consisting of SEQ ID NO: 14, SEQ ID NO: 15, SEQ ID NO: 16, SEQ ID NO: 17 and SEQ ID NO: 18.

In one embodiment, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the nucleic acid sequence comprises a poly(A) tail comprising about 150 adenosine bases. In one embodiment, the nucleic acid sequence comprises a 3'UTR comprising at least one repeat of a 3'UTR derived from human beta-globulin.

The present invention also provides a method of treating a cancer patient. The method comprises administering to the patient a T cell engineered to transiently express exogenous RNA, where the RNA comprises a nucleic acid encoding an extracellular domain, a transmembrane domain, a costimulatory signaling region, and a signaling domain of CD3-zeta. In one embodiment, the extracellular domain comprises an antigen binding moiety. In one embodiment, the antigen binding moiety binds to a tumor antigen. In one embodiment, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one embodiment, the method comprises repeating the administration of a T cell. In one embodiment, the method comprises administering a chemotherapeutic agent to the patient.

In one embodiment, the RNA is transcribed from an in vitro transcription vector, wherein the vector is pD-A.ss1.OF.BBZ.2bg.150A. In one embodiment, the vector comprises the nucleic acid sequence of SEQ ID NO: 4. In one embodiment, the DNA from which the RNA is transcribed comprises a sequence selected from the group consisting SEQ ID NO: 6, and SEQ ID NO: 8.

In one embodiment, the RNA is transcribed from an in vitro transcription vector, wherein the vector is pD-A.19.OF.2bg.150A. In one embodiment, the vector comprises the nucleic acid sequence of SEQ ID NO: 5. In one embodiment, the DNA from which the RNA is transcribed comprises a sequence selected from the group consisting of SEQ ID NO: 7, SEQ ID NO: 9, SEQ ID NO: 19, SEQ ID NO: 20, SEQ ID NO: 21, SEQ ID NO: 22, SEQ ID NO: 23 and SEQ ID NO: 24.

In one embodiment, the RNA is transcribed from an in vitro transcription vector, wherein the vector is pD-A.GD2.OF.8TMBBZ.2bg.150A. In one embodiment, the vector comprises the nucleic acid sequence of SEQ ID NO: 28. In one embodiment, the DNA from which the RNA is transcribed comprises a sequence selected from the group consisting of SEQ ID NO: 10, SEQ ID NO: 11, SEQ ID NO: 12 and SEQ ID NO: 13.

In one embodiment, the RNA is transcribed from an in vitro transcription vector, wherein the vector is pD-A.cMet.OF.8TMBBZ.2bgUTR.150A. In one embodiment, the vector comprises the nucleic acid sequence of SEQ ID NO: 27. In one embodiment, the DNA from which the RNA is transcribed comprises a sequence selected from the group consisting of SEQ ID NO: 14, SEQ ID NO: 15, SEQ ID NO: 16, SEQ ID NO: 17 and SEQ ID NO: 18.

In one embodiment, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In one embodiment, the nucleic acid sequence comprises a poly(A) tail comprising about 150 adenosine bases. In one embodiment, the nucleic acid sequence comprises a 3'UTR comprising at least one repeat of a 3'UTR derived from human beta-globulin.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is a schematic representation of ss1-bbz construct with different modifications of 5'UTR or 3'UTR. pGEM-based IVT vector containing ss1-bbz (pGEM-ss1bbz.64A) was modified as described elsewhere herein to add a 3'UTR (2bgUTR.64A), a 5'UTR (SP163.64A), a longer poly(A) tail (150A), or both 3'UTR and longer poly(A) (2bgUTR.150A). FIG. 1B is an image demonstrating that RNA made from the modified constructs was electroporated into T cells and the transgene expression was followed by flow cytometry including histograms of the transgene expression at day 1 after electroporation and an image depicting the mean fluorescence intensity (MFI) of the CAR for 4 d after electroporation. Data are representative of at least two independent experiments.

FIGS. 2A through 2C are images demonstrating that optimization of RNA capping enhances and sustains CAR expression on electroporated T cells. FIG. 2A is an image demonstrating that T cells were electroporated with IVT RNA capped by the indicated capping method, including using RC analogue, ARCA, or CE at a fixed RNA dose of 2.5 µg/100 µL T cells. Transgene expression was monitored by measuring MFI using flow cytometry at the indicated times after electroporation (EP). FIG. 2B is an image demonstrating that T cells from the above experiment were monitored by flow cytometry to determine the fraction of cells expressing the transgene. FIG. 2C is an image depicting T cells electroporated with IVT RNA encoding ss1-bbz capped by different capping methods, including ARCA, CE, CE with addition poly(A) (CE+A), CE system-generated cap1 RNA (CE1), or CE system-generated cap1 RNA plus enzymatic poly(A) (CE1+A) at an RNA dose of 10 µg RNA/100 µL T cells. Transgene expression was monitored by flow cytometry (MFI) for 3 d after electroporation. Data are representative of two independent experiments.

FIG. 3A is an image demonstrating that antigen-specific T-cell activation was detected by the induction of 4-1BB expression. FIG. 3B is an image demonstrating that IL-2 production was measured by ELISA. FIG. 3C is an image demonstrating that stimulated T cells were electroporated with clinical-grade RNA (10 µg RNA/100 µL T cells) generated from pD-A.ss1.OF (top) or pD-A.19.OF (bottom) and the transgene expression was monitored at the time as indicated. FIG. 3D is an image demonstrating that 1 d after electroporation, RNA-engineered T-cell function was tested by measuring CD107a surface translocation after T cells expressing the indicated RNA CAR were cocultured for 4 h with K562-CD19 or K562-meso targets. The effector cells were gated on CD3. Data are representative of at least two independent experiments.

FIG. 4A is an image demonstrating that flank tumors were established by M108 injection (s.c.) in NOD/scid/γc(−/−) (NSG) mice (n=6). Sixty-six days after tumor inoculation, mice were randomized to equalize tumor burden and treated with ss1-bbz RNA-electroporated T cells. The T cells ($10 \times 10^6$ to $15 \times 10^6$) were injected intratumorally every 4 d for a total of four injections using the same healthy donor; mice treated with saline served as controls (n=3). Tumor size was measured weekly. FIG. 4B is an image demonstrating that disseminated i.p. tumors were established in NSG mice (n=6 per group) by i.p. injection with $8 \times 10^6$ M108-Luc cells. Beginning on day 58, RNA CAR-electroporated T cells ($1 \times 10^7$) expressing ss1-bbz were injected twice weekly for 2 wk. RNA-engineered T cells expressing CD19-bbz RNA CAR or saline were injected as controls. On day 78, the luminescence signal was significantly decreased in the ss1-bbz mice compared with the CD19-bbz mice (P<0.01). FIG. 4C is an image depicting BLI from a single mouse treated with a single injection on day 58 of T cells ($1 \times 10^7$) expressing the ss1-bbz CAR using a lentiviral vector. BLI data for the experiment described in FIG. 4B are plotted. Bars, SE. *, P<0.05; **, P<0.01. The BLI signal in the saline group is truncated at the high end due to saturation of the imaging system.

FIG. 5, comprising FIGS. 5A through 5C, is a series of images demonstrating that multiple injections of autologous RNA-engineered T cells control the growth of advanced disseminated cancer in a xenogeneic mouse model. FIG. 5A is an image demonstrating that NOD/scid/γc(−/−) mice (n=30) were injected with $8 \times 10^6$ M108-Luc tumor cells (i.p.) and the mice were randomized into three groups before beginning therapy with RNA-electroporated autologous T cells ($10^7$ per injection) expressing ss1-bbz CAR, control CD19-bbz CAR, or saline on day 56 after tumor inoculation. Autologous T cells were injected i.p. and images were performed on surviving animals as indicated. Imaging commenced 5 d before the start of T-cell treatment. Tumor BLI significantly decreased in the ss1 CAR mice (38.6%) compared with both the CD19 CAR (243.6%) and the saline mice (237.1%) after the first six doses (P<0.001). FIG. 5B is an image demonstrating a Kaplan-Meier analysis. Median survival was significantly greater in the ss1 CAR mice compared with the CD19 CAR and saline mice (P<0.05). FIG. 5C is an image demonstrating that significantly less ascites accumulated in the ss1 CAR mice, as the mean change in total body weight was lower compared with both the CD19 CAR and the saline groups of mice (P<0.001).

CE1+A, capping enzyme 1 plus long poly(A); CE1, capping enzyme 1 with 64 poly(A); CE+A, capping enzyme plus long poly(A) 150; RC, regular capping analog; NoEP, mock electroporated. Data are representative of 2 independent experiments.

Figure 8:
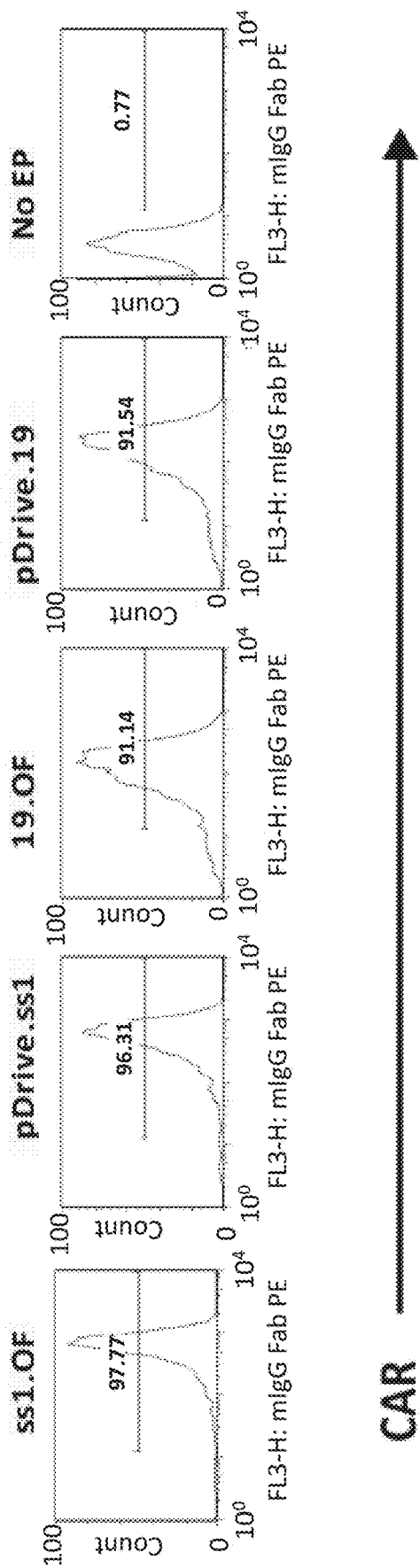

FIG. 8 is an image depicting transgene expression of T cells electroporated with RNAs generated from clinical grade IVT vector pD-A.ss1.OF (ss1.OF) and pD-A.19.OF (19.OF), compared to their parental vectors pDrive-ss1.2bgUTR.150A (pDrive.ss1) and pDrive-19.2bgUTR.150A (pDrive.19) 20 hours post electroporation. Data are representative of at least 2 independent experiments.

Figure 9:
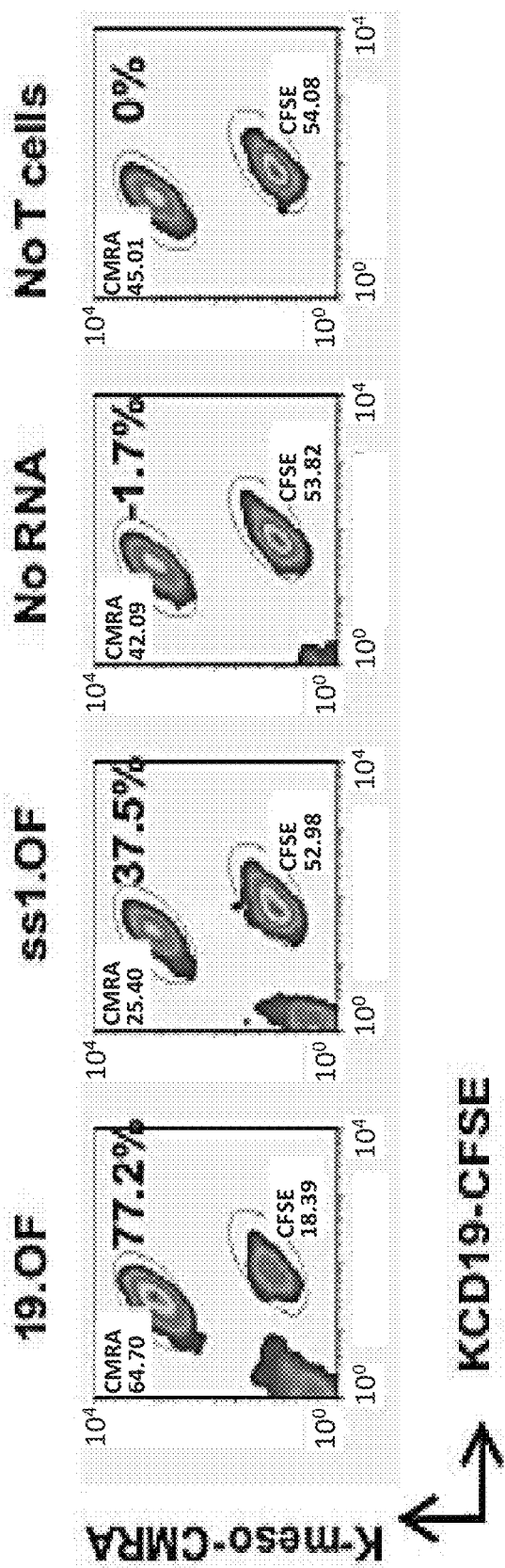

FIG. 9 is an image depicting specific lytic activity of T cells electroporated with ss1-bbz or 19-bbz CAR RNA. 20 hours after electroporation, a 4 hr flow-based CTL assay containing a mixture of labeled K562-CD19 or K562-meso targets at an effector:target ratio of 10:1 was used. Percentage values listed on upper right quadrant are calculated specific killing for the relevant target. Data are representative of at least 2 independent experiments.

Figure 4A:
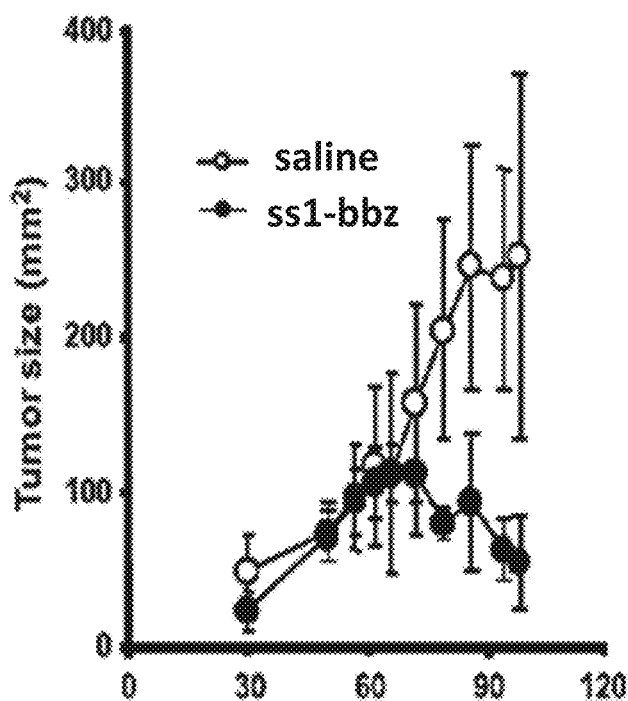
FIGS. 4A, 4B, and 4C are images demonstrating regression of advanced vascularized tumors in mice treated with RNA-engineered T cells.
Figure 10:
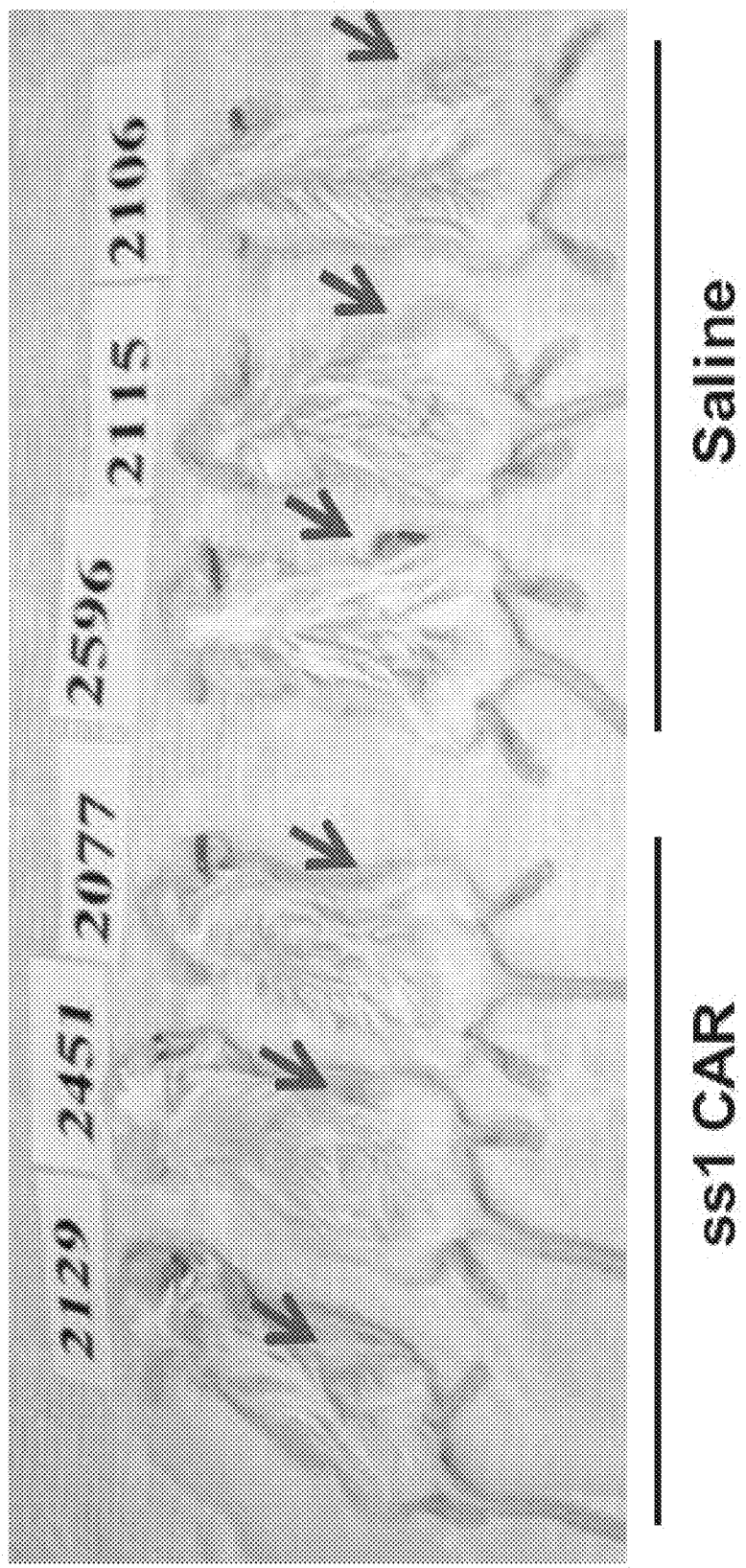

FIG. 10 is an image demonstrating that mice treated as shown in FIG. 4A were sacrificed on day 98 after tumor inoculation and photographed. Arrows point to the tumors.

FIG. 11 is an image depicting the schedule of BLI and T cell injections for experiment testing multiple injections of RNA-engineered T cells that were autologous to the tumor as described in FIG. 5. 30 mice were injected with $8\times10^6$ M108-Luc tumor cells (IP) and the mice were randomized into 3 groups before beginning therapy with autologous T cells electroporated with the indicated CAR on day 56. T cell injections ($1\times10^7$ T cells per injection) and the times of BLI are indicated. BLI commenced 5 days prior to T cell injections to provide a baseline measurement of tumor burden.

Figure 12A:
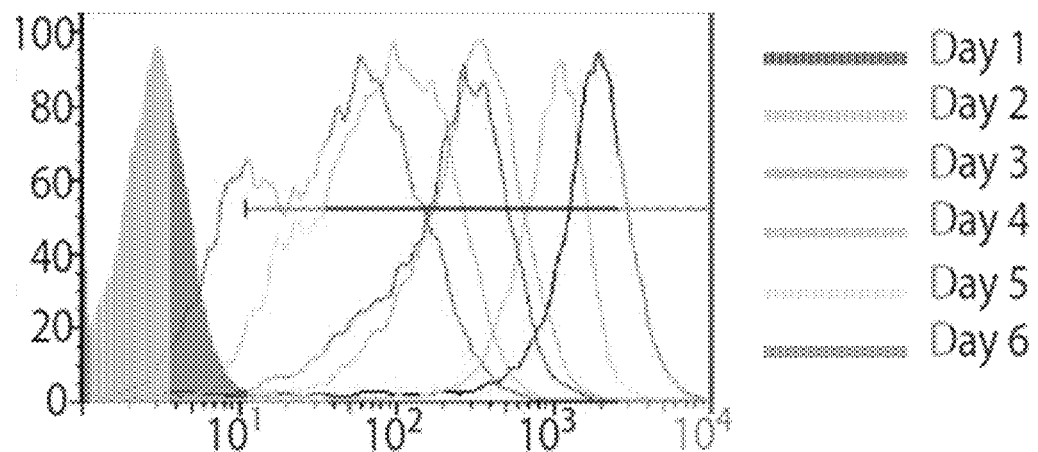
Figure 12B:
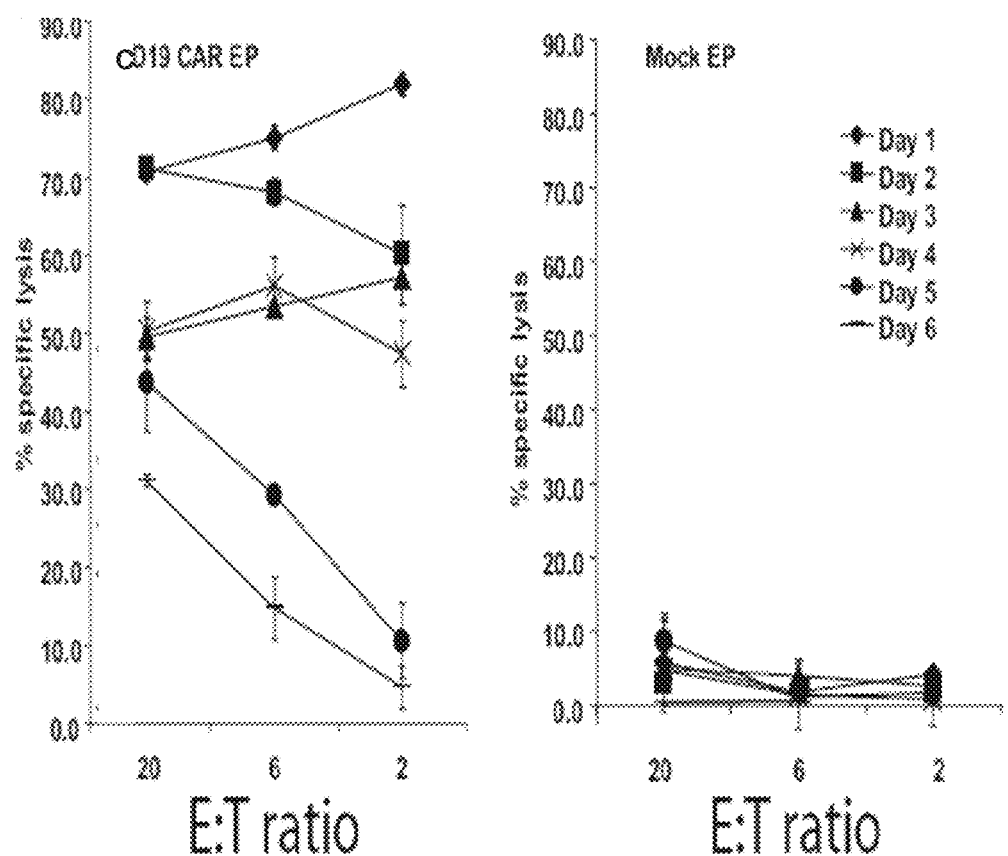
Figure 12C:
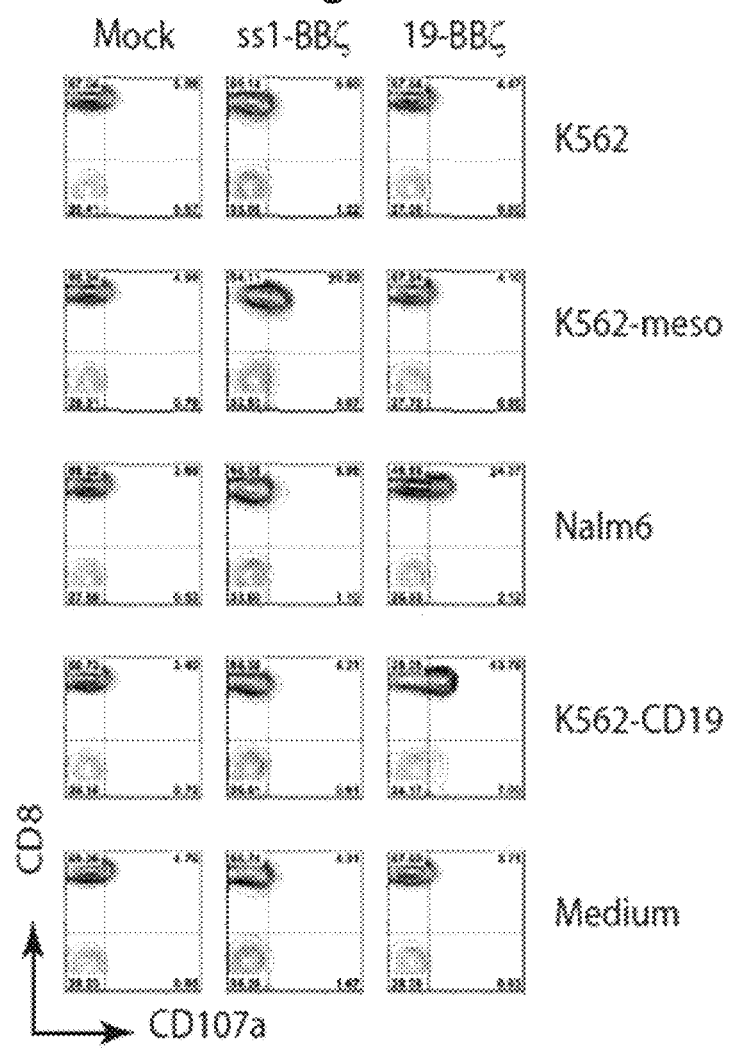
Figure 12D:
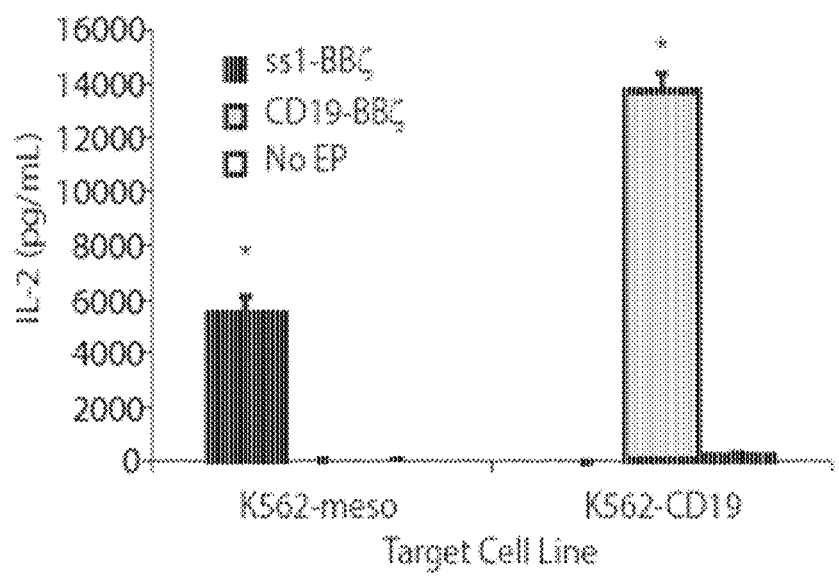

FIGS. 12A, 12B, 12C, and 12D are images demonstrating that optimized mRNA electroporation procedure results in uniform high level surface expression and specific function of RNA-engineered T cells in vitro. FIG. 12A is an image depicting CAR expression as measured by mean fluorescent intensity (MFI) at different time points after electroporation with CD19-BBz mRNA in anti-CD3 and CD28 stimulated peripheral blood T cells (open histograms); non-electroporated T cells were used as negative control (filled histogram). FIG. 12B is an image demonstrating that RNA CAR+ T cells specifically kill CD19 targets. A flow based CTL assay was conducted on the indicated day post electroporation with K562-CD19 as target and K562-meso as control. FIG. 12C is an image demonstrating that PBLs were electroporated with ss1-BBz, CD19-BBz or with no mRNA (Mock). Four hours post electroporation, the T cells were co-cultured with K562, NALM-6, or K562 expressing either CD19 (K562-CD19) or mesothelin (K562-meso) and analyzed for CD107a staining. CD3 positive T cells were gated. Only antigen specific CD107a expression is observed. FIG. 12D is an image demonstrating that four hours post electroporation, T cells electroporated with mRNA encoding for CD19-BBz or ss1-BBz were co-cultured with K562-meso or K562-CD19 target cells for 16 hours. IL-2 production was measured in the supernatant by ELISA, with significant increases in IL-2 production in an antigen specific manner (*=p<0.01). Data are representative of at least 2 independent experiments.

Figure 13A:
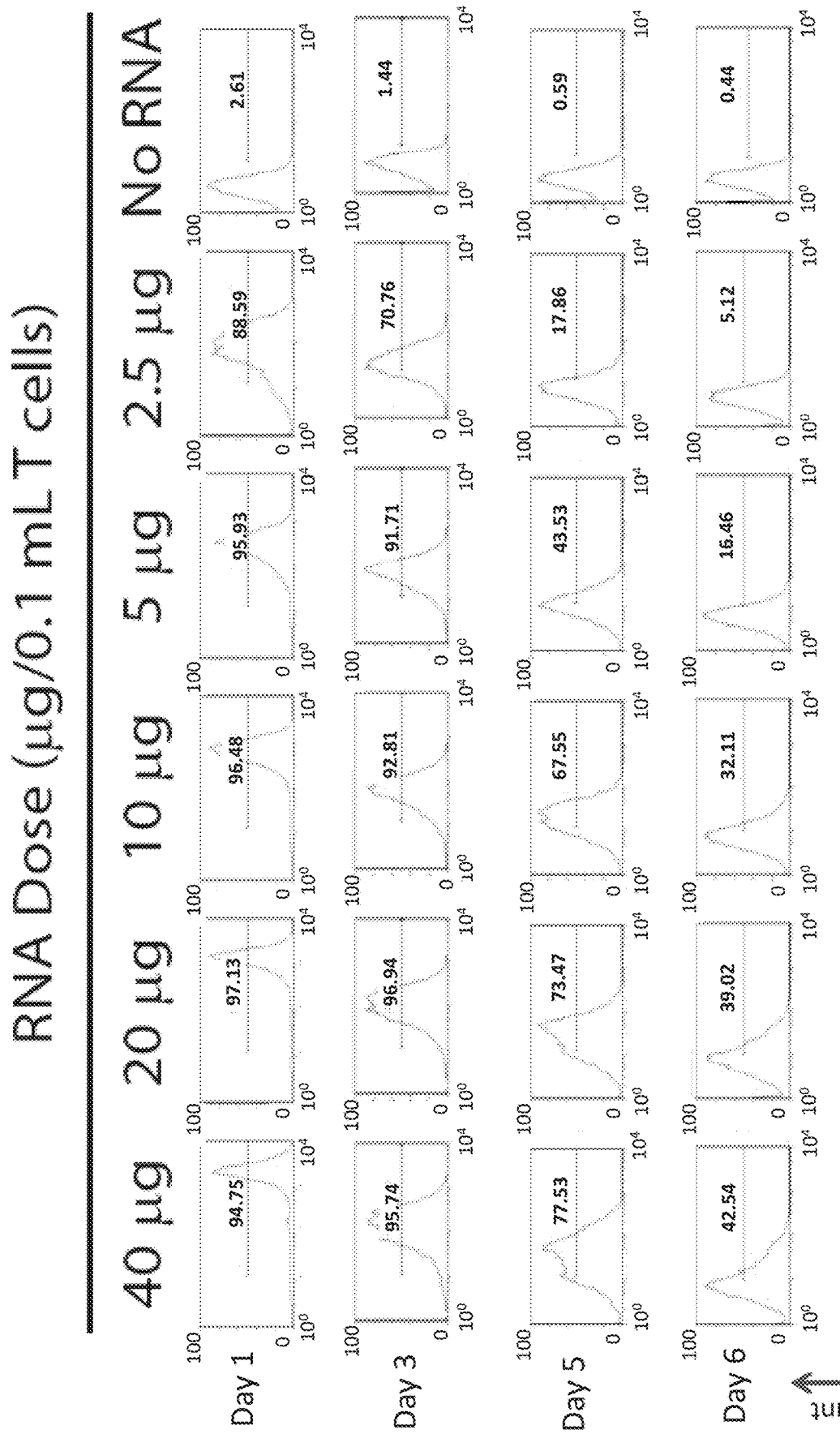
Figure 13D:
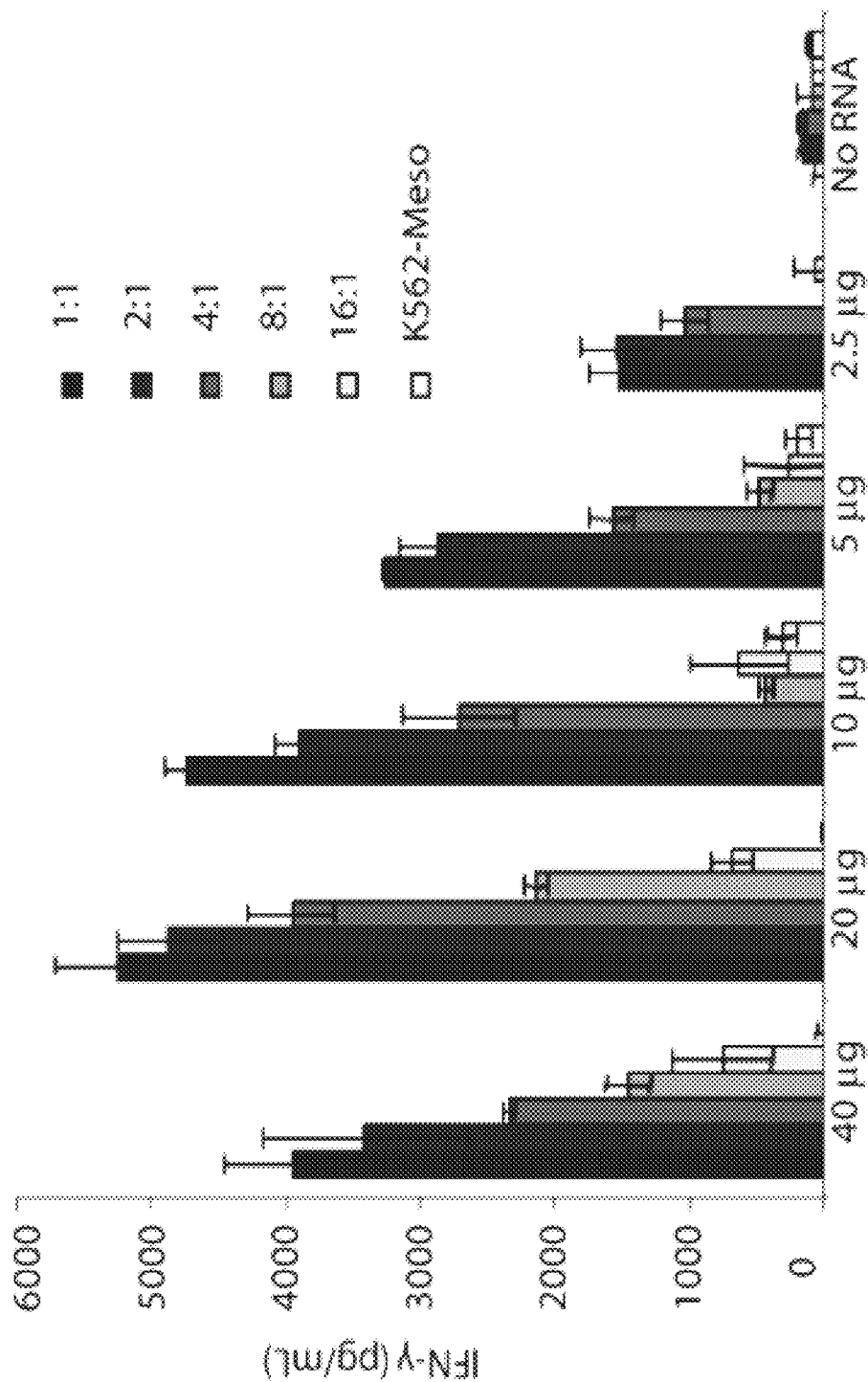

FIGS. 13A, 13B, 13C, and 13D are images depicting potentially tunable transgene expression and effector functions of RNA CAR+ T cells. FIG. 13A is an image demonstrating that transgene expression of RNA CAR+ T cells electroporated with the indicated amount of CD19-BBz RNA is shown as a function of time. Histograms of transgene expression of electroporated 19-BBz CAR mRNA. FIG. 13B is an image depicting transgene expression data from FIG. 13A plotted as a line graph. Rate of decline is similar despite different MFI seen in FIG. 13A. FIG. 13C is an image depicting specific lysis of CD19+ tumor cells with CAR T cells electroporated with the indicated amounts of RNA. Lysis measured using a flow cytometric CTL assay using K562-CD19 as targets on day 1 (left panel) and day 3 (right panel) after electroporation. While little difference exists on Day 1, by Day 3 a dose dependent decrease in specific lysis relative to RNA dose is observed. FIG. 13D is an image depicting IFN-γ secretion by RNA-engineered T cells (4 hours after electroporation) with indicated amount of RNA co-cultured overnight with serially diluted target cells (K562-CD19) or control targets (K562-meso at 1:1) assayed by ELISA. IFN-γ secretion titrates with amount of target, and is not statistically significantly different among CD19 CAR positive groups though a trend toward lower cytokine secretion with lower RNA doses is suggested.

Figure 14A:
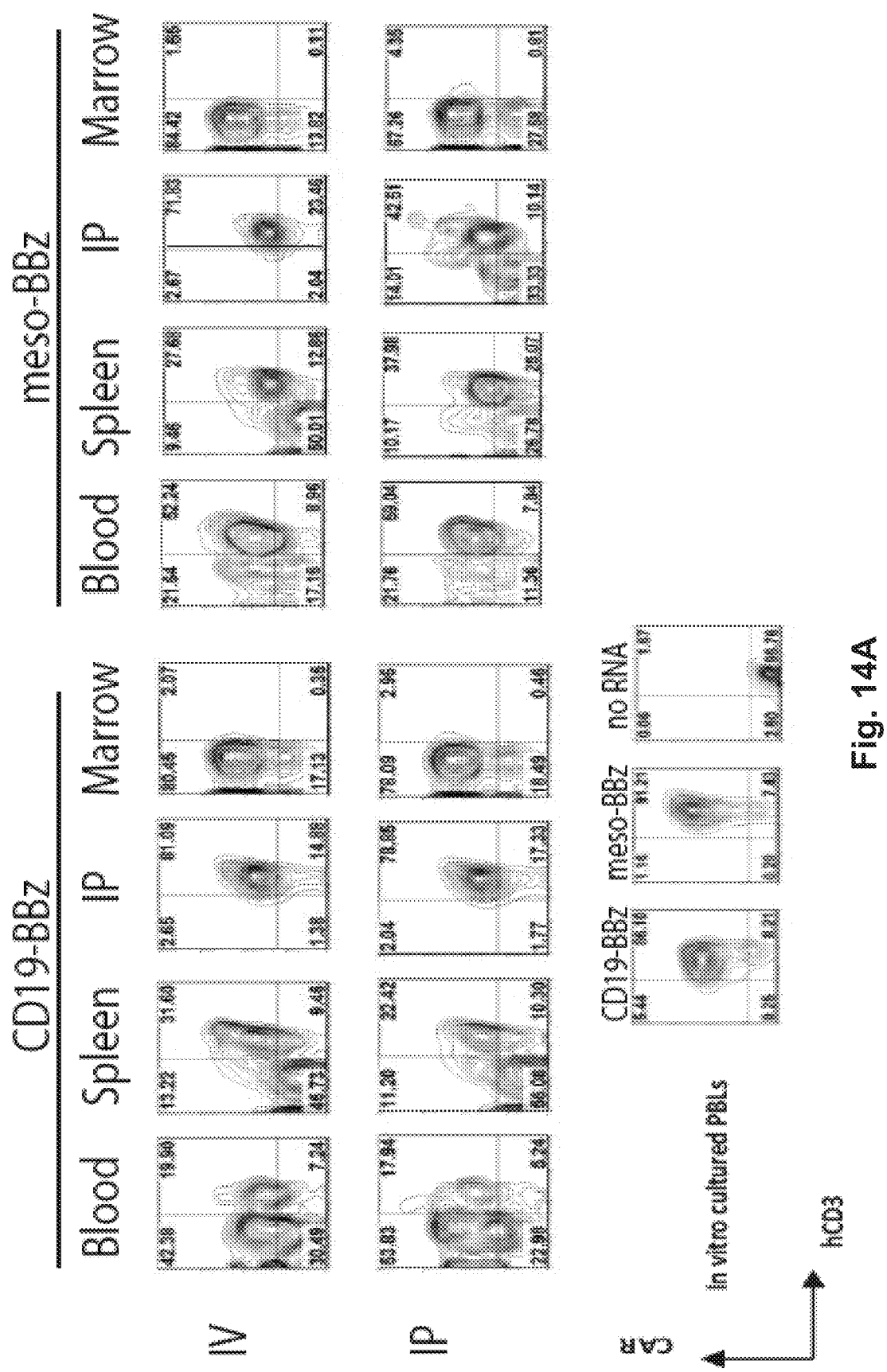
Figure 14B:
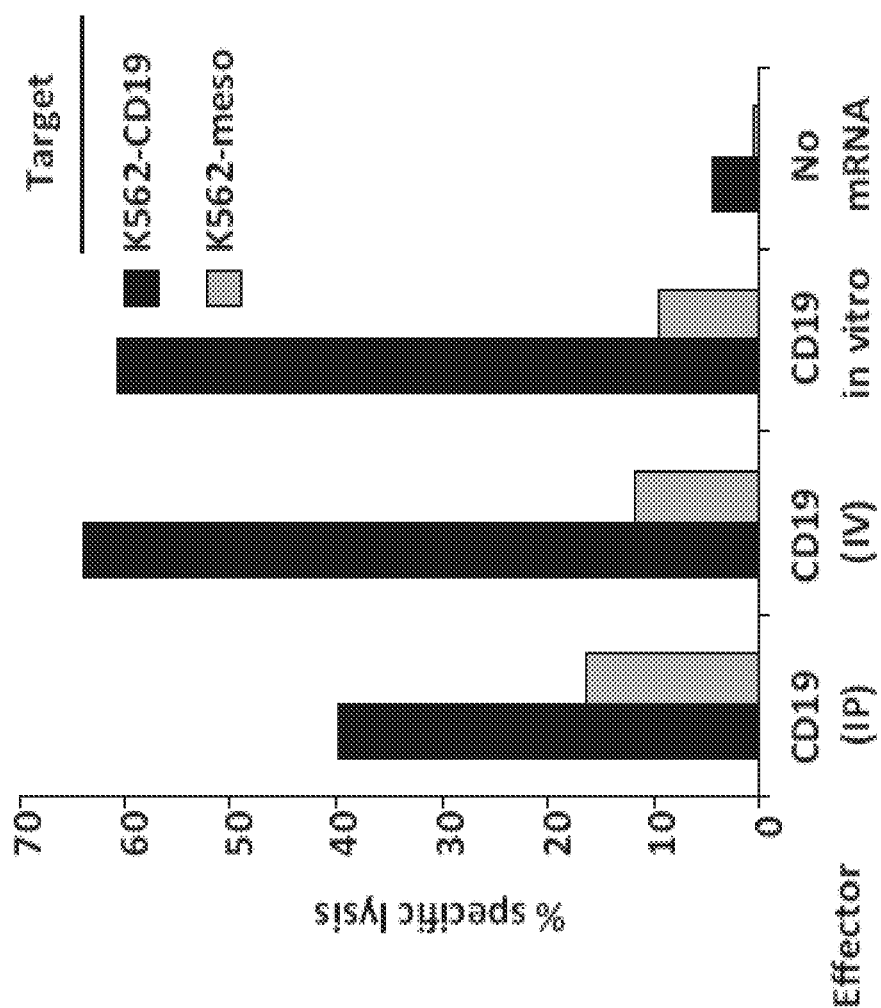

FIGS. 14A and 14B are images depicting the expression and function of RNA CARs in vivo. FIG. 14A is an image demonstrating that NOD/SCID/gc$^{-/-}$ null (NSG) mice were injected with $10^7$ PBLs either IV or intraperitoneally (IP) four hours afterelectroporation with ss1-BBz or CD19-BBz. Mice were sacrificed after 48 hours and human PBLs were isolated from peripheral blood, spleen, bone marrow and intraperitoneal washing (IP) by using a T cell negative selection kit (Dynal Magnetic Beads). The purified cells were stained for human CD3 and CAR expression (via a panspecific goat anti-mouse IgG) and analyzed by flow cytometry. Significant background staining of mouse marrow precursor cells is observed in the bone marrow compartment despite negative selection. CD3+CAR+ cells are recovered from blood, spleen and a peritoneal washing but rarely from the femoral bone marrow at this time point. FIG. 14B is an image depicting that purified T cells recovered from intraperitoneal washings 2 days after injection of mice by IV or IP route with CD19-BBz were used in a flow based CTL assay. CD19-BBz RNA electroporated T cells that had been cultured in vitro for two days (CD19 In Vitro) and mock electroporated T cells (no mRNA) were used as controls. Graph shows percentage lysis of the purified PBLs against K562-CD19 or K562-meso targets. Target specific lysis observed in recovered CAR CTLs comparable to that of in vitro cultured CAR+ PBLs and is significantly higher than no mRNA controls (p<0.01).

Figure 15A:
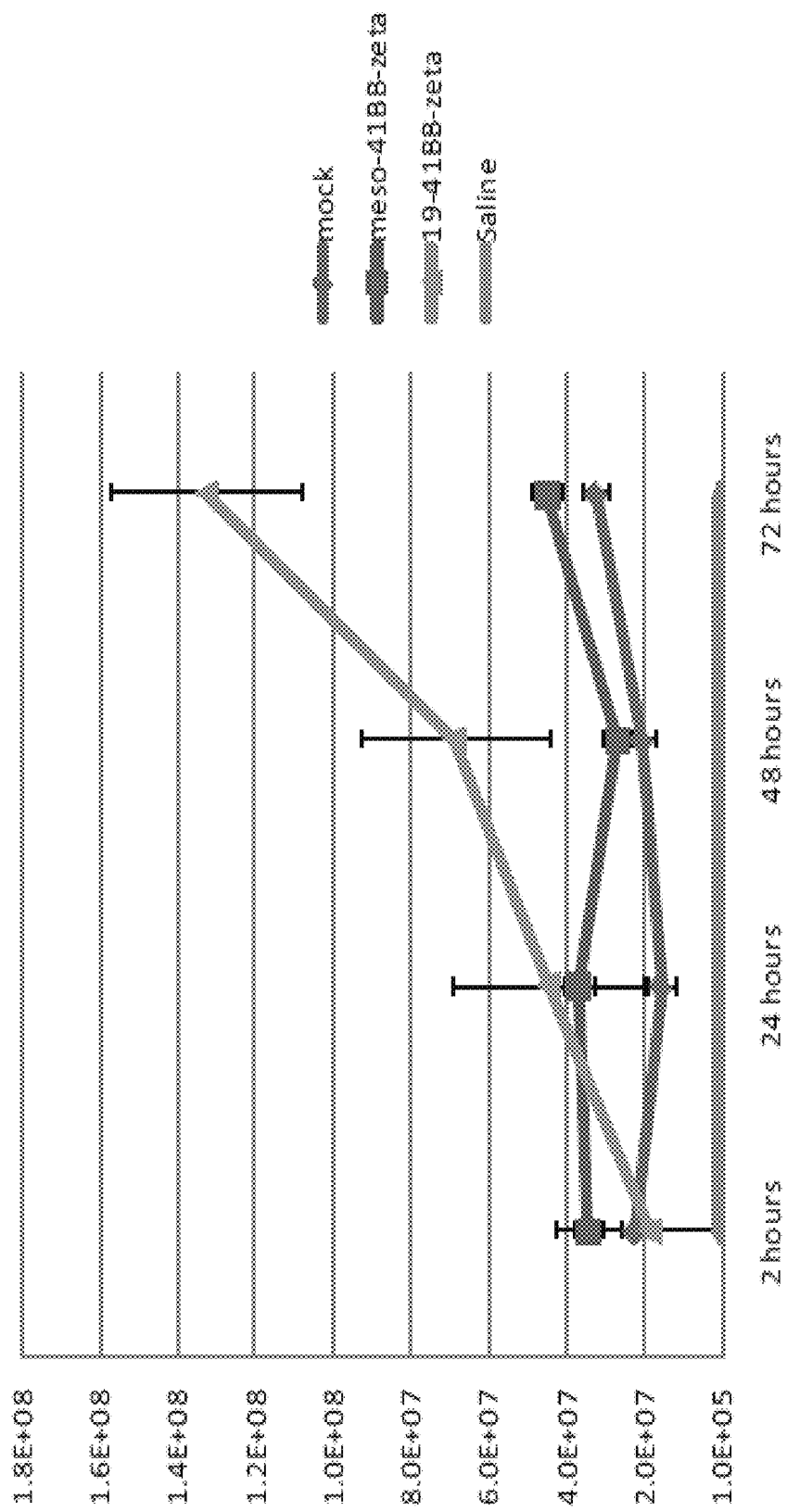

FIGS. 15A and 15B are images depicting specific trafficking and proliferation of RNA CARs in tumor bearing mice. FIG. 15A is an image demonstrating that NOD/SCID/γc$^{-/-}$ (NSG) mice were injected IV with $10^6$ Nalm-6 cells followed seven days later with $5\times10^6$ T cells four hours after electroporation with indicated mRNA constructs. The T cells had been stably transfected with a lentiviral construct to express firefly luciferase, and mice were imaged for bioluminescence. The graph indicates average of individual total photon flux±the standard error for each of the indicated groups (n=8). FIG. 15B is an image demonstrating that CD19 RNA CARs exhibit increasing bioluminescence signal and anatomic distribution consistent with migration to sites of disease and RNA-engineered T cell proliferation. Photon density heat maps on day 3 post injection suggest that mock T cells, or T cells expressing RNA CARs with irrelevant specificity against mesothelin pool passively in the spleen (left flank on heat map) and do not increase in photon density, indicating a lack of proliferation. Note that the 5×10⁶ cells produce a p/s/cm² flux of ~2×10⁷, equivalent among all groups immediately after injection. Saline treated mice represent the background autoluminescence of 5×10⁵ p/s/cm².

FIGS. 16A, 16B, 16C, and 16D, are images depicting therapeutic efficacy and specificity of a single injection of RNA CAR+ T cells in Nalm-6 xenograft model.

Figure 16A:
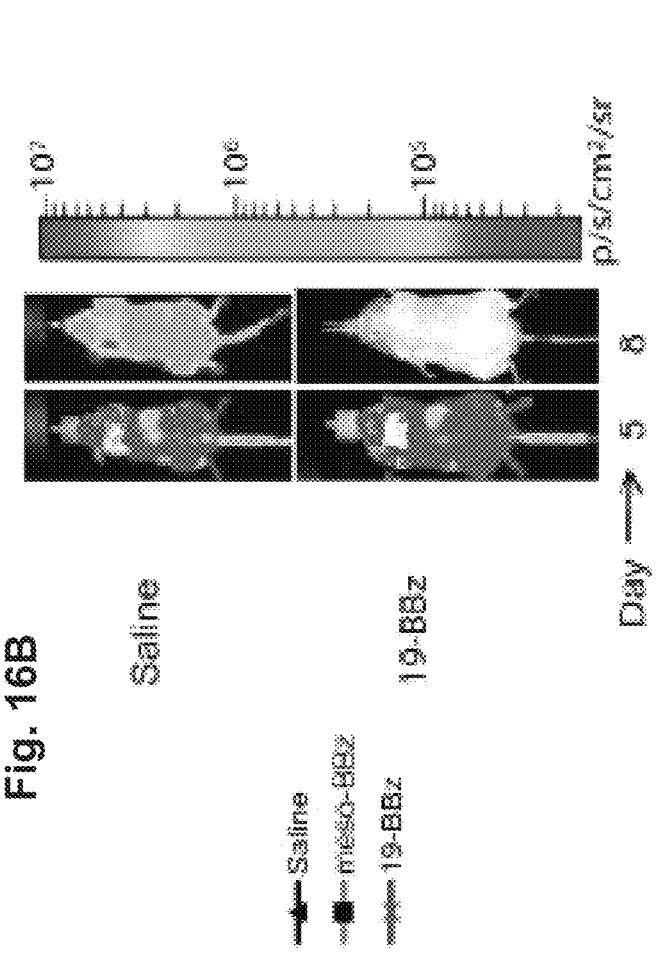
Figure 16B:
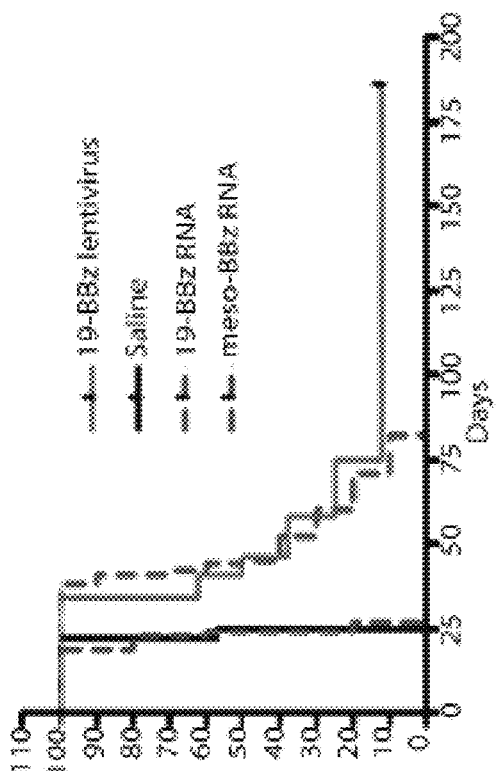
Figure 16C:
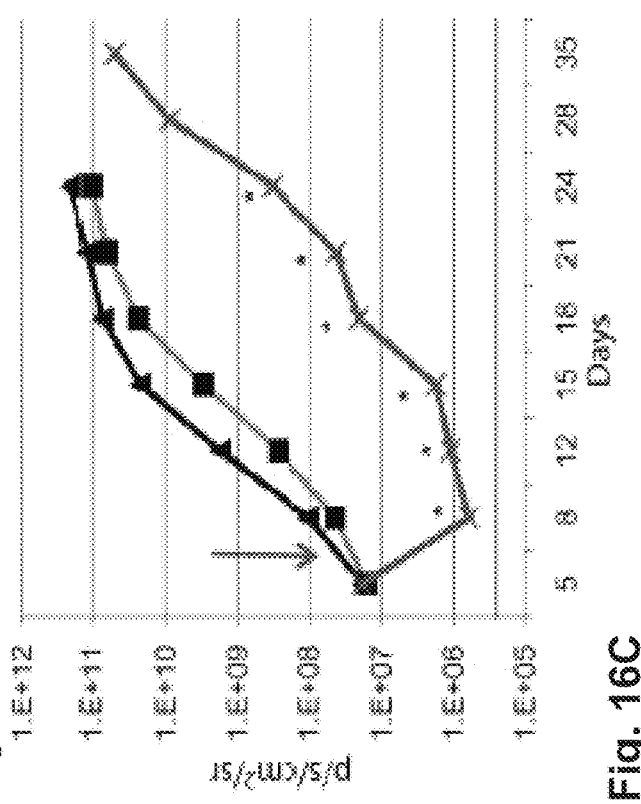
Figure 16D:
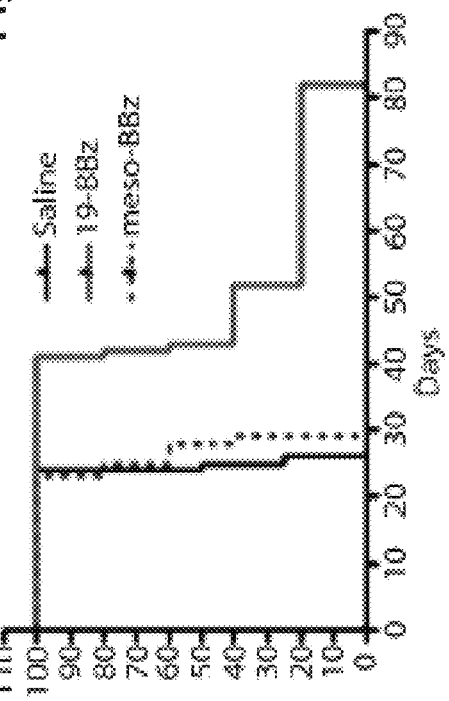

FIG. 16A is an image demonstrating that NSG mice were injected with 10⁶ Nalm-6 transduced to stably express firefly luciferase as in FIG. 17, followed by a single tail vein injection of 2.5×10⁷ T cells electroporated with CD19-BBz or meso-BBz mRNA seven days later (arrow). Animals were imaged at the indicated time points post injection, with total photon flux±SE indicated on the Y-axis; 5×10⁵ p/sec/cm²/sr represents mice with no luciferase containing cells. (*=p<0.01). FIG. 16B is an image depicting photon density heat maps of firefly luciferase positive leukemia in representative mice at Day 5 (2 days pre-treatment) and Day 8 (24 hours post CAR+ PBLs). Mice start with equal burden of leukemia but CD19 directed CAR+ PBLs reduce disease burden by 2 logs (but do not eliminate it) as measured by photon density. FIG. 16C is an image depicting survival for those mice treated with CD19-BBz RNA CAR+ T cells is significantly prolonged compared to saline controls and meso-BBz RNA CAR T cell groups. (p<0.01 by log rank analysis). FIG. 16D is an image depicting survival with RNA CAR CTLs compares favorably to that of lentiviral generated CAR CTLs in the same model though no long term survivors are noted with a single infusion of RNA CAR CTL's, consistent with our observation that single injection does not entirely eliminate disease (n=12, summation of 2 independent experiments).

Figure 17:
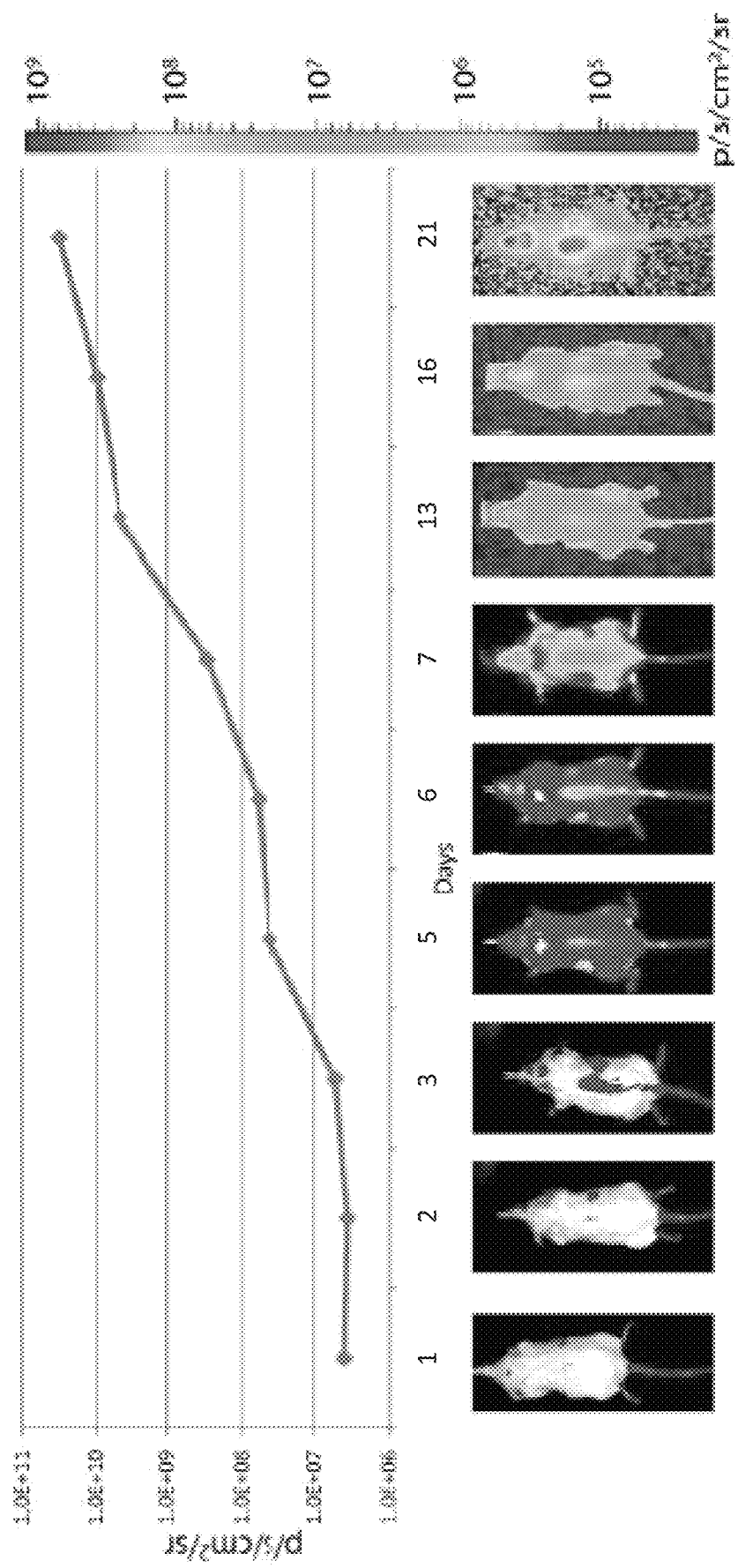

FIG. 17 is an image depicting rapid tumor growth and lethality of Nalm-6 in xenografted NSG mice. NSG mice (n=8) were injected with 10⁶ Nalm-6 cells transduced to stably express firefly luciferase. Animals were imaged at the indicated time points post injection, with total photon flux indicated on the Y-axis; 5×10⁵ p/sec/cm²/sr represents background of mice with no luciferase containing cells. Images are of a representative mouse followed through all time points; the animal became moribund on Day 24.

Figure 18B:
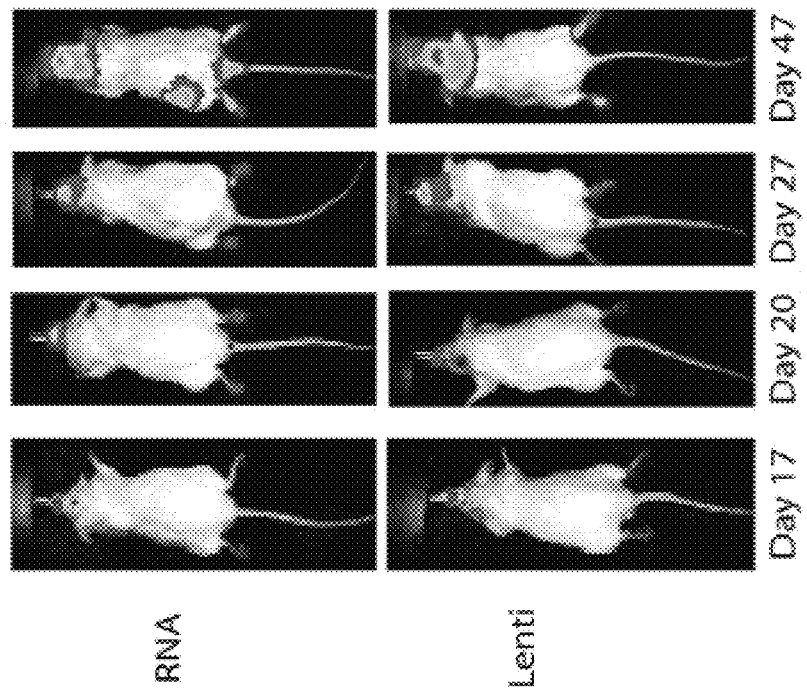
Figure 18A:
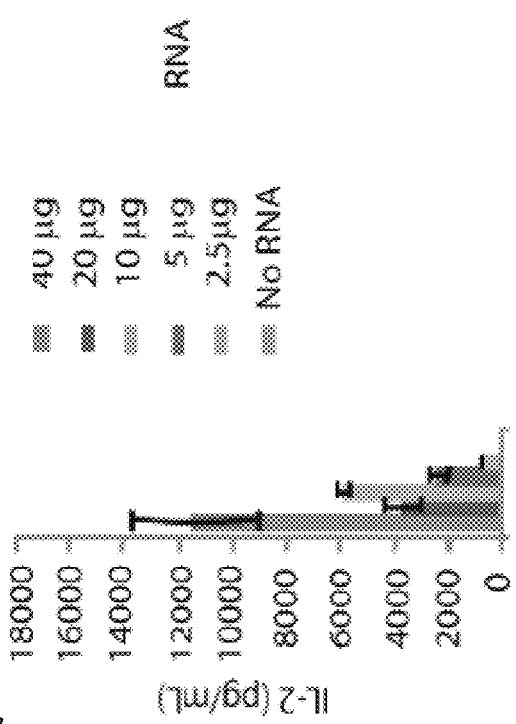
Figure 18C:
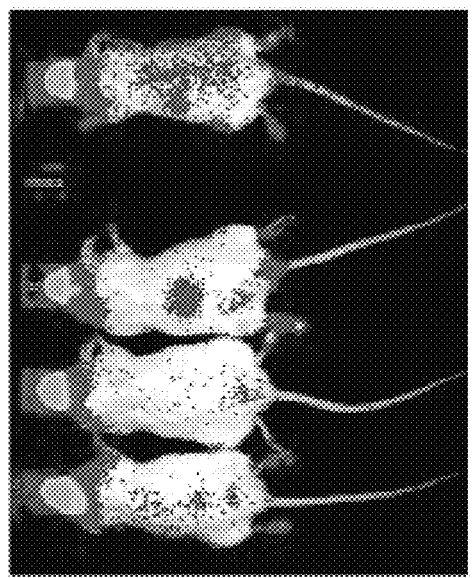

FIGS. 18A, 18B, and 18C are images depicting RNA titration results in potentially tunable IL-2 secretion. FIG. 18A is an image depicting IL-2 secretion by RNA-engineered T cells (4 hours after electroporation) with indicated amount of RNA co-cultured overnight with target cells (K562-CD19) at an E:T ration of 2:1 measured by Luminex array. FIG. 18B is an image depicting time course and site of relapse in mice representative of RNA CAR CTLs or Lentiviral CAR CTLs. Mice were treated as described in FIG. 16. The periodontal region is a harbor site for leukemia in both RNA and lentiviral CTL treated mice. Over time, mice treated with RNA-engineered T cells systemically relapse, whereas lentiviral treated mice die of local complications and/or systemic relapse unless the periodontal and paraspinal regions can be cleared. FIG. 18C is an image of mice at Day 35 showing the variability of relapse even with the consistent periodontal harbor site. The right-most mouse shows a building diffuse relapse with signal over the spleen, vertebrae and femurs. The third mouse shows a budding paraspinal relapse which eventually results in hind-limb paralysis.

Figure 19:
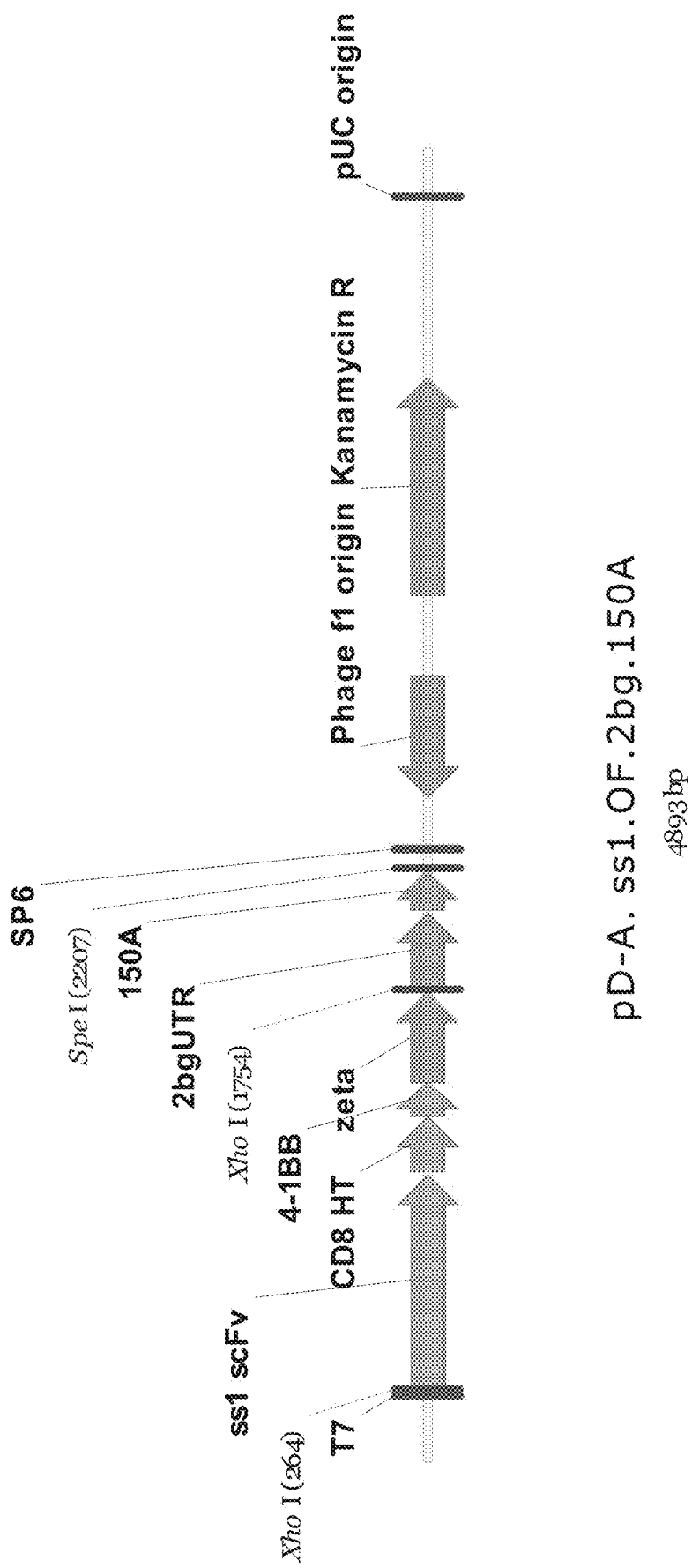

FIG. 19 is a schematic of the pD-A.ss1.OF.BBZ.2bg.150A plasmid (SEQ ID NO: 4).

Figure 20:
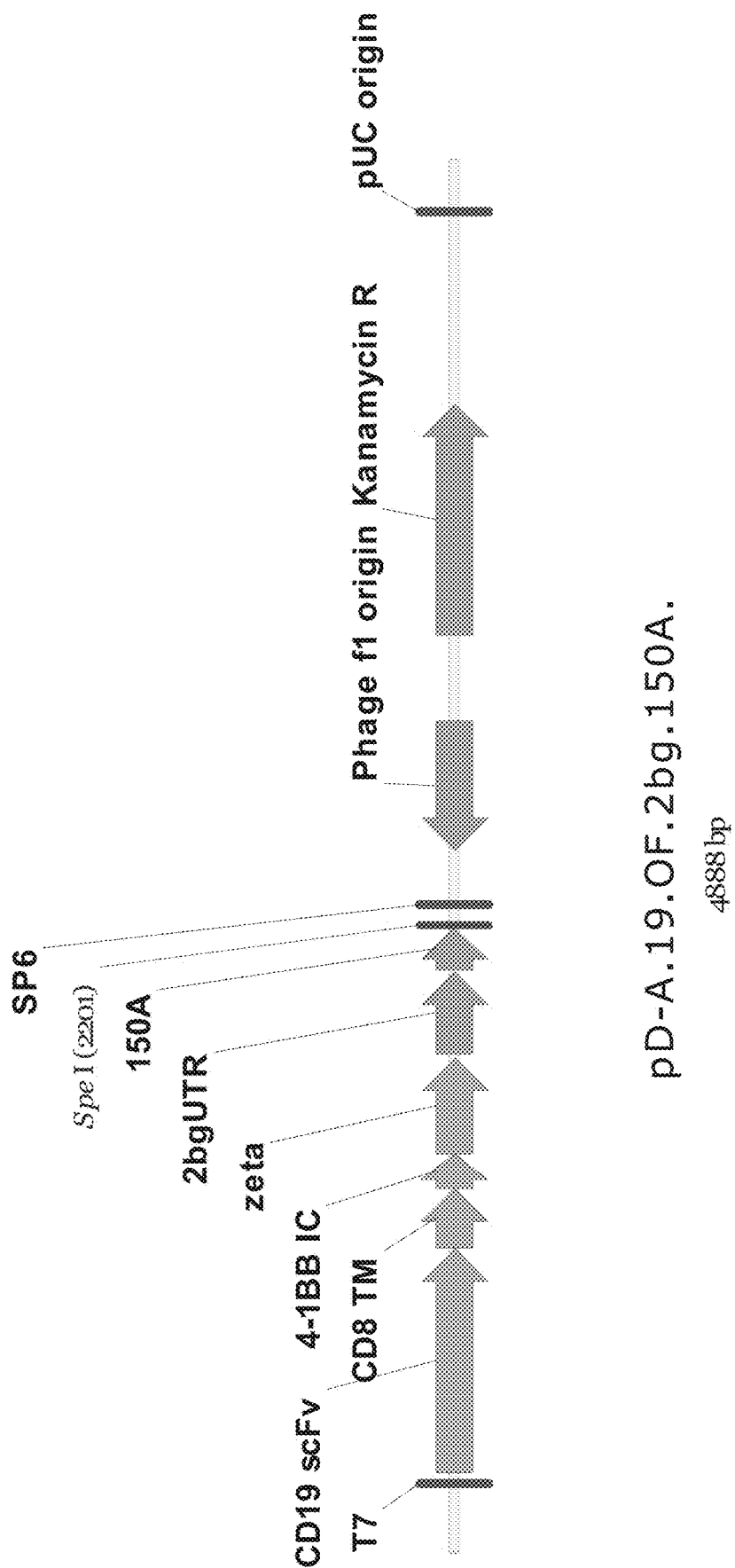

FIG. 20 is a schematic of the pD-A.19.OF.2bg.150A plasmid (SEQ ID NO: 5).

Figure 21:
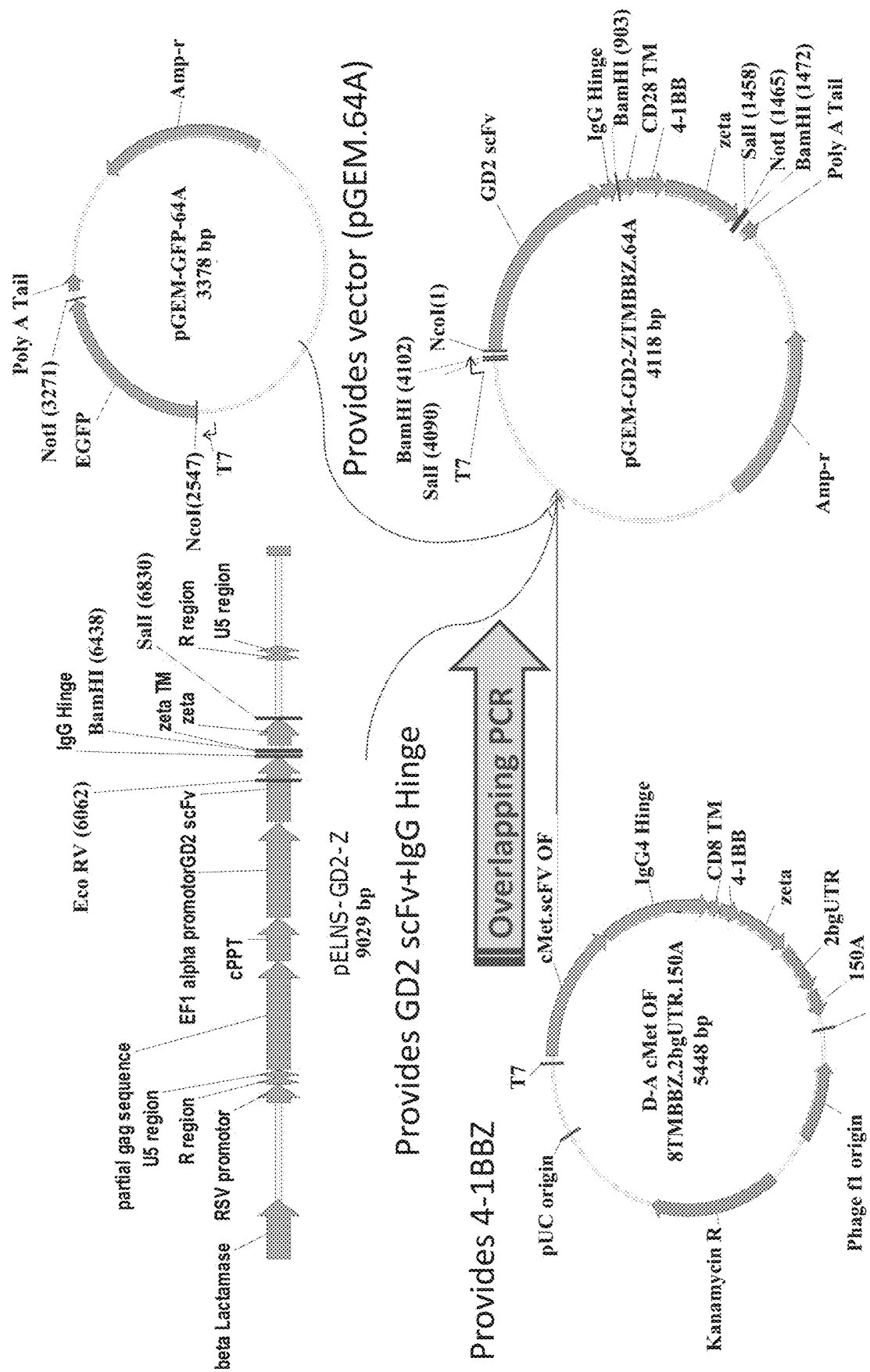

FIG. 21 is a schematic of the construction of pGEM-64A based IVT GD2– BBZ vectors.

Figure 22:
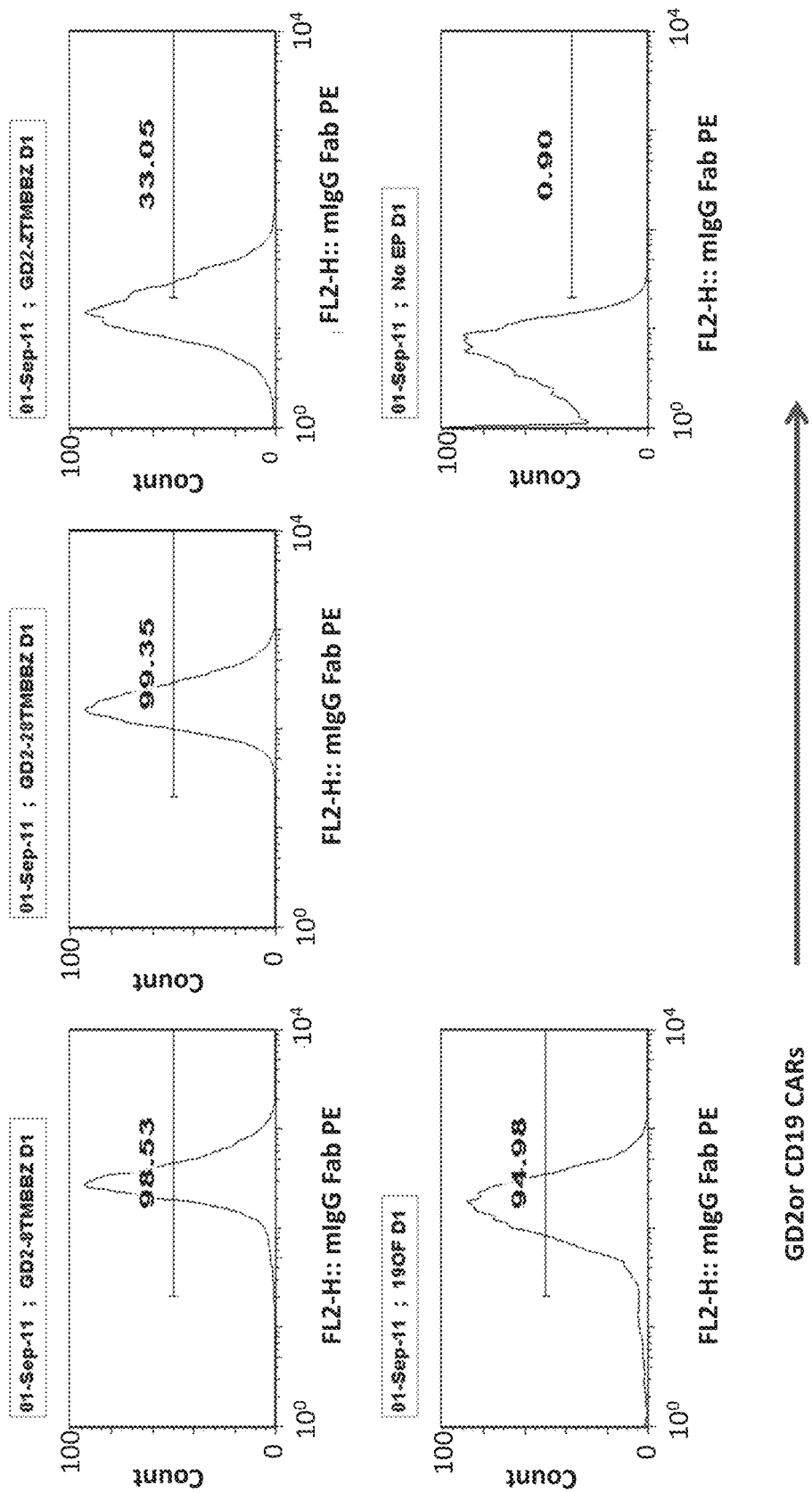

FIG. 22 is a set of graphs illustrating the expression of GD2 directed CARs one day after electroporation.

Figure 23:
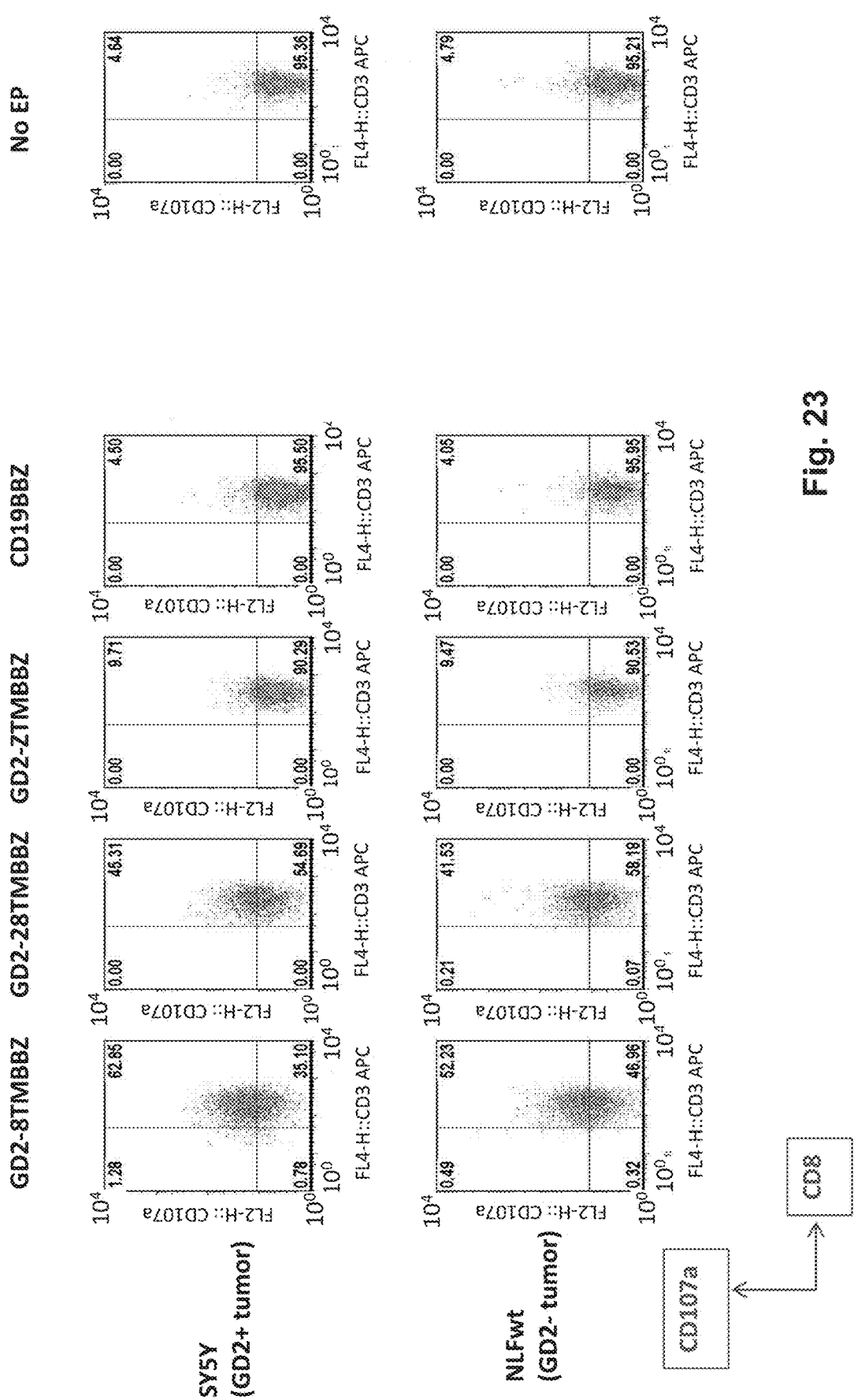

FIG. 23 depicts the results of an experiment examining the function of GD2 RNA CAR T cells using a CD107a assay. Cells electroporated with various GD2 directed CAR RNA were co-cultured with SYSY (GD2+ tumor cell line) or NLFwt (GD2– tumor cell line), and CD107a expression was detected by flow cytometry in a 4 hour culture assay.

Figure 24:
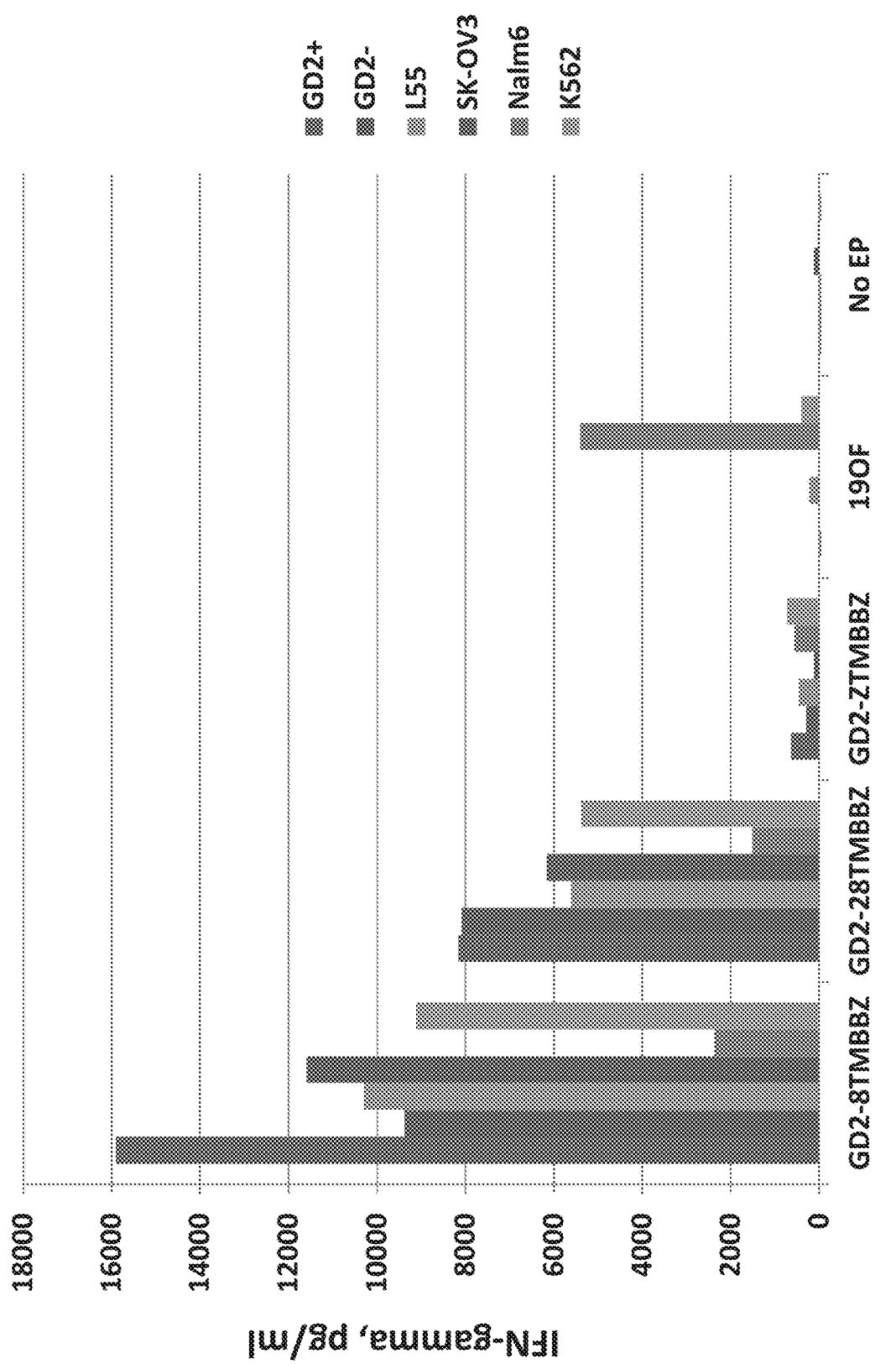

FIG. 24 is a graph depicting the levels of IFN-gamma produced and secreted by electroporated T cells upon co-culture with SYSY (GD2+ tumor cell line) or NLFwt (GD2– tumor cell line). Supernatant was harvested 24 hours post co-culture and IFN-gamma was detected by ELISA.

Figure 25:
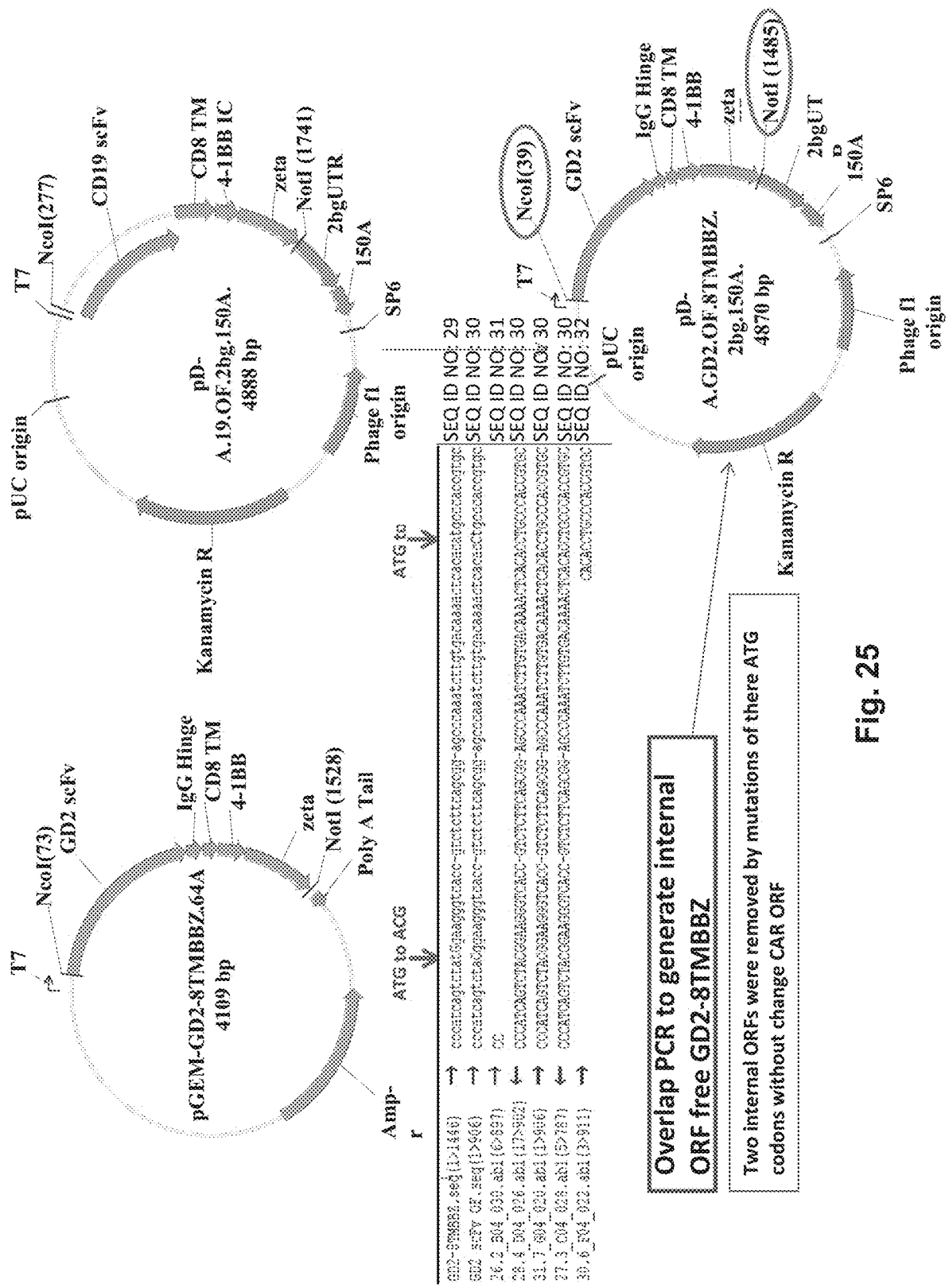

FIG. 25 is a schematic depicting the construction of pD-A.GD2.OF.8TMBBZ.abg.150A vectors for GD2 CAR GMP RNA production. Overlapping PCR was used to generate internal ORF free (OF) GD2-8TMBBZ. Two internal ORFs were removed by PCR mutations of the ATG codons without altering the CAR open reading frame.

Figure 26:
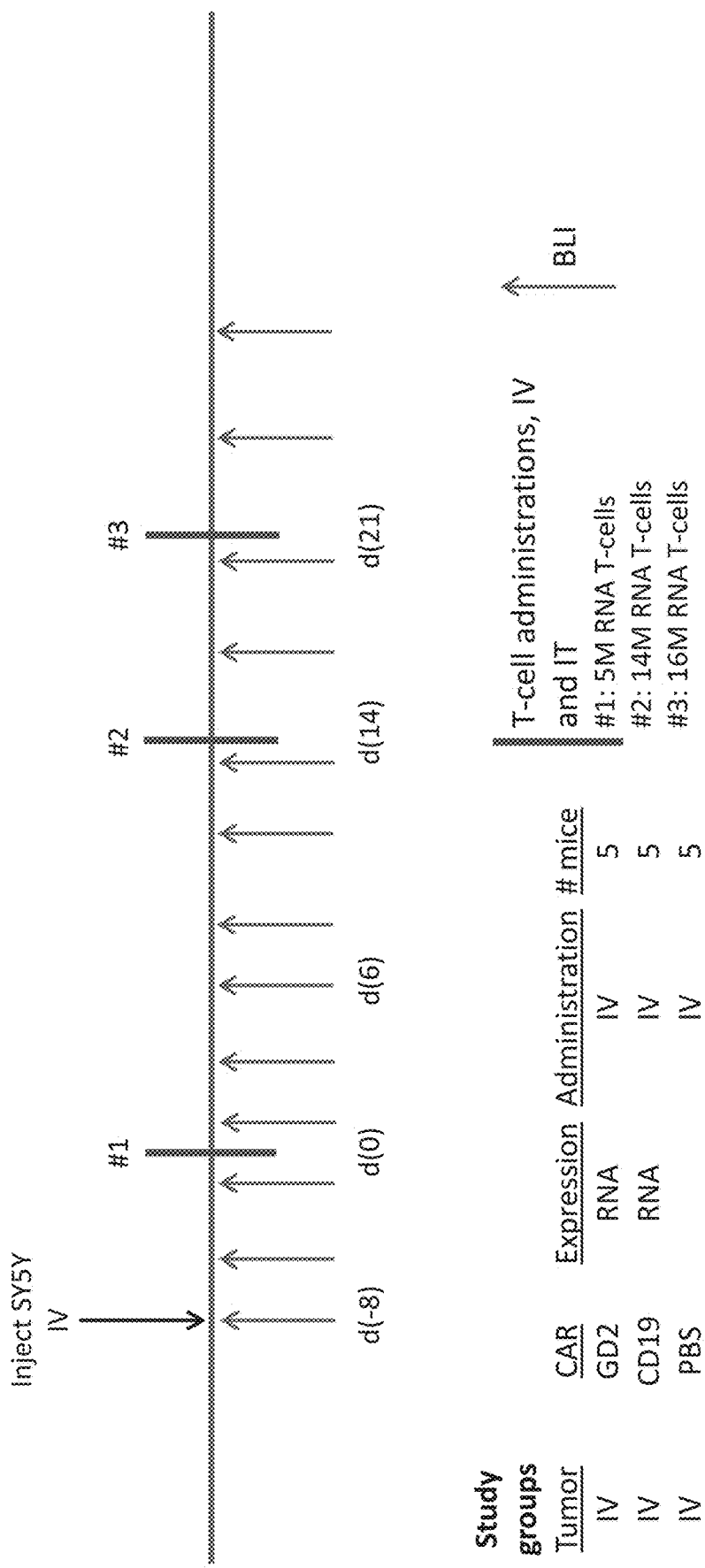

FIG. 26 is an image depicting a timeline of a neuroblastoma GD2 RNA CAR animal study.

Figure 27:
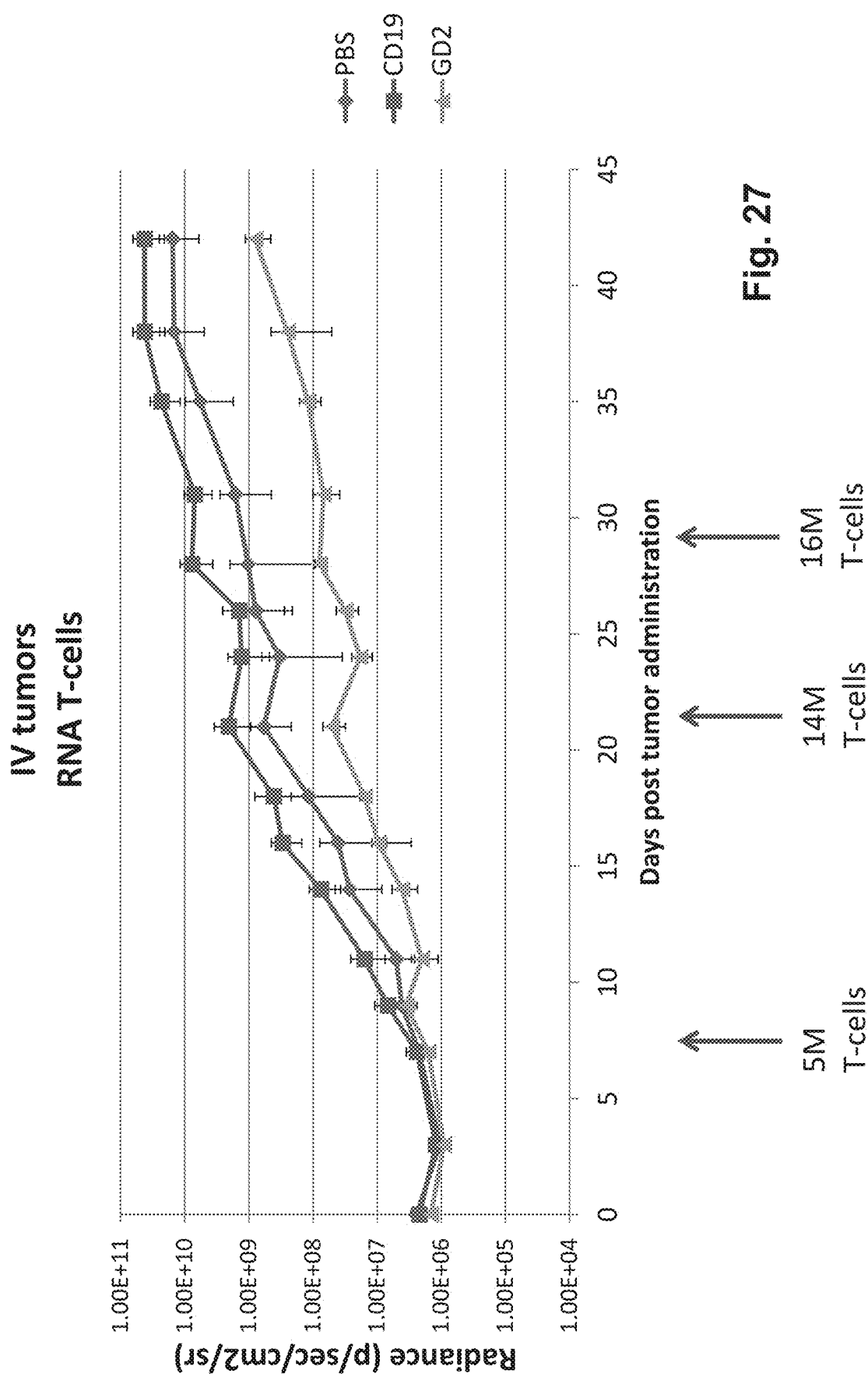

FIG. 27 is a graph illustrating the extent of tumor burden throughout the timecourse of treatment with T cells electroporated to receive RNA encoding GD2 directed CARs or CD19 directed CARs compared to PBS treated as negative control.

Figure 28:
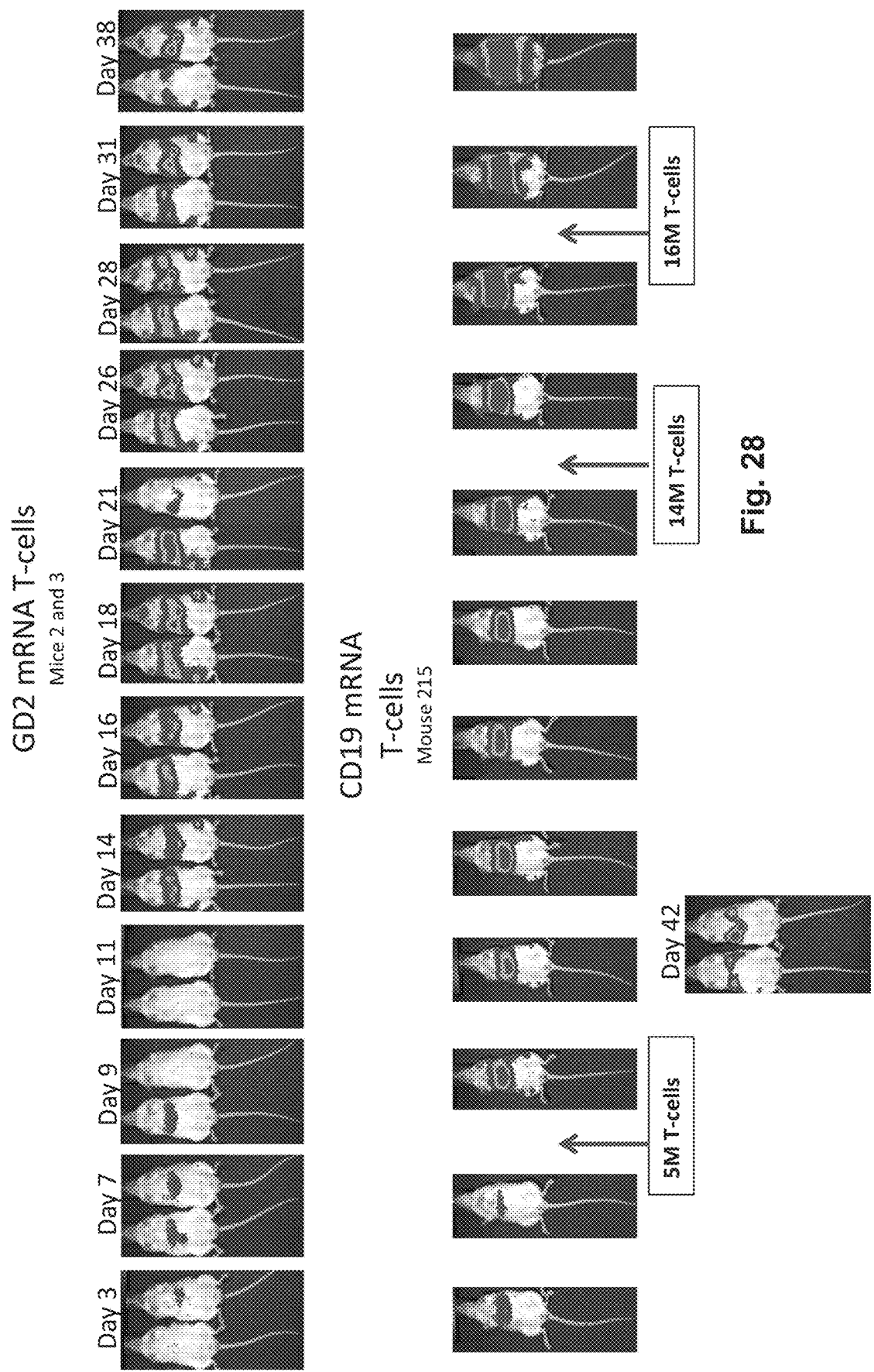

FIG. 28 is a set of images illustrating the presence of tumor cells in GD2 RNA CAR and CD19 RNA CAR treated mice.

Figure 29:
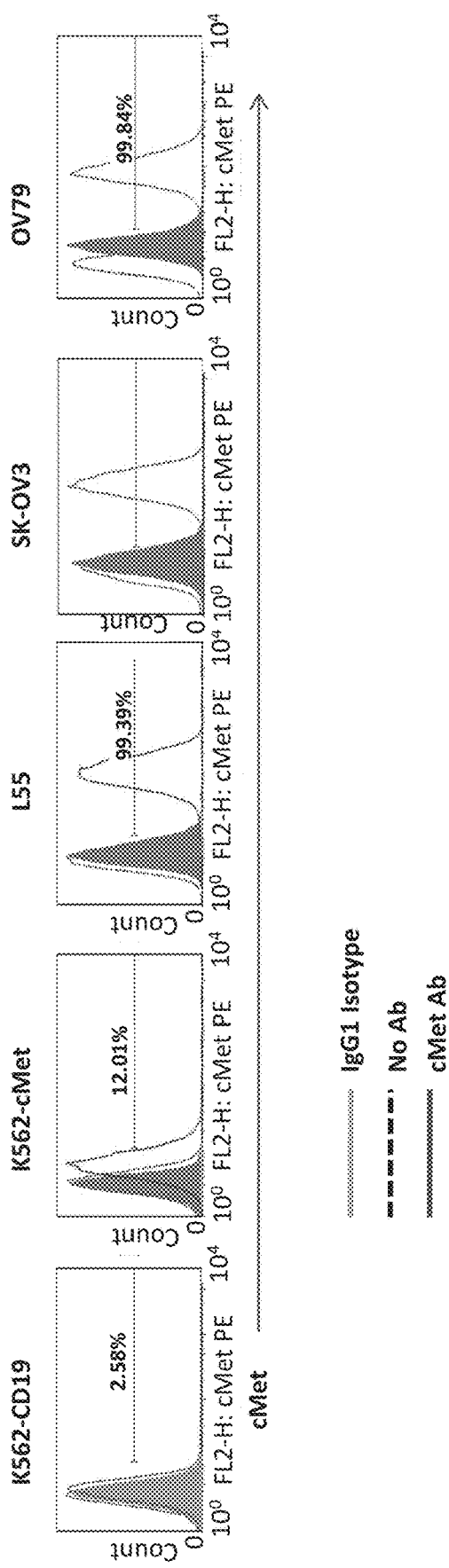

FIG. 29 is a set of graphs depicting the level of cMet expression in K562-CD19, K562-cMet, L55, SK-OV3, and OV79 cell lines.

Figure 30:
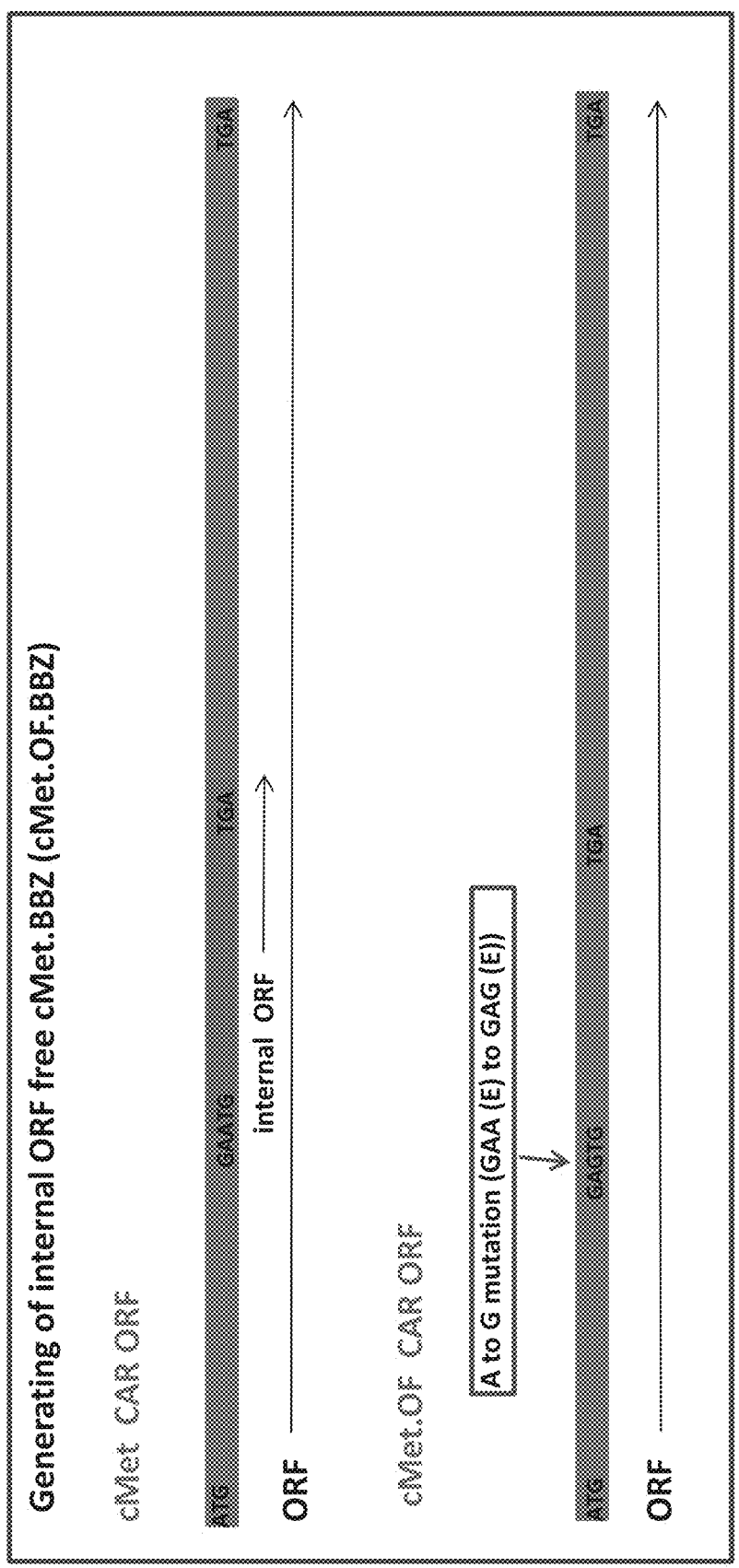

FIG. 30 is a schematic detailing the construction of internal ORF free (OF) cMet.BBZ CAR constructs.

FIGS. 31A and 31B depict the results of experiments examining the expression and function of clinical versions of cMet directed RNA CARs. FIG. 31A is a set of graphs illustrating the results of a CD107a assay examining the function of various cMet RNA CARs when co-cultured with either a cMet positive cell line (L55 or SK-OV3), or a cMet negative cell line (K562-CD19). CD107a was detected by flow cytometry in a 4 hour culture assay. FIG. 31B depicts a set of graphs showing CAR expression 24 hours after electroporation.

Figure 32B:
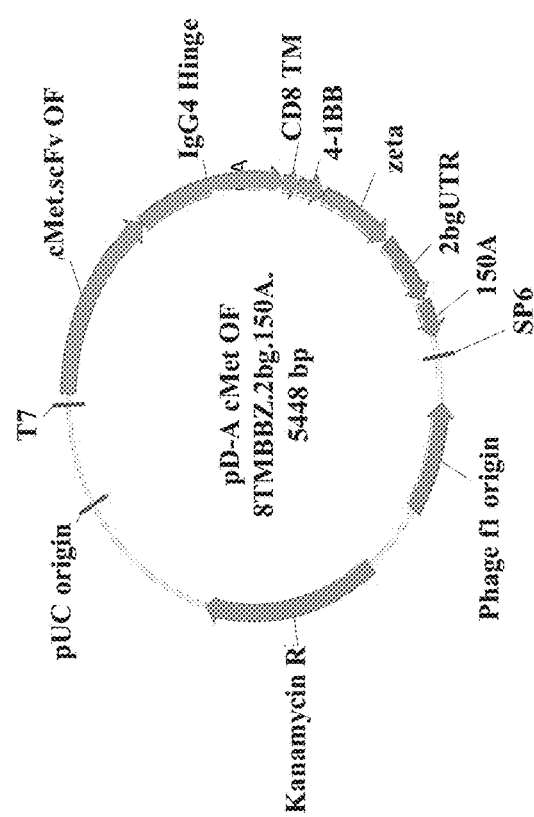
Figure 32A:
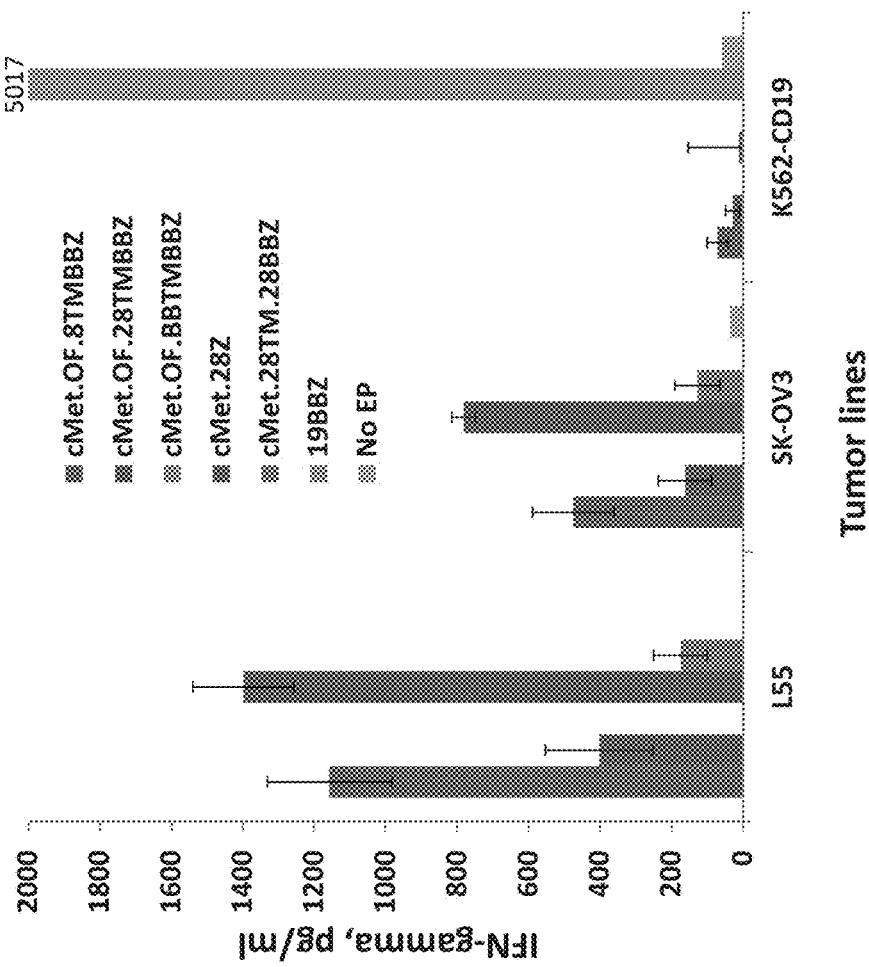

FIGS. 32A and 32B depict the results of experiments examining IFN-gamma production of cMet RNA CAR electroporated T cells when co-cultured with tumor cell lines. FIG. 32A depicts a graph illustrating the results of experiments where T cells were electroporated with IVT RNA encoding one of the various cMet CARs and were then co-cultured with either a cMet positive tumor cell lines (L55 or SK-OV3) or a cMet negative cell line (K562-CD19). Supernatant was harvested 24 hours post co-culture and was subjected to ELISA to detect secreted IFN-gamma. FIG. 32B depicts the map of the pD-A.cMet.OF.8TMBBZ.2bgUTR.150A construct which was chosen for animal experiments and potential clinical trial based upon its transgene expression and functionality.

Figure 33:
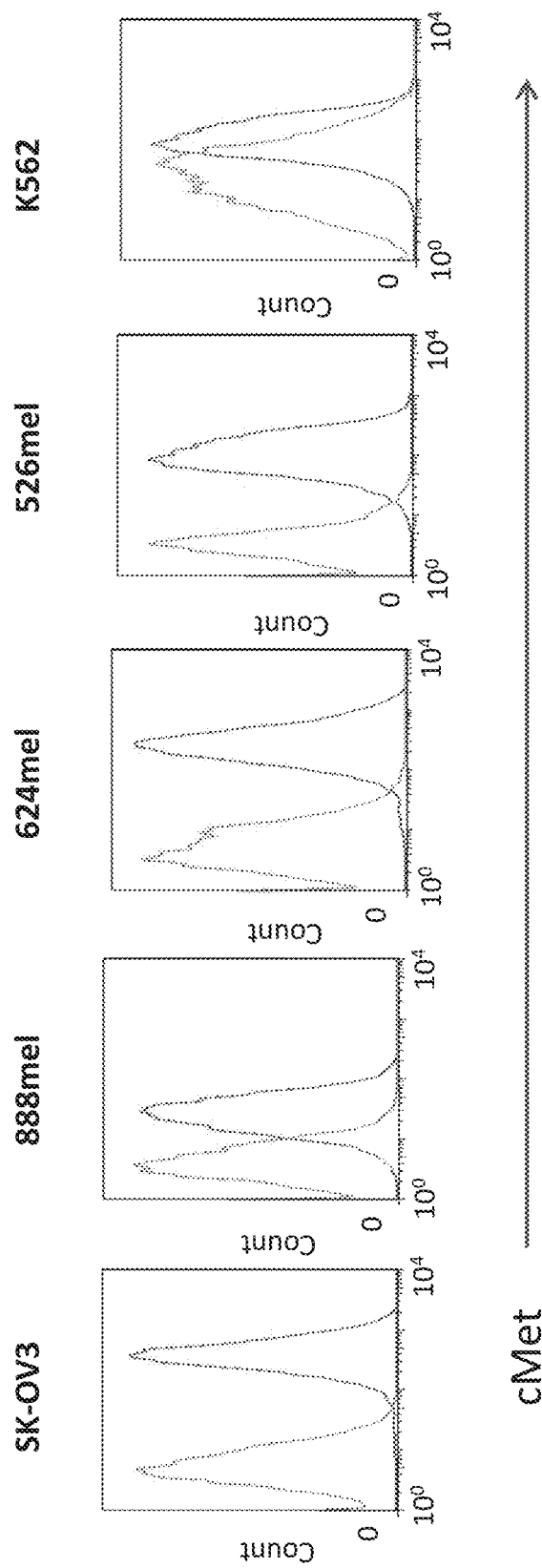

FIG. 33 is a set of graphs depicting the level of cMet expression in SK-OV3, 888mel, 624mel, 526mel, and K562 tumor cell lines.

Figure 34:
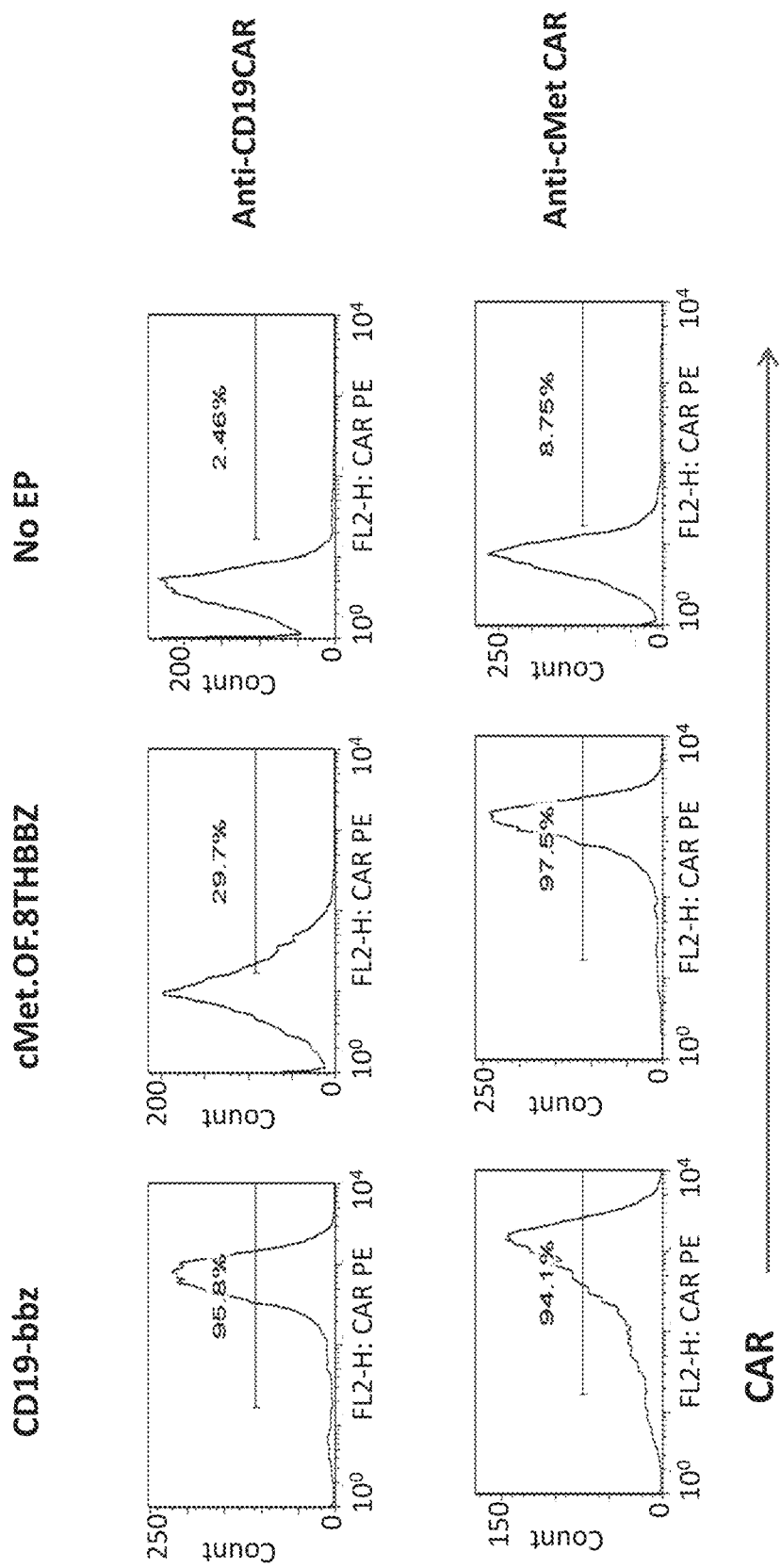

FIG. 34 is a set of graphs depicting the level of CAR expression in electroporated T cells. Day 10 stimulated T cells were electroporated with CD19 CAR RNA, or cMet CAR RNA or without electroporation (No EP). After overnight culturing, CD19 CAR or cMet CAR expression was detected by flow cytometry.

Figure 35:
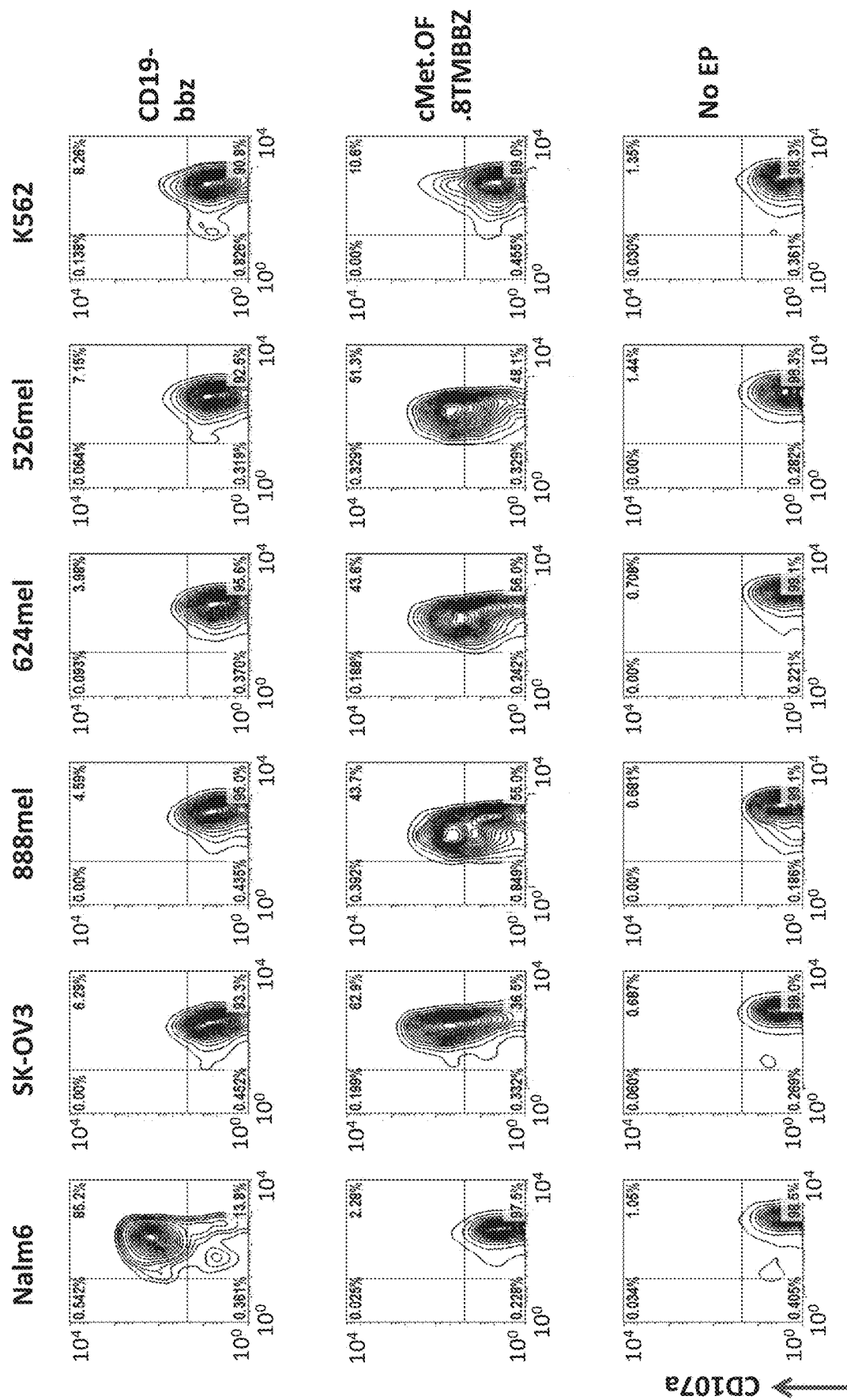

FIG. 35 is a set of graphs illustrating CD107a expression of melanoma stimulated cMet RNA CAR electroporated T cells. RNA electroporated T cells were stimulated with indicated tumor cell lines, including CD19+ Nalm6, cMet+ SK-OV3 and cMet+ melanoma lines (888mel, 624mel and 526mel). K562 was used as CD19− and cMet− control. After 4 h stimulation, CD107a expression was monitored by flow cytometry. Cells were CD8+ gated.

Figure 36:
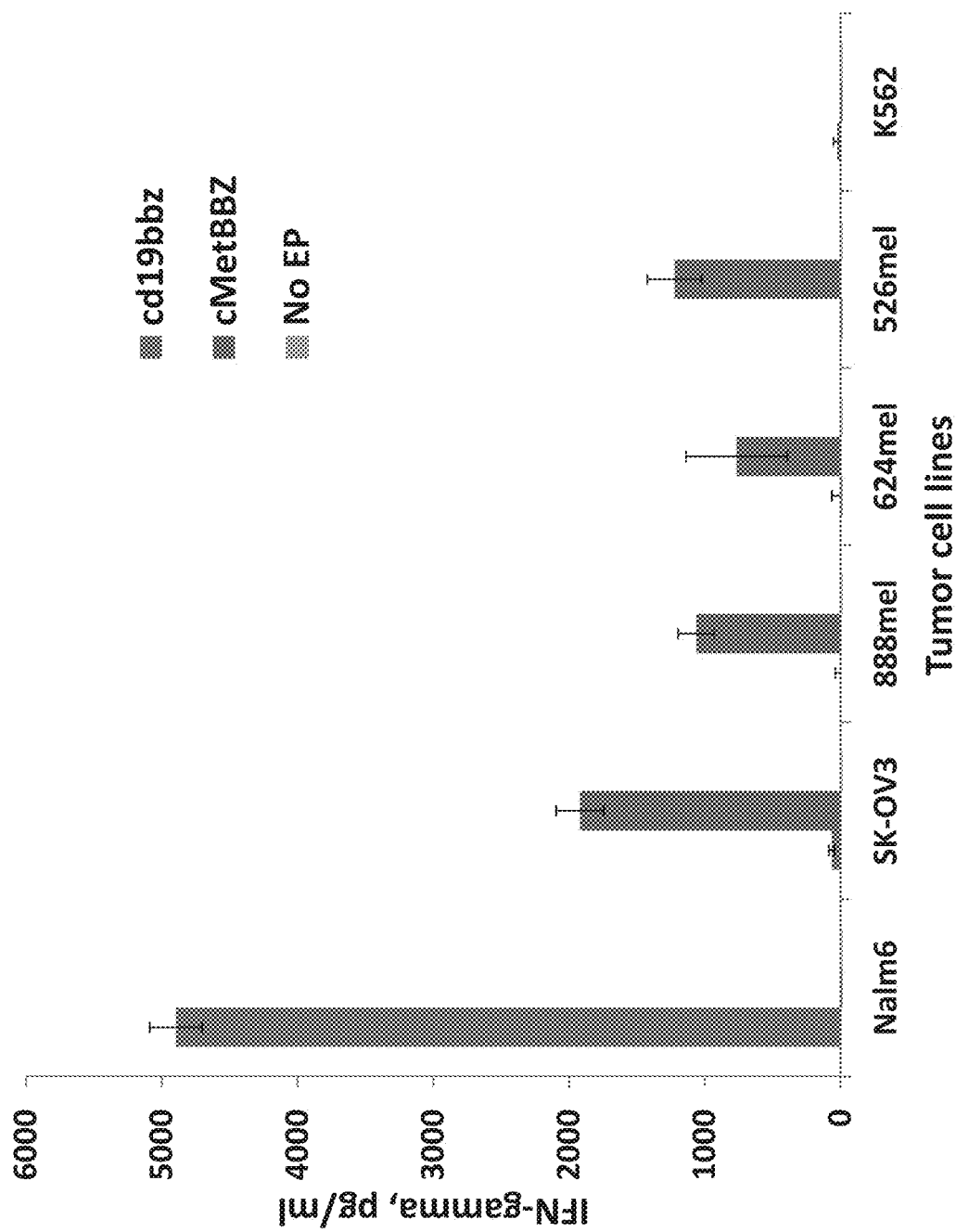

FIG. 36 is a graph depicting the amount of IFN-gamma production of melanoma stimulated cMet RNA CAR electroporated T cells. RNA electroporated T cells were stimulated with indicated tumor cell lines, including CD19+ Nalm6, cMet+ SK-OV3 and cMet+ melanoma lines (888mel, 624mel and 526mel). K562 was used as CD19− and cMet− control. After 24 h stimulation, IFN-gamma production was assayed by ELISA.

FIG. 37 depicts the design of an in vivo experiment examining the therapeutic effect of cMet RNA CARs.

Figure 38:
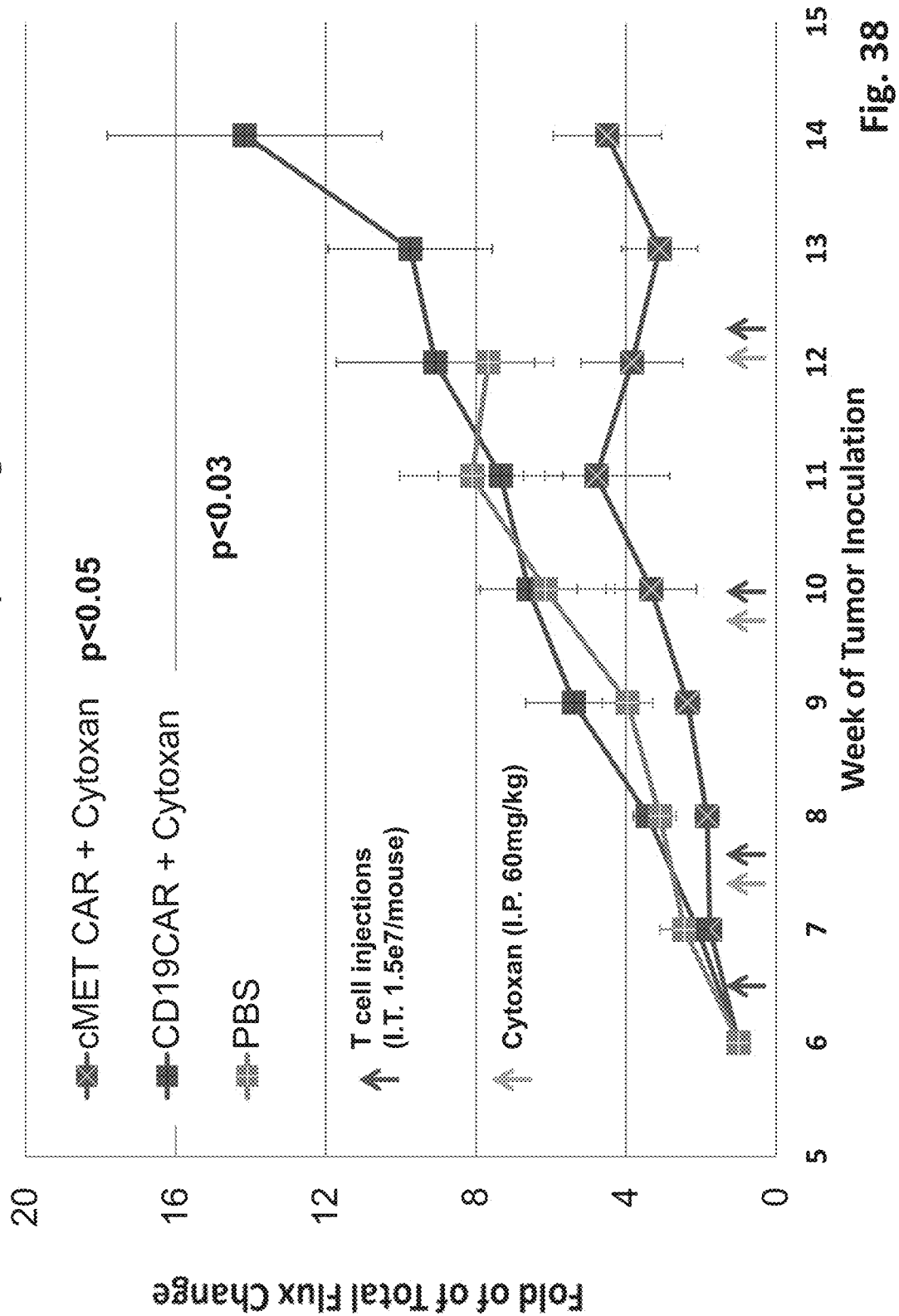

FIG. 38 is a graph illustrating the tumor burden of mice treated with PBS (as negative control), cMet RNA CAR electroporated T cells, or CD19 RNA CAR electroporated T cells. CAR T cell therapy was combined with Cytoxan treatment (I.P. 60 mg/kg) given one day prior to T cell injection.

Figure 39:
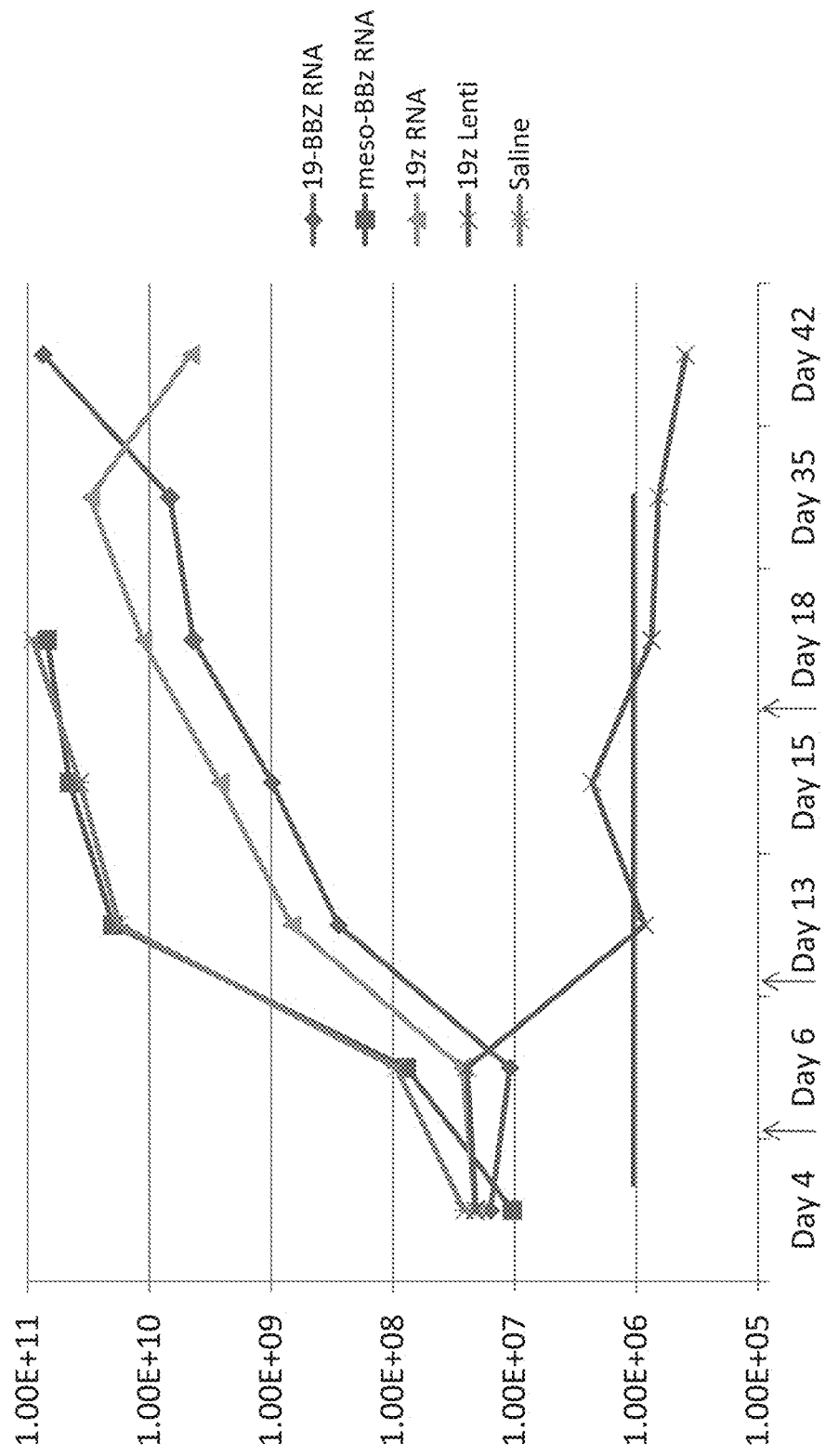

FIG. 39 is graph depicting tumor burden in mice with CD19 positive leukemia, treated with CARs delivered by either IVT RNA or lentiviral vectors. CD19 RNA electroporated T cells exhibit reduced tumor burden compared to control, but does not clear the tumor as seen by lentiviral delivered CD19 CARs. Arrows designate the times of injection of RNA CAR electroporated T cells.

Figure 40:
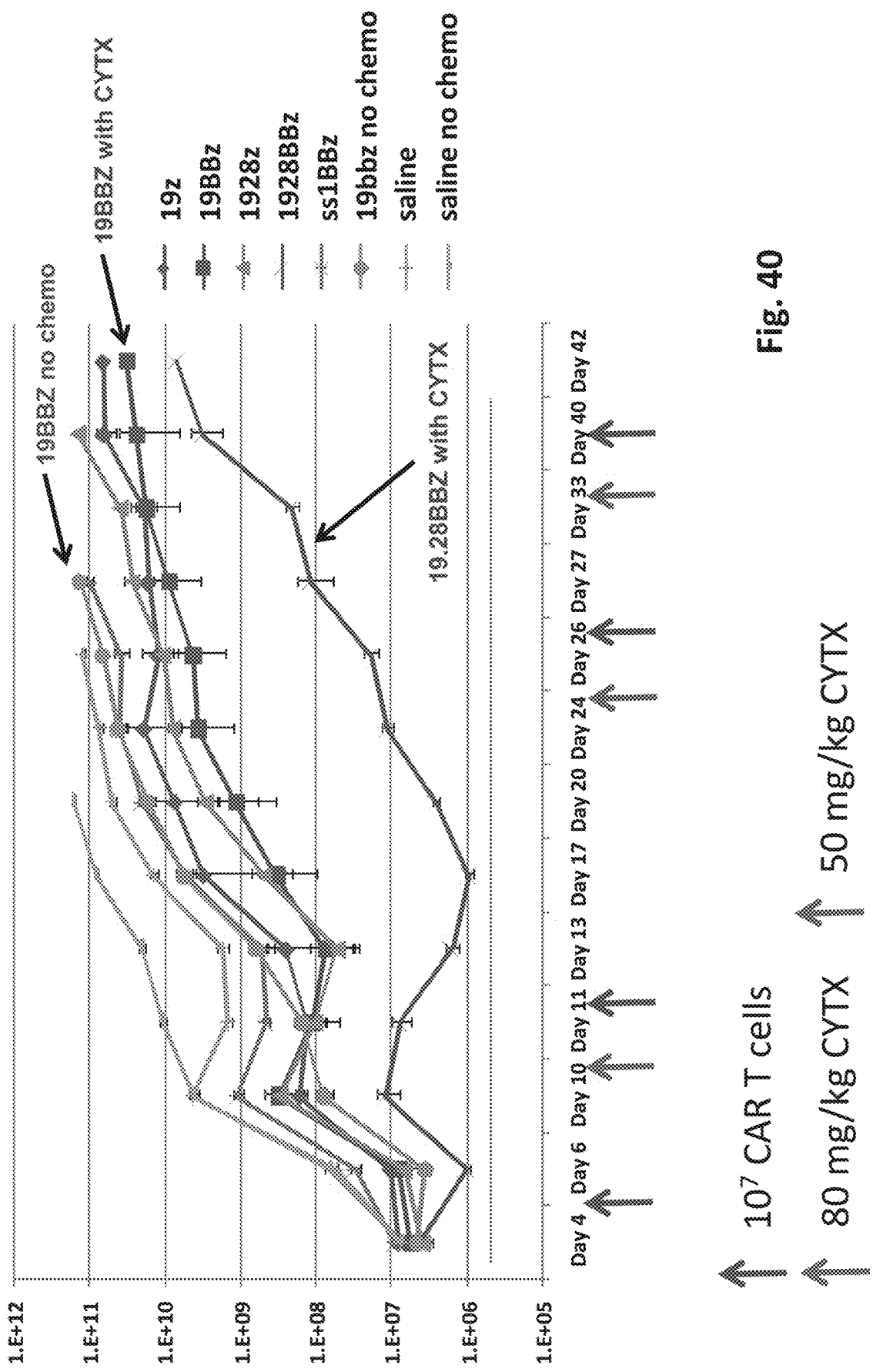

FIG. 40 is a graph depicting tumor burden in mice treated with RNA CAR electroporated T cells with or without combined Cytoxan treatment. Mice received the combined Cytoxan (chemo) and CAR treatment unless otherwise noted. The data presented demonstrates that depletion of previous CAR T cells by Cytoxan enhances the treatment conferred by repeat infusions of RNA CAR T cells.

Figure 41:
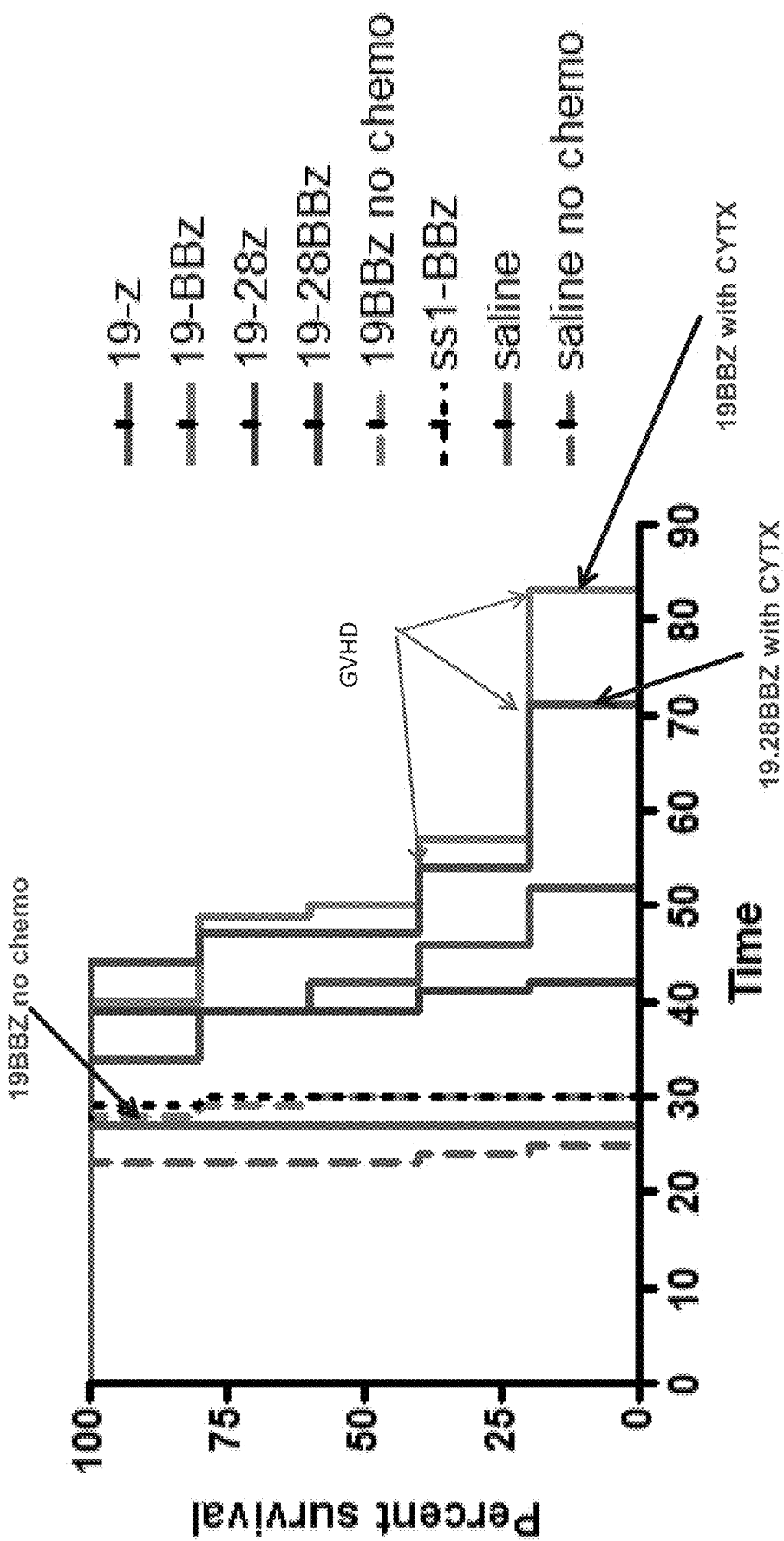

FIG. 41 is a graph depicting the percent survival of mice treated with RNA electroporated T cells with or without combined Cytoxan treatment. Mice received the combined Cytoxan (chemo) and CAR treatment unless otherwise noted. The data illustrates that overall survival is prolonged in the combined Cytoxan and repeated infusions of RNA CAR T cells therapies.

Figure 42:
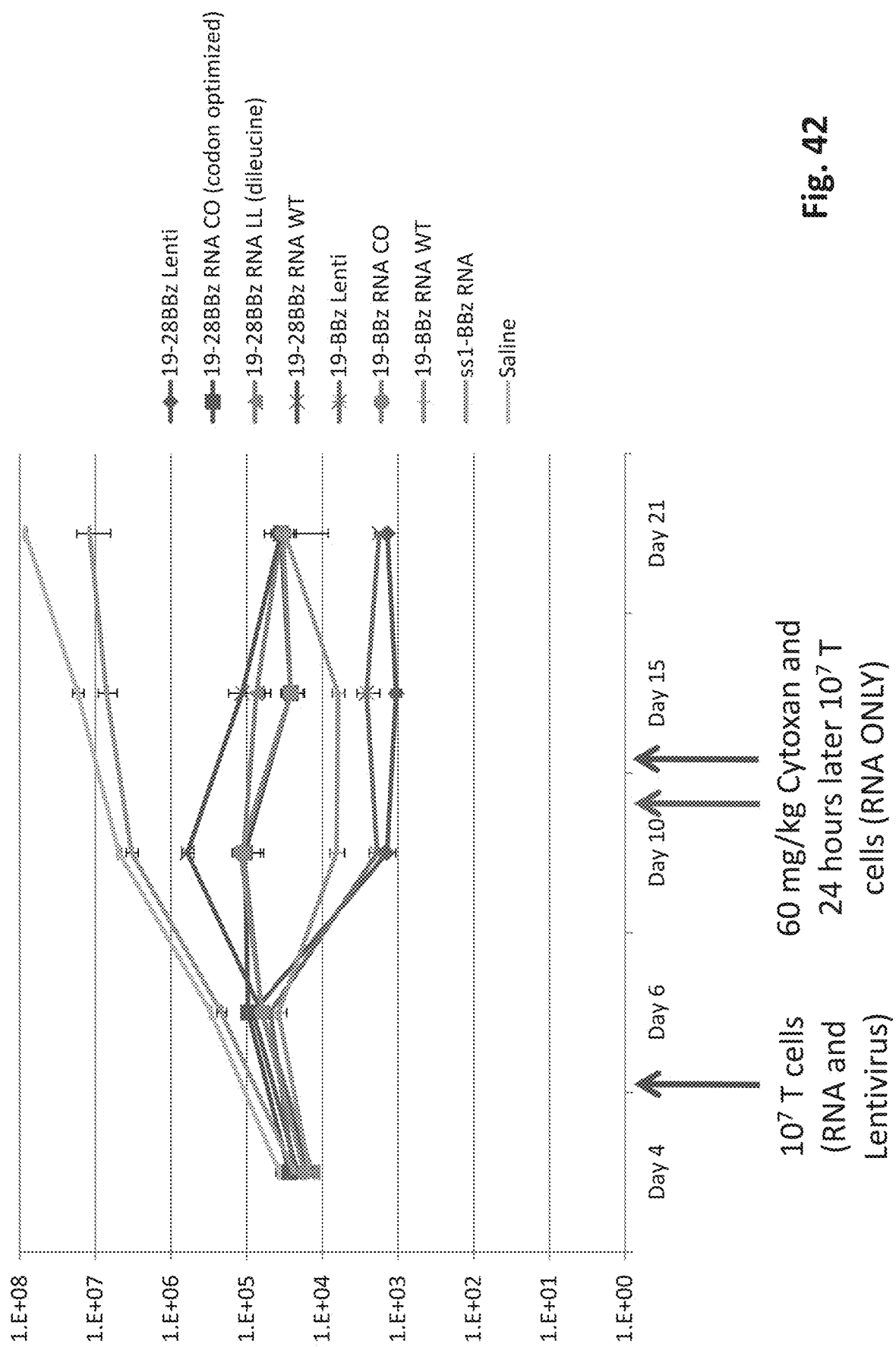

FIG. 42 is a graph depicting the extent of tumor burden in mice treated with CAR T cells, where the CAR is delivered either through lentiviral vector or by IVT RNA. For RNA groups, therapy was combined with 60 mg/kg Cytoxan delivered 24 hours before a second infusion of RNA CAR T cells. The CAR constructs used were either wildtype (WT), codon optimized (CO), or were mutated to remove a dileucine motif (LL).

Figure 43:
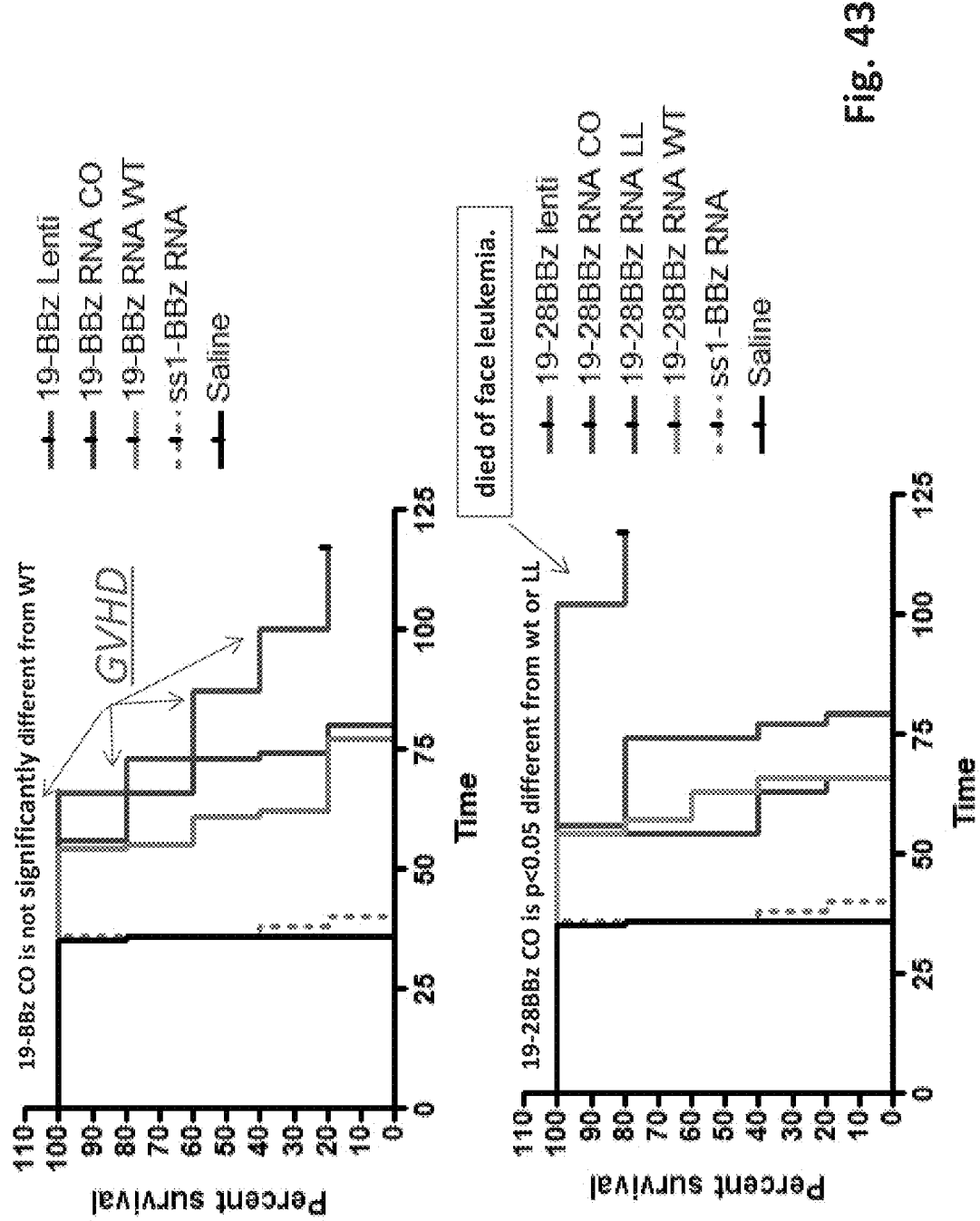

FIG. 43 is a set of graphs depicting the percent survival of mice treated with CD19-BBZ CAR T cells (top) and with CD19-28BBZ CAR T cells. For RNA groups, therapy was combined with 60 mg/kg Cytoxan delivered 24 hours before a repeat infusion of RNA electroporated CAR T cells. The CAR constructs used were either wildtype (WT), codon optimized (CO), or were mutated to remove a dileucine motif (LL).

Figure 44:
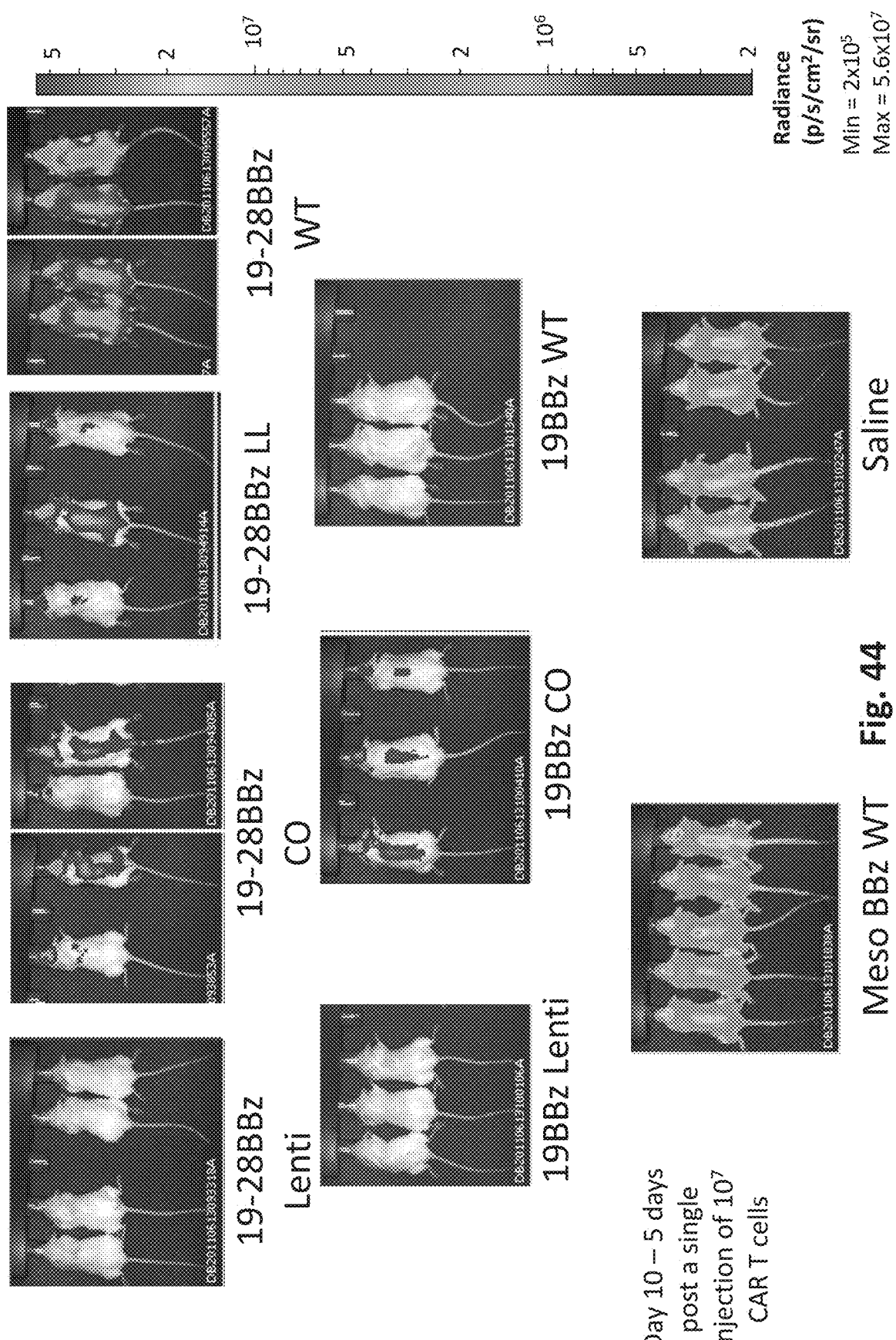

FIG. 44 is a set of images depicting the extent of tumors, as measured through bioluminescence, in mice 5 days after a single injection of CART cells. T cells were modified through delivery of IVT RNA encoding the CAR, unless where noted to be delivered by lentiviral vector (lenti). The CAR constructs used were either wildtype (WT), codon optimized (CO), or were mutated to remove a dileucine motif (LL).

Figure 45:
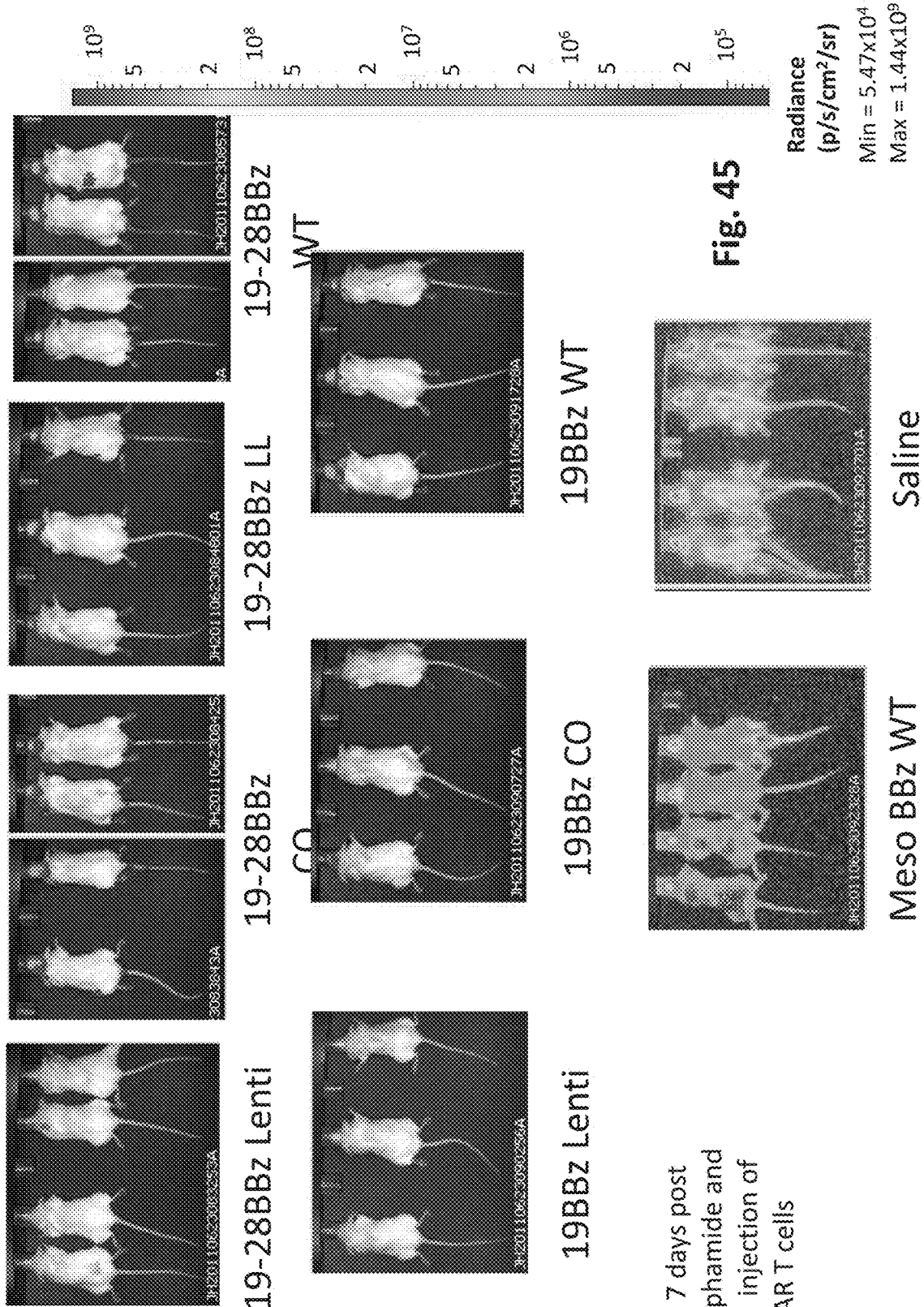

FIG. 45 is a set of images depicting the extent of tumors, as measured through bioluminescence, in mice on day 21, 7 days after combined treatment of the second infusion of CAR T cells and Cytoxan treatment. T cells were modified through delivery of IVT RNA encoding the CAR, unless where noted to be delivered by lentiviral vector (lenti). Lentiviral treated animals did not receive the Cytoxan or second infusion of T cells. The CAR constructs used were either wildtype (WT), codon optimized (CO), or were mutated to remove a dileucine motif (LL).

Figure 46:
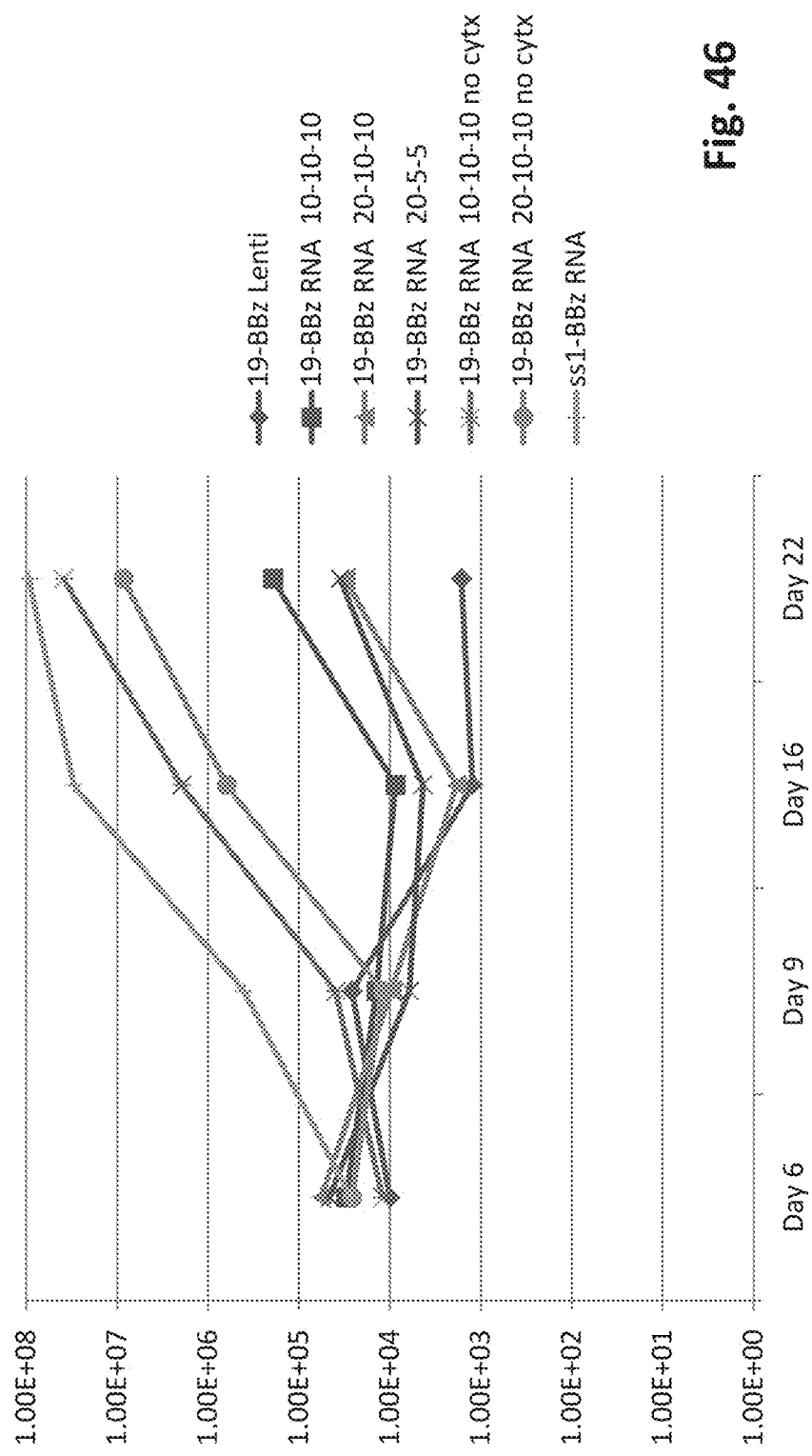

FIG. 46 is a graph depicting tumor burden in mice treated with 19-BBz CAR T cells. Mice were treated with a single dose of lentiviral delivered 19-BBz T cells or with multiple doses of 19-BBz RNA CAR T cells. RNA CAR T cells were either delivered alone, or in combination with Cytoxan treatment (given 1 day prior to T cell infusion). Multiple dosing strategies of the RNA CAR T cells were examined, where the number of T cells in each infusion was varied.

FIG. 47 is a set of images depicting the extent of tumors on day 22 in mice treated with 19-BBz CAR T cells. Mice were treated with a single dose of lentiviral delivered 19-BBz T cells or with multiple doses of 19-BBz RNA CAR T cells. RNA CAR T cells were either delivered alone, or in combination with Cytoxan treatment (given 1 day prior to T cell infusion). Multiple dosing strategies of the RNA CAR T cells were examined, where the number of T cells in each infusion was varied.

Figure 48:
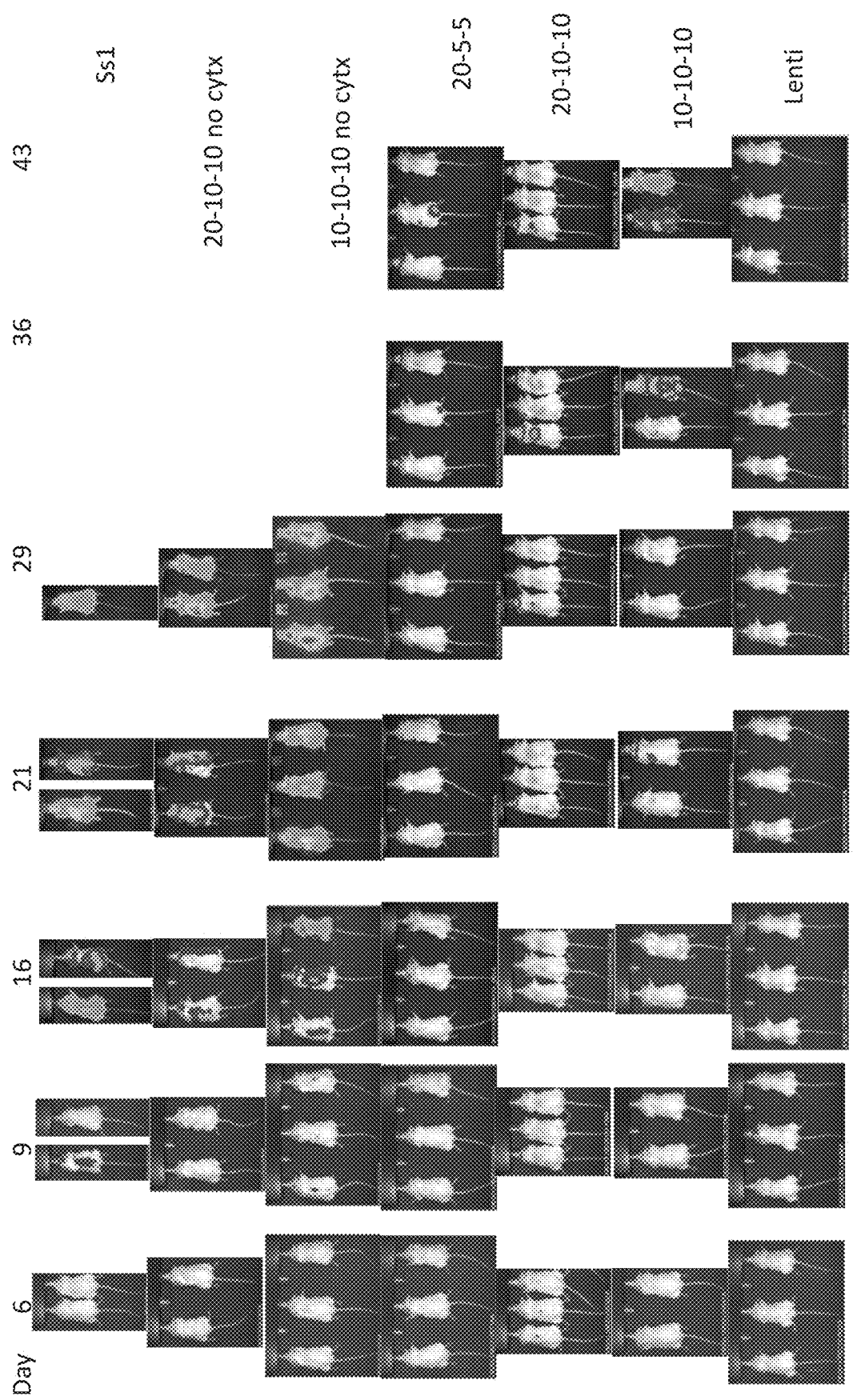

FIG. 48 is a set of images depicting the extent of tumors throughout the study time course in mice treated with 19-BBz CAR T cells. Mice were treated with a single dose of lentiviral delivered 19-BBz T cells or with multiple doses of 19-BBz RNA CAR T cells. RNA CAR T cells were either delivered alone, or in combination with Cytoxan treatment (given 1 day prior to T cell infusion). Multiple dosing strategies of the RNA CAR T cells were examined, where the number of T cells in each infusion was varied.

Figure 49:
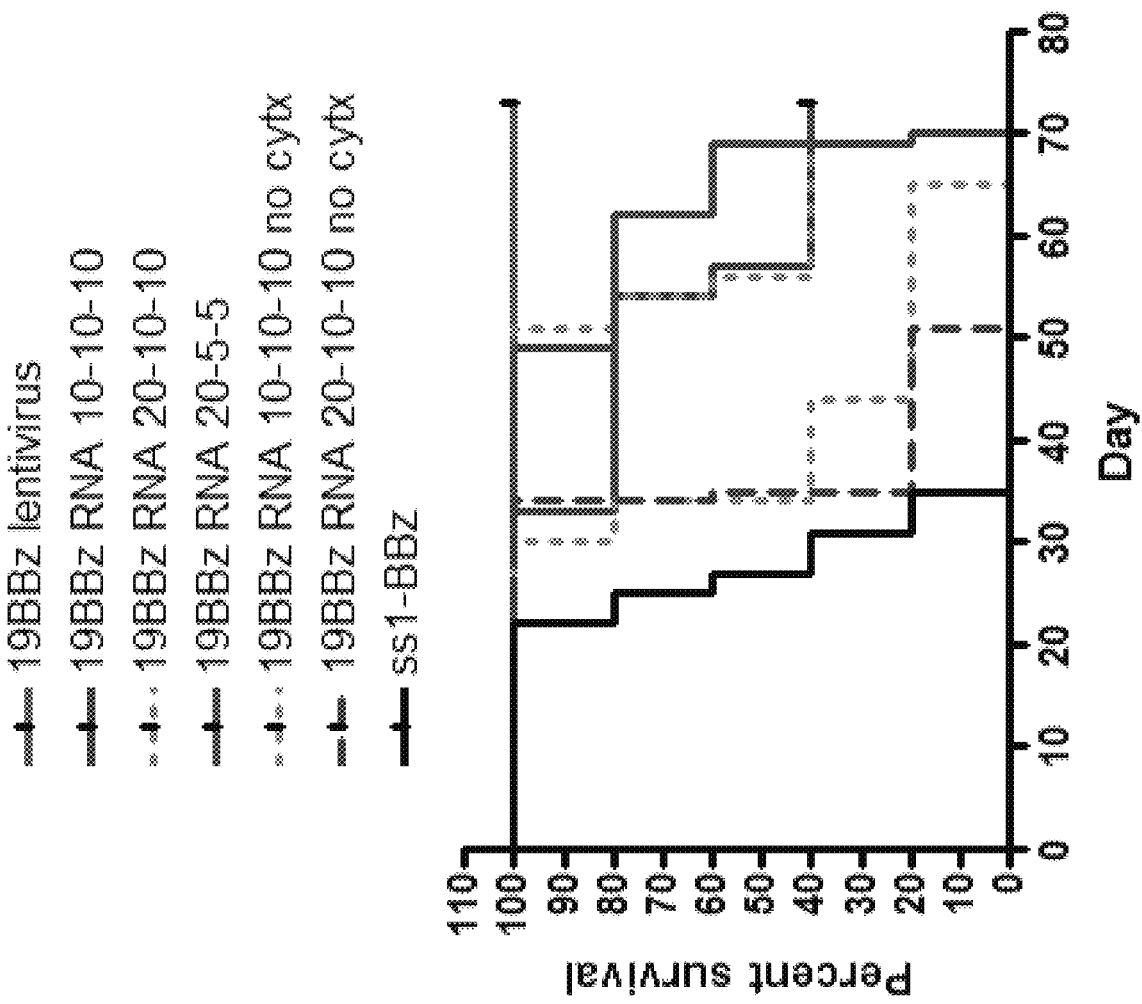

FIG. 49 is a graph depicting the percent survival in mice treated with 19-BBz CART cells. Mice were treated with a single dose of lentiviral delivered 19-BBz T cells or with multiple doses of 19-BBz RNA CAR T cells. RNA CAR T cells were either delivered alone, or in combination with Cytoxan treatment (given 1 day prior to T cell infusion). Multiple dosing strategies of the RNA CAR T cells were examined, where the number of T cells in each infusion was varied.

Figure 50:
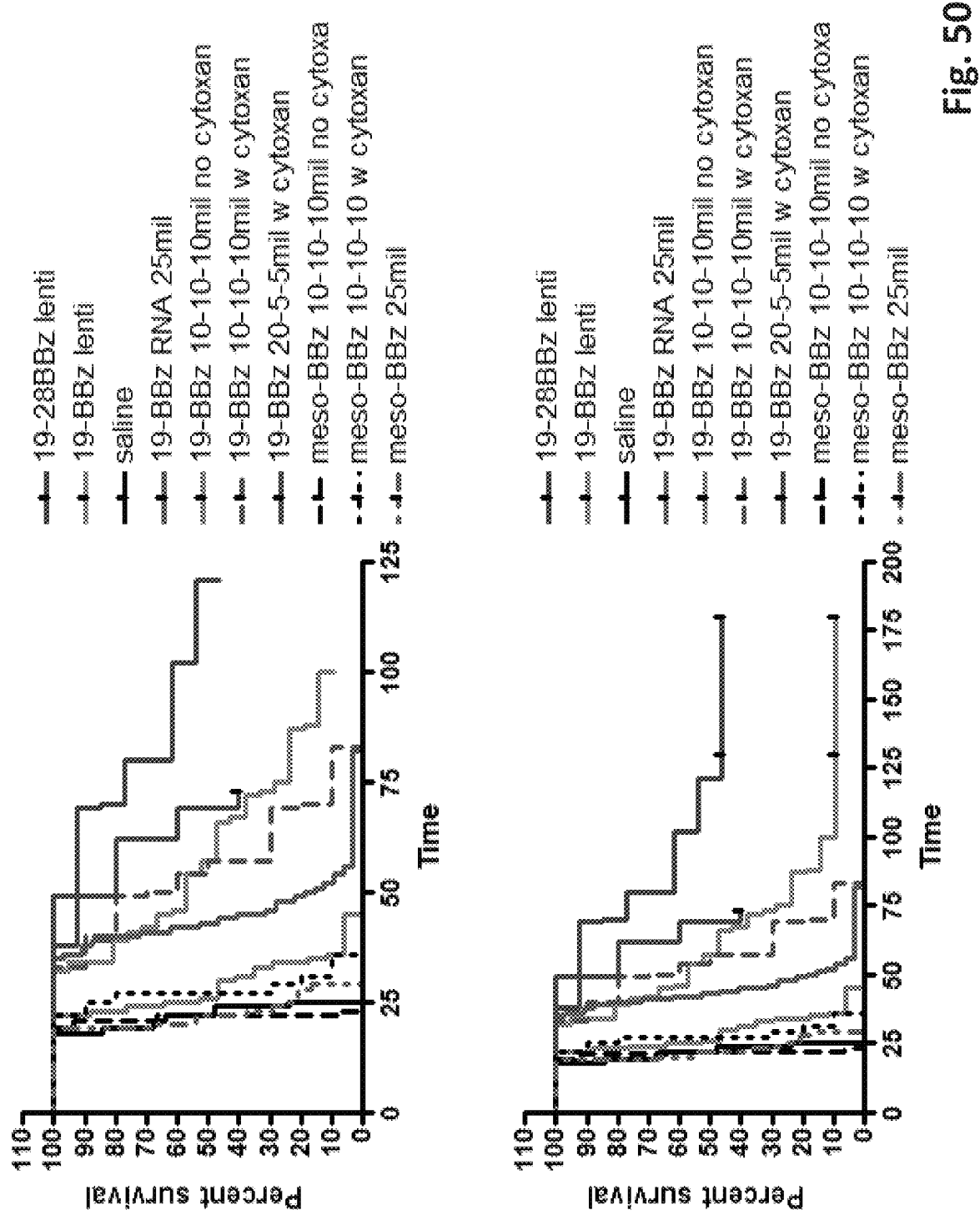

FIG. 50 is a set of graphs depicting the percent survival in mice treated with 19-BBz CAR T cells, 19-28BBz CAR T cells, or meso-BBz CAR T cells. Mice were treated with a single dose of lentiviral delivered CAR T cells or with multiple doses of RNA CAR electroporated T cells. RNA CAR electroporated T cells were either delivered alone, or in combination with Cytoxan treatment (given 1 day prior to T cell infusion). Multiple dosing strategies of the RNA CAR T cells were examined, where the number of T cells in each infusion was varied.

DETAILED DESCRIPTION

The present invention relates to the discovery that autologous T cells from a cancer patient can be engineered with RNA to provide an effective therapy to treat the patient. RNA-engineered T cells provide a novel approach for adoptive cell transfer that allows for a flexible platform for the treatment of cancer. In some instances, the RNA-engineered T cells can be used as a complement to the use of retroviral and lentiviral engineered T cells. The use of RNA-engineered T cells can increase the therapeutic index of T cells engineered to express powerful activation domains without the associated safety concerns of the use of viral vectors that have the potential to integrate into the host cell genome.

The present invention relates generally to the use of T cells transfected with RNA encoding a Chimeric Antigen Receptor (CAR). T cells transfected with RNA encoding a CAR are referred to herein as RNA-engineered T cells. CARs combine an antigen recognition domain of a specific antibody with an intracellular signaling molecule. For example, the intracellular signaling molecule can comprise one or more of CD3-zeta chain, 4-1BB and CD28 signaling modules. Accordingly, the invention provides RNA-engineered T cells and methods of their use for adoptive therapy.

An advantage of using RNA-engineered T cells is that the CAR is expressed for a limited time in the cell. Following transient expression of CAR, the phenotype of the cell returns to wild type. Thus, the duration of treatment can be controlled using cells that are transiently transfected with CAR.

In one embodiment, the invention includes autologous cells that are electroporated with mRNA that expresses an anti-CD19 CAR, an anti-mesothelin CAR, an anti-GD2 CAR, or an anti-cMet CAR. However, the invention should not be limited to CD19, mesothelin, GD2, and cMet as the target molecule. Rather, any antigen binding domain directed against any target molecule can be used in the context of the CAR. Preferably, the CAR of the invention combines an antigen recognition domain of a specific antibody with an intracellular domain of the CD3-zeta chain or FcγRI protein into a single chimeric protein. The invention therefore includes RNA encoding such combinations.

In one embodiment, the CAR further comprises a 4-1BB signaling domain. For example, the RNA-engineered T cells of the invention can be generated by introducing an in vitro transcribed mRNA of a CAR, for example αCD19, CD8a hinge and transmembrane domain, and human 4-1BB and CD3-zeta signaling domains into the cell. The RNA-engineered T cells of the invention can be infused into a patient for therapeutic purposes. In some instances, the CAR can further comprise CD28.

In one embodiment, the present invention provides a method of treating a patient using adoptive T cell therapy, wherein the T cells are modified to comprise an RNA sequence encoding a CAR. The method may be used to treat any number of disorders including cancers and immune disorders. In some instances, the method comprises administering RNA modified T cells multiple times over the course of a therapy. In one embodiment, the method comprises further administering an additional therapeutic composition. For example, in one embodiment, the method comprises administering a chemotherapeutic agent.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eulcaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eulcaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides an alternative strategy to the use of a virus for the expression of a CAR in a cell. The present invention is directed to RNA encoding CAR that is transfected into a cell and transiently expressed therein. Transient, non-integrating expression of CAR in a cell mitigates concerns associated with permanent and integrated expression of CAR in a cell. The present invention therefore provides an additional CAR-based therapy where CAR expression in a cell can be reversible. Such reversal of CAR expression in a cell may be more desirable in certain clinical circumstances than non-reversible expression of CAR. Thus, the present invention provides certain desirable advantages over permanent expression of CAR in certain clinical circumstances.

The present invention provides compositions and methods for generating transiently expressing CAR cells and also provides compositions and methods for administering such cells to a subject.

In comparison to longterm (integrating) expression systems, RNA transfection facilitates more rapid iterative changes in CAR design that is suitable for a GMP-compliant system. Manufacturing costs are far less. Release testing is less complex.

Compositions

The present invention includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells.

In one embodiment the RNA construct comprises a 3'UTR comprising at least one 3'UTR derived from human beta-globulin. In one embodiment, the RNA construct comprises a 3'UTR comprising two repeats of 3'UTR derived from human beta-globulin (2bgUTR). In one embodiment, the RNA construct comprise a poly(A) tail comprising 150 adenosine bases (150A). In one embodiment, the RNA construct comprise a 5'UTR comprising a 5' cap. In one embodiment the 5' cap comprises anti-reverse cap analogue (ARCA). In one embodiment the 5' cap comprises cap1. The present invention is partly based upon the discovery that the particular structure of the 5'UTR, 3'UTR, and poly(A) tail influence RNA production and resultant CAR expression.

In one embodiment, the template includes sequences for the CAR. Preferably, the CAR comprises an extracellular domain, a transmembrane domain and a cytoplasmic domain. The extracellular domain and transmembrane domain can be derived from any desired source of such domains.

Antigen Binding Domain

The extracellular domain may be obtained from any of the wide variety of extracellular domains or secreted proteins associated with ligand binding and/or signal transduction. In one embodiment, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity that is distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

The extracellular domain can be directed to any desired antigen. For example, when an antitumor CAR is desired, the extracellular domain chosen to be incorporated into the CAR can be an antigen that is associated with the tumor. The tumor may be any type of tumor as long as it has a cell surface antigen which is recognized by the CAR. In another embodiment, the CAR may one for which a specific monoclonal antibody currently exists or can be generated in the future.

In one embodiment, the template for the RNA CAR is designed to be directed to an antigen of interest by way of engineering a desired antigen into the CAR. In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, neuroblastoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

Tumor antigens are proteins that are produced by tumor cells that elicit an immune response, particularly T-cell mediated immune responses. In one embodiment, the tumor antigen of the present invention comprises one or more antigenic cancer epitopes immunologically recognized by tumor infiltrating lymphocytes (TIL) derived from a cancer tumor of a mammal. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as mesothelin, MART-1, tyrosinase and GP 100 in melanoma and prostatic acid phosphatase (PAP) and prostate-specific antigen (PSA) in prostate cancer. Other non-limiting examples of target molecules belong to the group of transformation-related molecules such as the oncogene HER-2/Neu/ErbB-2. Yet other non-limiting examples of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success but are deemed useful in the present invention.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

GD2 is a disialoganglioside which is expressed on the tumors of neuroectodermal origin, including neuroblastoma and melanoma, and is another target useful in the present invention. Further, the receptor tyrosine kinase cMet is another target useful in the present invention, as it is often overexpressed in a variety of carcinomas, including non-small cell lung carcinoma (NSCLC), gastric, ovarian, pancreatic, thyroid, breast, head and neck, colon and kidney carcinomas.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. Although analogs or artificially modified epitopes are not listed, a skilled artisan recognizes how to obtain or generate them by standard means in the art. Other antigens, identified by antibodies and as detected by the Serex technology (see Sahin et al. (1997) and Chen et al. (2000)), are identified in the database of the Ludwig Institute for Cancer Research.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention.

Transmembrane Domain

With respect to the transmembrane domain, the template for the RNA CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain is selected from the CD8 transmembrane domain, the CD28 transmembrane domain, the 4-1BB transmembrane domain, or the CD3-zeta transmembrane domain. In some instances the transmembrane domain may also comprise a hinge domain. In one embodiment, the hinge domain is a CD8a hinge domain. In another embodiment, the hinge domain is an IgG hinge domain.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the template for the RNA CAR can be designed to comprise the 4-1BB signaling domain by itself or combined with any other desired cytoplasmic domain(s) useful in the context of the CAR of the invention.

In one embodiment, the cytoplasmic domain is designed to comprise the signaling domain of CD3-zeta and the signaling domain of 4-1BB. In another embodiment, the cytoplasmic domain is designed to comprise the signaling domain of CD3-zeta, the signaling domain of 4-1BB, and the signaling domain of CD28.

In one embodiment, the template for the RNA CAR comprises the extracellular domain of a single chain variable domain of an anti-CD 19 monoclonal antibody, the transmembrane domain comprises the hinge and transmembrane domain of CD8a, and the cytoplasmic domain comprises the signaling domain of CD3-zeta and the signaling domain of 4-1BB.

In one embodiment, the template for the RNA CAR comprises the extracellular domain of a single chain variable domain of an anti-CD 19 monoclonal antibody, the transmembrane domain comprises the hinge and transmembrane domain of CD8a, and the cytoplasmic domain comprises the signaling domain of CD3-zeta, the signaling domain of CD28, and the signaling domain of 4-1BB.

In one embodiment, the template for the RNA CAR comprises the extracellular domain of a single chain variable domain of an anti-mesothelin monoclonal antibody, the transmembrane domain comprises the hinge and transmembrane domain of CD8a, and the cytoplasmic domain comprises the signaling domain of CD3-zeta and the signaling domain of 4-1BB.

In one embodiment, the template for the RNA CAR comprises the extracellular domain of a single chain variable domain of an anti-GD2 monoclonal antibody, the transmembrane domain comprises the transmembrane domain of CD8, and the cytoplasmic domain comprises the signaling domain of CD3-zeta and the signaling domain of 4-1BB.

In one embodiment, the template for the RNA CAR comprises the extracellular domain of a single chain variable domain of an anti-GD2 monoclonal antibody, the transmembrane domain comprises the transmembrane domain of CD28, and the cytoplasmic domain comprises the signaling domain of CD3-zeta and the signaling domain of 4-1BB.

In one embodiment, the template for the RNA CAR comprises the extracellular domain of a single chain variable domain of an anti-GD2 monoclonal antibody, the transmembrane domain comprises the transmembrane domain of CD3-zeta, and the cytoplasmic domain comprises the signaling domain of CD3-zeta and the signaling domain of 4-1BB.

In one embodiment, the template for the RNA CAR comprises the extracellular domain of a single chain variable domain of an anti-cMet monoclonal antibody, the transmembrane domain comprises the transmembrane domain of CD8, and the cytoplasmic domain comprises the signaling domain of CD3-zeta and the signaling domain of 4-1BB.

In one embodiment, the template for the RNA CAR comprises the extracellular domain of a single chain variable domain of an anti-cMet monoclonal antibody, the transmembrane domain comprises the transmembrane domain of CD28, and the cytoplasmic domain comprises the signaling domain of CD3-zeta and the signaling domain of 4-1BB.

In one embodiment, the template for the RNA CAR comprises the extracellular domain of a single chain variable domain of an anti-cMet monoclonal antibody, the transmembrane domain comprises the transmembrane domain of 4-1BB, and the cytoplasmic domain comprises the signaling domain of CD3-zeta and the signaling domain of 4-1BB.

In one embodiment, the template for the RNA CAR comprises the extracellular domain of a single chain variable domain of an anti-cMet monoclonal antibody and the cytoplasmic domain comprises the signaling domain of CD3-zeta and the signaling domain of CD28.

In one embodiment, the template for the RNA CAR comprises the extracellular domain of a single chain variable domain of an anti-cMet monoclonal antibody, the transmembrane domain comprises the transmembrane domain of CD28, and the cytoplasmic domain comprises the signaling domain of CD3-zeta, the signaling domain of CD28, and the signaling domain of 4-1BB.

In some instances, the template is modified to remove internal open reading frames (ORFs) to produce templates that are internal open reading frame free (OF). In one embodiment, the template is codon optimized for use in a specific species. For example, in one embodiment, the template is codon optimized for use in humans. In one embodiment, the template is modified to remove dileucine motifs.

In one embodiment, the template is comprised within an IVT vector or plasmid. In one embodiment, the plasmid comprises a nucleotide sequence comprising a sequence selected from the group consisting of SEQ ID NO: 4 and SEQ ID NO: 5.

In one embodiment, the template comprises a nucleotide sequence comprising a sequence selected from the group consisting of SEQ ID NOs: 6-24. In another embodiment, the RNA construct of the invention is transcribed from a nucleotide sequence comprising a sequence selected from the group consisting of SEQ ID NOs: 6-24.

In one embodiment, the template comprises a poly(A) tail. In one embodiment, the poly(A) tail comprises 150 adenosine bases. In one embodiment the poly(A) tail comprises a nucleotide sequence comprising SEQ ID NO: 25.

In one embodiment, the template comprises a 3'UTR comprising at least one repeat of a 3'UTR derived from human beta-globulin. In one embodiment, the template comprises a 3'UTR comprising a nucleotide sequence comprising SEQ ID NO: 26.

RNA Transfection

Disclosed herein are methods for producing the in vitro transcribed RNA CARs of the invention. In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising a single chain variable domain of an anti-tumor antibody; a transmembrane domain; and a cytoplasmic domain comprising the signaling domain of CD3-zeta. In one embodiment, the template comprises a nucleotide sequence comprising a sequence selected from the group consisting of SEQ ID NOs 6-24.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In one embodiment, the present invention includes synthetic RNA and RNA-like analogs encoding a CAR. That is, the present invention includes CAR-encoding RNA and RNA-like constructs manufactured in any method known in the art, including, for example IVT RNA and synthesized RNA. In one embodiment, RNA is synthesized through known methods of oligonucleotide synthesis. Methods of oligonucleotide synthesis include, for example, H-phosphonate synthesis, phosphodiester synthesis, phosphotriester synthesis, phosphite triester synthesis, and the phosphoramidite method. In some instances, synthesis of the RNA construct includes the incorporation of nucleotide/nucleoside derivatives or analogs. As such, in one embodiment, the RNA of the invention comprises a nucleotide/nucleoside derivative or analog. For example, one type of analog is LNA, such as beta-D-oxy-LNA, alpha-L-oxy-LNA, beta-D-amino-LNA and beta-D-thio-LNA, and beta-D-oxy-LNA. Methods of producing synthesized RNA are well known in the art, described, for example, in U.S. Pat. Nos. 8,242,248, 6,111,095, U.S. Patent Application Publication No.: 2010/0324278, U.S. Patent Application Publication No.: 2010/0137010, and PCT International Publication No.: WO 2007/031081, each of which is incorporated by reference. Further, the present invention includes CAR-encoding RNA and RNA-like constructs manufactured via methods heretofore unknown, provided that the constructs comprise a sequence which encodes the components of the CAR described herein.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

RNA-Engineered T Cells

The in vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to modulation of cell activity in basic research and therapy, in the fields of cancer, stem cells, acute and chronic infections, and autoimmune diseases, including modulation of the developmental pathways.

The methods also provide the ability to control the level of expression over a wide range by changing the amount of input RNA, making it possible to individually regulate the expression level of each transfected gene. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

An advantage of the methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population. Thus, cells containing an RNA construct introduced according to the disclosed method can be used therapeutically. For example, a lymphocyte cell population is withdrawn from a patient, transfected with different RNA constructs, and then reintroduced into the patient. The transfected cell population then target lymphoma or other cancer cells which contain the CD19 or other target antigen. A benefit of the use of RNA transfected cells is that the RNA transgene has a limited half-life. The encoded protein will only be produced by the transfected cell for a limited period of time. This serves to reduce the risk of any unintended consequences when genetically modified cells are introduced into a patient.

In the preferred embodiment, the technology is used for personalized therapy. For example, for treatment of tumors, the patient's blood or cells is collected by an appropriate method such as apheresis, biopsy or venapuncture. The cells are cultured for at least 24 hours during which time the cells are transfected with an appropriate RNA construct to treat the tumor. The cells can be stored frozen before transfection, if necessary. They are then returned back to the patient at the appropriate time and in the appropriate dose. In one embodiment, RNA modified cells are administered to the patient multiple times.

Immune therapy with in vitro-transcribed RNA (IVT-RNA) makes use of two different strategies both of which have been successively tested in various animal models. Cells are transfected with in vitro-transcribed RNA by means of lipofection or electroporation and administered to the subject. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing a chain of A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than CD8+ T cells in dilute concentrations. In one embodiment, the concentration of cells used is 5×10⁶/ml. In other embodiments, the concentration used can be from about 1×10⁵/ml to 1×10⁶/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment with a non-cellular based treatment and the T cells are engineered to comprise the RNA CAR of the invention. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Prior to the transfection of the T cells, the cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments.

For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention includes a type of cellular therapy where T cells are genetically modified to transiently express a chimeric antigen receptor (CAR) and the RNA-engineered T cell is infused to a recipient in need thereof. The infused cell is able to kill tumor cells in the recipient. Without wishing to be bound by any particular theory, the anti-tumor immunity response elicited by the RNA-engineered T cells may be an active or a passive immune response. The response may be part of an adoptive immunotherapy approach in which RNA-engineered T cells, such as CART19 cells.

The RNA-engineered T cells of the invention may be a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing RNA CAR to the cells or iii) cryopreservation of the cells.

Ex vivo procedures are well known in the art and are discussed more fully below. Briefly, cells are isolated from a mammal (preferably a human) and genetically modified (i.e., transduced or transfected in vitro) with an RNA CAR of the invention. The RNA-engineered cell can be administered to a mammalian recipient to provide a therapeutic benefit. The mammalian recipient may be a human and the RNA-engineered cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The RNA-engineered T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The amount of T cells administered at each dose may vary. For example, in one embodiment, the first administration comprises a relatively high dose, where subsequent doses comprise a relatively low dose. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the compositions of the invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide (Cytoxan), or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. For example, it is discovered herein that combined Cytoxan therapy with multiple infusions of RNA CAR T cells improves tumor clearance and survival.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Electroporated Autologous T Cells Expressing a Chimeric Antigen Receptor Mediates Regression of Human Disseminated Tumor Redirecting T lymphocyte antigen specificity by gene transfer can provide large numbers of tumor-reactive T lymphocytes for adoptive immunotherapy. However, there may be safety concerns associated with viral vector production in the clinical application of T cells expressing chimeric antigen receptors (CAR). It is believed that T lymphocytes can be gene modified by RNA electroporation without integration-associated safety concerns. To establish a safe platform for adoptive immunotherapy, the vector backbone for RNA in vitro transcription was optimized to achieve high-level transgene expression. CAR expression and function of RNA-electroporated T cells was detected up to a week after electroporation. The results presented herein demonstrate that multiple injections of RNA CAR-electroporated T cells mediated regression of large vascularized flank mesothelioma tumors in NOD/scid/γc(−/−) mice. Dramatic tumor reduction also occurred when the preexisting intraperitoneal human-derived tumors, which had been growing in vivo for >50 days, were treated by multiple injections of autologous human T cells electroporated with anti-mesothelin CAR mRNA.

The materials and methods employed in these experiments are now described.

Materials and Methods

Construction of In Vitro Transcription mRNA Vectors for CARs

Mesothelin (ss1) and CD19 specific CARs (Carpenito et al., 2009, Proc Natl Acad Sci USA 106:3360-5; Milone et al., 2009, Mol Ther 17:1453-64) were PCR amplified using the primers ss1F (cctaagcttaccgccatggccttaccagtgac; SEQ ID NO: 1), CD19F (cctaagcttaccgccatggccttaccagtgaccgcc; SEQ ID NO: 2) and zetaR (cctgcggccgc ttagcgagggggcagggcc; SEQ ID NO: 3). The PCR products were subcloned into pGEM.64A based vector by replacing GFP of pGEM-GFP.64A (Zhao et al., 2006, Mol Ther 13:151-9) to produce pGEM.64A based ss1 and CD19 vectors. To add 5' or 3' un-translational regions (UTR) and longer poly(A) to the constructs, the 64 poly(A) sequence in pGEM.ss1.bbz.64A or pGEM-CD19.bbz.64A vectors was replaced by two repeats of 3' UTR from beta globulin (2bgUTR) with or without 150 poly(A) sequences (150A) synthesized by PCR and further confirmed by sequencing. However, pGEM based vectors use ampicillin for selection, and this is not compatible with FDA regulatory guidance for GMP production and later clinical application. Thus, the CAR cDNA with UTRs were transferred to pDrive (Qiagen), which also uses kanamycin for selection. First, ss1.bbz.2bgUTR.150A or CD19.bbz.2bgUTR.150A was cut from the pGEM vector by Hind III and NdeI digestion (fill-in blunt end) and subcloned into pDrive by KpnI and NotI (fill-in blunt end). The insert with correct orientation was confirmed by sequencing to generate pDrive.ss1.bbz.2bgUTR.150A and pDrive.CD19.bbz.2bgUTR.150A. There were two steps to finalize the vectors for potential clinical use: 1) The ampicillin resistance gene in the pDrive vectors was deleted by double digestion with AhdI and BciVI; 2) Internal open reading frames in both CD19.bbz and ss1.bbz were deleted by mutagenesis PCR to produce pD-A.19.OF.2bg.150A (SEQ ID NO: 5) and pD-A.ss1.OF.2bg.150A (SEQ ID NO: 4).

RNA In Vitro Transcription

Three RNA IVT systems were used to compare RNA quality, quantity and cost: mMESSAGE mMACHINE® T7 Kit (Ambion, Inc) that uses the regular cap (RC) analog 7-methylGpppG; mMESSAGE mMACHINE® T7 Ultra (Ambion, Inc) that generates IVT RNA with Anti-Reverse Cap Analog (ARCA, 7-methyl(3'-O-methyl) GpppG)m7G (5')ppp(5')G), and the mScript™ RNA System (Epicentre, Madison, Wis.) that uses capping enzyme (CE) and 2'-O-Methyltransferase capping enzyme to generate Cap 1 IVT RNA (Epicentre). The RC is incorporated with a capping efficiency of up to 40%, while the ARCA increases capping efficacy up to 80% and the CE system can result in up to 100% capping efficiency. The various IVT RNA products were purified using an RNeasy Mini Kit (Qiagen, Inc., Valencia, Calif.) and purified RNA was eluted in RNase-free water at 1-2 mg/ml.

Preparation of Clinical Grade IVT RNA

To generate regulatory compliant plasmid DNA vectors containing the CAR open reading frames (ORF) without internal ORFs, DNA inserts for CAR cDNA with UTR and poly-A sequences were subcloned from the pGEM based vectors to pDrive vector that contains a kanamycin selection marker to generate pdrive.19bbz (for CD19− bbz) and pDrive.ss1bbz (for ss1-bbz) as described above. To eliminate potential aberrant proteins translated from internal ORFs nested inside the CAR ORF, all internal ORF in both CD19-bbz and ss1-bbz larger than 60 bp in size were mutated by mutagenesis PCR. Thus pD-A.19.OF and pD-A.ss1.OF that are free of internal ORFs were generated for 19-bbz and ss1-bbz respectively. Ss1-bbz RNA which contain parental ORFs were transcribed from a nucleotide sequence comprising SEQ ID NO: 6. Internal ORF free ss1-bbz constructs were transcribed from a nucleotide sequence comprising SEQ ID NO: 8. 19-bbz RNA which contain parental ORFs were transcribed from a nucleotide sequence comprising SEQ ID NO: 7. Internal ORF free CD19-bbz constructs were transcribed from a nucleotide sequence comprising SEQ ID NO: 9.

T-Cell Culture

Anonymous healthy donors donated lymphocytes, and T cells were purified by elutriation. In some experiments, cryopreserved T cells and tumor cells from the same patient were used. "Patient 108" had malignant mesothelioma. As part of an earlier clinical trial, this patient underwent leukapheresis and had tumor cells generated from his malignant pleural effusion. T cells were activated by addition of CD3/CD28 beads (Invitrogen) and a single cycle of stimulation as described (Levine et al., 1997, J Immunol 159: 5921-30). For the experiment shown in FIGS. 5A, 5B, and 5C, patient 108 T cells were stimulated with irradiated artificial antigen-presenting cells expressing 4-1BBL and loaded with anti-CD3 monoclonal antibody (mAb) OKT3 and CD28 mAb 9.3 as described (Suhoski et al., 2007, Mol Ther 15:981-8). T cells were maintained at a density of $0.8 \times 10^6$ to $1 \times 10^6$ cells/mL in RPMI 1640 with 10% FCS and 1% penicillin-streptomycin (R10) after bead stimulation.

RNA Electroporation of T Cells

On day 10 of culture, the activated T cells were collected and electroporated. Two electroporation systems were used: BTX CM830 (Harvard Apparatus BTX, Holliston, Mass., USA), and Maxcyte (Maxcyte Inc, Rockville, Md., USA). For electroporation using BTX EM830, the stimulated T cells subjected to electroporation were washed three times with OPTI-MEM (Invitrogen) and resuspended in OPTI-MEM at the final concentration of $1-3 \times 10^8$/ml. Subsequently, 0.1 to 0.2 ml of the cells was mixed with 10 μg/0.1 ml T cells of IVT RNA (or as indicated) and electroporated in a 2-mm cuvette (Harvard Apparatus BTX, Holliston, Mass., USA). For electroporation using Maxcyte, the instruction manual was followed using OC-400 processing chamber (Maxcyte Inc, Rockville, Md., USA) with integrated programs.

CAR Detection on Electroporated T Cells

Cells were washed and suspended in FACs buffer (PBS plus 0.1% sodium azide and 0.4% BSA). Biotin-labeled polyclonal goat anti-mouse F(ab)2 antibodies (anti-Fab, Jackson Immunoresearch, West Grove, Pa.) were added to the tube and the cells were incubated at 4° C. for 25 minutes and washed twice. The cells were then stained with phycoerythrin-labeled streptavidin (BD Pharmingen, San Diego, Calif.).

ELISA

Target cells were washed and suspended at $10^6$ cells/mL in R10. One hundred thousand of each target cell type were added to each of 2 wells of a 96 well round bottom plate (Corning). Effector T cell cultures were washed and suspended at $10^6$ cells/mL in R10. One hundred thousand effector T cells were combined with target cells in the indicated wells of the 96 well plate. In addition, wells containing T cells alone were prepared. The plates were incubated at 37° C. for 18 to 20 hours. After the incubation, supernatant was harvested and subjected to an ELISA assay using standard methods (Pierce, Rockford, Ill.).

CD107a Staining

Cells were plated at an E:T of 1:1 ($10^5$ effectors: $10^5$ targets) in 160 µl of complete RPMI medium in a 96 well plate. 20 µl of phycoerythrin-labeled anti-CD107a Ab (BD Pharmingen, San Diego, Calif.) was added and the plate was incubated at 37° C. for 1 hour before adding Golgi Stop and incubating for another 2.5 hours. After 2.5 hours 10 FITC-anti-CD8 and APC-anti-CD3 was added and incubated at 37° C. for 30 min. After incubation, the samples were washed once with FACS buffer. Flow cytometry acquisition was performed with a BD FacsCalibur (BD Biosciences), and analysis was performed with FlowJo (Treestar Inc, Ashland, Oreg.).

Flow CTL

A slightly modified version of a flow cytometry cytotoxicity assay was used (Cao et al., 2010 Cytometry Part A 77:534-45). In this assay, the cytotoxicity of target cells is measured by comparing survival of target cells relative to the survival of negative control cells. The negative control cells and the target cells are combined in the same tube with effector T cells. Target cells were prepared by transducing parental K562 cells with human CD19 or mesothelin as described (Carpenito et al., 2009, Proc Natl Acad Sci USA 106:3360-5; Milone et al., 2009, Mol Ther 17:1453-64). In the experiments, the cytolytic effects of CD19-CAR T cells and Meso-CAR T cells were tested using a mixture of both target cells (K562-CD19 or K562-meso). K562-meso were suspended in R10 medium at a concentration of $1.5 \times 10^6$ cells/mL, and the fluorescent dye CellTracker™ Orange CMRA (Invitrogen) was added at a concentration of 5 µM. The cells were mixed and then incubated at 37° C. for 30 minutes. The cells were then washed and suspended in R10. Next, the K562-meso were incubated at 37° C. for 60 min. The cells were then washed twice and suspended in R10. K562-CD19 were suspended in PBS+0.1% BSA at $1 \times 10^6$ cells/mL. The fluorescent dye carboxyfluorescein diacetate succinimidyl ester (CFSE) (Invitrogen) was added to this cell suspension at a concentration of 1 µM. The cells were incubated for 10 min at 37° C. After the incubation, the labeling reaction was stopped by adding a volume of FBS that was equal to the volume of cell suspension and the cells were incubated for 2 min at RT. The cells were washed and suspended in R10. Cultures were set up 96 well culture plate in duplicate at the following T cell:target cell ratios: 10:1, 3:1, and 1:1. The target cells were always 10,000 K562-meso in 0.1 ml. Each culture also contained $10^4$ K562-CD19 negative control cells. In addition, cultures were set up that contained only K562-CD19 plus K562-meso cells. The cultures were incubated for 4 hrs at 37° C. Immediately after the incubation, 7AAD (7-aminoactinomycin D) (BD Pharmingen) was added as recommended by the manufacturer, and flow cytometry acquisition was performed with a BD Calibur (BD Biosciences). Analysis was gated on 7AAD-negative (live) cells, and the percentages of live K562-CD19 and live K562-meso cells were determined for each T cell+target cell culture. The percent survival of K562-meso was determined by dividing the percent live K562-meso by the percent live K562-CD19 control cells. The corrected percent survival of K562-meso was calculated by dividing the percent survival of K562-meso in each T cell+target cell culture by the ratio of the percent K562-meso target cells:percent K562-meso negative control cells in tubes containing only K562-meso target cells and K562-CD19 control cells without any effector T cells. This correction was necessary to account for variation in the starting cell numbers and for spontaneous target cell death. Cytotoxicity was calculated as the percent cytotoxicity of K562-meso=100−corrected percent survival of K562-meso. For all effector:target ratios, the cytotoxicity was determined in duplicate and the results were averaged.

Mouse Xenograft Studies

Studies were performed as previously described with certain modifications (Teachey et al., 2006, Blood 107:1149-55; Teachey et al., 2008, Blood 112:2020-3). Briefly, 6-10 week old NOD-SCID-γc−/− (NSG) mice were obtained from the Jackson Laboratory (Bar Harbor, Me.) or bred in house under an approved institutional animal care and use committee (IACUC) protocol and maintained under pathogen-free conditions. The derivation of M108 human mesothelioma from patient 108 was and used to establish flank tumors using $5 \times 10^6$ cells as previously described (Carpenito et al., 2009, Proc Natl Acad Sci USA 106:3360-5). M108 tumor cells were also engineered with a lentiviral vector to express firefly luciferase, yielding the M108-Luc cell line. Animals were injected intraperitoneally (IP) with $8 \times 10^6$ viable M108-Luc. Tumor growth was monitored by size using caliper measurements for flank tumors, and by bioluminescent imaging and body weight for IP tumors.

Bioluminescence Imaging (BLI)

Tumor growth was monitored by BLI. Anesthetized mice were imaged using a Xenogen Spectrum system and Living Image v3.2 software. Mice were given an IP injection of 150 mg/kg body weight D-luciferin (Caliper Life Sciences, Hopkinton, Mass.) suspended in sterile PBS at a concentration of 15 mg/mL (100 µL luciferin solution/10 g mouse body weight). Previous titration of M108-Luc indicated the time to peak of photon emission to be five minutes, with peak emission lasting for 6-10 minutes. Each animal was imaged alone (for photon quantitation) or in groups of up to 5 mice (for display purposes) in the anterior-posterior prone position at the same relative time point after luciferin injection (6 minutes). Data were collected until the mid range of the linear scale was reached (600 to 60000 counts) or maximal exposure settings reached (f/stop 1, large binning and 1-2 seconds), and then converted to photons/second/cm2/steradian to normalize each image for exposure time, f/stop, binning and animal size. For anatomic localization, a pseudocolor map representing light intensity was superimposed over the grayscale body-surface reference image. For data display purposes, mice without luciferase containing cells were imaged at maximal settings and a mean value of $3.6 \times 10^5$ p/s/cm$^2$/sr was obtained.

Statistical Considerations

Analysis was performed with STATA version 10 (StataCorp) or Prism 4 (GraphPad Software). In vitro data represent means of duplicates, and comparisons of means were made via Mann-Whitney test. For comparison among multiple groups, Kruskal-Wallis analysis was performed with Dunn multiple comparison tests to compare individual groups. Survival curves were compared using the log-rank test with a Bonferroni correction for comparing multiple curves.

The results of the experiments are now described.

Electroporation of RNA CARs Mediates Variable Expression in Stimulated T Cells

Figure 6:
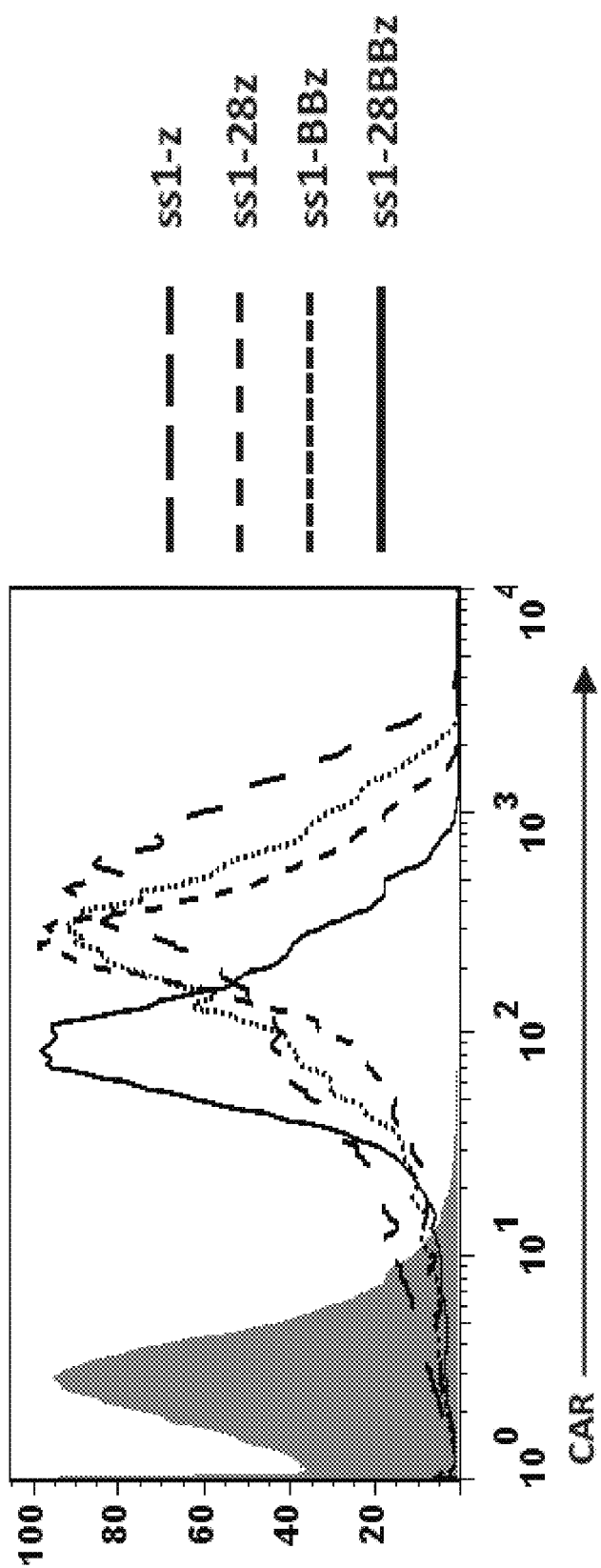
FIG. 6 is an image depicting varying levels of CAR transgene expression on T cells. Activated T cells were electroporated with RNA encoding anti-mesothelin scFv ss1 CARS with the indicated signaling moieties, and flow cytometry used to measure surface expression 19 hours after electroporation. T cells electroporated without RNA were used as negative control. Data are representative of at least 2 independent experiments.

It has been previously reported that anti-mesothelin ss1 scFv CARs with combinations of CD3ζ, CD28, and 4-1BB activation domains are highly and stably expressed in T cells when introduced using lentiviral vector technology (Carpenito et al., 2009, Proc Natl Acad Sci USA 106:3360-5). Human T cells were activated for 10 days as previously described (Levine et al., 1997, J Immunol 159:5921-30), and as the cells returned to a near resting state, they were electroporated with RNA encoding the ss1 scFv with the previously described combinations of signaling moieties. The level of transgene expression was found to be not uniform (FIG. 6), as T cells electroporated with CAR bearing CD3ζ alone (ss1-z) showed the highest transgene expression, followed by nearly equivalent levels of ss1-28z (CD28+CD3ζ) and ss1-bbz (4-1BB+CD3ζ) expression. Because "second-generation" CARs containing costimulation domains seem superior in several preclinical and early-stage clinical trials when expressed with viral vector systems (Carpenito et al., 2009, Proc Natl Acad Sci USA 106:3360-5; Milone et al., 2009, Mol Ther 17:1453-64; Zhao et al., 2009, J Immunol 183:5563-74; Zhong et al., 2009, Mol Ther 18:413-20), it was decided not to optimize expression of the "first-generation" ss1-z CAR. Rather, the second-generation ss1-bbz and CD19-bbz CARs were chosen for further optimization using RNA electroporation because they are being tested in a clinical trial using lentiviral vector technology.

Figure 1A:
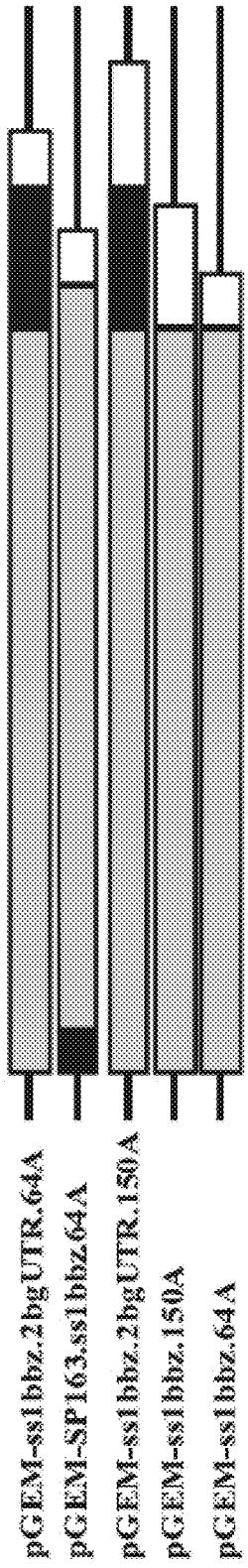
FIGS. 1A and 1B are images demonstrating that optimization of mRNA by modification of the UTRs confers high-level expression of CARs in electroporated T cells.
Figure 1B:
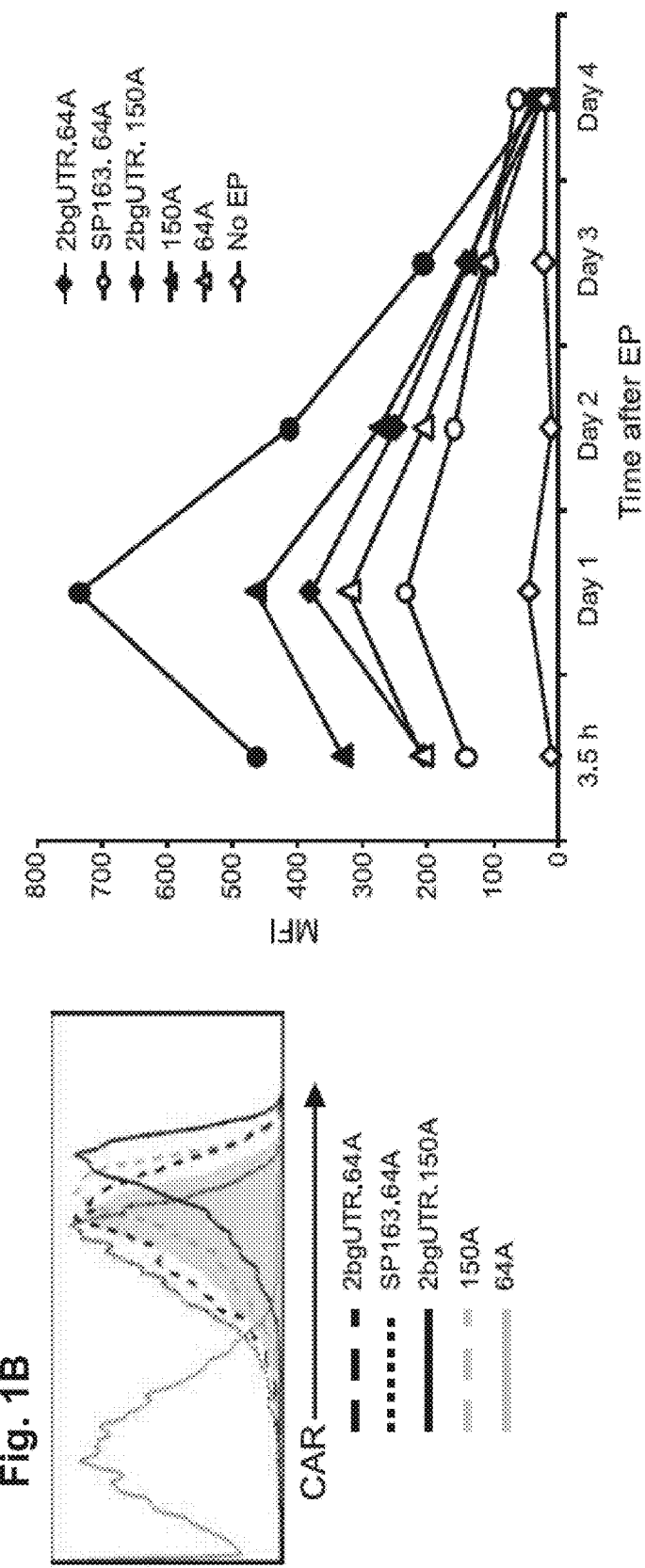

Optimization of RNA Constructs Improves Transgene Expression in Stimulated T Cells Structural modification of noncoding regions by incorporation of two repeats of 3' untranslated regions (UTR) from β-globulin and longer poly(A) sequences has been shown to enhance RNA stability, translational efficiency, and the function of RNA-transfected dendritic cells (Holtkamp et al., 2006, Blood 108:4009-17). However, these strategies have not been systematically evaluated in RNA-electroporated T cells. To test if this approach applies to human T lymphocytes, the IVT vector (pGEM-ss1bbz.64A) was modified by adding 5'UTR (SP163) or 3'UTR [two repeats of 3'UTR derived from human β-globin (2bgUTR) or a prolonged poly(A) (150A) sequence as shown in FIG. 1A]. The SP163 translational enhancer is derived from the 5'UTR of the vascular endothelial growth factor gene and is reported to increase expression levels 2- to 5-fold compared with promoter alone (Stein et al., 1998, Mol Cell Biol 18:3112-9). RNA made from these constructs was electroporated into stimulated T cells. As shown in FIG. 1B, compared with the basic IVT construct containing a 64-poly(A) tract, addition of 3'UTR from β-globulin (2bgUTR) and longer poly(A) (150A) tailing enhanced the transgene expression, especially when combined (2bgUTR.150A). In contrast, incorporation of the SP163 sequence at the 5' end of ss1-bbz repressed transgene expression, which might be due to reduced capping efficiency when the SP163 sequence was added.

Optimization of the 5' Cap Structure Enhances the Expression and Function of CARs in Electroporated T Cells The 5' cap located at the end of mRNA molecule consists of a guanine nucleotide connected to the mRNA via a 5' to 5' triphosphate linkage. Several cap structures have been described, including caps 0 and 1 (Banerjee, 1980, Microbiol Rev 44:175-205). Several methods have been used to incorporate the 5' cap structure onto the transgene and poly(A) tail construct. Commercially available systems incorporate cap 0 or 1 using cotranscriptional or enzymatic approaches to produce capped mRNA. This process is important to optimize to enhance translational efficiency and because of the considerable expense of the various capping systems. RNA made using the different capping systems was electroporated into stimulated T cells, and the transgene expression was monitored by flow cytometry (FIGS. 2A and 2B). The results showed that the transgene expression of T cells electroporated with RNA capped by anti-reverse cap analogue (ARCA) was 3-fold higher than regular cap (RC) analogue capped RNA at 4 hours. The transgene persistence of ARCA capped RNA was also improved, as at day 5 after electroporation >50% of the T cells still expressed the CAR as shown in FIG. 2B.

Next, enzymatic addition of caps 0 and 1 to nonenzymatic addition of the ARCA was compared. The potential advantage of using the capping enzyme (CE) system is that this approach includes CE and mScript 2'-O-methyltransferase that work together to produce the cap1 structure, which is very similar to ARCA and provides superior translation efficiency in many in vivo systems. To evaluate the efficiency of cap 0 or 1 RNA encoding ss1-bbz, human T cells were electroporated with RNA made by ARCA, CE, cap1 CEs, or CEs plus additional poly(A). As shown in FIG. 2C, the CAR expression using cap1 RNA electroporation was equivalent to ARCA IVT mRNA. The transgene expression was further enhanced by incorporation of the longer poly(A) tail, consistent with the results in FIGS. 1A and 1B.

Figure 7:
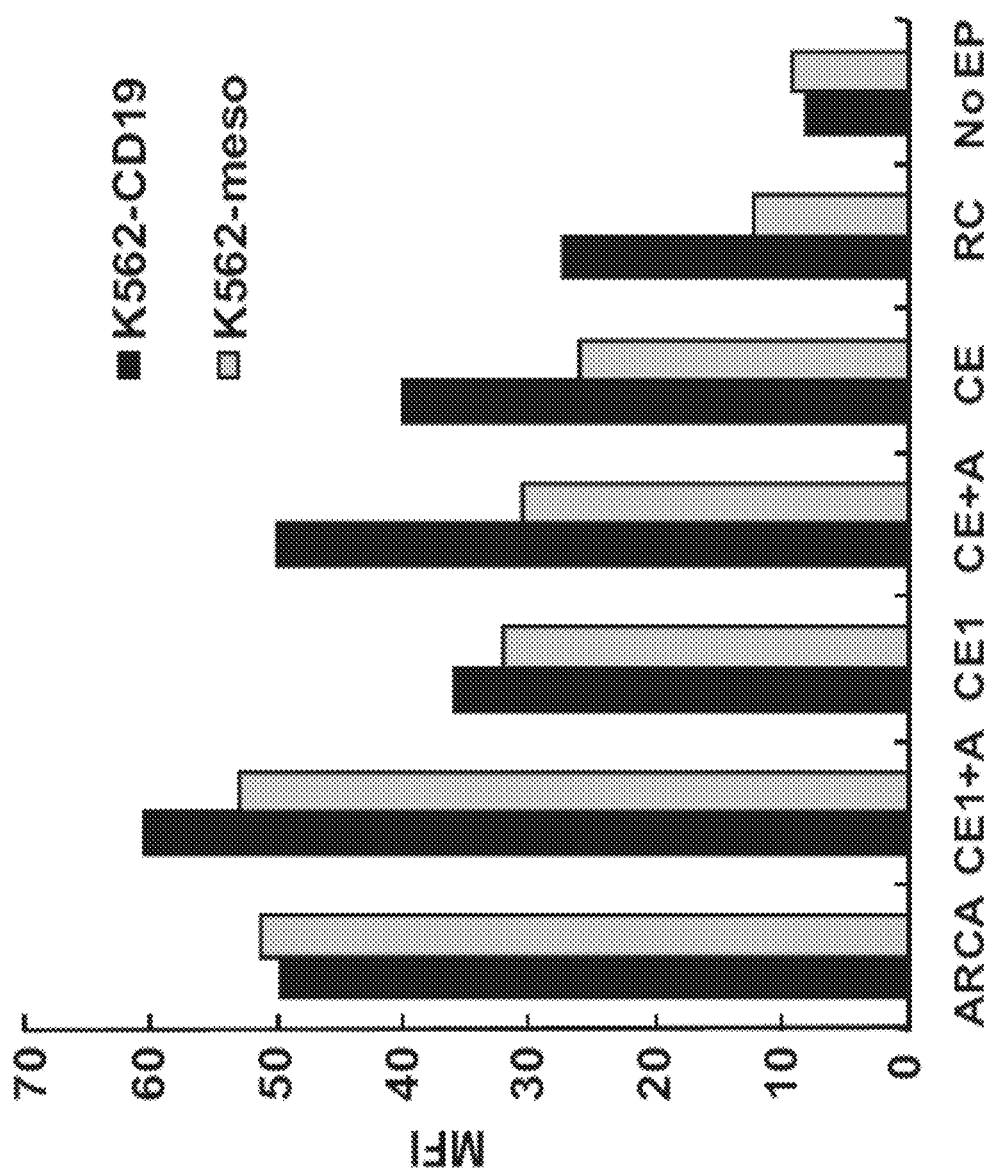
FIG. 7 is an image depicting T cells electroporated with ss1 RNA CARs generated by different methods were co-cultured 1:1 with targets expressing mesothelin (K562-meso) or control targets (K562-CD19) at day 1 post electroporation and cultured for 48 hours before the surface transgene expression (MFI) was measured by flow cytometry. Abbreviations: ARCA, anti-reverse capping analog.

One potential functional advantage of optimized IVT RNA is that CAR expression could be sustained, as translation of additional CAR could lead to more persistent expression and overcome downregulation induced by target recognition or homeostatic expansion. Activated T cells were electroporated with various RNA preparations encoding ss1-bbz, and then cocultured with K562-meso or control K562-CD19 target cells for 2 days (FIG. 7). T cells electroporated with ARCA and CE1 or CE1+A capped ss1-bbz RNA could still maintain their transgene expression after being stimulated with the K562-meso cell line compared with the same T cells cocultured with control target cells. In contrast, T cells electroporated with ss1-bbz RNA capped by the RC analogue did not have detectable CAR on the surface after cocultured with antigen-bearing target.

Based on the above results and other data, it can be concluded that RNA capped with ARCA or with cap1 and a long poly(A) tail is the best RNA production system among the RNAs tested. For large-scale GMP production of IVT RNA, when the production cost is also considered, cap1 is preferred.

In Vitro Function of Optimized IVT RNA CARs

Figure 3A:
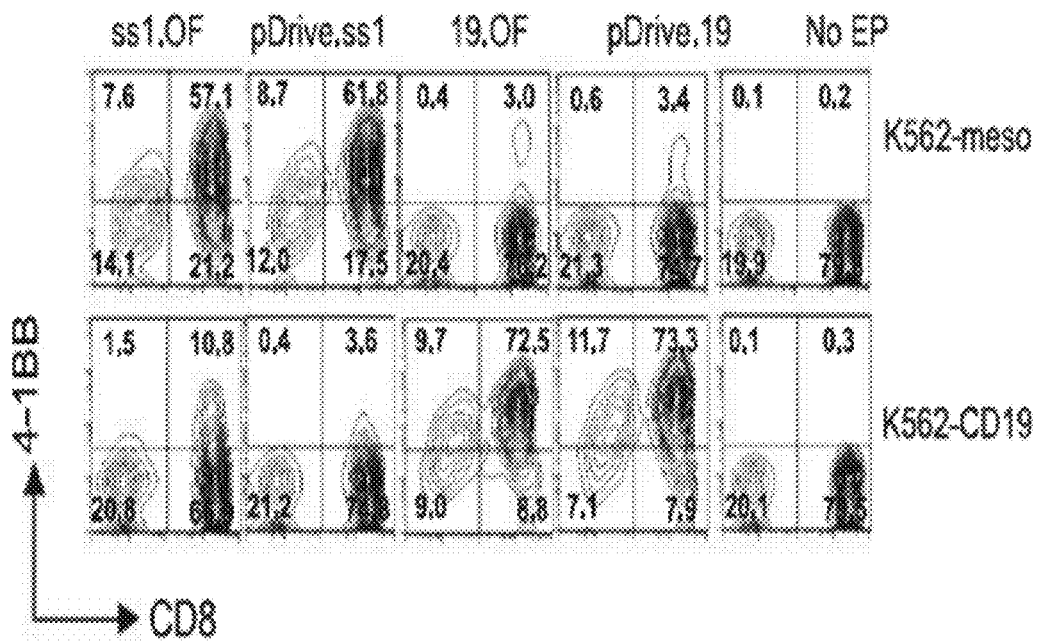
FIGS. 3A, 3B, 3C, and 3D are images demonstrating sustained RNA CAR expression and function using RNA generated from regulatory-compliant vector constructs. Four hours after electroporation, the T cells electroporated with the indicated RNA were cocultured with K562-meso or K562-CD19 for 16 h.
Figure 3B:
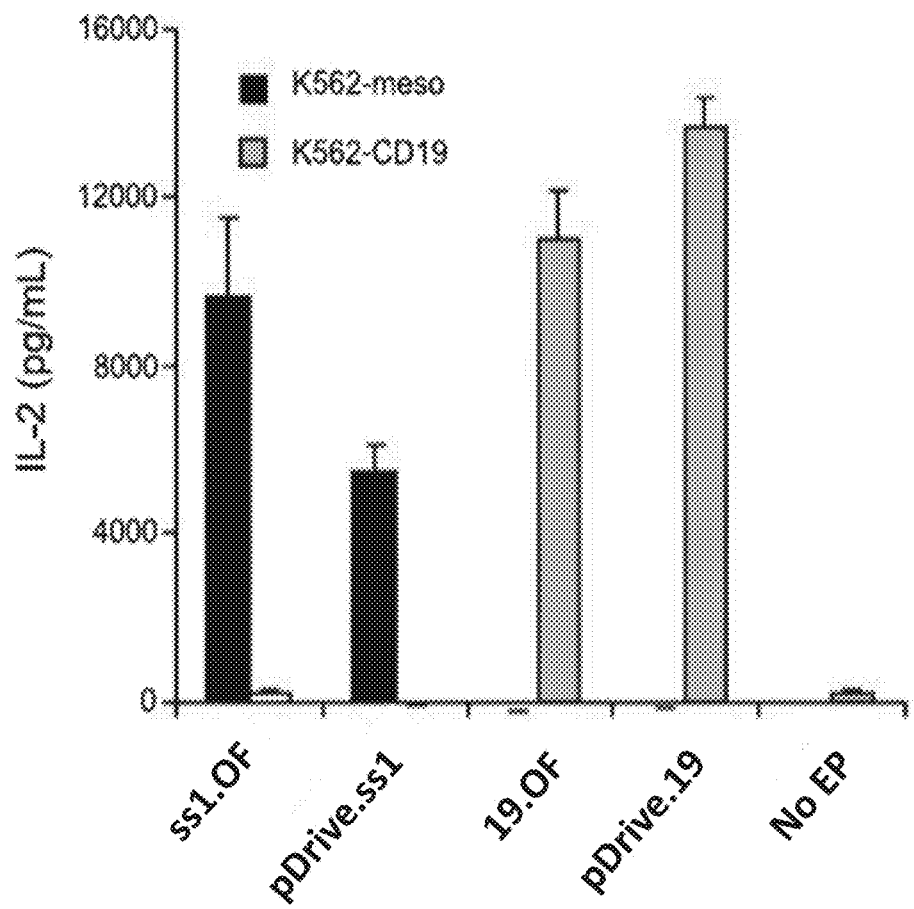
Figure 3C:
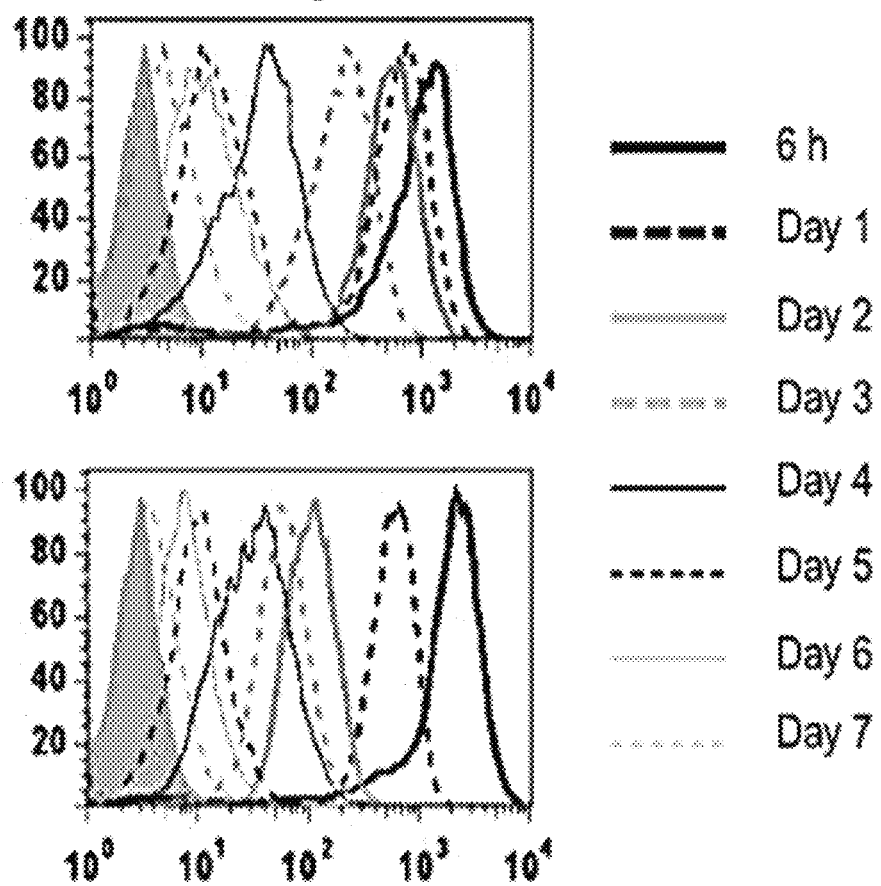

RNAs prepared from both plasmids bearing parental or internal ORF-free CAR sequences were electroporated into T cells, and it was found that the transgene expression from the RNAs with internal ORF-free electroporated T cells was equivalent to the T cells electroporated with RNAs with parental sequences (FIG. 8) at 20 hours after electroporation. However, substantial prolongation of CAR expression was observed in activated T cells electroporated with clinical-grade RNA generated from internal ORF-free pD-A.ss1.OF or pD-A.19.OF RNAs using the CE system that incorporated both cap1 and prolonged poly(A) into the IVT RNAs (FIGS. 3A, 3B, 3C, and 3D). Transgene expression of the optimized IVT RNA could be detected as long as 7 days after RNA electroporation for both meso and CD19 RNA CARs as shown in FIG. 3C.

Figure 3D:
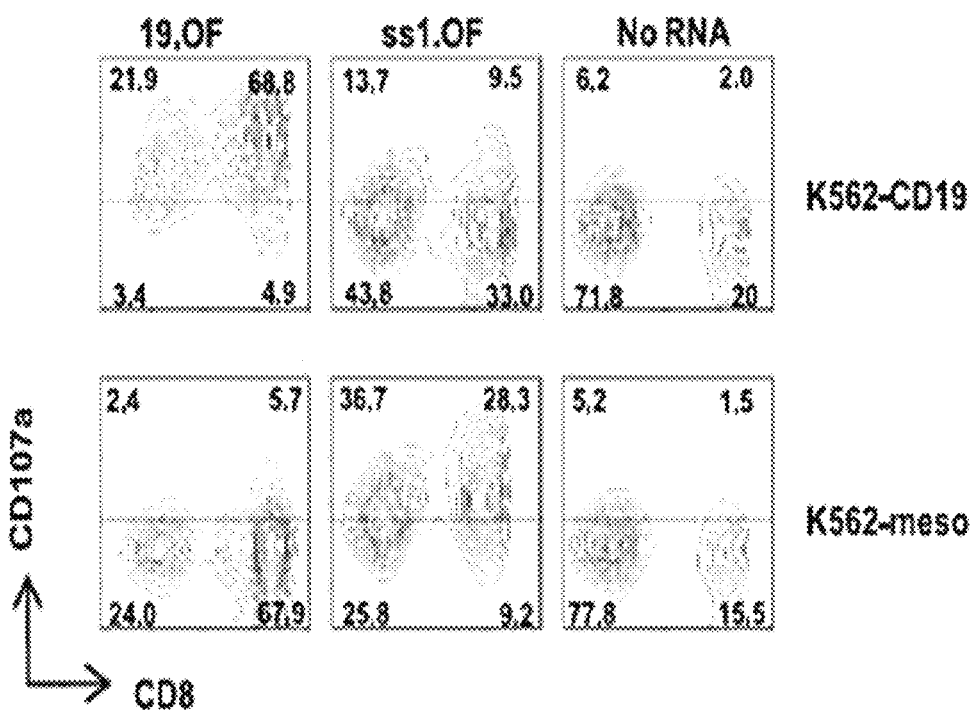

Previous studies have shown that 4-1BB is upregulated on $CD8^+$ T cells after T-cell receptor stimulation (Wolff et al., 2007, Blood 110:201-10). Bulk T cells electroporated with ss1-bbz or CD19-bbz RNA were incubated with target cells expressing either mesothelin or CD19, and found robust upregulation of 4-1BB, particularly on $CD8^+$ T cells, which was target specific (FIG. 3A). The T cells expressing RNA CARs also secreted substantial amounts of interleukin-2 (IL-2) and translocated CD107a on target-specific recognition (FIGS. 3B and 3D). Finally, in a flow-based lytic assay, it was found that both CD19 (19.OF) and ss1 (ss1.OF) CAR RNA-electroporated T cells could specifically lyse target cells efficiently (FIG. 9).

RNA-Electroporated T Cells Mediate Regression of Human Disseminated Mesothelioma Xenografts A pilot experiment was first conducted to evaluate the therapeutic potential of T cells expressing optimized RNA CARs in mice bearing large pre-established tumors. Mesothelin-positive tumors were established in NSG mice as previously reported (Carpenito et al., 2009, Proc Natl Acad Sci USA 106:3360-5). Sixty-six days after tumor inoculation, $10 \times 10^6$ to $15 \times 10^6$ ss1-bbz RNA CAR-electroporated T cells from a healthy donor were injected intratumorally, twice weekly for 2 weeks. The biweekly administration schedule was based on the in vitro expression data shown in FIGS. 3A, 3B, 3C, and 3D. As seen in FIG. 4A, the tumors regressed in the mice treated with ss1 RNA-electroporated T cells, whereas progressive tumor growth was observed in the control group of mice. At the time the mice were sacrificed on day 98, tumor size was substantially smaller in all of the mice treated with electroporated T cells than that of the mice treated with saline (FIG. 10). These results indicate therapeutic potential of multiple injections of RNA-engineered T cells; however, they are not as potent in the same mouse model using lentiviral transduced T cells, where two intratumoral injections of T cells were able to cure most mice (Carpenito et al., 2009, Proc Natl Acad Sci USA 106:3360-5).

Figure 4B:
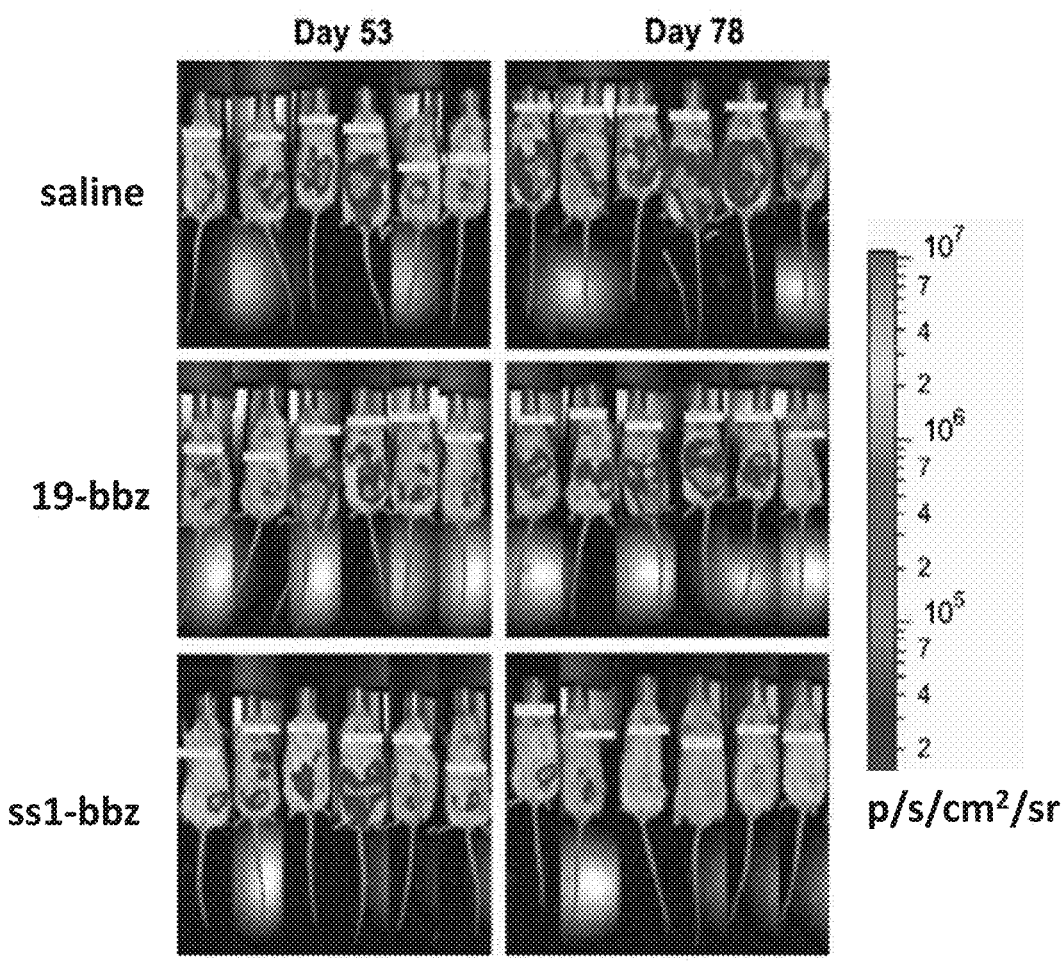
Figure 4C:
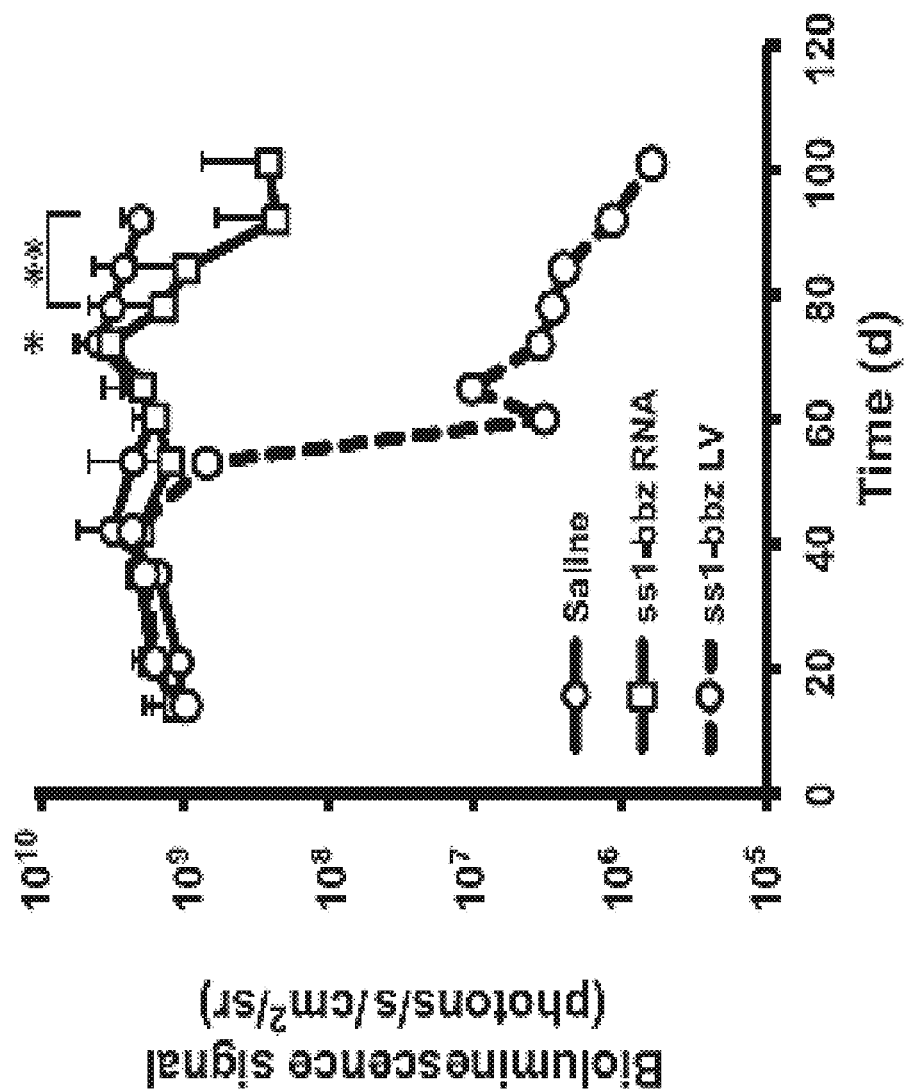

The M108-Luc model was developed to test if RNA CAR-electroporated T cells are capable of treating mice bearing large disseminated tumors. M108 parental cells were stably transduced with firefly luciferase to allow for bioluminescence imaging (BLI), and in preliminary experiments, it was found that NSG mice develop widely disseminated disease with progressive ascites and that all mice die or become moribund by day 100. NSG mice (n=18) were injected with M108-Luc, and they were randomized into three i.p. treatment groups. On day 58 day after tumor injection, when all mice had large vascularized tumors with ascites and metastatic nodules lining the peritoneal cavity, ss1-bbz RNA CAR-electroporated T cells from a healthy donor were injected (i.p.) into the mice, twice weekly, for 2 weeks. As a control for CAR specificity, a group of mice was injected with CD19-bbz RNA-engineered T cells, and another group was treated with saline. Tumor burden in the ss1-bbz RNA CAR group progressively decreased from baseline on day 53. Furthermore, on day 78 after tumor inoculation, the tumor growth in the ss1-bbz RNA-engineered T-cell-treated group was significantly repressed (P<0.01) compared with both saline or CD19-bbz RNA T-cell-treated groups (FIG. 4B). In a side by side experiment, a mouse treated with ss1-bbz CAR T cells expressed using a lentiviral vector exhibited a more robust treatment effect (FIG. 4C), similar to previously published data (Carpenito et al., 2009, Proc Natl Acad Sci USA 106:3360-5). However, the ss1-bbz RNA-engineered T-cell-treated group had a survival advantage and a significant slowing of tumor growth between days 72 and 92, at which point all of the control mice died from tumor progression (FIG. 4C).

Figure 5A:
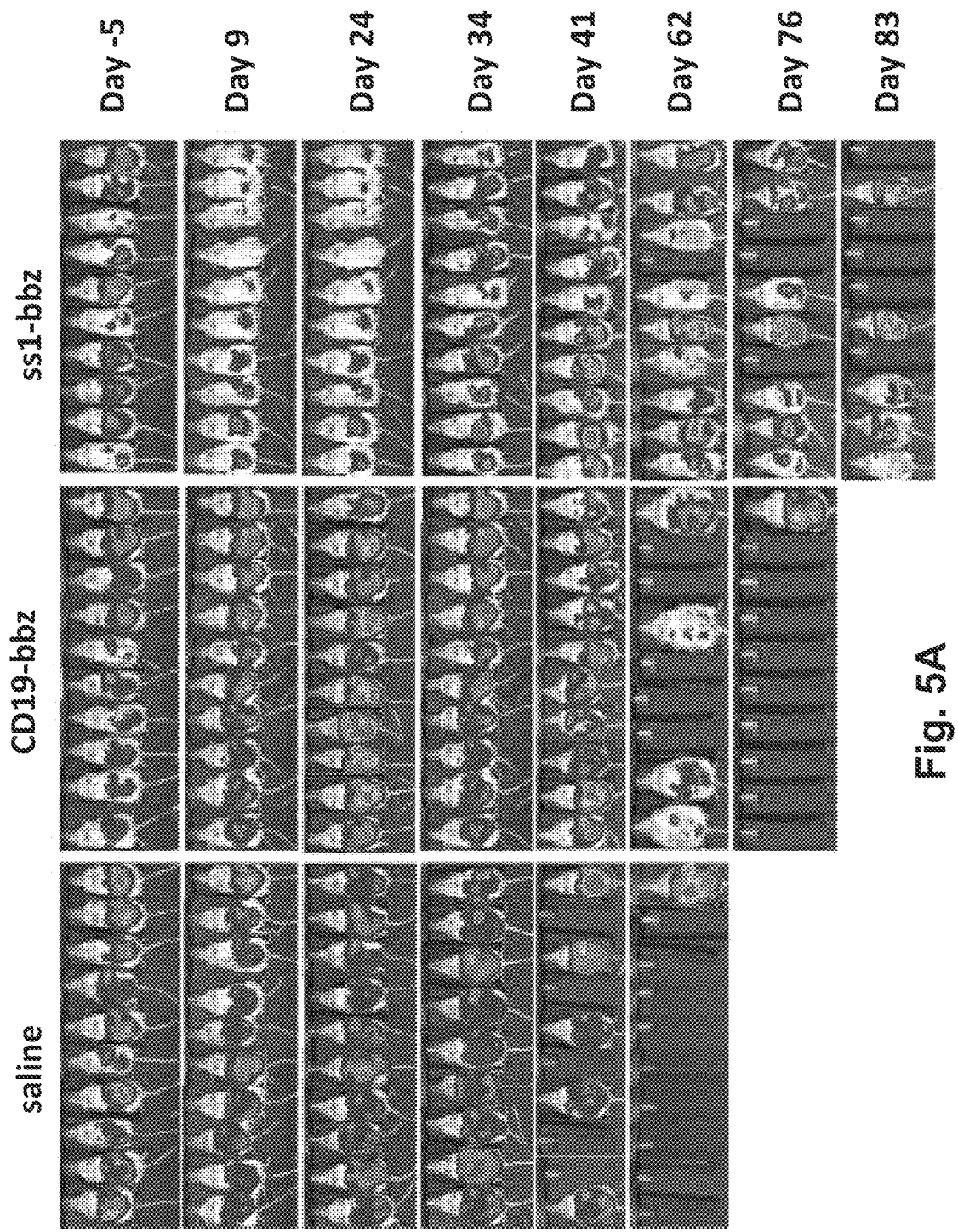

RNA CAR-Electroporated Autologous T Cells Mediate Regression of Disseminated Mesothelioma The above studies indicate that biweekly injections of RNA-engineered T cells can control advanced flank and i.p. tumors, and that the inhibition is dependent on the CAR specificity, as T cells expressing the CD19 RNA CAR were not effective. However, the T cells in those experiments were obtained from healthy donors and were allogeneic to the tumor. Because allogeneic antitumor effects were observed with repeated long-term administration of RNA CAR T cells, autologous peripheral blood mononuclear cells from the patient from whom the M108 tumor was derived were used. T cells were stimulated and electroporated using GMP grade RNA. Thirty NSG mice were randomized into three i.p. treatment groups, as depicted in the diagram in FIG. 11. Mice were inoculated with M108-Luc (i.p.) on day 0 and treated with ss1-bbz or CD19– bbz RNA CAR T cells or with saline control, and tumor burden was monitored by serial BLI and body weight as indicated. Therapy was started on day 56 when the tumor was advanced based on the finding of ascites on physical examination and high BLI signals. Tumor burden was dramatically reduced in the group treated with T cells electroporated with ss1-bbz RNA CAR T cells, whereas the tumor continued to grow in the control mice treated with either CD19-bbz RNA CAR T cells or saline (FIGS. 5A and 5C). Even in this setting, where the T cells are autologous to the tumor, there was still a modest CD19 CAR treatment effect, which may be due to the RNA backbone, as this is unlikely to be related to the CD19 scFv CAR given that there were no B cells in these mice. However, after the first six doses of T cells, imaging revealed a lower mean change tumor bioluminescence in the ss1 CAR mice (39%) compared with both the CD19 CAR (244%) and the saline mice (237%; P<0.001). The 50% median survival after T-cell injection was significantly (P<0.05) greater in the ss1 CAR mice (73 days) compared with the CD19 CAR (62 days) and saline mice (36 days; FIG. 5B). After the first six doses were given, the mean change in total body weight was lower in the ss1 RNA CAR mice (1.62 g) compared with both the CD19 CAR (6.21 g) and the saline mice (11.4 g; P<0.001; FIG. 5C). Although disease stability and even "cures" by imaging in some of the ss1 CAR mice was observed, tumor eventually recurred. Despite giving an additional eight doses of treatment, tumor progression was observed in the ss1 CAR mice. Thus, repeated injections of ss1-bbz RNA CAR T cells can provide a survival benefit for advanced disseminated tumors. The mechanism for tumor recurrence in spite of continued therapy is under investigation.

Multiple Injections of Activated T Cells Expressing Electroporated RNA CARs

The goal of these experiments was to determine the therapeutic potential of activated T cells expressing electroporated RNA CARs. The results presented herein show that mRNA CARs provide a platform that is expected to be safer and more economical than retroviral or lentiviral vectors for the evaluation of new targets. In the event of toxicity, injections of RNA CAR T cells can be terminated, and the toxicity would be expected to rapidly abate. However, the RNA CAR T cells have a substantial treatment potential, especially in compartmentalized tumors such as mesothelioma. RNA CAR T cells are expected to complement therapies currently being developed with retroviral and lentiviral CARs.

The approach was to first optimize RNA expression and then test a multiple dosing strategy in robust tumor models. This is the first report indicating that retargeted T cells can have potent in vivo antitumor effects without the use of an integrating vector system. Using optimized IVT mRNA, the results presented herein show that RNA CAR T cells have potent antitumor effects on advanced flank and intraperitoneal tumors. Further, these studies are the first to show that autologous T cells obtained from a patient with advanced cancer can be engineered and shown to control metastatic tumor in robust preclinical models.

It has previously been shown that RNA electroporation can modify T-cell function in vitro (Smits et al., 2004, Leukemia 18:1898-902; Schaft et al., 2006, Cancer Immunol Immunother 55:1132-41; Zhao et al., 2006, Mol Ther 13:151-9). Mitchell and colleagues (Mitchell et al., 2008, Hum Gene Ther 19:511-21) reported that T cells can be functionally modified by RNA transfection of the chemokine receptor CXCR2 to migrate efficiently toward a variety of CXCR2-specific chemokines in vitro and in vivo. Yoon and colleagues (Yoon et al., 2009, Cancer Gene Ther 16:489-97) recently showed that adoptive transfer of Her2/neu RNA CAR-electroporated T cells in the SKOV3 xenograft model led to a decreased rate of tumor growth compared with transfer of mock-transfected T cells. A recent report showed the feasibility of mRNA transfection of a CD19 chimeric receptor into a natural killer cell line, but without a preclinical model or demonstration of in vivo effect (Li et al., 2010, Cancer Gene Ther 17:147-54). However, none of these reports demonstrate in vivo regression of large advanced tumors and survival extension using RNA-electroporated T cells.

There are a variety of nonintegrating approaches to engineer T cells (June et al., 2009, Nat Rev Immunol 9:704-16). A temporary expression approach toward CAR immunotherapy, such as mRNA transfection, runs counter to the common efforts of the field. However, the improving technology for RNA transfection may compliment the use of CARs that are stably expressed by integrating viral vector or transposon systems. By systematic comparison of 3'UTR and 5'UTR, incorporation of longer poly(A) tails, efficient capping of RNA, and removal of internal ORFs we were able to achieve high-level and longer expression of RNA CARs in electroporated T cells.

The prevailing paradigm in the adoptive transfer field is that long-term persistence of the cells within the patient is key to efficacy (June, 2007, J Clin Invest 117:1466-76; Rosenberg et al., 2008, Nat Rev Cancer 8:299-308). However, it is being increasingly realized that transferred cells can lose their ability to function within the tumor microenvironment rather quickly (Teague et al., 2006, Nat Med 12:335-41). The data presented herein, suggest that it may be possible to give multiple, more frequent injections of T cells that only temporarily express the transgenes of choice, avoiding the accumulation of CAR T cells that have become tolerized, and therefore achieve antitumor efficacy with an improved safety profile. Alternatively, the improving technology for RNA transfection may complement the use of CARs that are stably expressed by integrating viral vector or transposon systems.

Several adverse events have been observed and others are theoretically possible with CAR T-cell therapy. Two deaths have recently been reported following treatment with retrovirally modified CAR T cells, and the early toxic events have been related to systemic effects from cytokine release (Brentjens et al., 2010, Mol Ther 18:666-8; Morgan et al., 2010, Mol Ther 18:843-51). As a consequence of these clinical events, recent editorials have discussed the need for safer CARs (Heslop, 2010, Mol Ther 18:661-2; Buning et al., 2010, Hum Gene Ther 21:1039-42). Other toxicities encountered with stably transduced CAR T cells have been on-target, off-organ effects such as the depletion of normal B cells following CD19 CAR therapy, or the induction of hepatic toxicity following carbonic anhydrase IX therapy (Lamers et al., 2006, J Clin Oncol 24:e20-2). Without wishing to be bound by any particular theory, it is believed that repeated administration of RNA CARs would be required to elicit this form of toxicity, and that the toxicity would resolve following discontinuation of RNA CAR T-cell infusions. Finally, concerns over the lentiviral or retroviral introduction of CARs into CTLs include the known risk of malignant transformation from insertional mutagenesis (Nienhuis et al., 2006, Mol Ther 13:1031-49; Bushman et al., 2007, J Clin Invest 117:2083-6). As there is no integration into the host cell genome and the CAR expression is self-limited, these concerns are circumvented by mRNA transfection.

Without wishing to be bound by any particular theory, it is believed that the primary potential limitation of CAR therapy is the relatively short persistence of RNA CARs. This can be expected to be exacerbated when the RNA CAR T cells are administered to hosts that have been lymphodepleted, which would be expected to result in the induction of homeostatic proliferation of the CART cells and, as a consequence, the accelerated loss of CAR expression at the T-cell surface. Thus, RNA CAR T cells may be more effective when given for compartmentalized tumors such as mesothelioma or central nervous system tumors. Furthermore, more frequent administration of RNA CARs may be required in lymphodepleted hosts.

In addition to providing a form of toxicity management discussed elsewhere herein, there are several potential opportunities for RNA CAR T-cell therapy. First, RNA CARs offer the potential to accelerate the pace of CAR development, by providing a flexible and more rapid path to the clinic, and thereby enabling an efficient iterative approach to optimize CAR design and potency. Based on the data presented herein, it is planned to open a phase I trial testing anti-mesothelin RNA CARs. The regulatory approval process is less cumbersome with RNA CARs than with stably expressed CARs that require genomic integration. Clinical-grade mRNA is less costly to produce than integrating retroviral or lentiviral vectors, although more expensive than plasmid DNA that is being used in transfection or transposon-based protocols (Till et al., 2008, Blood 112: 2261-71; Singh et al., 2008, Cancer Res 68:2961-71). Second, it may be attractive to combine RNA CAR "knockdown" therapy using potent but potentially toxic CARs for remission induction, with consolidation and maintenance therapy using stably expressed CARs as a strategy to provide CAR cells with a potential for memory.

In summary, multiple injections of RNA-engineered T cells are a novel approach for adoptive cell transfer, providing a cost-efficient and flexible platform for the treatment of cancer diseases. In addition, this approach may increase the therapeutic index of T cells engineered to express powerful activation domains without the associated safety concerns of integrating viral vectors.

Example 2: Treatment of Advanced Leukemia in Mice with mRNA Engineered T Cells

While Cytotoxic T lymphocytes (CTLs) bearing stably expressed CARs generated by integrating viral vectors are efficacious and have potential long-term persistence, an alternative therapy is to use transiently expressing CARs where T cells are electroporated with an optimized in vitro transcribed RNA encoding a CAR against a desired target (e.g. CD19). The results presented herein demonstrate that T cells expressing an anti-CD19 CAR introduced by electroporation with optimized mRNA were potent and specific killers of CD19 target cells. CD19 RNA CART cells given to immunodeficient mice bearing xenografted leukemia rapidly migrated to sites of disease and retained significant target-specific lytic activity. Unexpectedly, a single injection of CD19 RNA CAR T cells reduced disease burden within 1 day after administration, resulting in a significant prolongation of survival in an aggressive leukemia xenograft model. The surface expression of the RNA CARs may be titrated, giving T cells with potentially tunable levels of effector functions such as cytokine release and cytotoxicity. RNA CARs are a genetic engineering approach that should not be subject to genotoxicity, and provide a platform for rapidly optimizing CAR design before proceeding to more costly and laborious stable expression systems.

The materials and methods employed in these experiments are now described.

Materials and Methods

Construction of In Vitro Transcription (IVT) Vectors and RNA Electroporation.

CD19 and mesothelin (meso)-targeted CARs with 4-1BB and CD3ζ signaling domains (19-BBz and ss1-BBz, respectively) have been described previously (Milone, et al., 2009, Mol Ther 17(8):1453-1464; Carpenito et al., 2009, Proc Natl Acad Sci USA 106(9):3360-3365). The PCR products were subcloned into pGEM.64A based vector by replacing GFP from pGEM-GFP.64A (Zhao, et al., 2006, Mol Ther 13(1): 151-159) with restriction enzyme digested PCR products with Hind III and Not I to produce pGEM-ss1.bbz.64A and pGEM-CD19bbz.64A. Similarly, third generation versions of the CARs were constructed utilizing the CD28 signaling domain. The replaced CAR cDNAs were confirmed by direct sequencing and linearized by SpeI digestion prior to RNA IVT. mScript RNA System (Epicentre, Madison, Wis.) was utilized to generate capped IVT RNA. The IVT RNA was purified using an RNeasy Mini Kit (Qiagen, Inc., Valencia, Calif.) and purified RNA was eluted in RNase-free water at 1-2 mg/ml. Human T cells were stimulated by CD3/CD28 beads as described (Carpenito et al., 2009, Proc Natl Acad Sci USA 106(9):3360-3365). The stimulated T cells were washed three times with OPTI-MEM and resuspended in OPTI-MEM at the final concentration of $1-3\times10^8$/ml prior to electroporation. Subsequently, the stimulated T cells were mixed with 10 µg/0.1 ml T cells of IVT RNA (as indicated) and electroporated in a 2-mm cuvette (Harvard Apparatus BTX, Holliston, Mass., USA) using an ECM830 Electro Square Wave Porator (Harvard Apparatus BTX). Viability post transfection ranged from 50 to 80%, and in all cases viable T cells for injection had >99% CAR expression at time of use. For the trafficking experiments, T cells were stably transduced with a firefly luciferase lentiviral construct prior to mRNA transfection.

Construction of Lentiviral Vectors with Different CARs.

Lentiviral vectors that encode the various CARs under the transcriptional control of the EF-1α promoter were generated as previously described (Imai et al., 2004, Leukemia 18(4): 676-684; Milone, et al., 2009, Mol Ther 17(8):1453-1464). CAR-expressing lentiviral vectors in which the CAR sequences were preceded in frame by either an eGFP sequence or firefly luciferase (FFluc) followed by the 2A ribosomal skipping sequence from FMDV were also generated. These vectors permit dual expression of GFP or FFluc and the CARs from a single RNA transcript. All constructs were verified by sequencing.

CAR Detection on Electroporated T Cells

Cells were washed and suspended in FACS buffer (phosphate buffered saline (PBS) with 0.1% sodium azide and 0.4% bovine serum albumin (BSA)). Cells were incubated at 4° C. for 25 minutes with Biotin-labeled polyclonal goat anti-mouse F(ab)2 antibodies (anti-Fab, Jackson Immunoresearch, West Grove, Pa.) and then washed twice with FACS buffer. Cells were then stained with phycoerythrin-labeled streptavidin (BD Pharmingen, San Diego, Calif.). Flow cytometry acquisition was performed with a BD FacsCalibur (BD Biosciences), and analysis was performed with FlowJo (Treestar Inc, Ashland, Oreg.).

ELISA and Luminex Assays

Target cells were washed and suspended at $10^6$ cells/mL in C10 (RPMI 1640 supplemented with 10% Fetal Calf Serum (FCS), Invitrogen). $10^5$ target cells of each type were added to each of 2 wells of a 96 well round bottom plate (Corning). Effector T cell cultures were washed and suspended at $10^6$ cells/mL in C10. $10^5$ effector T cells were combined with target cells in the indicated wells of the 96 well plate. In addition, wells containing T cells alone were prepared. The plates were incubated at 37° C. for 18 to 20 hours. After the incubation, an ELISA assay was performed on the supernatant using manufacturer's instructions (Pierce, Rockford, Ill.). 50 microliters of culture supernatant were tested in duplicate, and the results reported in pg/ml.

CD107a Staining

Cells were plated at an effector:target (E:T) of 1:1 ($10^5$ effectors:$10^5$ targets) in 160 µl of C10 medium in a flat bottom 96 well plate. Controls included wells without target cells to assess background levels of CD107a. 20 µl of phycoerythrin-labeled anti-CD107a Ab (BD Pharmingen, San Diego, Calif.) was added, the plate was gently agitated and incubated at 37° C. for 1 hour. Golgi Stop solution was added and plates incubated for another 2.5 hours. Cells were then stained with 10 µl FITC-anti-CD8 and APC-anti-CD3 (BD Pharmingen, San Diego, Calif.), and washed. Flow cytometry acquisition was performed with a BD FacsCalibur (BD Biosciences), and analysis was performed with FlowJo (Treestar Inc, Ashland, Oreg.).

Flow Cytometric Cytotoxic T Lymphocyte Assay

A slightly modified version of a flow cytometric cytotoxicity assay was used (Hermans et al., 2004, J Immunol Methods 285(1):25-40). In this assay, the cytotoxicity of target cells is measured by comparing survival of target cells relative to the survival of negative control cells within the same tube as the effector cells. In the experiments described herein, the target cells were K562 cells expressing human CD19 (K562-CD19), and the negative control cells were K562 cell expressing mesothelin (K562-meso). K562-meso were labeled with the fluorescent dye 5-(and-6)-(((4-chloromethyl)benzoyl)amino) tetramethylrhodamine (CMTMR). (Invitrogen) K562-CD19 cells were labeled with carboxyfluorescein diacetate succinimidyl ester (CFSE). (Invitrogen) Cultures were set up 96 well culture plate in duplicate at the following T cell:target cell ratios: 10:1, 3:1, and 1:1, using $10^4$ CD19+ target cells and $10^4$ meso+ control cells. For some experiments in which both K562-CD19 and K562-meso were used as target cells and were labeled with CFSE, a myeloma cell line NSO that is negative for CD19 was labeled with CMRA as a negative control. The cultures were incubated for 4 hours at 37° C. Immediately after the incubation, 7-AAD (7-aminoactinomycin D) (BD Pharmingen) was added as recommended by the manufacturer. Analysis was gated on 7AAD-negative (live) cells, and the percentages of live K562-CD19 and live K562-meso cells were determined for each Tcell+target cell culture. For each culture, the percent survival of K562-CD19 was determined by dividing the percent live K562-CD19 by the percent live K562-meso control cells. The corrected percent survival of K562-CD19 was calculated by dividing the percent survival of K562-CD19 in each T cell+target cell culture by the ratio of the percent K562-CD19 target cells:percent K562-meso negative control cells in tubes containing only K562-CD19 target cells and K562- meso negative control cells without any effector T cells. This correction was necessary to account for variation in the starting cell numbers and for spontaneous target cell death. Cytotoxicity was calculated as 100−(corrected percent survival of K562-CD19). For all effector:target ratios, the cytotoxicity was determined in duplicate and the results were averaged.

Mouse Xenograft Studies

Studies were performed as previously described with certain modifications (Teachey, et al., 2006, Blood 107(3): 1149-1155 Teachey, et al., 2008, Blood 112(5): 2020-2023). Briefly, 6-10 week old NOD-SCID-$\gamma c^{-/-}$ (NSG) mice were obtained from the Jackson Laboratory (Bar Harbor, Me.) or bred in house under an approved institutional animal care and use committee (IACUC) protocol and maintained under pathogen-free conditions. The CD19+ human ALL line Nalm-6 was obtained from American Type Culture Collection (ATCC, Manassas, Va.). Animals were injected via tail vein with $10^6$ viable Nalm-6 cells in 0.2 mL sterile PBS. T cells were injected via tail vein at $5\times10^6$, $1\times10^7$ or $2.5\times10^7$ cells in a volume of 0.2 mL sterile PBS 7 days after injection of Nalm-6. Nalm-6 at this dose reliably produces fatal leukemia in the NSG mouse in 22-25 days if left untreated. Previous experiments demonstrated that the earliest reliable detection of disease (>0.1%) in femoral bone marrow was 7 days after injection, and thus this time point is chosen for therapeutic intervention and correlated with bioluminescent disease. Animals were closely monitored for signs of graft-versus-host disease and other toxicity as evidenced by >10% weight loss, loss of fur, diarrhea or conjunctivitis as well as for leukemia related hind limb paralysis. Peripheral blood was obtained by retro-orbital bleeding, and presence of ALL and T cell engraftment was determined by flow cytometry using BD Trucount (BD Biosciences) tubes as described in the manufacturer's instructions. CD19, CD20, CD4, CD3, CD10 and/or CD8 expression (as required) was detected by staining with fluorescently-conjugated monoclonal antibodies (BD Biosciences). Expression of the CD19 or SS1 scFv CARs was detected using the biotinylated F(ab')2 fragment from goat anti-mouse IgG sera (specific for scFvs of murine origin) (Jackson ImmunoResearch) followed by staining with streptavidin-PE (BD Biosciences/Pharmingen).

Bioluminescent Imaging

Anesthetized mice were imaged using a Xenogen Spectrum system and Living Image v4.0 software. Mice were given an intraperitoneal injection of 150 mg/kg D-luciferin (Caliper Life Sciences, Hopkinton, Mass.). Previous titration of both Nalm-6 and human T cells transduced with the firefly luciferase vector indicated time to peak of photon emission to be five minutes, with peak emission lasting for 6-10 minutes. Each animal was imaged alone (for photon quantitation) or in groups of up to 5 mice (for display purposes) in the anterior-posterior prone position at the same relative time point after luciferin injection (6 minutes). Data were collected until the mid range of the linear scale was reached (600 to 60000 counts) or maximal exposure settings reached (f stop 1, large binning and 120 seconds), and then converted to photons/second/cm$^2$/steradian to normalize each image for exposure time, f stop, binning and animal size. For anatomic localization, a pseudocolor map representing light intensity was superimposed over the grayscale body-surface reference image. For data display purposes, mice without luciferase containing cells were imaged at maximal settings and a mean value of $3.6\times10^5$ p/s/cm$^2$/sr was obtained. Mice with luciferase-containing Nalm-6 typically became moribund with leukemia when photon flux approached $5\times10^{11}$ p/s/cm$^2$/sr, giving a detection range of 6 orders of magnitude. Similarly, luciferase-expressing versions of the various CARs were used to detect trafficking of the T cells to tumor sites and to assess expansion of the transferred T cells in the host mouse.

Cell Line Identity Testing

Nalm-6 and K562 parent cell lines were obtained from ATCC (Manassas, Va.) and genotyped by short tandem repeat analysis (Masters, et al., 2001, Proc Natl Acad Sci USA 98(14):8012-8017). Cell lines were verified every six months, or after any genetic modification such as CD19 or luciferase transduction to insure identity.

Statistical Considerations

Analysis was performed with STATA version 10 (Statacorp, College Station, Tex.) or Prism 4 (Graphpad Software, La Jolla, Calif.). In vitro data represent means of duplicates, and comparisons of means were made via Mann-Whitney test. For comparison among multiple groups, Kruskal-Wallis analysis was performed with Dunn Multiple Comparison tests to compare individual groups. Survival curves were compared using the log-rank test with a Bonferroni correction for comparing multiple datasets.

The results of the experiments are now described.

Generation of CAR Expressing T Cells by mRNA Transfection Results in Up to 10 Days of Surface Expression with Detectable Lytic Activity.

The persistence of expression and cytolytic activity of mRNA-transfected CAR+ CTLs (RNA CARs) were evaluated in vitro. High surface expression persisted for 6 days in vitro before drifting down toward baseline non-expressing cells by 10 days (FIG. 1A and data not shown). This prolonged high transgene persistence was different from most reports of peak and duration of expression of a surface antigen after mRNA transfection (Birkholz et al., 2009, Gene Ther 16(5):596-604; Rabinovich, et al., 2009, Hum Gene Ther 20(1):51-61; Yoon, et al., 2009, Cancer Gene Ther 16(6):489-497; Li, et al., 2010, Cancer Gene Ther 17(3):147-154), possibly due to the optimized IVT vector and RNA production (data not shown). In parallel, the cytotoxic potential of CAR-expressing T cells in vitro was assessed with a flow cytometry based killing assay. Specific lysis of more than 50% of target cells at an E:T ratio of 2:1 was noted from Days 1-4. While cytotoxic activity declined on Days 5 to 6, even with a 2-3 log reduction in surface expression of the CAR, some lytic activity was observed and was well over that of background lysis of mock transfected cells (FIG. 12B). Specific lytic activity declined in parallel with declining MFI of the expressed transgene, but significant lytic activity (p<0.05) over nonelectroporated controls at an E:T ratio of 20:1 was observed 6 days after electroporation.

To further assess the lytic activity of the RNA CAR+ T cells, they were stimulated and electroporated as above, then co-cultured with various targets cells 4 hours after electroporation to examine cytolytic potential and target specificity. Expression of CD107a was used as a marker of cytolytic cell degranulation. (Betts and Koup, 2004, Methods Cell Biol 75:497-512) In addition to the target of interest (CD19), CAR directed against the irrelevant antigen mesothelin (not expressed on lymphocytes) was used as a control. K562 cells do not express either CD19 or mesothelin, but are easily transduced to express a variety of genes making them flexible target cells for in vitro cytotoxicity assessments (Suhoski et al., 2007, Mol Ther 15(5):981-988). CD19- directed RNA CAR+ T cells degranulate and express CD107a only in the presence of CD19$^+$ target, indicating antigen-specific recognition and lytic function (FIG. 12C). This included both the CD19$^+$ target leukemia cell line Nalm-6 as well as K562 cells transduced to express CD19. As a control, CAR recognizing mesothelin only specifically lyse mesothelin+ K562 cells, as measured by the same CD107a assay. Mesothelin-directed CAR+ T cells do not express CD107a in the presence of mesothelin-negative parent K562, the CD19+/mesothelin-ALL line Nalm-6, or K562 transduced to express surface CD19 but not mesothelin. A co-culture experiment using both an anti-meso CAR with 4-1BB and TCR zeta signaling domains (BBz) and an anti-CD19-BBz CAR also demonstrated specific release of interleukin-2 (IL-2) in the presence of appropriate target as measured by ELISA of the supernatant suggesting antigen-specific T cell activation (FIG. 12D).

Relationship of CAR Expression Level to Input RNA Dose

Recent reports of serious adverse events after administration of CAR T cells engineered by retroviral gene transfer (Brentjens et al., 2010, Molecular Therapy 18(4):666-668; Morgan, et al., 2010, Mol Ther 18(4):843-851) suggest that a platform for expressing CARs with pre-determined levels of surface expression or which ensures self limited expression (such as RNA) might be desirable. By titrating the mRNA dose, approximately a 100-fold variation of RNA CAR surface expression by MFI is observed (FIG. 13A). Despite the variation in surface MFI, the rate of decline of expression (expressed as percentage) is similar (FIG. 13B). RNA CAR+ T cells exhibit similar lytic activity on Day 1 post electroporation (FIG. 13C, left panel) and secretion of IFN-γ (FIG. 13D). Secretion of IL-2 was also tested). This is consistent with a recent report using a different methodology (James, et al., 2010, The Journal of Immunology 184(8):4284). By Day 3, however, a dose dependent decline in lytic activity is observed where lower RNA doses are less effective compared to their effects on Day 1 while higher doses (40 and 20 μg) have similar lytic profiles at each E:T ratio on Day 3 as on Day1. This suggests that the initial surface expression, which appears proportional to the input RNA, could dictate the time and degree of lytic activity. This may be useful in controlling the duration of effect and potentially the duration of cytokine release, though this remains to be studied.

In Vivo Trafficking of CAR+ CTLs

Based on the above in vitro data demonstrating RNA CAR expression for up to a week, the cytolytic function of mRNA-transfected CAR+ T cells after 48 hours in a xenograft mouse model was assessed. NSG mice were inoculated by tail vein with the CD19+ ALL line Nalm-6 seven days prior to infusion of $10^7$ 19-BBz or anti-meso (SS1)-BBz RNA CAR+ T cells (FIGS. 14A and 14B). Mice were sacrificed 48 hours after T cell infusion, and T cells were recovered and enriched from peripheral blood, spleen, femoral bone marrow and a peritoneal washing using a negative selection protocol. After 48 hours of in vivo proliferation and exposure to a CD19+ Nalm-6 targets, T cells expressing the CAR could still be detected in peripheral blood, spleen and peritoneum. Surface anti-CD19 CAR expression is modestly lower than that of companion control cultured T cells in vitro (FIG. 14A). Meso-BBz CAR T cells that had not been exposed to targets expressing the cognate mesothelin surrogate antigen were also recovered from these compartments. The overall CAR positive populations from the spleen were 75% (as a percentage of total human CD3+ cells recovered) for CD19 and 68% for mesothelin at this time point. So while the CD19 CAR CTLs were expanding based on bioluminescence (FIGS. 15A and 15B) and the mesothelin CAR CTLs were not, the proliferating CD19 CAR CTLs appear to be producing CAR+ progeny. If CAR mediated proliferation were resulting in CAR negative progeny, the percentage of CD19 CAR positive cells should be lower than that for the non-proliferating mesothelin CAR CTLs. Few human CD3+ cells for either construct were recovered from femoral bone marrow at this time point, likely due in part to the diluted distribution of T cells throughout unaccessible regions of marrow (vertebral bodies, calvarium). The goat-anti-mouse IgG sera used to stain for the CAR also cross-reacts with many bone marrow precursor cells giving a high background in the evaluation of this compartment.

Cells recovered from the 48-hour peritoneal washings were used, which had the most human CD3+ and CAR+ enriched population regardless of whether the T cells were administered IP or IV, for further in vitro characterization. T cells recovered from the peritoneum of mice 48 hours after injection of $10^7$ CAR+ T cells were tested for antigen-specific cytotoxicity in a flow cytometry based CTL assay (FIG. 14B). Significant antigen-specific target lysis was obtained with RNA CAR+ T cells recovered from mice after 48 hours, comparable to those that were cultured in vitro for 48 hours.

Next, the anatomic distribution of RNA CAR CTLs was evaluated for 3 days using in vivo bioluminescence. Mice were infused with Nalm-6 and on day 7, with 5×$10^6$ RNA CAR+ T cells (50% CD4+ and 50% CD8+, both IV). To evaluate the effects of antigen recognition and CAR signaling on biodistribution, RNA CAR+ T cells expressing 19-BBz, ss1-BBz, as well as mock transfected T cells were compared. T cells that were stably transduced with a firefly luciferase lentiviral construct prior to mRNA transfection were used to allow for in vivo bioluminescent tracking and relative quantitation. Retention at sites of disease and subsequent proliferation as indicated by increasing total bioluminescent signal as well as heat maps over known disease sites required recognition of a target antigen (FIGS. 15A and 15B). T cells with CARs against antigens not present in the model (mesothelin) or mock-transfected cells concentrated in the spleen and showed no increase in bioluminescence over time from injection. The lack of increase of bioluminescence activity suggests a lack of T cell expansion in vivo as luminescent signal is directly proportional to cell number (Zhao, et al., 2005, J Biomed Opt 10(4):41210; Dobrenkov et al., 2008, J Nucl Med 49(7):1162-1170). T cells with 19-BBz migrated to, were retained and proliferated at sites of disease (axial skeleton and femoral bone marrow, spleen as well as likely the liver in the right flank) (FIG. 15B). In addition, the total bioluminescent signal increased over the whole mouse as well as sites of known involvement by Nalm-6, consistent with proliferative expansion of the T cell number (FIG. 15A). A time course experiment with Nalm-6 stably transduced with firefly luciferase revealed that disease is present in the same locations (axial skeleton, femoral bone marrow, spleen and liver), and that a 4 log increase in bioluminescent signal corresponded to an increasing disease burden (FIGS. 17, 18A, and 18B). Consistent with previous experiments, there were few, if any, CTLs present in the peripheral blood compartment during the initial 3 days after T cell injection, with <10 human T cells/μL detected by TruCount quantitation, while large numbers of human T cells are detected in the peripheral blood at later time points. Similarly, appearance of Nalm-6 in the peripheral blood is a late event in this model, with mice showing <10 human ALL cells/μL of peripheral blood until shortly before the animals become moribund, typically by day 21 (data not shown). Over multiple repeats of this experimental model, this remains the consistent finding, highlighting the sensitivity of bioluminescence over traditional evaluation using flow cytometry to quantitate CTLs or blasts in the peripheral blood.

In Vivo Efficacy of CAR+ CTLs Against CD19+ ALL in a Xenograft Model

In order to assess potential in vivo efficacy of RNA CAR CTLs, animals were treated as before, but given a single higher dose of T cells ($2.5 \times 10^7$) on Day 7 post tumor inoculation. A dose of $2.5 \times 10^7$ was chosen instead of $10^7$ cells by hypothesizing that, since the receptor expression was self-limited to a few days, the CAR-driven expansion of cells would similarly be limited and a higher starting cell dose might be required to demonstrate efficacy in a high tumor burden. Preclinical models using stably transduced CD19 CAR+ T cells with retroviruses have utilized a 3 or 4 separate injections schedule with $3-4 \times 10^7$ total T cells in similar models. (Shaffer, et al., 2011, Blood 117(16):4304-14; Brentjens et al., 2007, Clin Cancer Res 13(18 Pt 1):5426-5435) Surprisingly, a 2 log reduction of bioluminescent signal was observed as early as 24 hours after injection, a reduction that was sustained over time ($p<0.01$, FIG. 5A). The bioluminescence signal was globally reduced, without evidence of a reservoir that the CTLs fail to penetrate (FIG. 16B), though signal never reached undetectable levels indicating it was not cleared entirely. Of note, two dimensional heat maps are not capable of separating CNS disease from other sites so ex vivo imaging of the brain, skull, spine and vertebrae was done, which revealed that the CNS appears not significantly involved at this time point (Day 5). Rather, the calvarium/skull base and vertebral bodies are involved with leukemia giving rise to the heat maps over the head and back of the mouse. This is consistent with other reports of the early migration of human hematopoietic cells in immunodeficient mice evaluated by optical imaging (Kalchenko, et al., 2006, J Biomed Opt 11(5):050507).

Mesothelin-directed CAR CTLs had no significant effect on bioluminescent disease burden, indicating little non-specific allogeneic or xenogeneic effect. The initial reduction in disease burden is rapid but short lived as bioluminescent disease begins to rise within 4 days of injection. The degree of disease reduction and the subsequent delay in reaching fatal disease burden ($>2 \times 10^{11}$ p/s/cm$^2$/sr) correlates directly with survival. Finally, RNA CAR+CTL injection resulted in significant prolongation ($p<0.01$ by log rank test of survival data) of survival compared to control animals who received no CTLs and control animals which received the same dose of $2.5 \times 10^7$ RNA CAR+ CTLs directed against the irrelevant antigen mesothelin (FIG. 16C). Together, these results indicate that RNA CAR+ CTLs exhibit robust antitumor effects by specifically killing target cells after migration and proliferation in mice with advanced, disseminated leukemia xenografts. Importantly, the survival of RNA CAR+ CTLs were compared to that of stably expressed, lentiviral generated CAR CTLs in the same Nalm-6 model. In this case, CAR CTLs were generated by lentiviral transduction to contain the same 19-BBz CAR as the RNA generated CTLs. $10^7$ lentiviral CAR CTLs were injected on Day 7 after Nalm-6, based on dosing previously determined. Mice were followed as before, and median survival was not different between RNA CAR or lentiviral CAR CTLs, although one long term survivor was seen with the persistently expressing lentiviral CAR CTLs (FIG. 5D).

Treatment of Advanced Leukemia in Mice with mRNA Engineered T Cells

Results from recent clinical trials indicate improved clinical results with CARs introduced with retroviral vectors (Pule, et al., 2008, Nat Med 14(11):1264-1270; Till, et al., 2008, Blood 112(6):2261-2271). Recent editorials have discussed the need for safer CARs (Buning et al., 2010, Human Gene Therapy 21(9):1039-42; Heslop, 2010, Molecular Therapy 18(4):661-662). The data described herein describes the development of a platform that has the potential to increase the therapeutic window with CARs that contain increasingly potent signaling domains. The findings presented herein are the first to demonstrate therapeutic effects of RNA CAR+ CTLs for disseminated leukemia in a pre-clinical model.

A temporary expression approach towards CAR immunotherapy such as mRNA transfection runs counter to our previous efforts and to those of most investigators in the field. The data described herein is the first to indicate that a single injection of mRNA transfected CAR+ T cells can achieve a systemic effect, expanding and persisting sufficiently in vivo to migrate to distant sites of disseminated leukemia and to retain their cytotoxic effects. Massive, CAR-driven expansion of the T cells is observed during the period of CAR expression. The present results demonstrate a 2-log reduction of leukemic burden and extended survival an aggressive xenograft model characterized by rapid human ALL engraftment. Importantly, the survival of mice bearing xenografted leukemia administered a single injection of RNA CAR CTLs is comparable to survival achieved by stable lentivirus CAR CTLs. The sites and timing of relapse are similar between these groups, though only stable expressed CARs result in long term cures (>180 days). Survival in the RNA CAR model is directly correlated with degree of initial disease reduction, though the periodontal and paraspinal regions remain the first sites of relapse in both RNA and lentiviral CAR models.

The current finding that CAR surface expression is relatively mRNA dose-independent, with resulting relatively mRNA dose-dependent IFN-γ and IL-2 cytokine secretion over time, raises the future possibility of tailoring expression levels to mitigate the release of cytokines that may result in toxicity. Other toxicities encountered with stably transduced CAR T cells have been on-target/off-organ effects, such as the expected depletion of normal B cells following CD19 CAR therapy, or the induction of hepatic toxicity following carbonic anhydrase IX therapy (Lamers, et al., 2006, J. Clin Oncol. 24(13):e20-e22). Without wishing to be bound by any particular theory, it is believed that repeated administration of RNA CARs would be required to elicit this form of toxicity. Finally, concerns over the lentiviral or retroviral introduction of CARs into CTLs include the theoretical possibility of malignant transformation from insertional mutagenesis, a subject of significant regulatory oversight even for mature T cells (Nienhuis, et al., 2006, Molecular Therapy 13(6):1031-1049; Bushman, 2007, J Clin Invest 117(8):2083-2086). As there is no integration into the host cell genome and the CAR expression is self-limited, these concerns are potentially circumvented by mRNA transfection. Also importantly, since RNA expressed CARs seem to function similarly to stably expressed CARs both in vitro and in vivo in preclinical animal models in the short term, this platform provides a potentially more rapid way to evaluate iterations in CAR design that could be translated back to the stable expression systems.

It is reassuring that the data with the RNA CAR CTLs examined herein, show all the target based cytotoxic properties of their lentiviral counterparts (Carpenito et al., 2009, Proc Natl Acad Sci USA 106(9):3360-3365; Milone, et al., 2009, Mol Ther 17(8):1453-1464). The RNA CAR CTLs exhibited antigen specificity with concomitant ability to migrate to and expand at sites of disseminated leukemia after a single IV injection. Trafficking of CAR CTLs to sites of disease is critical to their anti-tumor function, as has been demonstrated in a prostate cancer xenograft model (Dobrenkov et al., 2008, J Nucl Med 49(7):1162-1170), and this work is the first to demonstrate CD19 RNA CAR CTLs can traffic to and function at all sites of disseminated leukemia after a single tail vein injection. Importantly, it is described herein, that RNA CARs are still expressed at high levels after circulation and expansion in a tumor bearing xenograft, indicating functional CTLs despite potential receptor internalization and dilution of RNA from proliferation after antigen engagement. There are several potential opportunities for RNA CAR CTL therapy. First, they offer a potential strategy for toxicity mitigation (self-limited expression) that is not possible with stably expressed CARs, with the possible exception of the incorporation of suicide systems with stably expressed CARs (Marktel, et al., 2003, Blood 101 (4):1290-1298; Sato, et al., 2007, Mol. Ther. 15(5):962-970). Second, RNA CARs offer the potential to accelerate the pace of CAR development, by providing a lexible and more rapid path to the clinic, and thereby enable an efficient iterative approach to optimize CAR design and potency. The regulatory approval process has the potential to be less cumbersome with RNA CARs than with stably expressed CARs that require genomic integration. Clinical grade mRNA is far less costly to produce than integrating retroviral or lentiviral vectors, and somewhat more expensive than plasmid DNA that is being used in transfection or transposon based protocols (Singh, et al., 2008, Cancer Research 68(8):2961-2971; Till, et al., 2008, Blood 112(6): 2261-2271). How the true cost-effectiveness plays out will ultimately be determined by the number of T cells, number of infusions and duration of response—factors not yet known. Finally, it may be attractive to combine RNA CAR "knock down" therapy, using potent but potentially toxic CARs for remission induction, with consolidation and maintenance therapy using stably expressed CARs as a strategy to provide memory CAR+ cells. In summary, a short-term expression platform whose development is described herein provides an alternative for cell therapy, may have advantages for certain applications, and with repeated infusions over time it may be possible to achieve long term disease control or eradication of otherwise treatment resistant leukemia.

Example 3: Clinical Trial of Autologous Re-Directed T Cells

The investigational agent in this protocol is autologous T cells transfected with chimeric anti-mesothelin immunoreceptor scFv. To maximize safety, the trial uses T-cells electroporated with the mesothelin CAR mRNA. A representative CAR mRNA can be generated by in vitro transcription of the pD-A.ss1.OF.BBZ.2bg.150A plasmid (see FIG. 19) or pD-A.19.OF.2bg.150A (see FIG. 20). As discussed elsewhere herein, using CAR mRNA allows for only a limited expression period. If side effects are noted, T cell infusions can be terminated and toxicity can rapidly be abated because expression of the mRNA CAR is limited to a few days, thus making side effects more transient and manageable.

This protocol is designed to determine the safety of IV autologous anti-mesothelin redirected CAR T-cell administration. The primary toxicity that may be anticipated is that engineered T cells may cause inflammation, i.e. serositis, on the peritoneum and pleura-pericardial surfaces due to normal low-level mesothelin expression on these serosal surfaces.

The materials and methods employed in these experiments are now described.

Materials and Methods

Plasmid

Derivation of the final plasmid construct was a multi-step process that entailed cloning into intermediate plasmids. Two different plasmids were utilized to clone the ss1.bbz fragment. The mesothelin scFv fragment (ss1) was first cloned by the Translational Research Program (TRP) laboratory from the previously published construct of Dr. Pastan (Chowdhury et al., 1998). The human CD8a hinge and transmembrane domain together with 41BB and CD3ζ sequence was cloned by PCR from the pELNS.CD19-BB-ζ plasmid described previously (Milone et al., 2009). The ss1.bbz fragment was first cloned in pGEM.GFP.64A vector. This vector was modified by addition of two 3'UTR beta globin repeats and 150 bp of polyA sequence (replacing the 64 polyA sequence in pGEM.GFP.64A) for enhanced transgene expression (Holtkamp 2006). The GMP-compliant plasmid for clinical use was derived by subcloning the ss1.bbz.2bgUTR.150A fragment from pGEM into the pDrive vector. The pDrive cloning vector (Qiagen) is designed for highly efficient cloning of PCR products through UA hybridization. It allows for both ampicillin and kanamycin selection of recombinant clones, and comes with universal sequencing primer sites, and both T7 and SP6 promoters for in vitro transcription. First, ss1.bbz.2bgUTR.150A was cut from pGEM vector by Hind III and NdeI (Fill-in blunt) and subcloned into pDrive cut by KpnI and NotI (Fill-in blunt). The insert with correct orientation was sequence confirmed to generate pDrive.ss1.bbz.2bgUTR.150A. Ampicillin resistance gene in pDrive vectors was deleted by double digestion with AhdI and BciVI. To eliminate potential aberrant proteins translated from internal open reading frames (ORF) inside the CAR ORFs, all internal ORF that were larger than 60 bp in size were mutated by mutagenesis PCR, while the ORF of ss1 CAR was maintained intact. The resulting plasmid was designated pD-A.ss1.bbz.OF.2bg.150A.

Bacterial Transformation

The final pD-A.ss1.bbz.OF.2bg.150A construct was introduced into OneShot TOP10 Chemically Competent *E Coli* cells (Invitrogen) as per CVPF SOP 1188. A master cell bank was generated and the cells were testing for safety, purity, and identity as described in TCEF SOP 1190.

DNA Preparation

Up to 10 mg plasmid DNA prepared as one batch was generated using the QIAfilter Plasmid Giga DNA isolation kit as per SOP 1191, from two 1.25 liters of LB-media containing 100 µg/ml kanamycin. 1 mg of DNA at a time was linearized with SpeI restriction enzyme overnight at 37° C. Linearization was confirmed by gel electrophoresis prior to large scale purification using the Qiagen Plasmid Maxi Kit. The release criteria for DNA includes appearance, concentration purity, sterility, and gel confirmation of linearization.

RNA Preparation

To test translational efficiency, RNA was generated from a number of different commercially available systems as described elsewhere herein. Compared to co-transcriptional systems, the mScript mRNA system was selected because it provides virtually 100% capping of transcripts, 100% proper cap orientation, and incorporates a Cap 1 translation boosting structure that may enhance translational efficiency. A custom lot of the mScript™ mRNA System accompanied by the Certificate of Analysis for the kit was provided. The RNA was isolated using the RNeasy Maxi kit (Qiagen). The in vitro transcribed RNA was cryopreserved in aliquots of 0.5 mL at a concentration of 1 mg/mL. RNA quality and quantity was analyzed by 1% agarose gel electrophoresis after 15 min denaturation at 70° C. in mRNA denaturation buffer (Invitrogen, Carlsbad, Calif.) and quantified by UV spectrophotometry (OD260/280). Evaluation of transgene expression of T cells electroporated with this mRNA was also performed as part of functional characterization.

CAR T Cells Product Manufacturing

CD3+ T-cells are enriched from a leukapheresis product by depletion of monocytes via counterflow centrifugal elutriation on the CaridianBCT Elutra, which employs a single use closed system disposable set. On day 0, the T cell manufacturing process is initiated with activation with anti-CD3/CD28 monoclonal antibody-coated magnetic beads, and expansion is initiated in a static tissue culture bag. At day 5, cells can be transferred to a WAVE bioreactor if needed for additional expansion. At the end of the culture, cells are depleted of the magnetic beads, washed, and concentrated using the Haemonetics Cell Saver system. The post-harvest cells are incubated overnight at 37° C. for electroporation the next morning. Cells are washed and resuspended in Electroporation Buffer (Maxcyte) and loaded into the Maxcyte processing assembly. Cells are electroporated with the ss1 RNA, and allowed to recover for 4 hours and then formulated in infusible cryopreservation media.

The total number of cells during harvest of the electroporated cells can be used to calculate the six doses that can be cryopreserved. With a CD3+ release criteria of ≥80% and an in-process criteria of ≥80% viability prior to cryopreservation and ≥70% for the sentinel vial, all subjects can be administered the same amount of viable and CD3+ T cells+/−20%. Samples can be taken at the time of cryopreservation to measure CAR expression using flow cytometry, however this information is not available in real-time. Therefore, while the percent of CAR positive cells can be subsequently calculated and used as a release criteria, the final product doses cannot be normalized to the number of CAR positive cells. Only those final products that meet release criteria of ≥20% positive for CAR expression, and meet other release criteria as stated in the protocol will be administered.

Additionally, approximately 10 vials of the SS1 T cells can be cryopreserved and retained as sentinel vials, for performing an endotoxin gel clot and viability count at the time of the first infusion, and for assessment of viability at each subsequent infusion. Remaining vials can be used to conduct the "for information only (FIO)" functional assays. All cryopreserved cells can be stored in a monitored freezer at ≤−130° C.

CAR expression following electroporation is part of the release criteria for the final cell product. This is done by surface staining of the cells with a goat anti-mouse IgG, F(ab')2 antibody (Jackson ImmunoResearch) followed by PE-labeled streptavidin (BD Pharmingen) and flow cytometry analysis. The release criterion is set to ≥20% positive cells.

CAR T Cells Product Stability

The ss1 CAR T cells will be cryopreserved 4 hours post-electroporation, and thawed and administered within a three month window after T cell manufacturing. It has been demonstrated that mesothelin scFv expression of the cryopreserved ss1 CAR T cells approximately 30 days at ≤−130° C. was 97.4%, almost identical to time of cryopreservation (96.9%), and other cryopreserved T cell products are stable for at least 6 months. Viability post-thaw, based on Trypan blue counts was 75.2% as compared to 98.7%. The expression data suggests that the final product is stable during storage for the trial, and that the sentinel vial for additional doses should meet release criteria of 70% viability and ≥20% CAR expression. Additional vials of ss1 CAR T cells will be thawed at 3, 6, 9, and 12 months post cryopreservation, and viability and transgene expression tested to generate further product stability data.

CAR T Cell IV Administration

The infusion will take place in an isolated room in the CTRC, using precautions for immunosuppressed patients.

One or two bags of transfected T cells will be transported by the protocol coordinator or nurse on wet ice from the Clinical Cell and Vaccine Production Facility (CVPF) to Investigational Drug Services (IDS) at the University of Pennsylvania Hospital.

IDS will log in the product for accountability, verify the patient's name and identifier as provided by the clinical trial coordinator, and tear off one label from the 2-part perforated label affixed to the bag to maintain in the IDS records. The transfected T cells will be transported by the protocol coordinator or nurse from IDS to the subject's bedside at the CTRC.

Transfected T cells will be thawed by a member of CVPF staff in a 37° C. water bath at subject bedside immediately after transport from IDS. If the CAR T cell product appears to have a damaged or leaking bag, or otherwise appears to be compromised, it should not be infused, and should be returned to the CVPF as specified below.

Cells will be infused to the subject while cold by a CTRC nurse within approximately 10-15 minutes after thaw. The transfected T cells (in a volume of ~100 mL) will be infused intravenously rapidly through an 18 gauge latex free Y-type blood set with 3-way stopcock. Dosing will take place by gravity infusion. If the infusion rate by gravity is too slow, the transfected T cell drug product may be drawn into a 50 mL syringe via the stopcock and manually infused at the required rate. There should be no frozen clumps left in the bag.

Prior to the infusion, two individuals will independently verify the information in the label in each bag in the presence of the subject and confirm that the information correctly matches the participant.

Patients will be monitored during and after infusion of the transfected T cells. Blood pressure, heart rate, respiratory rate, and pulse oximetry will be obtained and recorded immediately prior to dosing and every 15 minutes for 2 hours following infusion completion. A crash cart must be available for an emergency situation.

If no symptoms occur and subject's vital signs remain normal 3 hours after the infusion, the subject will be discharged home with instructions to return to the hospital should any symptoms develop. If a vital sign measurement is not stable, it will continue to be obtained approximately every 15 minutes until the subject's vital signs stabilize or the physician releases the patient. The subject will be asked not to leave until the physician considers it is safe for him or her to do so.

Within 60 minutes (±5 minutes) following completion of transduced CAR T cell dosing, a blood sample will be obtained for a baseline determination of transduced CIRT cell number.

Subjects will be instructed to return to the CTRC in 24 hours for blood tests and follow up examination.

Without wishing to be bound by any particular theory, it is believed that the proposed study should minimize fatal risks for several reasons: 1) a pre-infusion lymphodepletion regimen is not being utilized; 2) T cell transduction will occur with mRNA, not retroviruses, thereby reducing the persistence of these cells to several days; 3) mesothelin has limited native expression to serosal surfaces in the pericardium, pleural and peritoneal cavities. In the event of mesothelin cross reaction and inflammatory process leading to fluid accumulation, these cavities can be quickly and readily accessed in a minimally invasive fashion to remove the fluid as anti-lymphocyte therapy is initiated (steroids).

This is a first-in-human clinical trial of a new molecular entity; however, other phase I trials have been conducted with similar CAR T cells. The pharmacologically effective dose (PED) of the CAR T cells in the NOD/SCID/γc−/− mouse tumor xenograft is $1 \times 10^7$ CAR T cells/mouse. At this dose, some of the mice develop xenogeneic graft versus host disease.

Cohort 1 patients (n=3) receive a single infusion of $1 \times 10^8$ using flat dosing with anti-meso RNA CAR T cells on day 0 and one infusion of $1 \times 10^9$ RNA CAR T cells on day 7, providing the patients meet the protocol-specified safety assessments before the day 7 infusion.

Cohort 2 subjects (n=6) are given 2 cycles of modified CAR T cells separated by one week to assess infusion toxicity. One cycle consists of 3 infusions every other day (Monday, Wednesday, Friday). Cycle 1 consists of 3 doses of $1 \times 10^8$ CAR T cells dosed on MWF (day 0, 2, 4), and after passing safety assessments, cycle 2 consists of 3 doses of $1 \times 10^9$ CART cells dosed on MWF (day 14, 16, 18). If an unforeseen circumstance prevents infusion from starting on Day 14 as scheduled, Cycle 2 of Cohort 2 may be postponed until Day 21. Days 21 through 35 will also be re-schedule accordingly. Months 2, 3, 6 remain the same.

Subjects on cohort 1 can be enrolled in cohort 2 at the end of their monitoring period (3 months following last infusion) if they satisfy all the inclusion/exclusion criteria. Patient enrollment can be staggered in the cohorts, so that a new patient is not treated until the previous patient completes safety assessments. Subjects cam be enrolled serially with each subject having to complete both treatment cycles followed by a seven-day toxicity observation period for cohort 1 (Day 14) and a 10 day toxicity observation period for cohort 2 (Day 28) prior to treatment of subsequent patients.

In the event of DLTs, the dose can be de-escalated by 10-fold. Thus, if toxicity occurs during cycle 1 at $10^8$ CAR T cells, then all infusions (doses 1 to 6) would be reduced to $10^7$ CIRs. In the event of unmanageable toxicity at $10^7$ CAR T cells, the trial would be stopped.

The target dose per infusion is $1 \times 10^8 \pm 20\%$ cells for the first cycle (one dose for Cohort 1 and three doses for Cohort 2) and $1 \times 10^9 \pm 20\%$ cells for the second cycle (one dose for Cohort 1 and three doses for Cohort 2). The minimally acceptable dose is $1 \times 10^8$. If the total cell expansion is lower than the total acceptable cell dose, the patient may undergo a second apheresis in an attempt to expand more cells and fulfill the total target dose. If there are contraindications for the second apheresis or if the second apheresis and expansion fails to produce the minimally acceptable dose, the dose will be deemed a manufacturing failure.

Example 4: Compassionate Use of RNA-Engineered CAR T Cells

This protocol was designed to test IV injection of RNA CAR T cells that are specific for mesothelin. After determination of tolerability of up to 9 planned injections by IV ROA, the subject will receive an IT administration of RNA CAR T cells×2. Cycles of IV and IT RNA CAR T cells will be repeated as tolerated at ~6 to 8 week intervals in absence of progressive disease. The results from this patient will guide the subsequent development of a fully developed phase I proof of concept protocol.

The major question in the development of CAR T cells for cancer therapy is to determine the safety of the therapeutic window, in this case the balance of potential antitumor effects and serositis that might occur by targeting mesothelin. RNA CAR T cells have been developed for this purpose, so that antitumor effects can be observed in preclinical 2 robust pre-clinical models. The toxicity management plan is guided by the fact that in the event of toxicity, the RNA CAR T cells will rapidly disappear within 2 to 3 days after discontinuation of CAR T cell injection. This compassionate use pilot study will determine the safety, tolerability and engraftment potential of mesothelin specific T cells in a patient with metastatic pancreatic cancer. The safety and feasibility of IT and IV routes of administration will be identified in this protocol. The general protocol schema is shown in FIG. 21.

The study consists of 1) a screening phase, 2) followed by an ~8 week intervention/treatment phase consisting of phlebotomy/apheresis, infusion and injection of T cells, tumor biopsy, and 3) staging and follow up. Repeat cycles of cells will be offered to the subject if evaluation has stable disease or better.

Apheresis/Phlebotomy

The patient or twin donor will have the standard leukapheresis screening prior to the procedure. For IT T cells 100 ml phlebotomy may provide sufficient lymphocytes for manufacturing. A 7 to 12 liter apheresis may be required for the IV dose of T cells in order to collect approximately $1 \times 10^9$ T cells or more. Subjects with poor venous access may have a temporary catheter placement for apheresis use. This catheter will be inserted prior to apheresis and removed once the apheresis procedure is completed. Peripheral samples will be taken for baseline immunoassays. Baseline blood leukocytes for FDA look-back requirements and for research are also obtained and cryopreserved.

Pre-Injection Assessment

In the week prior to dosing with the study agent, the patient will have interval history and physical exam, concomitant medication review, ECOG performance status, AE screen. The following must be done within 2 weeks prior to dosing: EKG and CXR (baseline screen for serositis), CBC, chemistry (LFTs), CEA and CA-19-9.

Preparation and Administration of Study Drug

The T cells are prepared in the Clinical Cell and Vaccine Production Facility (CVPF) and are not released until FDA specified release criteria for the infused cells (e.g., cell purity, sterility, pyrogenicity, etc.) are met.

IV Administration in the Clinical and Translational Research Center (CTRC)

T cells in one or two bags as appropriate for the dose will be transported on cold packs if fresh and on dry ice if cryopreserved to the subject's bedside at the CTRC. The cells are given by rapid intravenous infusion at a flow rate of approximately 10 to 20 ml per minute through an 18-gauge or comparable latex free Y-type blood set with a 3-way stopcock. The bag will be gently massaged until the cells have just thawed. There should be no frozen clumps left in the container. The duration of the infusion will be approximately 15 minutes. Each infusion bag will have affixed to it a label containing the following: "FOR AUTOLOGOUS/SYNGENEIC USE ONLY." In addition the label will have at least two unique identifiers such as the subject's initials, birth date, and study number. Prior to the infusion, two individuals will independently verify all this information in the presence of the subject and so confirm that the information is correctly matched to the participant. If the T cell product appears to have a damaged or leaking bag, or otherwise appears to be compromised, it should not be infused.

Emergency medical equipment (i.e., emergency trolley) will be available during the infusion in case the subject has an allergic response, or severe hypotensive crisis, or any other reaction to the infusion. Vital signs (temperature, respiration rate, pulse, and blood pressure) will be taken before and after infusion, then every 15 minutes for at least one hour and until these signs are satisfactory and stable. Details are as follows:

Concomitant medications will be reviewed.

T cells will be transported on cold packs from the Clinical Cell and Vaccine Production Facility (CVPF) to the patient's bedside.

The infusion will take place in the CTRC.

If frozen, autologous T cells will be thawed in a 37° C. water bath at patient-subject bedside. Cells will be infused within approximately 10-40 minutes after thaw. The T cells (in a volume of ~50-100 mL if cryopreserved and 100-300 mL if fresh) will be infused intravenously at a rate of approximately 10 mL/minute through an 18 gauge or equivalent latex free Y-type blood set with 3 way stop-cock. Dosing will take place by gravity infusion. If the infusion rate by gravity is too slow, the autolgous T cell drug product may be drawn into a 50 mL syringe via the stopcock and manually infused at the required rate.

Blood pressure, heart rate, respiratory rate and pulse oximetry will be obtained and recorded immediately prior to dosing and every 15 minutes for 2 hours following the start of infusion. A crash cart must be available for an emergency situation.

Within 15 minutes (±5 minutes) following completion of dosing with T cells, a blood sample will be obtained for a baseline determination of the number of infused T cells.

If no symptoms occur and patient-subject's vital signs remain normal 1 hour after the injection, the patient-subject will be discharged. If a vital sign measurement is not stable, it will continue to be obtained approximately every 15 minutes until the patient-subject's vital signs stabilize or the physician releases the patient.

Patient-will be admitted for observation overnight after initial infusion. Infusions are given on a qod M-W-F basis, and once tolerability determined, then subject will be infused on an outpatient basis if possible, and subject will be instructed to return in 24 hours for blood tests and follow up according to the SOE.

Premedication

Side effects following T cell infusions include transient fever, chills, fatigue and/or nausea. It is recommended that prior to infusion the subject be pre-medicated with acetaminophen 650 mg by mouth and diphenhydramine hydrochloride 25-50 mg by mouth or IV, prior to the infusion of T cells. These medications may be repeated every six hours as needed. A course of non-steroidal anti-inflammatory medication may be prescribed if the patient continues to have fever not relieved by acetaminophen. It is recommended that patient not receive systemic corticosteroids such as hydrocortisone, prednisone, prednisolone (Solu-Medrol) or dexamethasone (Decadron) at any time, except in the case of a life-threatening emergency, since this may have an adverse effect on T cells. If corticosteroids are required for an acute infusional reaction, an initial dose of hydrocortisone 100 mg is recommended. For IT injection, patients will not routinely receive pre-medications, other than anesthetics for injection pain.

IV T Cell Injections

Prior to study agent injection, patient will have ECOG performance status, AE screen, CBC, and LFTs reviewed. The objective is to administer T cells thrice weekly, i.e. MWF, for 3 weeks. It is likely that intervening medical complications or holidays, for example, could alter the schedule; scheduled infusions will be adjusted prn with the goal of 3 injections per week as tolerated.

The subject will receive infusions in an isolated room. The cells are thawed at the patient's bedside. The thawed cells will be given at an infusion rate as quickly as tolerated so that the duration of each infusion will be approximately 10-15 minutes. In order to facilitate mixing, the cells will be administered simultaneously using a Y-adapter. A blood sample for determination of baseline T cell level is obtained before infusion and 20 minutes post infusion. Subject will be infused and premedicated as appropriate. Subject's vital signs will be assessed and pulse oximetry will be done prior to dosing, at the end of the infusion and every 15 minutes thereafter for 1 hour and until these are stable. Patient will be hospitalized overnight following the first infusion. Later infusions will be administered on an outpatient basis as permitted. Patient-subject will be instructed to return to the HUP offices in 24 hours for blood tests and follow up.

The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management. 3) Hypotension requiring pressor support. 4) Active Infection: Positive blood cultures for bacteria, fungus, or virus within 48-hours of T cell infusion.

Following study agent infusion, blood should be obtained ~20 min after injection/infusion for cytokines and flow cytometry. Serum will be obtained for measurement of cytokines.

Interventional Radiology (IT Injection) T Cell Injection and Tumor Biopsy

T cells will be injected into the tumor lesions using ultrasonic guidance or other imaging as recommended by invasive radiology. Patient may be premedicated with an anxiolytic (i.e. ativan) or injected under conscious sedation. Patient may have 2.5 to 5.0 grams of lidocaine/prilocaine cream (EMLA) applied to the injection site at least 30 minutes before the procedure for local anesthesia. The area of skin to be injected will be cleansed with betadine, and after, more lidocaine (1%) will be injected in the skin, and subcutaneous tissues, and the tumor and peritumoral area infiltrated with the T cells, attempting to inject from tumor margins to central areas.

Prior to CAR T cell injection, core needle biopsies using a 16 Ga needle will be obtained to serve as baseline for mesothelin expression and the other parameters listed in secondary endpoints. Peripheral blood prior to and should be obtained after injection for cytokines and flow cytometry.

Tumor response assessments will begin at +4 and +8 weeks by abdominal imaging (PET/CT, CT or MRI) and then according to standard care and practices every 2 months for 2 years after T cell infusions or until the patient requires alternative therapy for his disease. It is expected that the metabolic activity of the T cells may obscure the interpretation of PET scans, as it may be difficult to interpret tumor metabolic activity from the inflammation triggered by the T cells.

Additional T Cell Therapy

In the absence progressive disease, IT and IV T cells infusions may be given on continued 6 to 8 week cycles. In the event of humoral immune responses to CART cells, then systemic (IV) injections of T cells will not be continued. However, in the absence of disease progression, patient may continue to receive monthly IT T cell injections to sites of active disease as tolerated.

Subjects will return on month 3 and 6 post T cell infusion. At these study visits, subject will undergo the following: physical exam, documentation of adverse events and blood draws for hematology, chemistry, urinalysis, CA-19-9, and research labs.

Example 5: GD2 Directed RNA CAR

GD2 is a disialoganglioside expressed on tumors with neuroectodermal origin, including neuroblastomas and melanomas. The tumor specificity of GD2 allows for its use to target genetically modified CTLs expressing an RNA CAR. The data presented herein demonstrates that CTLs electroporated with IVT RNA encoding a CAR comprising an GD2 scFv (where the scFv binds to GD2) effectively detects and treats GD2 expressing tumors.

pGEM-64A vectors were used to create IVT GD2-BBZ vectors. Overlapping PCR was used to generate pGEM-GD2-8TMBBZ, pGEM-GD2-28TMBBZ and pGEM-GD2-ZTMBBZ, using a lentiviral vector harboring GD2-zeta CAR that provides GD2 scFv and IgG hinge and pD-A.cMet.OF.8TMBBZ that provides 4-1BB-zeta (FIG. 21). Each transmembrane was introduced by PCR primers. The IVT RNA produced with these vectors each comprise an GD2 scFv antigen binding domain, as well as 4-1BB and CD3-zeta intracellular signaling domains. Additionally, three different vectors were produced, each differing in the identity of the transmembrane domain. As such, GD2 RNA CARs comprised either a CD8 transmembrane domain, a CD28 transmembrane domain, or a CD3-zeta transmembrane domain.

GD2-8TMBBZ RNA (containing the CD8 transmembrane domain) is transcribed from a nucleotide sequence comprising SEQ ID NO: 10. GD2-28TMBBZ (containing the CD28 transmembrane region) is transcribed from a nucleotide sequence comprising SEQ ID NO: 11. GD2-ZTMBBZ (containing the CD3-zeta transmembrane domain) is transcribed from a nucleotide sequence comprising SEQ ID NO: 12.

Flow cytometry was used to determine the surface expression of the various GD2 CAR compositions one day after electroporation. As shown in FIG. 22, GD2-8TMBBZ and GD2-28TMBBZ were highly expressed on electroporated cells.

To examine the function of GD2 RNA CART cells, a CD107a assay was performed on electroporated T cells. T cells were electroporated with different GD2 CAR RNA as indicated (using a CD19 CAR as a control) and were co-cultured with either a GD2 positive tumor line (SYSY) or a negative control (NLFwt). CD107a upregulation was detected by flow cytometry in a 4 h culture assay, as described elsewhere herein. FIG. 23 demonstrates upregulation of CD107a in GD2 RNA CAR electroporated cells indicating target recognition.

Electroporated T cells were also evaluated for IFN-gamma secretion following co-culture with various tumor cell lines. T cells electroporated with different GD2 CAR RNA as indicated (using a CD19 CAR as a control) were co-cultured with GD2 positive tumor line (SYSY), and negative control (NLFwt). Supernatant was harvested 24 hours post co-culture and was subjected to ELISA assay for the detection of IFN-gamma secretion. FIG. 24 illustrates that GD2 RNA CAR electroporated cells, but not cells electroporated with CD19 CAR or non-electroporated cells, secreted IFN-gamma following incubation with GD2 expressing tumors.

In order to remove internal open reading frames (ORFs) that existed within the GD2-8TMBBZ construct, overlapping PCR was used to generate pD-A.GD2.OF.8TMBBZ. pGEM-GD2-8TMBBZ was used as a template and the PCR product was subcloned into pD-A vector from pD-A.190F.2bgUTR.150A. Two internal ORFs were removed by PCR mutations of the ATG codons without producing a change in the CAR ORF (FIG. 25). The internal open reading frame free GD2.OF.8TMBBZ is transcribed from a nucleotide sequence comprising SEQ ID NO: 13

To evaluate the effectiveness of GD2 RNA CARs to treat GD2 expressing tumors in vivo, and animal study was performed using mice injected with SYSY neuroblastoma cells, modified to express luciferase. T cells were electroporated with RNA made from pD-A.GD2.OF.8TMBBZ.2bg.150A. This vector comprises two repeats of a 3'UTR derived from human beta-globulin and a poly(A) tail comprising 150 A bases. The pD-A.GD2.OF.8TMBBZ.2bg.150A vector comprises a nucleotide sequence comprising SEQ ID NO: 28. FIG. 26 depicts the study time line where tumors were injected 8 days prior to the first administration of electroporated T cells (5M RNA T cells). Subsequent doses of electroporated T cells was given intravenously on day 14 (14M RNA T cells) and day 16 (16M RNA T cells. Bioluminescence imaging (BLI) was done throughout the time course of the study as depicted.

Quantification of the amount of the GD2 expressing neuroblastoma in the tumor injected mice is depicted in FIG. 27. Mice injected with T cells electroporated with GD2 CAR RNA demonstrated decreased tumor burden compared to those electroporated with CD19 CAR RNA and those treated with only PBS. FIG. 28 provides heat maps of the tumor cells in mice treated with GD2 RNA CAR and CD19 RNA CAR, demonstrating reduced tumors in the GD2 RNA CAR treated animals.

Example 6: cMet Directed RNA CAR cMet is a receptor tyrosine kinase found on numerous types of cancers including non-small cell carcinoma (NSCLC), gastric, ovarian, pancreatic, thyroid, breast, head and neck, colon, and kidney carcinomas. Thus, as presented herein, the ability to develop IVT RNA CARs that target cMet would prove useful to treat a variety of forms of cancer.

cMet expression on variety of tumor lines was first examined. cMet expression of different cell lines was detected by flow cytometry using anti-cMet antibody (Anti-Human HGF R/c-MET Fluorescein MAb, R&D System). As depicted in FIG. 29, K562-cMet, L55, SK-OV3, and OV79 tumor cell lines all express cMet to some degree, and thus could be used in experiments examining the functional activity of cMet RNA CARs.

Based on initial screening tests, cMet.BBZ CARs with different transmembrane (TM) regions (TM regions from CD8, CD28 or 4-1BB) and with internal ORF free (cMet.OF) (FIG. 30) were generated by overlapping PCR and subcloned into pDrive based vector by replacing CD19.OF.BBZ of pD-A.190F.BBZ.2bgUTR.150A with cMet.OF.BBZs. The cMet RNACARs constructed and tested here are: cMet.OF.8TM.BBZ, cMet.OF.28TMBBZ, cMet.OF.BBTMBBZ, cMet.28TM28BBZ, and cMet.28Z. Thus, the constructs described herein all contain a cMet targeted scFv antigen binding domain, and at least one of CD28, 4-1BB, and CD3-zeta intracellular domains. cMet.OF.8TMBBZ is transcribed from a nucleotide sequence comprising SEQ ID NO: 14. cMet.OF.28TMBBZ is transcribed from a nucleotide sequence comprising SEQ ID NO: 15. cMet.OF.BBTMBBZ is transcribed from a nucleotide sequence comprising SEQ ID NO: 16. cMet.28TM28BBZ is transcribed from a nucleotide sequence comprising SEQ ID NO: 17. cMet.28Z is transcribed from a nucleotide sequence comprising SEQ ID NO: 18.

The functionality of the various forms of cMET RNA CAR was evaluated in a CD107a assay. T cells electroporated with different cMet CAR RNA as indicated in FIGS. 31A and 31B (using a CD19 CAR, CD19.OF BBZ as a control) were co-cultured with cMet positive tumor lines, L55 and SL-0V3, and negative control K562-CD19. CD107a upregulation was detected by flow cytometry in a 4 h culture assay (FIG. 31A). FIG. 31B shows the level of CAR expression 24 h post electroporation.

IFN-gamma production and secretion by cMet RNA CAR electroporated T cells was also examined after co-culture with various cell lines. T cells electroporated with different cMet CAR RNA, as indicated in FIG. 32 (using a CD19 CAR, 19BBZ as a control), were co-cultured with cMet positive tumor lines L55 and SL-0V3, and negative control K562-CD19. Supernatant was harvested 24 h post co-culture and was subjected to ELISA assay for IFN-gamma secretion (FIG. 32A). Based on both transgene expression and function cMet CAR RNA electroporated T cells, pD-A.cMet.OF.8TMBBZ 0.2bgUTR.150A (construct shown in FIG. 32B) was chosen for animal experiment and potential clinical trial. This vector comprises two repeats of a 3'UTR derived from human beta-globulin and a poly(A) tail comprising 150 A bases. The pD-A.cMet.OF.8TMBBZ 0.2bgUTR.150A vector comprises a nucleotide sequence comprising SEQ ID NO: 27. cMet.OF.8TMBBZ CAR is transcribed from a nucleotide sequence comprising SEQ ID NO: 14, and comprises a cMet scFv antigen binding domain, a CD8 transmembrane region, a 4-1BB intracellular signaling domain, and a CD3-zeta signaling domain.

For the next set of experiments, cMet.OF.8TMBBZ was used as the cMET RNA CAR. Additional melanoma tumor cell lines were evaluated for their surface expression of cMet (FIG. 33). Cells were stained with PE conjugated anti-cMet Ab or Isotype IgG Ab, which showed that SK-OV3, 888mel, 624mel, and 526mel cell lines all expressed cMet, while the K562 line did not.

CAR expression of the cMet.OF.8TMBBZ RNA CAR was evaluated by flow cytometry. Day 10 stimulated T cells were electroporated with either CD19 CAR RNA or cMet CAR RNA, or were not electroporated (No EP). After overnight culturing, CD19 CAR or cMet CAR expression was detected by flow cytometry, showing that T cells electroporated with cMet.OF.8TMBBZ had substantial CAR expression (FIG. 34).

Next, a CD107a assay was performed to examine the functional activity of the cMet.OF.8TMBBZ RNA CAR when co-cultured with a variety of tumor cell lines. RNA electroporated T cells were stimulated with a tumor cell line, including CD19+ Nalm6, cMet+ SK-OV3 and cMet+ melanoma lines (888mel, 624mel and 526mel). K562 was used as CD19− and cMet− control. After 4 h stimulation, CD107a expression was monitored by flow cytometry. Cells were CD8+ gated. As shown in FIG. 35, CD107a was upregulated in all conditions of cMet RNA CAR electroporated T cells co-cultured with a cMet+ tumor cell line.

IFN-gamma production and secretion by cMet RNA CAR electroporated T cells co-cultured with various tumor lines was evaluated. cMet.OF.8TMBBZ CAR RNA electroporated T cells were stimulated with a tumor cell line, including CD19+ Nalm6, cMet+ SK-OV3 and cMet+ melanoma lines (888mel, 624mel and 526mel). K562 was used as CD19− and cMet− control. After 24 h stimulation, IFN-gamma production was assayed by ELISA. As depicted in FIG. 36, IFN-gamma secretion is increased in all conditions of cMet RNA CAR electroporated T cells co-cultured with a cMet+ tumor cell line.

Next, an animal study was designed and conducted to evaluate the effectiveness of treating cMet+ tumors with cMet RNA CARs in vivo. FIG. 37 provides the study design where SKOV3-Luc tumor cells were implanted subcutaneously on day 0, and cMet.OF.8TMBBZ CAR RNA electroporated T cells were administered intratumorally at weeks 7, 9, and 11. Further, animals were treated with Cytoxan 24 hours before each T cell administration.

Quantification of tumor burden, as measured by fold of total flux change, is depicted in FIG. 38. It is shown that tumor burden is decreased in mice treated with cMet RNA CAR+Cytoxan. This data demonstrates that RNA CARs targeted to cMet are effective in treating cMet+ tumors.

Example 7: Combined Treatment of RNA CAR and Cytoxan

Based on multiple animal tumor treatment experiments with RNA CARs, it was found that a few days post treatment, both lenti-CD19z and CD19 RNA T cells showed similar treatment efficacy. While CD19 RNA CAR T cells showed significantly lower tumor burden than control T cells, or saline treated mice (1-2 log lower BLI), they do not clear the tumor as effectively as lentivirus encoding CD19 CARs (FIG. 39). Additional T cells injections (the second and the third) do not seem to add any additional treatment benefits, compared to Lenti-CD19Z T cells treated mice, which showed continuous tumor repression (FIG. 39). The treatment efficacy of multiple T cells injections is comparable to previous experiments using single dose T cells injection, indicating that the observed lack of treatment efficacy of re-injected T cells may be due to pre-existing non-functional T cells expanded from the first T cell injection. As presented herein, it is examined whether ablating those non-functional T cells prior new T cell injections enhances the treatment of multiple injections of RNA CAR T cells.

For initial experiments, T cells were electroporated with one of: CD19-z, CD19-BBz, CD19-28z, and CD19-28BBz. T cells electroporated with SS1-BBz was used a control. CD19-z is transcribed from a nucleotide sequence comprising SEQ ID NO: 19. CD19-BBZ is transcribed from a nucleotide sequence comprising SEQ ID NO: 7. CD19-28z transcribed from a nucleotide sequence comprising SEQ ID NO: 20. CD19-28BBz transcribed from a nucleotide sequence comprising SEQ ID NO: 21.

At day 5 post Nalm-6-Luc injection into NSG mice, $10^7$ RNA electroporated T cells were injected (iv). Seven days post the first T cell injection, chemotherapy (Cytoxan; CYTX, 80 mg/kg) was given (ip) to ablate the pre-existing T. One day after the Chemo, the second injection of $10^7$ T cells was given. Cytoxan (CYTX, 50 mg/kg) was given one day before the third and fourth T cells injections. Mice treated with saline or saline+chemo were used as controls. Mice were imaged and bled weekly to monitor the tumor and T cell burdens. FIG. 40 demonstrates that CYTX chemotherapy treatments enhances the tumor depletion mediated by repeated infusions of CD19 directed RNA CARs. FIG. 41 depicts the overall survival of animals in the various treatment groups, which shows that repeated infusions of RNA CAR T cells only prolongs survival when combined with Cytoxan based depletion of the previous infusion.

In the next set of experiments, 5 day Primary Leukemia-CBG/NSG mice were used. At day 5 post administration of cells from a primary leukemia cell line modified to express the click beetle green (CBG) gene, $10^7$ RNA electroporated T cells were injected (iv). Seven days post the first T cell injection, chemotherapy (Cytoxan, 60 mg/kg) was given (ip) to ablate the pre-existing T cells. One day after the Chemo, second injection of $10^7$ T cells was given. Cytoxan was given one day before the third T cell injections. Mice were imaged and bled weekly to monitor the tumor and T cell burdens. The following treatment groups were used: Lentiviral vector.19.28BBZ, IVT RNA. 19.28BBZ CO (codon optimized CD19-28BBZ CAR DNA sequence), IVT RNA 19.28BBZ LL (CD28 dileucine motif was mutated), IVT RNA 19.28BBZ wt (CD28 with dileucine motif), Lentiviral vector 19BBZ, IVT RNA 19BBZ CO (codon optimized CD19-BBZ CAR DNA sequence), IVT RNA 19BBZ wt. 19.28BBZ CO is transcribed from a nucleotide sequence comprising SEQ ID NO: 22. 19.28BBZ LL is transcribed from a nucleotide sequence comprising SEQ ID NO: 23. 19BBZ CO is transcribed from a nucleotide sequence comprising SEQ ID NO: 24.

T cells electroporated with IVT RNA ss1BBZ was used as a control. Multiple T cell injections were performed only in treatment groups with RNA electroporated T cells (not lentiviral transduced T cells). FIG. 42 depicts tumor burden over the first three weeks of the study, showing that the effect of Cytoxan was repeated and that tumor burden decreases further when multiple dosages of RNA CARs are combined with Cytoxan. FIG. 43 depicts the percent survival of treated animals.

FIG. 44 depicts heat maps of animals in each treatment group on day 10, 5 days after a single injection of $10^7$ CAR T cells, while FIG. 45 depicts heat maps for animals in each treatment group on day 21, 7 days after Cytoxan treatment and second injection of $10^7$ cells (second injection only in RNA CAR groups). The heat maps demonstrate that the combined treatment of Cytoxan and multiple RNA CAR injections reduces tumor cells similar to lentiviral CAR treatments.

The next study examined different dosing strategies of the amount of T cells administered in the multiple injections. Seven day Nalm-6-Luc/NSG mice were used. At day 7 post delivery of leukemia cells, RNA electroporated T cells were injected at different dose (iv). Seven days post the first T cell injection, chemotherapy (Cytoxan, 60 mg/kg) was given (ip) to ablate the pre-existing T. One day after the Chemo, the second injection of T cells was given. Cytoxan was applayed one day before the third T cells injection. Mice were imaged and bled weekly to monitor the tumor and T cell burdens. The following treatment groups were used: Lentiviral vector-CD19BBZ-10e6/mouse; CD19BBZ RNA, 10e6/mouse for all 3 injections; CD19BBZ RNA, 1st injection—20e6/mouse, 2nd and 3rd—10e6/mouse; CD19BBZ RNA, 1st injection-20e6/mouse, 2nd and 3rd—5e6/mouse; CD19BBZ RNA, 10e6/mouse for all 3 injections—without Cytoxan; CD19BBZ RNA, 1st injection—20e6/mouse, 2nd and 3rd—10e6/mouse—without Cytoxan. T cells electroporated with ss1BBZ RNA-1st injection: 20e6/mouse, 2nd and 3rd-10e6/mouse was used as a control. FIG. 46 depicts the tumor burden of animals in each treatment group over the first 3 weeks of the study. Data presented therein demonstrates that animals receiving multiple injections of CD19-BBz RNA CAR T cells combined with Cytoxan had less tumor burden than those receiving multiple injections of CD19-BBz RNA CART cells alone.

FIG. 47 provides heat maps of animals in each treatment group on day 22 of the study. It is seen that chemotherapy, as provided by Cytoxan is vital in the elimination of tumors in mice treated with multiple injections of RNA CAR. FIG. 48 provides additional heat maps of animals throughout the time course of the study, showing sustained reduction of tumors in the 20-5-5, and 20-10-10 groups, when combined with Cytoxan treatments.

The percent survival, as depicted in FIGS. 49 and 50, again shows that Cytoxan enhances the treatment conferred by multiple injections of RNA CAR T cells. Present results show that high dose RNA CAR regimen (20-5-5) with Cytoxan treatments results in about 40% survival at about 75 days post leukemia induction, while all treatment groups that did not include Cytoxan had a 0% survival by 65 days at the latest. The data presented herein demonstrate that chemotherapy drastically enhances treatment and tumor reduction conferred by RNA CARs.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An in vitro transcribed RNA or synthetic RNA, comprising a nucleic acid sequence encoding an extracellular domain, a transmembrane domain, a costimulatory signaling region, and a signaling domain of CD3-zeta, wherein the RNA is transcribed from an in vitro transcription vector or a DNA,
   wherein the in vitro transcription vector comprises the nucleic acid sequence of SEQ ID NO: 4, 5, 27, or 28, and
   wherein the DNA comprises the nucleic acid sequence of any one of SEQ ID NOs: 6-24.

2. The RNA of claim 1, wherein the extracellular domain comprises an antigen binding moiety.

3. The RNA of claim 2, wherein the antigen binding moiety binds to a tumor antigen.

4. The RNA of claim 3, wherein the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

5. The RNA of claim 1, wherein the vector comprises the nucleic acid sequence of SEQ ID NO: 4.

6. The RNA of claim 1, wherein the DNA comprises the nucleic acid sequence of SEQ ID NO: 6 or 8.

7. The RNA of claim 1, wherein the vector comprises the nucleic acid sequence of SEQ ID NO: 5.

8. The RNA of claim 1, wherein the DNA comprises a sequence selected from the group consisting of SEQ ID NO: 7, SEQ ID NO: 9, SEQ ID NO: 19, SEQ ID NO: 20, SEQ ID NO: 21, SEQ ID NO: 22, SEQ ID NO: 23 and SEQ ID NO: 24.

9. The RNA of claim 1, wherein the vector comprises the nucleic acid sequence of SEQ ID NO: 28.

10. The RNA of claim 1, wherein the DNA comprises a sequence selected from the group consisting of SEQ ID NO: 10, SEQ ID NO: 11, SEQ ID NO: 12 and SEQ ID NO: 13.

11. The RNA of claim 1, wherein the vector comprises the nucleic acid sequence of SEQ ID NO: 27.

12. The RNA of claim 1, wherein the DNA comprises a sequence selected from the group consisting of SEQ ID NO: 14, SEQ ID NO: 15, SEQ ID NO: 16, SEQ ID NO: 17 and SEQ ID NO: 18.

13. The RNA of claim 1, wherein the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

14. The RNA of claim 1, wherein the nucleic acid sequence comprises a poly(A) tail comprising about 150 adenosine bases.

15. The RNA of claim 1, wherein the nucleic acid sequence comprises a 3'UTR comprising at least one repeat of a 3'UTR derived from human beta-globin.

* * * * *